US011021534B2

(12) United States Patent
Hall et al.

(10) Patent No.: US 11,021,534 B2
(45) Date of Patent: Jun. 1, 2021

(54) MYCOBACTERIAL ANTIGEN COMPOSITION

(71) Applicant: Secretary of State for Health and Social Care, London (GB)

(72) Inventors: Yper Hall, Salisbury (GB); Joanna Bacon, Salisbury (GB); Philip Marsh, Salisbury (GB)

(73) Assignee: SECRETARY OF STATE FOR HEALTH AND SOCIAL CARE, London (GB)

( * ) Notice: Subject to any disclaimer, the term of this patent is extended or adjusted under 35 U.S.C. 154(b) by 63 days.

(21) Appl. No.: 15/672,085

(22) Filed: Aug. 8, 2017

(65) Prior Publication Data

US 2018/0066043 A1 Mar. 8, 2018

Related U.S. Application Data

(62) Division of application No. 15/110,932, filed as application No. PCT/GB2015/050100 on Jan. 16, 2015, now abandoned.

(30) Foreign Application Priority Data

Jan. 17, 2014 (GB) ..................................... 1400819

(51) Int. Cl.

| | |
|---|---|
| ***C07K 16/12*** | (2006.01) |
| ***A61K 39/04*** | (2006.01) |
| ***A61K 39/00*** | (2006.01) |
| ***G01N 33/569*** | (2006.01) |

(52) U.S. Cl.

CPC .......... *C07K 16/1289* (2013.01); *A61K 39/04* (2013.01); *G01N 33/5695* (2013.01); *A61K 39/00* (2013.01); *A61K 2039/53* (2013.01); *A61K 2039/57* (2013.01); *A61K 2039/6006* (2013.01); *C07K 2319/21* (2013.01); *G01N 2333/35* (2013.01)

(58) Field of Classification Search

None

See application file for complete search history.

(56) References Cited

U.S. PATENT DOCUMENTS 6,294,328 B1 * 9/2001 Fleischmann .......... C12Q 1/689 435/6.15

FOREIGN PATENT DOCUMENTS

| | | | |
|---|---|---|---|
| EP | 2 196 473 | A1 | 6/2010 |
| RU | 2244933 | C2 | 1/2005 |
| WO | 02/077183 | A2 | 10/2002 |
| WO | 2004/074310 | A2 | 9/2004 |
| WO | 2005/090988 | A2 | 9/2005 |
| WO | 2014/009438 | A2 | 1/2014 |

OTHER PUBLICATIONS

Ellis (Vaccines, W.B. Saunders Company, Chapter 29, 1988, pp. 568-574).*

Boslego et al (Vaccines and Immunotherapy, 1991, Chapter 17).*

Skolnick et al. (Trends in Biotechnology 18: 34-39, 2000).*

Greenspan et al. 1999 (Nature Biotechnology, 17:936-937).*

Great Britain Search Report Under Section 17(5), dated Sep. 30, 2014, issued in corresponding Application No. GB 1400819.7, filed Jan. 17, 2014, 261 pages.

Great Britain Search Report Under Section 17(6), dated Oct. 30, 2014, issued in corresponding Application No. GB 1400819.7 (Invention (b)), filed Jan. 17, 2014, 88 pages.

Great Britain Search Report Under Section 17(6), dated Dec. 1, 2014, issued in corresponding Application No. GB 1400819.7 (Invention (d)), filed Jan. 17, 2014, 26 pages.

Great Britain Search Report Under Section 17(6), dated Dec. 1, 2014, issued in corresponding Application No. GB 1400819.7 (Invention (e)), filed Jan. 17, 2014, 2 pages.

Great Britain Search Report Under Section 17(6), dated Dec. 1, 2014, issued in corresponding Application No. GB 1400819.7 (Invention (f)), filed Jan. 17, 2014, 159 pages.

Great Britain Search Report Under Section 17(6), dated Dec. 1, 2014, issued in corresponding Application No. GB 1400819.7 (Invention (g)), filed Jan. 17, 2014, 132 pages.

Great Britain Search Report Under Section 17(6), dated Dec. 1, 2014, issued in corresponding Application No. GB1400819.7 (Invention (h)), filed Jan. 17, 2014, 2 pages.

Great Britain Search Report Under Section 17(6), dated Dec. 17, 2014, issued in corresponding Application No. GB 1400819.7 (Invention (i)), filed Jan. 17, 2014, 298 pages.

Murphy, D.J., and J.R. Brown, "Identification of Gene Targets Against Dormant Phase *Mycobacterium tuberculosis* Infections," BMC Infectious Diseases 7:84, Jul. 2007, 16 pages.

Wang, L., et al., "Prokaryotic Essential Gene #22228," Nucleic Acid Sequence Accession No. ACA40571, submitted Jun. 19, 2003 to Integrated Biotechnological Information Services (IBIS) <http://ibis.internal.epo.org/exam/dbfetch.jsp?id=GSP:ABU36701> [retrieved May 20, 2015], 1 page.

(Continued)

*Primary Examiner* — Robert A Zeman

(74) *Attorney, Agent, or Firm* — Christensen O'Connor Johnson Kindness PLLC

(57) ABSTRACT

The present invention provides an antigenic composition for use as a mycobacterial vaccine, said composition comprising (i) a first mycobacterial antigenic polypeptide, wherein said first mycobacterial antigenic polypeptide comprises a polypeptide sequence having at least 70% amino acid sequence identity to the amino acid sequence of SEQ ID NO: 6, 12, 2, 18, 8, 10, 16, 4, or a fragment thereof having at least 50 consecutive amino acids thereof; or (ii) a first mycobacterial polynucleotide, wherein said first mycobacterial polynucleotide comprises a polynucleotide sequence encoding said first mycobacterial antigenic polypeptide, or wherein said first mycobacterial polynucleotide comprises a polynucleotide sequence selected from SEQ ID NO: 5, 11, 1, 17, 7, 9, 15, 3.

10 Claims, 2 Drawing Sheets

Specification includes a Sequence Listing.

(56) References Cited

OTHER PUBLICATIONS

Wang, L., et al., "Protein Encoded by Prokaryotic Essential Gene #22228," Nucleic Acid Sequence Accession No. ABU36701, submitted Jun. 19, 2003 to Integrated Biotechnological Information Services (IBIS), last updated Jun. 16, 2007, <http://ibis.internal.epo.org/exam/dbfetch.jsp?id=GSP:ACA40571> [retrieved May 21, 2015], 1 page.
Zahrt, T.C., et al., "Functional Analysis of the *Mycobacterium tuberculosis* MprAB Two-Component Signal Transduction System," Infection and Immunity 71(12):6962-6970, Dec. 2003.
Written Opinion and International Search Report dated Aug. 26, 2015, issued in corresponding International Application No. PCT/GB2015/050100, filed Jan. 16, 2015, 15 pages.
Second Written Opinion dated Feb. 2, 2016, issued in corresponding International Application No. PCT/GB2015/050100, filed Jan. 16, 2015, 7 pages.
International Preliminary Report on Patentability dated Jun. 22, 2016, issued in corresponding International Application No. PCT/GB2015/050100, filed Jan. 16, 2015, 16 pages.
Cole, S.T., et al., "Deciphering the Biology of *Mycobacterium tuberculosis* From the Complete Genome Sequence," Nature 393:537-544, 1998.
Extended European Search Report dated Dec. 1, 2017, issued in corresponding European Application No. 17192244.6, 8 pages.
Russian Federation Search Report, issued in Application No. 2016133598, filed Jan. 16, 2015, 2 pages.
Second Chinese Office Action dated Aug. 16, 2019, issued in Chinese Application No. 201580009239.8, 6 pages.
GenPept [Online], Aug. 29, 2013, "acyl-CoA dehydrogenase [*Mycobacterium tuberculosis* complex]," Accession WP_003412771.1, 1 page.
GenBank [Online], Dec. 14, 2017, "*Mycobacterium tuberculosis* H37Rv, Complete Genome," Accession NC_000962.3, 2 pages.

* cited by examiner

MYCOBACTERIAL ANTIGEN COMPOSITION

CROSS-REFERENCES TO RELATED APPLICATIONS

This application is a division of U.S. patent application Ser. No. 15/110,932, filed Jul. 11, 2016, (now abandoned) which is a national stage of International Application No. PCT/GB2015/050100, filed Jan. 16, 2015, both of which are incorporated herein by reference in their entirety.

STATEMENT REGARDING SEQUENCE LISTING

The sequence listing associated with this application is provided in text format in lieu of a paper copy and is hereby incorporated by reference into the specification. The name of the text file containing the sequence listing is MASQ164196_Seq_Rev_20210412_ST25.txt. The text file is 140 KB; was created on Apr. 12, 2021; and is being submitted via EFS-Web with the filing of the specification.

BACKGROUND

The present invention relates to mycobacterial polynucleotides and polypeptides, to fragments or variants thereof, to antibodies that bind thereto, to vectors and microbial carriers, to therapeutic compositions such as vaccines against mycobacterial infections, and to compositions and methods for detecting mycobacterial infection.

Microorganisms such as species of *Salmonella, Yersinia, Shigella, Campylobacter, Chlamydia* and *Mycobacterium* are capable of causing intracellular infections. These infections may be exclusively intracellular, or may contain both intracellular and extracellular components. Generally, these microorganisms do not circulate freely in the body (e.g. in the bloodstream) and are often not amenable to drug treatment regimes.

The difficulties associated with treating intracellular infection have been exacerbated by the development of multiple drug-resistant microorganisms. Vaccine therapies have not proved effective against intracellular microorganisms because of the difficulties in the ability of the host defenses to access the pathogen.

*Mycobacterium tuberculosis* (MTB) and closely related species make up a small group of mycobacteria known as the *Mycobacterium tuberculosis* complex (MTC). This group comprises five distinct species: *M. tuberculosis, M. microti, M. bovis, M. caneti*, and *M. africanum. M. avium* subsp. paratuberculosis causes Johne's disease in ruminants, *M. bovis* causes tuberculosis in cattle, *M. avium* and *M. intracellulare* cause tuberculosis in immunocompromised patients (eg. AIDS patients, and bone marrow transplant patients), and *M. leprae* causes leprosy in humans. Another important mycobacterial species is *M. vaccae.*

As the aetiological agent of tuberculosis infection, *Mycobacterium tuberculosis* (*M. tuberculosis*) is the leading cause of death by bacterial infectious disease worldwide—latent infection affecting as much as one third of the world's population. The World Health Organisation (WHO) estimates that over eight million new cases of TB, and over one million deaths, occur globally each year. The largest number of new TB cases in 2005 occurred in South-East Asia (34% of incident cases globally), and the estimated incidence rate in sub-Saharan Africa is nearly 350 cases per 100,000 population. However, TB infection is not limited to the developing world: the UK has seen a resurgence of tuberculosis since the late 1980s and there are currently over 8000 new cases each year—a rate of 14.0 per 100,000 population. About 40% of these new cases occur in the London region, where the rate of infection is 44.8 per 100,000 population.

Optimal patient management requires early initiation of drug therapy and isolation of infectious individuals as soon as possible. Left untreated, each person with active TB disease will infect on average between 10 and 15 people every year. TB infection can normally be treated by a 6 month course of antibiotics; however, patient compliance to long-term drug treatment is varied, with patients often stopping therapy when their symptoms cease. Failure to complete the treatment can promote the development of multiple drug-resistant mycobacteria.

The term 'latency' is synonymous with 'persistence', and describes a reversible state of low metabolic activity in which mycobacterial cells can survive for extended periods with limited or no cell division. During latency (ie. latent infection), the clinical symptoms associated with a mycobacterial infection do not become manifest. However, reactivation of latent mycobacteria may be induced by environmental stimuli. During active infection, mycobacteria demonstrate high metabolic activity and replicate rapidly, resulting in the development of active infection with clinical symptoms.

In vitro studies have demonstrated that mycobacteria such as *M. tuberculosis* are able to adapt to and survive under nutrient- and oxygen-depleted conditions, and can grow over a range of nutrient availabilities and oxygen tensions. Adaptation to carbon starvation and/or to a low dissolved oxygen tension in vitro triggers transition to a non-replicating persistent state that may be analogous to latency in vivo. Intracellular survival and multiplication of mycobacteria is suspected to be a main supportive factor for mycobacterial disease progression. The presence of a large reservoir of asymptomatic individuals latently-infected with mycobacteria is a major problem for the control of mycobacterial infections, especially *M. tuberculosis* infections. In addition, conventional methods for the detection of a latent mycobacterial infection by skin testing may be compromised by BCG vaccination and by exposure to environmental mycobacteria.

The effectiveness of vaccine prevention against *M. tuberculosis* has varied widely. The current *M. tuberculosis* vaccine, BCG, is an attenuated strain of *M. bovis*. It is effective against severe complications of TB in children, but it varies greatly in its effectiveness in adults in different countries, particularly across ethnic groups. BCG vaccination has been used to prevent tuberculous meningitis and helps prevent the spread of *M. tuberculosis* to extra-pulmonary sites, but does not prevent infection. The limited efficacy of BCG and the global prevalence of TB has led to an international effort to generate new, more effective vaccines. This, in turn, requires the identification of new vaccine candidates. In view of the increasing threat and global prevalence of mycobacterial infection, new strategies are required for more effective prevention, treatment, and diagnosis of mycobacterial infection.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
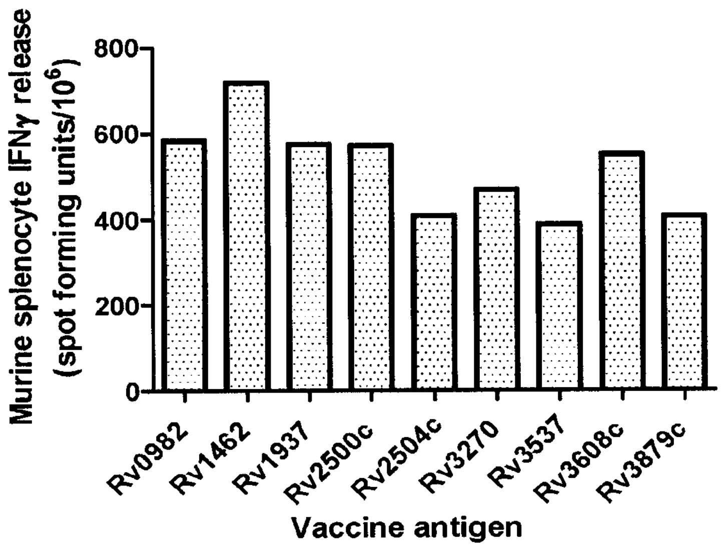
FIG. 1 graphically illustrates the murine splenocyte interferon-gamma (IFN-γ) release for various vaccine antigens.

The invention provides an antigenic composition comprising a mycobacterial antigen, wherein said antigen comprises:

(i) a polypeptide sequence having at least 70% amino acid sequence identity to the amino acid sequence of a polypeptide selected from SEQ ID NOs: 2, 4, 6, 8, 10, 12, 14, 16 and 18, or a fragment thereof having at least 50 consecutive amino acids thereof; or (ii) a polynucleotide sequence encoding a polypeptide sequence according to (i); or a polynucleotide sequence having at least 70% nucleotide sequence identity to the nucleic acid sequence of a polynucleotide selected from SEQ ID NOs: 1, 3, 5, 7, 9, 11, 13, 15 and 17, or a fragment thereof having at least 150 consecutive nucleotides thereof.

As used herein, the term "mycobacterial" or "*mycobacterium*" embraces the species *M. phlei, M. smegmatis, M. africanum, M. caneti, M. fortuitum, M. marinum, M. ulcerans, M. tuberculosis, M. bovis, M. microti, M. avium, M. paratuberculosis, M. leprae, M. lepraemurium, M. intracellulare, M. scrofulaceum, M. xenopi, M. genavense, M. kansasii, M. simiae, M. szulgai, M. haemophilum, M. asiaticum, M. malmoense, M. vaccae, M. caneti*, and *M. shimoidei*. Of particular interest are the members of the MTC, such as *M. tuberculosis*.

The term antigen means any substance that can be recognized by the immune system and/or that stimulates an immune response. For example, an antigen may stimulate a cell mediated immune response and/or may stimulate the generation of antibodies.

In one embodiment, a mycobacterial antigen of the invention provides a cell mediated response to infection involving immune cells such as T cells (CD4+ and/or CD8+ T cells) and/or the ability to respond with Th1-type cytokines such as IFN-γ. In one embodiment, a mycobacterial antigen induces IFN-γ-secreting cells (eg. predominantly CD4+ T cells). In this regard, recent studies suggest that immune cell responses (particularly T cell immune responses in, for example, the lung) may be critical for protection against pulmonary mycobacterial disease.

In one embodiment, a mycobacterial antigen of the invention provides protection (such as long term protection) against challenge by mycobacteria such as *M. tuberculosis*. By way of example, a mycobacterial antigen of the invention may induce 'memory T cells', which can continue to stimulate protective immunity in the long term (eg. for decades). Memory immune responses have been attributed to the reactivation of long-lived, antigen-specific T lymphocytes that arise directly from differentiated effector T-cells and persist in a quiescent state. Memory T cells are heterogeneous; at least two subsets have been identified, having different migratory capacity and effector function. Memory T cells of the first subset are known as 'effector memory T cells' (TEM) because they resemble the effector T cells generated in the primary response, in that they lack the lymph node-homing receptors for migration into inflamed tissues. Upon re-encounter with antigen, the TEM rapidly produce IFN-γ or IL-4, or release pre-stored perforin. Memory T cells of the second subset (known as 'central memory cells' (TCM)) express L-selectin and CCR7 and lack immediate effector function. The TCM have a low activation threshold and proliferate and differentiate to effectors when re-stimulated in secondary lymphoid organs.

In one embodiment, a mycobacterial antigen provides a neutralizing antibody response to mycobacterial (eg. *M. tuberculosis*) infection. In one embodiment, each mycobacterial antigen in the antigenic composition of the present invention independently induces an effective immune response (eg. a cell mediated immune response or antibody response). Thus, in accordance with this embodiment, following administration of the antigenic composition to a subject, an immune response is induced in the subject to each mycobacterial antigen in the antigenic composition.

In one embodiment, a mycobacterial antigen comprises (eg. consists of) a polypeptide sequence. Alternatively, or in addition, a mycobacterial antigen comprises a polynucleotide (e.g. DNA or RNA) sequence.

The specific sub-set of mycobacterial polypeptides represented by SEQ ID NOs: 2, 4, 6, 8, 10, 12, 14, 16 and 18 are 'latency-regulated polypeptides'. The specific subset of mycobacterial polynucleotides represented by SEQ ID NOs: 1, 3, 5, 7, 9, 11, 13, 15 and 17 are 'latency-regulated polynucleotides'.

In one embodiment, 'a latency-regulated polypeptide' is encoded by a 'latency-regulated polynucleotide'. By way of example, the latency-regulated polypeptide SEQ ID NO: 2 is encoded by latency-regulated polynucleotide SEQ ID NO: 1; SEQ ID NO: 4 is encoded by SEQ ID NO: 3; SEQ ID NO: 6 is encoded by SEQ ID NO: 5; SEQ ID NO: 8 is encoded by SEQ ID NO: 7; SEQ ID NO: 10 is encoded by SEQ ID NO: 9; SEQ ID NO: 12 is encoded by SEQ ID NO: 11; SEQ ID NO: 14 is encoded by SEQ ID NO: 13; SEQ ID NO: 16 is encoded by SEQ ID NO: 15; and SEQ ID NO: 18 is encoded by SEQ ID NO: 17.

The expression or activity of a latency-regulated polypeptide or polynucleotide is modulated in response to mycobacterial latency—eg. in response to growth of mycobacteria (eg. MTB) under conditions that induce or maintain mycobacterial latency.

In one embodiment, "modulation" of expression or activity of the latency-regulated polypeptide or polynucleotide in response to conditions of mycobacterial latency means that the expression or activity is induced or upregulated in response to latency. Thus, the latency-regulated polypeptide or polynucleotide may be a 'latency-induced' or 'latency-upregulated' polypeptide or polynucleotide.

For example, the expression or activity of a latency-upregulated polypeptide or polynucleotide may be up-regulated by at least 1.5-fold, 2-fold, 5-fold, 10-fold, 20-fold or 50-fold under latency conditions as compared to non-latency conditions. Alternatively, vaccine efficacy of the polypeptides/polynucleotides of the present invention may be measured in terms of murine splenocyte interferon-gamma (IFN-γ) release—for example, said polypeptide/polynucleotide demonstrate at least 380, at least 400, at least 420, at least 450, at least 500, at least 550, at least 600 or higher spot forming units/$10^6$ (murine splenocyte IFN-γ release)—see FIG. 1. Alternatively, vaccine efficacy of the polypeptides/polynucleotides of the present invention may be measured in terms of protective efficacy (%) relative to BCG alone (i.e. when administered as a boost to a BCG prime vaccine)—for example, said polypeptide/polynucleotide demonstrates at least 120, at least 150, at least 180, at least 200, at least 220, at least 250, at least 300% increase in protective efficacy, such as measured by bacterial load (eg. in murine spleen and/or lung)—see FIGS. 2 & 3.

The expression or activity of latency-induced and latency-upregulated polypeptides and polynucleotides may be induced or upregulated in vivo during latency in the *mycobacterium*'s natural environment. As such, the present inventors believe that latency-induced or latency-upregulated mycobacterial polypeptides and polynucleotides represent good vaccine candidates for preventing the establishment, spread and reactivation of disease and/or make good diagnostic tools for latent infection.

In one embodiment, the mycobacterial antigen comprises (or consists of) a polypeptide sequence having at least 70% amino acid sequence identity (such as at least 75, 80, 82, 84, 86, 88, 90, 92, 94, 96, 98, 99 or 100% amino acid sequence identity) to the amino acid sequence of a polypeptide selected from SEQ ID NOs: 2, 4, 6, 8, 10, 12, 14, 16 and 18, or a fragment thereof having at least 50 consecutive amino acids thereof. SEQ ID NOs: 2, 4, 6, 8, 10, 12, 14, 16 and 18 are defined in Table 1, below:

TABLE 1

| SEQ ID No. | Polypeptide name |
|---|---|
| 2 | Rv0982 |
| 4 | Rv1462 |
| 6 | Rv1937 |
| 8 | Rv2500c |
| 10 | Rv2504c |
| 12 | Rv3270 |
| 14 | Rv3537 |
| 16 | Rv3608c |
| 18 | Rv3879c |

Thus, in the context of the present application, an "Rv0982 polypeptide antigen" comprises or consists of SEQ ID NO: 2 (or a sequence 'variant' or 'fragment' thereof as defined herein); an "Rv1462 polypeptide antigen" comprises or consists of SEQ ID NO: 4 (or a sequence 'variant' or 'fragment' thereof as defined herein); an "Rv1937 polypeptide antigen" comprises or consists of SEQ ID NO: 6 (or a sequence 'variant' or 'fragment' thereof as defined herein); an "Rv2500c polypeptide antigen" comprises or consists of SEQ ID NO: 8 (or a sequence 'variant' or 'fragment' thereof as defined herein); an "Rv2504c polypeptide antigen" comprises or consists of SEQ ID NO: 10 (or a sequence 'variant' or 'fragment' thereof as defined herein); an "Rv3270 polypeptide antigen" comprises or consists of SEQ ID NO: 12 (or a sequence 'variant' or 'fragment' thereof as defined herein); an "Rv3537 polypeptide antigen" comprises or consists of SEQ ID NO: 14 (or a sequence 'variant' or 'fragment' thereof as defined herein); an "Rv3608c polypeptide antigen" comprises or consists of SEQ ID NO: 16 (or a sequence 'variant' or 'fragment' thereof as defined herein); and an "Rv3879c polypeptide antigen" comprises or consists of SEQ ID NO: 18 (or a sequence 'variant' or 'fragment' thereof as defined herein).

In one embodiment, the amino acid sequence identity exists over a region of the polypeptide sequences that is at least 50 consecutive amino acid residues in length (eg. at least 75, 100, 150, 200, 250, 300 consecutive amino acid residues in length). Conventional methods for determining amino acid sequence identity are discussed in more detail later in the specification.

In the context of the first mycobacterial antigen, a fragment of a polypeptide comprises (or consists of) at least 50 consecutive amino acid residues of said polypeptide (eg. at least 75, 100, 125, 150, 175, 200, 225, 250, 275, 300 consecutive amino acid residues of said polypeptide). Said fragment includes at least one epitope of the polypeptide. A fragment of a polypeptide has a sequence length that is at least 25%, 50%, 60%, 70%, 80%, or 90% of that of the sequence of the full-length polypeptide.

In one embodiment, in the context of the first mycobacterial antigen, a fragment of a polypeptide comprises (or consists of) a truncated form of said polypeptide. For example, a fragment of a polypeptide may have an N-terminal truncation (as compared with the polypeptide), or a fragment of a polypeptide may have a C-terminal truncation (as compared with the polypeptide).

In one embodiment, in the context of the first mycobacterial antigen, a fragment of a polypeptide comprises (or consists of) a mature form of the polypeptide. For example, the polypeptide may comprise a signal sequence (ie. a secretion/targeting sequence) (eg. at the N-terminus), and a fragment of the polypeptide may lack this signal sequence. In one embodiment, the fragment is formed by cleavage of a signal sequence from the polypeptide.

In one embodiment, a fragment of polypeptide SEQ ID NO: 2 is an N-terminally truncated form of SEQ ID NO: 2. In one embodiment, a fragment of polypeptide SEQ ID NO: 2 has an N-terminal truncation of 50, 100, 150, 200 or 250 amino acid residues as compared with the amino acid sequence of SEQ ID NO: 2. In one embodiment, a fragment of SEQ ID NO: 2 comprises at least the C-terminal 50, 100, 150, 200 or 250 amino acid sequence of SEQ ID NO: 2. Similarly, in one embodiment, a fragment of polypeptide SEQ ID NO: 4, 6, 8, 10, 12, 14, 16, 18 is an N-terminally truncated form of SEQ ID NO: 4, 6, 8, 10, 12, 14, 16, 18 (respectively). In one embodiment, a fragment of SEQ ID NO: 4, 6, 8, 10, 12, 14, 16, 18 is a mature polypeptide sequence, which differs from the sequence of SEQ ID NO: 4, 6, 8, 10, 12, 14, 16, 18 (respectively) by removal of an N-terminal signal sequence. In one embodiment, a fragment of polypeptide SEQ ID NO: 4, 6, 8, 10, 12, 14, 16, 18 has an N-terminal truncation of 5, 10, 15, 20, 25, 30, 35, 40, 50, 100, 150, 200 or 250 amino acid residues as compared with the amino acid sequence of SEQ ID NO: 4, 6, 8, 10, 12, 14, 16, 18 (respectively). In one embodiment, a fragment of SEQ ID NO: 4, 6, 8, 10, 12, 14, 16, 18 comprises at least the C-terminal 50, 100, 150, 200 or 250 amino acid sequence of SEQ ID NO: 4, 6, 8, 10, 12, 14, 16, 18 (respectively).

In one embodiment, the mycobacterial antigen of the invention comprises a polypeptide or fragment thereof that has a common antigenic cross-reactivity and/or substantially the same in vivo biological activity as a polypeptide selected from SEQ ID NOs: 2, 4, 6, 8, 10, 12, 14, 16, 18. As used herein, 'common antigenic cross-reactivity' means that the mycobacterial polypeptide or fragment of the invention and the latency-regulated polypeptide selected from SEQ ID NOs: 2, 4, 6, 8, 10, 12, 14, 16, 18 share a common ability to induce a "recall response" of an immune cell such as a T-lymphocyte (eg. CD4+, CD8+, effector T cell or memory T cell such as a TEM or TCM), which has been previously exposed to an antigenic component of a mycobacterial infection. New immunological assays for measuring and quantifying immune cell responses (eg. T cell responses) have been established over the last 10+ years. For example, the interferon-gamma (IFN-γ) ELISPOT assay is useful as an immunological readout because the secretion of IFN-γ from antigen-specific immune cells such as T cells is a good correlate of protection against *M. tuberculosis*. Furthermore, the ELISPOT assay is a very reproducible and sensitive method of quantifying the number of IFN-γ secreting antigen-specific immune cells such as T cells. Alternatively, or in addition, 'common antigenic cross-reactivity' means that an antibody capable of binding to the mycobacterial polypeptide or fragment of the invention would also be capable of binding to the corresponding latency-regulated polypeptide (SEQ ID NO: 2, 4, 6, 8, 10, 12, 14, 16, 18).

In one embodiment, the mycobacterial antigen comprises, or consists of, a polynucleotide sequence that encodes the corresponding mycobacterial polypeptide as defined above.

Thus, in one embodiment, the first mycobacterial antigen comprises (or consists of) a polynucleotide sequence that encodes a polypeptide that comprises (or consists of) an amino acid sequence having at least 70% amino acid sequence identity (such as at least 75, 80, 82, 84, 86, 88, 90, 92, 94, 96, 98, 99 or 100% amino acid sequence identity) to the amino acid sequence of a latency-regulated polypeptide selected from SEQ ID NOs: 2, 4, 6, 8, 10, 12, 14, 16, 18, or a fragment thereof having at least 50 consecutive amino acids thereof (eg. as defined above). In one embodiment, the mycobacterial antigen comprises (or consists of) a polynucleotide sequence having at least 70% nucleotide sequence identity (at least 75, 80, 82, 84, 86, 88, 90, 92, 94, 96, 98, 99 or 100% nucleotide sequence identity) to the nucleic acid sequence of a latency-regulated polynucleotide selected from SEQ ID NOs: 1, 3, 5, 7, 9, 11, 13, 15, 17, or a fragment thereof having at least 150 consecutive nucleotides thereof. In use, said polynucleotide is in a form (e.g. vector) that provides corresponding mycobacterial antigenic peptide/protein. Thus, in one embodiment, the mycobacterial antigen is a 'mycobacterial polynucleotide' (or fragment), as defined above. SEQ ID NOs: 1, 3, 5, 7, 9, 11, 13, 15 and 17 are defined in Table 2, below:

TABLE 2

| SEQ ID No. | Polynucleotide name |
|---|---|
| 1 | Rv0982 |
| 3 | Rv1462 |
| 5 | Rv1937 |
| 7 | Rv2500c |
| 9 | Rv2504c |
| 11 | Rv3270 |
| 13 | Rv3537 |
| 15 | Rv3608c |
| 17 | Rv3879c |

Thus, in the context of the present application, an "Rv0982 polynucleotide antigen" comprises or consists of SEQ ID NO: 1 (or a sequence 'variant' or 'fragment' thereof as defined herein); an "Rv1462 polynucleotide antigen" comprises or consists of SEQ ID NO: 3 (or a sequence 'variant' or 'fragment' thereof as defined herein); an "Rv1937 polynucleotide antigen" comprises or consists of SEQ ID NO: 5 (or a sequence 'variant' or 'fragment' thereof as defined herein); an "Rv2500c polynucleotide antigen" comprises or consists of SEQ ID NO: 7 (or a sequence 'variant' or 'fragment' thereof as defined herein); an "Rv2504c polynucleotide antigen" comprises or consists of SEQ ID NO: 9 (or a sequence 'variant' or 'fragment' thereof as defined herein); an "Rv3270 polynucleotide antigen" comprises or consists of SEQ ID NO: 11 (or a sequence 'variant' or 'fragment' thereof as defined herein); an "Rv3537 polynucleotide antigen" comprises or consists of SEQ ID NO: 13 (or a sequence 'variant' or 'fragment' thereof as defined herein); an "Rv3608c polynucleotide antigen" comprises or consists of SEQ ID NO: 15 (or a sequence 'variant' or 'fragment' thereof as defined herein); and an "Rv3879c polynucleotide antigen" comprises or consists of SEQ ID NO: 17 (or a sequence 'variant' or 'fragment' thereof as defined herein).

In one embodiment, the nucleotide sequence identity exists over a region of the polynucleotide sequences that is at least 150 consecutive nucleotide residues in length (eg. at least 200, 250, 300, 350, 400, 450, 500, 550, 600, 650, 700 or 750 consecutive nucleotide residues in length). Conventional methods for determining nucleotide sequence identity are discussed in more detail later in the specification.

In the context of the mycobacterial antigen, a fragment of said polynucleotide comprises (or consists of) at least 150 consecutive nucleotide residues of said polynucleotide (eg. at least 200, 250, 300, 350, 400, 450, 500, 550, 600, 650, 700 or 750 consecutive nucleotide residues of said polynucleotide). In one embodiment, the length of the sequence of the polynucleotide fragment is at least 25%, 50%, 60%, 70%, 80%, or 90% that of the polynucleotide.

In one embodiment, in the context of the mycobacterial antigen, a fragment of a polynucleotide comprises (or consists of) a truncated form of said polynucleotide. In one embodiment, a fragment of a polynucleotide is truncated at the 5' end and/or the 3' end, as compared with the full-length polynucleotide sequence. In one embodiment, a fragment of a polynucleotide encodes a truncated form of said polypeptide. For example, a fragment of a polynucleotide may encode a polypeptide that is N-terminally truncated and/or C-terminally truncated polypeptide (as compared with the polypeptide encoded by the full-length polynucleotide). In one embodiment, in the context of the first mycobacterial antigen, a fragment of a polynucleotide encodes a polypeptide that comprises (or consists of) a mature polypeptide. For example, the full-length polypeptide comprises a signal sequence (ie. a secretion/targeting sequence) (eg. at the N-terminus), and the polynucleotide fragment encodes a mature polypeptide that lacks this signal sequence.

In one embodiment, a fragment of polynucleotide SEQ ID NO: 1 is a 5' truncated form of SEQ ID NO: 1. In one embodiment, a fragment of polynucleotide SEQ ID NO: 1 has a 5' truncation of 100, 200 or 300 nucleotide residues as compared with the nucleotide sequence of SEQ ID NO: 1. In one embodiment, a fragment of polynucleotide SEQ ID NO: 1 encodes an N-terminally truncated form of SEQ ID NO: 2. In one embodiment, a fragment of polynucleotide SEQ ID NO: 1 encodes a polypeptide having an N-terminal truncation of 50, 100, 150, 200 or 250 amino acid residues as compared with the amino acid sequence of SEQ ID NO: 2. In one embodiment, a fragment of SEQ ID NO: 1 comprises the 3' terminal 100, 200 or 300 nucleotide residues as compared with the nucleotide sequence of SEQ ID NO: 1. In one embodiment, a fragment of polynucleotide SEQ ID NO: 1 encodes a polypeptide comprising at least the C-terminal 50, 100, 150, 200, 250 or 300 amino acid sequence of SEQ ID NO: 2.

In one embodiment, a fragment of polynucleotide SEQ ID NO: 3, 5, 7, 9, 11, 13, 15, 17 is a 5' truncated form of SEQ ID NO: 3, 5, 7, 9, 11, 13, 15, 17 (respectively). In one embodiment, a fragment of polynucleotide SEQ ID NO: 3, 5, 7, 9, 11, 13, 15, 17 has a 5' truncation of 25, 50, 75, 100 or 125 nucleotide residues as compared with the nucleotide sequence of SEQ ID NO: 3, 5, 7, 9, 11, 13, 15, 17 (respectively). In one embodiment, a fragment of polynucleotide SEQ ID NO: 3, 5, 7, 9, 11, 13, 15, 17 encodes an N-terminally truncated form of SEQ ID NO: 4, 6, 8, 10, 12, 14, 16, 18 (respectively). In one embodiment, a fragment of polynucleotide SEQ ID NO: 3, 5, 7, 9, 11, 13, 15, 17 encodes a mature polypeptide sequence, which differs from the sequence of SEQ ID NO: SEQ ID NO: 4, 6, 8, 10, 12, 14, 16, 18 (respectively) by removal of an N-terminal signal sequence. In one embodiment, a fragment of polynucleotide SEQ ID NO: 3, 5, 7, 9, 11, 13, 15, 17 encodes a polypeptide that has an N-terminal truncation of 5, 10, 15, 20, 25, 30, 35, 40, 50, 100, 150, 200 or 250 amino acid residues as compared with the amino acid sequence of SEQ ID NO: 4, 6, 8, 10, 12, 14, 16, 18 (respectively). In one embodiment, a fragment of SEQ ID NO: 3, 5, 7, 9, 11, 13, 15, 17 comprises the 3' terminal 150, 300, 450, 600 or 750 nucleotide residues as compared with the nucleotide sequence of SEQ ID NO: 3, 5, 7, 9, 11, 13, 15, 17 (respectively). In one embodiment, a fragment of SEQ ID NO: 3, 5, 7, 9, 11, 13, 15, 17 encodes a polypeptide that comprises at least the C-terminal 50, 100, 150, 200 or 250 amino acid sequence of SEQ ID NO: 4, 6, 8, 10, 12, 14, 16, 18 (respectively).

In one embodiment, said mycobacterial polynucleotide, or fragment thereof, encodes a polypeptide that has a common antigenic cross-reactivity and/or substantially the same in vivo biological activity as a latency-regulated polypeptide selected from SEQ ID NOs: 2, 4, 6, 8, 10, 12, 14, 16, or 18. For example, said first mycobacterial antigen may comprise (or consist of) a polynucleotide sequence that encodes a polypeptide sequence that is capable of evoking a protective immune cell response (eg. T-cell response) against mycobacterial infection. By way of example, the polypeptide encoded by the first mycobacterial polynucleotide or fragment shares, with the latency-regulated polypeptide, a common ability to induce a “recall response” of an immune cell such as a T-lymphocyte (eg. CD4+, CD8+, effector T cell or memory T cell such as TEM or TCM) that has previously been exposed to an antigenic component of a mycobacterial infection. In this regard, the secretion of IFN-γ from antigen-specific immune cells such as T cells is a good correlate of protection against *M. tuberculosis*. Accordingly, the interferon-gamma (IFN-γ) ELISPOT assay is a useful immunological readout, and enables reproducible and sensitive quantification of IFN-γ secreting antigen-specific immune cells such as T cells. Alternatively, or in addition, an antibody capable of binding to a polypeptide encoded by the mycobacterial polynucleotide or fragment of the invention would also be capable of binding to the latency-regulated polypeptide (SEQ ID NO: 2, 4, 6, 8, 10, 12, 14, 16 or 18).

The antigenic composition of the invention may comprise at least a second mycobacterial antigen, in addition to the first mycobacterial antigen. The second mycobacterial antigen may be any one of the aforementioned mycobacterial antigens, and is preferably different from said first mycobacterial antigen.

In one embodiment, the second mycobacterial antigen is capable of evoking a protective immune response (eg. a T-cell response) against mycobacterial infection. In one embodiment, the second mycobacterial antigen comprises (eg. consists of) a polypeptide sequence. In one embodiment, the second mycobacterial antigen comprises (eg. consists of) a polynucleotide sequence such as a DNA or RNA sequence, or a mycobacterial glycolipid, such as a mycobacterial sulphoglycolipid. In one embodiment, the second mycobacterial antigen comprises (eg. consists of) a mycobacterial carbohydrate antigen such as a mycobacterial saccharide or polysaccharide. Optionally, the saccharide may be linked (eg. chemically conjugated) to a carrier (eg. a polypeptide) to enhance immunogenicity.

In one embodiment, the ‘difference’ between the second mycobacterial antigen and the first mycobacterial antigen is defined by the specificity of the immune response to the first and second mycobacterial antigens. For example, in one embodiment, each of the first and second antigens induces an immune response that is substantially specific to that antigen. The ‘difference’ between the second mycobacterial antigen and the first mycobacterial antigen may be defined in terms of a substantial lack (eg. an absence) of common antigenic cross-reactivity between the first and second mycobacterial antigens. The ‘difference’ between the second mycobacterial antigen and the first mycobacterial antigen may alternatively (or in addition) be defined as a substantial lack (eg. an absence) of common in vivo biological activity between the first and second mycobacterial antigens.

For example, in one embodiment, the first and second mycobacterial antigens may exhibit (substantially) no common antigenic cross-reactivity. In one embodiment, the first and second mycobacterial antigens may exhibit (substantially) no common in vivo biological activity. For example, the first and second mycobacterial antigens induce different immune responses and/or have different in vivo biological activities.

In one embodiment, the first and second mycobacterial antigens comprise polypeptides (as defined herein), and the second mycobacterial antigen has substantially no common antigenic cross-reactivity with the first mycobacterial antigen and/or has a substantially different in vivo biological activity from the first mycobacterial antigen. In one embodiment, the first and second mycobacterial antigens comprise polynucleotides (as defined herein), and the second mycobacterial antigen encodes a polypeptide that has substantially no common antigenic cross-reactivity with the polypeptide encoded by the first mycobacterial antigen. In one embodiment, the first and second mycobacterial antigens comprise polynucleotides (as defined herein), and the second mycobacterial antigen has a substantially different in vivo biological activity from the first mycobacterial antigen and/or encodes a polypeptide that has a substantially different in vivo biological activity from the polypeptide encoded by the first mycobacterial antigen.

In one embodiment, the first mycobacterial antigen comprises a polypeptide and the second mycobacterial antigen comprises a polynucleotide (as defined herein), and the second mycobacterial antigen or polypeptide encoded thereby has substantially no common antigenic cross-reactivity with the first mycobacterial antigen and/or has a substantially different in vivo biological activity from the first mycobacterial antigen.

In one embodiment, the first mycobacterial antigen comprises a polynucleotide and the second mycobacterial antigen comprises a polypeptide (as defined herein), and the second mycobacterial antigen has substantially no common antigenic cross-reactivity with the first mycobacterial antigen or polypeptide encoded thereby, and/or has a substantially different in vivo biological activity from the first mycobacterial antigen or polypeptide encoded thereby. By way of example, in one embodiment, the first and second mycobacterial antigens do not share a common ability to induce a “recall response” of an immune cell such as a T-lymphocyte (eg. CD4+, CD8+, effector or memory T cell such as TEM or TCM) that has previously been exposed to an antigenic component of a mycobacterial infection. In other words, in one embodiment, the first and second mycobacterial antigens are 'different' because they induce recall responses in different immune cells (eg. T cells).

In one embodiment, the second mycobacterial polypeptide comprises (or consists of) an antigenic mycobacterial polypeptide—ie. a mycobacterial polypeptide that is capable of evoking a protective T-cell response against mycobacterial infection.

In one embodiment, the second mycobacterial antigen comprises a polypeptide that is selected from the same group of polypeptides as discussed above in connection with the first mycobacterial antigen (preferably the second mycobacterial polypeptide is different from the first mycobacterial polypeptide).

Thus, in one embodiment, the second mycobacterial antigen comprises (or consists of) a polypeptide sequence having at least 70% amino acid sequence identity (such as at least 75, 80, 82, 84, 86, 88, 90, 92, 94, 96, 98, 99 or 100% amino acid sequence identity) to the amino acid sequence of a latency-regulated polypeptide selected from SEQ ID NOs: 2, 4, 6, 8, 10, 12, 14, 16, 18, or a fragment thereof having at least 50 consecutive amino acids thereof (such as at least 75, 100, 125, 150, 175, 200, 225 or 250 consecutive amino acid residues thereof).

In one embodiment, the second mycobacterial antigen comprises a polypeptide that is not selected from the same group of polypeptides as discussed above in connection with the first mycobacterial antigen. For example, in one embodiment, the second mycobacterial antigen comprises (or consists of) a polypeptide sequence having at least 70% amino acid sequence identity (such as at least 75, 80, 82, 84, 86, 88, 90, 92, 94, 96, 98, 99 or 100% amino acid sequence identity) to an amino acid sequence selected from SEQ ID NOs: 19-41, or a fragment thereof having at least 50 consecutive amino acids thereof. SEQ ID NOs: 19-41 are illustrated in Table 3, below:

TABLE 3

| SEQ ID NO: | Polypeptide name: |
|---|---|
| 19 | Ag85A/Rv3804c |
| 20 | Ag85B/Rv1886c |
| 21 | ESAT-6/Rv3875 |
| 22 | TB10.4/Rv0288 |
| 23 | Rv0125 |
| 24 | PPE18/Rv1196 |
| 25 | P27/Rv1411c |
| 26 | Hsp65/Rv0440 |
| 27 | HBHA/Rv0475 |
| 28 | Rv2659c |
| 29 | Rv2660c |
| 30 | HspX/Rv2031c |
| 31 | RPFA/Rv0867c |
| 32 | RPFB/Rv1009 |
| 33 | RPFC/Rv1884c |
| 34 | RPFD/Rv2389c |
| 35 | RPFE/Rv2450c |
| 36 | Rv1733 |
| 37 | Rv2029c |
| 38 | Rv2032 |
| 39 | Rv2626c |
| 40 | Rv2627c |
| 41 | Rv2628 |

The polypeptide "Ag85A" represented by SEQ ID NO: 19 of the present application (Accession Nos. CAA17868 and BX842584) is a member of a family of proteins ("the Ag85 complex"), which also comprises Ag85B (SEQ ID NO: 20 of the present application) and Ag85C. This family of proteins is secreted by *M. tuberculosis, M. bovis* BCG, and many other species of mycobacteria. Ag85A is highly conserved amongst all mycobacterial species and is immunodominant in animal and human studies.

The polypeptides represented by SEQ ID NOs: 30 and 36-41 are comprised within the DosR regulon (also known as the DevR regulon), which includes the polypeptides represented by Rv2623-2631 and Rv3126-3134. The expression of these polypeptides is regulated via DosR (DevR). The polypeptides represented by SEQ ID NOs: 31-35 are members of the RPF family of polypeptides (RPFA, RPFB, RPFC, RPFD and RPFE, respectively).

In one embodiment, the amino acid sequence identity exists over a region of the polypeptide sequences that is at least 50 consecutive amino acid residues in length (eg. at least 75, 100, 125, 150, 175, 200, 225 or 250 consecutive amino acid residues in length). In one embodiment, in the context of the second mycobacterial antigen, a fragment of said polypeptide comprises at least 50 consecutive amino acid residues of said polypeptide sequence. In one embodiment, the fragment comprises (or consists of) at least 75, 100, 125, 150, 175, 200, 225 or 250 consecutive amino acid residues of said polypeptide sequence. In one embodiment, a fragment of a polypeptide is at least 20%, 30%, 40%, 50%, 60%, 70%, 80%, or 90% of the length of the mycobacterial polypeptide. A fragment of a polypeptide includes at least one epitope of the polypeptide.

In one embodiment, in the context of the second mycobacterial antigen, a fragment of a polypeptide comprises (or consists of) a truncated form of said polypeptide. For example, a fragment of a polypeptide may have an N-terminal truncation (as compared with the polypeptide), or a fragment of a polypeptide may have a C-terminal truncation (as compared with the polypeptide). In one embodiment, in the context of the second mycobacterial antigen, a fragment of a polypeptide comprises (or consists of) a mature form of the polypeptide. For example, the polypeptide may comprise a signal sequence (ie. a secretion/targeting sequence) (eg. at the N-terminus), and a fragment of the polypeptide may lack this signal sequence. In one embodiment, the fragment is formed by cleavage of a signal sequence from the polypeptide.

In one embodiment, a fragment of polypeptide SEQ ID NO: 19-41 is an N-terminally truncated form of SEQ ID NO: 19-41. In one embodiment, a fragment of SEQ ID NO: 19-41 is a mature polypeptide sequence, which differs from the sequence of SEQ ID NO: 19-41 by removal of an N-terminal signal sequence. In one embodiment, a fragment of polypeptide SEQ ID NO: 19-41 has an N-terminal truncation of 10, 20, 30 or 40 amino acid residues as compared with the amino acid sequence of SEQ ID NO: 19-41. In one embodiment, a fragment of SEQ ID NO: 19-41 comprises at least the C-terminal 50, 100, 150, 200 or 250 amino acid sequence of SEQ ID NO: 19-41. In one embodiment, the second mycobacterial polypeptide or fragment thereof has a common antigenic cross-reactivity and/or substantially the same in vivo biological activity as the polypeptide selected from SEQ ID NOs: 19-41. In one embodiment, 'common antigenic cross-reactivity' means that the second mycobacterial polypeptide, or fragment, shares a common ability, with the polypeptide selected from SEQ ID NOs: 19-41, to induce a "recall response" of an immune cell such as a T-lymphocyte which has been previously exposed to an antigenic component of a mycobacterial infection. For example, the interferon-gamma (IFN-γ) ELISPOT assay is useful as an immunological readout because the secretion of IFN-γ from antigen-specific immune cells such as T cells is a good correlate of protection against *M. tuberculosis*. Furthermore, the ELISPOT assay is a very reproducible and sensitive method of quantifying the number of IFN-γ secreting antigen-specific immune cells such as T cells. Alternatively, or in addition, 'common antigenic cross-reactivity' means that an antibody capable of binding to the second mycobacterial polypeptide, or fragment, would also be capable of binding to the polypeptide selected from SEQ ID NOs: 19-41.

In one embodiment, the second mycobacterial polynucleotide comprises (or consists of) an antigenic mycobacterial polynucleotide that is capable (following translation) of evoking a protective immune cell response (eg. T-cell response) against mycobacterial infection. In one embodiment, the second mycobacterial polynucleotide encodes an antigenic mycobacterial polypeptide that is capable of evoking a protective immune cell response (eg. T-cell response) against mycobacterial infection. Thus, in one embodiment, the second mycobacterial antigen is a 'second mycobacterial polynucleotide' (or fragment), as defined above. In one embodiment, the second mycobacterial antigen comprises a polynucleotide selected from the polynucleotides discussed above in connection with the first mycobacterial antigen (though preferably different from the first mycobacterial polynucleotide).

Thus, in one embodiment, the second mycobacterial antigen comprises (or consists of) a polynucleotide sequence that encodes a polypeptide selected from the polypeptides discussed above in connection with the first mycobacterial antigen (though the polypeptide encoded by the second mycobacterial polynucleotide is different from the polypeptide encoded by the first mycobacterial polynucleotide). Thus, said second mycobacterial polynucleotide comprises a polynucleotide sequence (e.g. as a vector or plasmid) encoding a second mycobacterial polypeptide of the invention, as defined above.

In one embodiment, said encoded second mycobacterial polypeptide comprises a polypeptide sequence having at least 70% amino acid sequence identity to the amino acid sequence of SEQ ID NO: 2, 4, 6, 8, 10, 12, 14, 16, 18, or a fragment thereof having at least 50 consecutive amino acids thereof. In one embodiment, the second mycobacterial antigen comprises (or consists of) a polynucleotide sequence having at least 70% nucleotide sequence identity (such as at least 75, 80, 82, 84, 86, 88, 90, 92, 94, 96, 98, 99 or 100% nucleotide sequence identity) to the nucleic acid sequence of a latency-regulated polynucleotide selected from SEQ ID NOs: 1, 3, 5, 7, 9, 11, 13, 15, 17, or a fragment thereof having at least 150 consecutive nucleotides thereof (such as at least 200, 250, 300, 350, 400, 450, 500, 550, 600, 650, 700 or 750 consecutive nucleotides thereof). In one embodiment, the second mycobacterial polypeptide comprises (or consists of) a polynucleotide sequence having at least 70% nucleotide sequence identity to the nucleic acid sequence of SEQ ID NO: 1, 3, 5, 7, 9, 11, 13, 15, 17, or a fragment thereof having at least 150 consecutive nucleotides thereof. In one embodiment, the limitations discussed above with respect to the first mycobacterial polypeptide apply equally to this embodiment of the second mycobacterial polypeptide.

In one embodiment, the second mycobacterial antigen comprises a polynucleotide that is not selected from the same group of polynucleotides as discussed above in connection with the first mycobacterial antigen. In one embodiment, the second mycobacterial antigen comprises a polynucleotide that encodes a polypeptide that is not selected from the same group of polypeptides as discussed above in connection with the first mycobacterial antigen. In one embodiment, the second mycobacterial antigen comprises a polynucleotide sequence that encodes a second mycobacterial polypeptide as defined above.

Thus, in one embodiment, the second mycobacterial antigen comprises (or consists of) a polynucleotide sequence, wherein said polynucleotide sequence encodes a polypeptide that comprises (or consists of) an amino acid sequence having at least 70% amino acid sequence identity (such as at least 75, 80, 82, 84, 86, 88, 90, 92, 94, 96, 98, 99 or 100% amino acid sequence identity) to an amino acid sequence selected from SEQ ID NOs: 19-41, or a fragment thereof having at least 50 consecutive amino acid residues thereof. In one embodiment, the second mycobacterial antigen comprises (or consists of) a polynucleotide sequence having at least 70% nucleotide sequence identity (such as at least 75, 80, 82, 84, 86, 88, 90, 92, 94, 96, 98, 99 or 100% nucleotide sequence identity) to a nucleic acid sequence selected from SEQ ID NOs: 42-64, or a fragment thereof having at least 150 consecutive nucleotides thereof. SEQ ID NOs: 42-64 are illustrated in Table 4, below:

TABLE 4

| SEQ ID NO: | Polynucleotide name: |
|---|---|
| 42 | Ag85A/Rv3804c |
| 43 | Ag85B/Rv1886c |
| 44 | ESAT-6/Rv3875 |
| 45 | TB10.4/Rv0288 |
| 46 | Rv0125 |
| 47 | PPE18/Rv1196 |
| 48 | P27/Rv1411c |
| 49 | Hsp65/Rv0440 |
| 50 | HBHA/Rv0475 |
| 51 | Rv2659c |
| 52 | Rv2660c |
| 53 | HspX/Rv2031c |
| 54 | RPFA/Rv0867c |
| 55 | RPFB/Rv1009 |
| 56 | RPFC/Rv1884c |
| 57 | RPFD/Rv2389c |
| 58 | RPFE/Rv2450c |
| 59 | Rv1733 |
| 60 | Rv2029c |
| 61 | Rv2032 |
| 62 | Rv2626c |
| 63 | Rv2627c |
| 64 | Rv2628 |

The polynucleotide "Ag85A" represented by SEQ ID NO: 42 of the present application (Accession Nos. CAA17868 and BX842584) is a member of a family of genes ("the Ag85 complex"), which also comprises Ag85B (SEQ ID NO: 43 of the present application) and Ag85C. This family of genes encodes proteins that are secreted by *M. tuberculosis, M. bovis BCG, and many other species of mycobacteria. Ag*85A is highly conserved amongst all mycobacterial species and is immunodominant in animal and human studies.

The polynucleotides represented by SEQ ID NOs: 53 and 59-64 are comprised within the DosR regulon (also known as the DevR regulon), which includes the polynucleotides represented by Rv2623-2631 and Rv3126-3134. The expression of these polynucleotides is regulated via DosR (DevR). The polynucleotides represented by SEQ ID NOs: 54-49 are members of the RPF family of polynucleotides (RPFA, RPFB, RPFC, RPFD and RPFE, respectively).

In one embodiment, the nucleotide sequence identity exists over a region of the polynucleotide sequences that is at least 150 consecutive nucleotide residues in length (eg. at least 200, 250, 300, 350, 400, 450, 500, 550, 600, 650, 700 or 750 consecutive nucleotide residues in length).

In one embodiment, in the context of the second mycobacterial antigen, a fragment of a polynucleotide comprises at least 150 consecutive nucleotide residues of said polynucleotide sequence. In one embodiment, the fragment comprises (or consists of) at least 200, 250, 300, 350, 400, 450, 500, 550, 600, 650, 700 or 750 consecutive nucleotide residues of said polynucleotide sequence. In one embodiment, a fragment of said polynucleotide is at least 20%, 30%, 40%, 50%, 60%, 70%, 80%, or 90% of the length of the polynucleotide.

In one embodiment, in the context of the second mycobacterial antigen, a fragment of a polynucleotide comprises (or consists of) a truncated form of said polynucleotide. For example, a fragment of a polynucleotide may have a 5' truncation and/or 3' truncation as compared with the polynucleotide. In one embodiment, in the context of the second mycobacterial antigen, a fragment of a polynucleotide encodes a polypeptide that is truncated as compared with the polypeptide sequence encoded by the full-length polynucleotide. For example, the polynucleotide fragment may encode a polypeptide that is N-terminally truncated and/or C-terminally truncated, as compared with the polypeptide encoded by the full-length polynucleotide. In one embodiment, in the context of the second mycobacterial antigen, a fragment of a polynucleotide encodes a mature polypeptide. For example, the polypeptide may comprise a signal sequence (ie. a secretion/targeting sequence) (eg. at the N-terminus), and the polynucleotide fragment may encode a polypeptide fragment that lacks this signal sequence.

In one embodiment, a fragment of polynucleotide SEQ ID NO: 42-64 is a 5' truncated form of SEQ ID NO: 42-64 (respectively). In one embodiment, a fragment of polynucleotide SEQ ID NO: 42-64 has an N-terminal truncation of 25, 50, 75, 100 or 125 nucleotide residues as compared with the nucleotide sequence of SEQ ID NO: 42-64 (respectively). In one embodiment, a fragment of polynucleotide SEQ ID NO: 42-64 comprises at least the C-terminal 150, 300, 450, 600 or 750 nucleotide residues of SEQ ID NO: 42-64 (respectively). In one embodiment, a fragment of polynucleotide SEQ ID NO: 42-64 encodes an N-terminally truncated form of SEQ ID NO: 42-64 (respectively). In one embodiment, a fragment of polynucleotide SEQ ID NO: 42-64 encodes a mature polypeptide sequence, which differs from the sequence of SEQ ID NO: 42-64 (respectively) by removal of an N-terminal signal sequence. In one embodiment, a fragment of polynucleotide SEQ ID NO: 42-64 encodes a polypeptide fragment of SEQ ID NO: 42-64 (respectively) that has an N-terminal truncation of 10, 20, 30, 40, 50, 100, 150 amino acid residues as compared with the amino acid sequence of SEQ ID NO: 42-64 (respectively). In one embodiment, a fragment of polynucleotide SEQ ID NO: 42-64 encodes a polypeptide fragment of SEQ ID NO: 42-64 (respectively) that comprises at least the C-terminal 50, 100, 150, 200 or 250 amino acid residues of SEQ ID NO: 42-64 (respectively). In one embodiment, a polypeptide encoded by the second mycobacterial polynucleotide or fragment has a common antigenic cross-reactivity and/or substantially the same in vivo biological activity as the polypeptide selected from SEQ ID NOs: 19-41. By way of example, the polypeptide encoded by the second mycobacterial polynucleotide, or fragment, shares a common ability, with the polypeptide selected from SEQ ID NOs: 19-41, to induce a "recall response" of an immune cell such as a T-lymphocyte which has been previously exposed to an antigenic component of a mycobacterial infection. For example, the interferon-gamma (IFN-γ) ELISPOT assay is useful as an immunological readout because the secretion of IFN-γ from antigen-specific immune cells such as T cells is a good correlate of protection against *M. tuberculosis*. Furthermore, the ELISPOT assay is a very reproducible and sensitive method of quantifying the number of IFN-γ secreting antigen-specific immune cells such as T cells. Alternatively, or in addition, an antibody capable of binding to a polypeptide encoded by the second mycobacterial polynucleotide, or fragment, would also be capable of binding to the polypeptide selected from SEQ ID NOs: 19-41.

In one embodiment, the antigenic composition comprises both an Rv0111 antigen (antigenic polypeptide or polynucleotide) and an Rv0198 antigen (antigenic polypeptide or polynucleotide).

In one embodiment, where there are multiple additional mycobacterial antigens (eg. 2 or more additional mycobacterial antigens, as well as the first and second mycobacterial antigens), each of said additional mycobacterial antigens is different from each other. In one embodiment, the 'difference' between the additional mycobacterial antigen(s) and the first and second mycobacterial antigens is defined by the specificity of the immune response to the mycobacterial antigens. For example, in one embodiment, each of the first, second and additional antigens induce an immune response that is substantially specific to that antigen. The 'difference' between the first, second and additional mycobacterial antigens may be defined in terms of a substantial lack (eg. an absence) of common antigenic cross-reactivity between the mycobacterial antigens. The 'difference' between the first, second and additional mycobacterial antigens may be alternatively (or in addition) be defined as a substantial lack (eg. an absence) of common in vivo biological activity between the mycobacterial antigens. For example, in one embodiment, the first, second and additional mycobacterial antigens (eg. first, second and additional mycobacterial antigenic polypeptides, or first, second and additional mycobacterial antigenic polynucleotides or polypeptide encoded thereby) may exhibit (substantially) no common antigenic cross-reactivity.

In one embodiment, the first, second and additional mycobacterial antigens (eg. first, second and additional mycobacterial antigenic polypeptides, or first, second and additional mycobacterial antigenic polynucleotides or polypeptide encoded thereby) exhibit (substantially) no common in vivo biological activity. For example, the first, second and additional mycobacterial antigens (eg. first, second and additional mycobacterial antigenic polypeptides, or first, second and additional mycobacterial antigenic polynucleotides or polypeptide encoded thereby) may each induce different immune responses and/or each have different in vivo biological activities. By way of example, in one embodiment, the first, second and additional mycobacterial antigens (eg. first, second and additional mycobacterial antigenic polypeptides, or first, second and additional mycobacterial antigenic polynucleotides or polypeptide encoded thereby) do not share a common ability to induce a "recall response" of an immune cell such as a T-lymphocyte (eg. CD4+, CD8+, effector or memory T cell-TEM or TCM) that has previously been exposed to an antigenic component of a mycobacterial infection. In other words, in one embodiment, the first, second and additional mycobacterial antigens are 'different' because they induce recall responses in different immune cells (eg. different T cells).

In one embodiment, the one or more additional mycobacterial antigen(s) is expressed or up-regulated under different culture conditions and/or mycobacterial infection states as compared with the first and/or second mycobacterial antigens. In one embodiment, the activity of the one or more additional mycobacterial antigen(s) is up-regulated under different culture conditions and/or mycobacterial infection states as compared with the first and/or second mycobacterial antigens. Thus, in one embodiment, the expression or activity of first mycobacterial antigen is up-regulated during conditions of mycobacterial latency, whereas the expression or activity of the second and/or additional mycobacterial antigen is up-regulated during active mycobacterial infection or upon re-activation from a latent state (and/or down-regulated during conditions of mycobacterial latency). In one embodiment, where there are multiple additional mycobacterial antigens (eg. 2 or more additional mycobacterial antigens, as well as the first and second mycobacterial antigens), each additional mycobacterial antigen is expressed/up-regulated at different stages of mycobacterial infection, or the activity of each additional mycobacterial antigen is up-regulated at different stages of mycobacterial infection.

In one embodiment, the one or more additional mycobacterial antigens are from a *mycobacterium* other than *M. tuberculosis*. For example, the one or more additional mycobacterial antigens may be from another member of the MTC, such as *M. microti, M. bovis, M. canetti* or *M. africanum*, or a non-MTC *mycobacterium* such as *M. avium-intracellulare, M. kansasii, M. marinum* or *M. ulcerans.*

In one embodiment, the antigenic composition comprises at least 1, 2, 3, 4 or 5 further mycobacterial antigens, in addition to the first and second mycobacterial antigens discussed above. In one embodiment, each of said at least 1, 2, 3, 4 or 5 additional mycobacterial antigens is different from each other and from the first and second mycobacterial antigens. In one embodiment, the antigenic composition comprises up to about 10 different mycobacterial antigens (eg. including the first and second mycobacterial antigens discussed above). In one embodiment, the antigenic composition comprises 1 additional mycobacterial antigen, and thus comprises a total of 3 different mycobacterial antigens (ie. the antigenic composition is trimeric). In one embodiment, the antigenic composition comprises 2 additional mycobacterial antigens, and thus comprises a total of 4 different mycobacterial antigens (ie. the antigenic composition is tetrameric). In one embodiment, the antigenic composition comprises 3 additional mycobacterial antigens, and thus comprises a total of 5 different mycobacterial antigens (ie. the antigenic composition is pentameric). In one embodiment, the antigenic composition comprises up to 8 additional mycobacterial antigens, and thus comprises up to a total of 10 different mycobacterial antigens (ie. the antigenic composition is up to decameric).

In one embodiment, the one or more additional mycobacterial antigens comprises (or consists of) a polypeptide sequence having at least 70% amino acid sequence identity to the amino acid sequence of a latency-regulated polypeptide selected from SEQ ID NOs: 1, 3, 5, 7 and 56, or a fragment thereof having at least 150 consecutive amino acids thereof, as defined above with respect to the first mycobacterial antigen (so long as the one or more additional mycobacterial antigens is different from the first mycobacterial antigen). Alternatively, or in addition, the one or more additional mycobacterial antigens may comprise (or consist of) a polypeptide sequence having at least 70% amino acid sequence identity to an amino acid sequence selected from SEQ ID NOs: 19-41, or a fragment thereof having at least 50 consecutive amino acids thereof, as defined above with respect to the second mycobacterial antigen (so long as the one or more additional mycobacterial antigens is different from the second mycobacterial antigen).

In one embodiment, the one or more additional mycobacterial antigens comprises (or consists of) a polynucleotide sequence that encodes a polypeptide sequence as described above with respect to the first mycobacterial antigenic polypeptide (preferably different from the first mycobacterial antigen). In one embodiment, the one or more additional mycobacterial antigens comprises (or consists of) a polynucleotide sequence that encodes a polypeptide sequence as described above with respect to the second mycobacterial antigenic polypeptide (preferably different from the second mycobacterial antigen).

In one embodiment, the one or more additional mycobacterial antigens comprises (or consists of) a polynucleotide sequence having at least 70% nucleotide sequence identity to the nucleic acid sequence of a latency-regulated polynucleotide selected from SEQ ID NOs: 1, 3, 5, 7, 9, 11, 13, 15, 17, or a fragment thereof having at least 150 consecutive nucleotides thereof, as described above with respect to the first mycobacterial antigen (so long as the one or more additional mycobacterial antigens is different from the first mycobacterial antigen). Alternatively, or in addition, the one or more additional mycobacterial antigens may comprise (or consist of) a polynucleotide sequence having at least 70% nucleotide sequence identity to a nucleic acid sequence selected from SEQ ID NOs: 42-64, or a fragment thereof having at least 150 consecutive nucleotides thereof, as described above with respect to the second mycobacterial antigen (so long as the one or more additional mycobacterial antigens is different from the second mycobacterial antigen).

In one embodiment, at least two of the mycobacterial antigens in the antigenic composition comprise (or consist of) a polypeptide sequence, and said at least two polypeptide sequences are optionally joined together to form a fusion protein. By way of example, in one embodiment, the first mycobacterial antigen and second mycobacterial antigen each comprise (or consist of) a polypeptide sequence, as defined above, and said first and second polypeptide sequences are optionally joined together to form a fusion protein.

In one embodiment, said fusion protein further comprises at least one additional mycobacterial antigenic polypeptide sequence, optionally joined to said first and/or second polypeptide sequences, wherein each of said further mycobacterial antigens is different from each other and from the first and second mycobacterial antigens. For example, the fusion protein may comprise at least 1, 2, 3, 4 or 5 further mycobacterial antigens, in addition to said first and second mycobacterial antigens, wherein each of said further mycobacterial antigens is different from each other and from the first and second mycobacterial antigens. In one embodiment, the fusion protein may comprise up to about 10 different mycobacterial antigens (eg. including the first and second mycobacterial antigens).

In one embodiment, the antigenic composition comprises at least one additional mycobacterial antigen (eg. at least 1, 2, 3, 4, 5, 6, 7, 8, 9 or 10 additional mycobacterial antigens) and the first mycobacterial antigen and said at least one additional mycobacterial antigen each comprise (or consist of) a polypeptide sequence, as defined above, and said polypeptide sequences are optionally joined together to form a fusion protein. In one embodiment, the antigenic composition comprises at least one additional mycobacterial antigen (eg. at least 1, 2, 3, 4, 5, 6, 7, 8, 9 or 10 additional mycobacterial antigens), and the second mycobacterial antigen and said at least one additional mycobacterial antigen each comprise (or consist of) a polypeptide sequence, as defined above, and said polypeptide sequences are optionally joined together to form a fusion protein. Alternatively, in one embodiment, the antigenic composition comprises at least two additional mycobacterial antigens (eg. at least 2, 3, 4, 5, 6, 7, 8, 9 or 10 additional mycobacterial antigens), and said at least two additional mycobacterial antigens each comprise (or consist of) a polypeptide sequence, as defined above, and said polypeptide sequences are optionally joined together to form a fusion protein.

In one embodiment, a recombinant fusion protein may be generated by expression of a recombinant polynucleotide sequence that encodes said fusion protein. By way of example, polynucleotide sequences encoding mycobacterial antigenic polypeptides of the invention may be positioned in the same reading frame downstream of a promoter in an expression vector, thereby allowing transcription through the polynucleotide sequences and translation as one protein product. In one embodiment, intervening 'linker' sequences are located between the polynucleotide sequence for each polypeptide antigen, arising from the inclusion of restriction sites. In general, the amino acids encoded by these linker sequences are not deleterious to the immunogenicity of the resultant fusion protein, and may even be beneficial to immunogenicity. Alternatively, a fusion protein of the invention may be produced as an epitope string, by expression of polynucleotide sequences that are linked without intervening nucleotides. The absence of intervening linker sequence avoids the presence of unnecessary nucleic acid and/or amino acid material. Alternatively, a fusion protein of the invention may be prepared by chemically conjugating the mycobacterial antigenic polypeptides of the invention. By way of example, the first and/or second and/or additional mycobacterial polypeptides of the invention may be coupled to each other using conventional chemical conjugation techniques.

In one embodiment, at least two of the mycobacterial antigens in the antigenic composition comprise (or consist of) a polynucleotide sequence, and said at least two polynucleotide sequences are optionally joined together to form a polycistronic nucleic acid sequence. By way of example, in one embodiment, the first mycobacterial antigen and second mycobacterial antigen each comprise (or consist of) a polynucleotide sequence, as defined above, and said first and second polynucleotide sequences are optionally joined together to form a polycistronic nucleic acid sequence.

In one embodiment, said polycistronic nucleic acid sequence comprises or consists of (in any order from the 5' to 3' end):

(i) a first mycobacterial polynucleotide, wherein said first mycobacterial polynucleotide comprises (or consists of) a polynucleotide sequence as hereinbefore defined; and (ii) a second mycobacterial polynucleotide, wherein said second mycobacterial polynucleotide comprises (or consists of) a polynucleotide sequence as hereinbefore defined.

In one embodiment, said polycistronic sequence further comprises at least one additional mycobacterial antigenic polynucleotide sequence, joined to said first and second polynucleotide sequences. Alternatively, in one embodiment, the antigenic composition comprises at least one additional mycobacterial antigen, and the first mycobacterial antigen and at least one additional mycobacterial antigen each comprise (or consist of) a polynucleotide sequence, as defined above, and said polynucleotide sequences are joined together to form a polycistronic nucleic acid sequence. Alternatively, in one embodiment, the antigenic composition comprises at least one additional mycobacterial antigen, and the second mycobacterial antigen and at least one additional mycobacterial antigen each comprise (or consist of) a polynucleotide sequence, as defined above, and said polynucleotide sequences are joined together to form a polycistronic nucleic acid sequence. Alternatively, in one embodiment, the antigenic composition comprises at least two additional mycobacterial antigens, and said at least two additional mycobacterial antigens each comprise (or consist of) a polynucleotide sequence, as defined above, and said polynucleotide sequences are joined together to form a polycistronic nucleic acid sequence.

In one embodiment, the polycistronic nucleic acid sequence of the invention is positioned downstream of a promoter in frame in a vector (eg. an expression vector or viral vector as discussed below), thereby allowing transcription through the polynucleotide sequences and optional translation as one 'fusion protein' product. Accordingly, in one embodiment, the polycistronic nucleic acid sequence encodes a fusion protein as discussed above. Alternatively, in one embodiment, the polycistronic nucleic acid sequence encodes separate mycobacterial antigenic polypeptide sequences, as discussed above. In one embodiment, the polycistronic nucleic acid sequence is operably linked to a nucleic acid sequence encoding a tag polypeptide, such that the encoded tag is covalently linked to the encoded antigenic polypeptide(s) upon translation. The tag may facilitate detection of antigenic polypeptide expression, or detection of clones that express the antigen, and/or may lead to increases in antigen efficacy. Suitable tag polypeptides include a PK tag, FLAG tag, MYC tag, polyhistidine tag or any detectable tag (eg. a tag that can be detected by an antibody such as a monoclonal antibody). Other examples of tags will be clear to skilled persons in the art. The nucleic acid sequence encoding the tag polypeptide may be positioned such that, following translation, the tag is located at the C-terminus of the expressed antigenic polypeptide (ie. in the order: antigenic polypeptide-tag). Alternatively, the nucleic acid sequence encoding the tag polypeptide may be positioned such that, following translation, the tag is located at the N-terminus of the expressed antigenic polypeptide (ie. in the order: tag-antigenic polypeptide). Alternatively, the nucleic acid sequence encoding the tag polypeptide may be positioned such that, following translation, the tag is located internally to the expressed antigenic polypeptide, or between the expressed antigenic polypeptides of an encoded fusion protein.

Nucleotides encoding a linker sequence may be inserted between the polycistronic nucleic acid sequence encoding the antigenic polypeptide(s) and the nucleic acid sequence encoding the tag polypeptide. In one embodiment, the linker sequence encodes the amino acid sequence Gly-Ser-Ile. In one embodiment, the encoded linker sequence is located between an expressed antigenic polypeptide and a tag polypeptide (ie. in the order: antigenic polypeptide-linker-tag, or tag-linker-antigenic polypeptide). In one embodiment, the nucleic acid sequence encoding the tag polypeptide and the nucleotides encoding the linker sequence are positioned such that, following translation, the linker sequence (eg. Gly-Ser-Ile) is located at the C-terminus of the expressed antigenic polypeptide and the tag is located at the C-terminus of the expressed linker sequence (ie. in the order antigenic polypeptide-linker-tag). Intervening 'linker' sequences may alternatively (or additionally) be located between the mycobacterial polynucleotide sequences of the polycistronic sequence, arising from the inclusion of restriction sites (eg. in the form: mycobacterial polynucleotide-linker-mycobacterial polynucleotide). However, to avoid the presence of unnecessary nucleic acid and/or amino acid material, the polynucleotide sequences may be linked without intervening nucleotides.

In one embodiment, the polycistronic nucleic acid sequence is operably linked to a leader sequence. For example, the leader sequence may be fused to the N-terminus of the polycistronic sequence (ie. in the form: leader-polycistronic sequence) or to the C-terminus of the polycistronic sequence (ie. in the form: polycistronic sequence-leader). A leader sequence may affect processing of a primary DNA transcript to mRNA, and/or may affect mRNA stability or translation efficiency. In one embodiment, a leader sequence ensures that the encoded polypeptide antigen is directed to the secretory machinery of a host cell. In one embodiment, a leader sequence enhances expression and/or immunogenicity of the antigen. Enhanced expression may be determined by a conventional assay, such as using an antibody (eg. monoclonal antibody) to detect the amount of protein produced. Enhanced immunogenicity may be determined using a conventional assay such as a cultured or ex vivo ELISPOT assay. In one embodiment, the presence of a leader sequence enhances the expression and/or immunogenicity of the mycobacterial antigenic polypeptide by 2-fold, 3-fold or more when compared with antigenic polypeptide expressed without the leader sequence. An example of a suitable leader sequence is t-PA (tissue plasminogen activator).

Accordingly, in one embodiment, the polycistronic nucleic acid sequence encoding said mycobacterial antigenic polypeptides is operably linked to a leader sequence and a tag sequence. For example, the leader sequence may be fused to the N-terminus of the polycistronic sequence and the tag sequence may be fused to the C-terminus of the polycistronic sequence (ie. in the form: leader-polycistronic sequence-tag. In one embodiment, a linker sequence is located between the polycistronic sequence and the nucleic acid sequence encoding the tag (ie. in the form leader-polycistronic sequence-linker-tag). In one embodiment, the leader sequence is a t-PA leader sequence and/or the tag sequence is a PK tag sequence (ie. in the form: t-PA leader-polycistronic sequence-PK tag). In one embodiment, a linker sequence is located between the polycistronic sequence and the nucleic acid sequence encoding the tag (ie. in the form t-PA leader-polycistronic sequence-linker-PK tag). In one embodiment, intervening leader sequences are located between one or more of the mycobacterial polynucleotide sequences of the polycistronic sequence (ie. in the form: mycobacterial polynucleotide-leader-mycobacterial polynucleotide). In one embodiment, the polycistronic nucleic acid sequence encoding the mycobacterial antigenic polypeptides is operably linked to an N-terminal leader sequence, internal leader sequence and a tag sequence (ie. in the form: leader-first mycobacterial polynucleotide-leader-second mycobacterial polynucleotide-tag). In one embodiment, a linker sequence is located between the polycistronic sequence and the nucleic acid sequence encoding the tag (ie. in the form: leader-first mycobacterial polynucleotide-leader-second mycobacterial polynucleotide-linker-tag). In one embodiment, the leader sequence is a t-PA leader sequence and/or the tag sequence is a PK tag sequence (ie. in the form: t-PA leader-first mycobacterial polynucleotide-t-PA leader-second mycobacterial polynucleotide-PK tag). In one embodiment, a linker sequence is located between the polycistronic sequence and the nucleic acid sequence encoding the tag (ie. in the form t-PA leader-first mycobacterial polynucleotide-t-PA leader-second mycobacterial polynucleotide-linker-PK tag). In one embodiment, the polycistronic nucleic acid sequence further comprises a polyadenylation signal, such as a bovine growth hormone (BGH) polyadenylation signal.

In one embodiment, the antigenic composition comprises one or more cells, wherein said cells comprise at least one of the mycobacterial antigens. In one embodiment, said one or more cells comprise a first mycobacterial antigen and/or a second mycobacterial antigen, as defined above. In one embodiment, said one or more cells comprises one or more of said additional mycobacterial antigens, as defined above. In one embodiment, one or more of said additional mycobacterial antigens comprises a polypeptide sequence as defined above. In one embodiment, one or more of said additional mycobacterial antigens comprises a polynucleotide sequence as filed above.

In one embodiment, said at least one mycobacterial antigen (eg. polypeptide) is at least partially exposed at the surface of the cell(s). In an alternative embodiment, the cell becomes degraded in vivo so that at least part of the mycobacterial antigen (eg. polypeptide) becomes exposed to a host's immune system. In an alternative embodiment, the cell at least partially releases (eg. secretes or exports) the mycobacterial antigen (eg. polypeptide) to the outside of the cell, so that it is exposed to a host's immune system. In one embodiment, said antigenic composition comprises an individual cell, wherein said cell comprises at least two of said mycobacterial antigens. By way of example, in one embodiment, said antigenic composition comprises an individual cell, wherein said cell comprises both said first mycobacterial antigen and said second mycobacterial antigen. In one embodiment, said individual cell further comprises one or more of said additional mycobacterial antigens.

In one embodiment, said antigenic composition comprises an individual cell, wherein said cell comprises said first mycobacterial antigen and said one or more additional mycobacterial antigens. In one embodiment, said antigenic composition comprises an individual cell, wherein said cell comprises said second mycobacterial antigen and said one more additional mycobacterial antigens. In one embodiment, said antigenic composition comprises an individual cell, wherein said cell comprises said at least two of said additional mycobacterial antigens. In an alternative embodiment, the antigenic composition comprises at least first and second cells, wherein said first cell comprises said first mycobacterial antigen (as defined above) and wherein said second cell comprises said second mycobacterial antigen (as defined above). In this embodiment, the first and second mycobacterial antigens are not present in the same cell; rather, the first and second mycobacterial antigens are in different cells. In one embodiment, said antigenic composition further comprises at least a third cell, wherein said cell comprises an additional mycobacterial antigen, as defined above.

In one embodiment, said at least one cell is an attenuated microbial carrier. An attenuated carrier is a cell (such as a bacterial cell) that is incapable of causing a significant pathological effect in an animal subject, typically a mammalian subject such as a human, bovine, porcine or equine subject. Suitable examples of attenuated microbial carriers include attenuated *salmonella*, attenuated *M. tuberculosis*, or attenuated *M. bovis* (eg. BCG strain).

In one embodiment, the antigenic composition comprises one or more vectors, wherein said vectors comprise at least one of the mycobacterial antigens. In one embodiment, said one or more vectors comprises a first mycobacterial antigen, as defined above. In one embodiment, said first mycobacterial antigen comprises a polypeptide sequence as defined above. In one embodiment, said one or more vectors comprises a second mycobacterial antigen, as defined above. In one embodiment, said vector comprises said first mycobacterial antigen and said second (and optionally additional) mycobacterial antigen. By way of example, said vector may comprise a first mycobacterial polynucleotide as defined herein and a second (and optionally additional) mycobacterial polynucleotide as defined herein. In one embodiment, said vector comprises:

(i) a first mycobacterial polynucleotide, wherein said first mycobacterial polynucleotide comprises (or consists of) a polynucleotide sequence as hereinbefore defined; and optionally (ii) a second mycobacterial polynucleotide, wherein said second mycobacterial polynucleotide comprises (or consists of) a polynucleotide sequence as hereinbefore defined.

In one embodiment, said one or more vectors comprises one or more of said additional mycobacterial antigens, as defined above. In one embodiment, one or more of said additional mycobacterial antigens comprises a polypeptide sequence as defined above. In one embodiment, one or more of said additional mycobacterial antigens comprises a polynucleotide sequence as filed above.

Examples of vectors include DNA vectors (e.g. Vaccinia virus vectors, such as MVA) and RNA vectors (e.g. Sinbis or Semiliki Forest virus vectors). The term ‘vector’ embraces expression vectors (which may be useful for preparation of mycobacterial antigens of the invention), and viral vectors (which may be useful for replication and/or delivery of mycobacterial antigens of the invention). The vectors optionally include appropriate control sequences such as a promoter and/or terminator. In one embodiment, the vector comprises one or more polynucleotide sequence(s) encoding said mycobacterial antigen(s). Said polynucleotide sequence may be operably linked to a nucleic acid sequence encoding a tag polypeptide, such that the encoded tag is covalently linked to the antigen upon translation. The tag may facilitate detection of antigen expression, or of clones that express the antigen, and/or may lead to increases in antigen efficacy. Suitable tag polypeptides include a PK tag, FLAG tag, MYC tag, polyhistidine tag or any detectable tag (eg. a tag that can be detected by an antibody such as a monoclonal antibody). The nucleic acid sequence encoding the tag polypeptide may be positioned such that, following translation, the tag is located at the C-terminus of the expressed antigen. Alternatively, the nucleic acid sequence encoding the tag polypeptide may be positioned such that, following translation, the tag is located at the N-terminus of the expressed antigen. Alternatively, the nucleic acid sequence encoding the tag polypeptide may be positioned such that, following translation, the tag is located internally to the expressed antigen. Nucleotides encoding a linker sequence may be inserted between the polynucleotide encoding the expressed antigen and the nucleic acid sequence encoding the tag polypeptide. In one embodiment, the encoded linker sequence is located between an expressed antigen polypeptide and a tag polypeptide. In one embodiment, the nucleic acid sequence encoding the tag polypeptide and the nucleotides encoding the linker sequence are positioned such that, following translation, the linker sequence is located at the C-terminus of the expressed antigen and the tag is located at the C-terminus of the expressed linker sequence.

In one embodiment, the vector comprises one or more polynucleotide sequences encoding mycobacterial antigenic polypeptide(s), wherein said polynucleotide sequence is operably linked to a leader sequence. A leader sequence may affect processing of the primary transcript to mRNA, and/or may affect mRNA stability or translation efficiency. In one embodiment, a leader sequence ensures that the encoded polypeptide antigen is directed to the secretory machinery of a host cell. In one embodiment, a leader sequence enhances expression and/or immunogenicity of the antigen. Enhanced immunogenicity may be determined using a conventional assay such as a cultured or ex vivo ELISPOT assay. Enhanced expression may be determined by a conventional assay, such as using an antibody (eg. monoclonal antibody) to detect the amount of protein produced. In one embodiment, the presence of a leader sequence enhances the expression and/or immunogenicity of the mycobacterial antigen by 2-fold, 3-fold or more when compared with antigen expressed without the leader sequence. An example of a suitable leader sequence is t-PA (tissue plasminogen activator). In one embodiment, the vector comprises a C-terminally truncated polynucleotide encoding said mycobacterial antigen fused to a t-PA leader sequence. In one embodiment, the vector comprises a C-terminally truncated polynucleotide encoding said mycobacterial antigen fused to a t-PA leader sequence and a PK tag sequence. For example, the leader sequence may be fused to the N-terminus of the polynucleotide encoding the antigen and the tag sequence may be fused to the C-terminus of the polynucleotide encoding the antigen. In one embodiment, a linker sequence (eg. Gly-Ser-Ile) is located between the polynucleotide encoding the antigen and the nucleic acid sequence encoding the tag.

In one embodiment, said antigenic composition comprises an individual vector, wherein said vector comprises both said first mycobacterial antigen and said second mycobacterial antigen. In one embodiment, said individual vector further comprises one or more of said additional mycobacterial antigens. In one embodiment, said antigenic composition comprises an individual vector, wherein said vector comprises said first mycobacterial antigen and said one or more additional mycobacterial antigens. In one embodiment, said antigenic composition comprises an individual vector, wherein said vector comprises said second mycobacterial antigen and said one more additional mycobacterial antigens. In one embodiment, said antigenic composition comprises an individual vector, wherein said cell comprises said one or more additional mycobacterial antigens. In an alternative embodiment, the antigenic composition comprises at least first and second vectors, wherein said first vector comprises said first mycobacterial antigen (as defined above) and wherein said second vector comprises said second mycobacterial antigen (as defined above). In this embodiment, the first and second mycobacterial antigens are not present in the same vector; rather, first and second mycobacterial antigens are in different vectors. In one embodiment, said antigenic composition further comprises at least a third vector, wherein said third vector comprises an (one or more) additional mycobacterial antigen(s), as defined above.

In one embodiment, the vector (or at least one of said vectors) is a viral vector. Viral vectors are usually non-replicating or replication-impaired vectors, which means that the viral vector cannot replicate to any significant extent in normal cells (eg. normal human cells), as measured by conventional means—eg. via measuring DNA synthesis and/or viral titre. Non-replicating or replication-impaired vectors may have become so naturally (ie. they have been isolated as such from nature) or artificially (eg. by breeding in vitro or by genetic manipulation). There will generally be at least one cell-type in which the replication-impaired viral vector can be grown—for example, modified vaccinia Ankara (MVA) can be grown in CEF cells. Typically, the viral vector is incapable of causing a significant infection in an animal subject, typically in a mammalian subject such as a human, bovine, porcine or equine patient. Examples of viral vectors that are useful in this context include attenuated vaccinia virus vectors such as modified vaccinia Ankara (MVA) and NYVAC, or strains derived therefrom. Other suitable viral vectors include poxvirus vectors, such as avipox vectors, for example attenuated fowlpox vectors (eg. FP9) or canarypox vectors (eg. ALVAC and strains derived therefrom). Alternative viral vectors useful in the present invention include adenoviral vectors (eg. non-human adenovirus vectors), alphavirus vectors, flavivirus vectors, herpes viral vectors, influenza virus vectors and retroviral vectors.

In one embodiment, the vector (or at least one of said vectors) is an expression vector. Expression vectors are nucleic acid molecules (linear or circular) that comprise one or more polynucleotide sequences encoding a polypeptide(s) of interest, operably linked to additional regulatory elements required for its expression. In this regard, expression vectors generally include promoter and terminator sequences, and optionally one or more enhancer sequences, polyadenylation signals, and the like. Expression vectors may also include suitable translational regulatory elements, including ribosomal binding sites, and translation initiation and termination sequences. The transcriptional and translational regulatory elements employed in the expression vectors of the invention are functional in the host cell used for expression, and may include those naturally associated with mycobacterial genes.

The selection of suitable promoters, terminators, selectable markers and other elements is a matter of routine design within the level of ordinary skill in the art. Promoters such as the trp, lac and phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and others. Appropriate non-native mammalian promoters may include the early and late promoters from SV40 or promoters derived from murine moloney leukemia virus, mouse mammary tumour virus, avian sarcoma viruses, adenovirus II, bovine papilloma virus or polyoma. In one embodiment, the expression vector comprises a CMV promoter.

Generally, "operably linked" means that the nucleic acid sequences being linked are contiguous and arranged so that they function in concert for their intended purposes—for example, transcription initiates in the promoter and proceeds through the coding polynucleotide segment to the terminator. Where necessary to join two protein coding regions, the polynucleotide coding sequences should be contiguous and in reading frame.

In one embodiment, the invention provides a host cell comprising an antigenic composition of the invention, as defined above. The host cell thus comprises the first mycobacterial antigen and second mycobacterial antigen of the invention, wherein said mycobacterial antigens may comprise polypeptide and/or polynucleotide sequences, as discussed above.

Accordingly, in one embodiment, a host cell comprises an antigenic composition comprising a first mycobacterial antigen and a second mycobacterial antigen; wherein said first mycobacterial antigen comprises:

(i) a first mycobacterial polypeptide sequence as hereinbefore defined; and optionally
(ii) a second (and optionally additional) mycobacterial polynucleotide sequence as hereinbefore defined;

and wherein said second mycobacterial antigen is different from said first mycobacterial antigen.

In one embodiment, said host cell comprises either:

(i) a first mycobacterial antigenic polypeptide as herein before defined; or
(ii) a first mycobacterial polynucleotide, wherein said first mycobacterial polynucleotide comprises a polynucleotide sequence encoding said first mycobacterial antigenic polypeptide;

and optionally either:

(iii) a second mycobacterial antigenic polypeptide as hereinbefore defined; or
(iv) a second mycobacterial polynucleotide, wherein said second mycobacterial polynucleotide comprises a polynucleotide sequence encoding said second mycobacterial polypeptide.

The antigenic compositions, polynucleotides or polypeptides of the present invention may be prepared by expressing the polynucleotide sequences of the invention in vectors or other expression vehicles in compatible prokaryotic or eukaryotic host cells using standard molecular biology methods (e.g., Sambrook et al. 1989, Molecular Cloning a Laboratory Manual, Second Edition, Cold Spring Harbor Laboratory Press, Cold Spring Harbor, New York; incorporated herein by reference).

The most commonly used prokaryotic hosts are strains of *E. coli*, although other prokaryotes, such as *B. subtilis* or *Pseudomonas* may be used. Mammalian or other eukaryotic host cells, such as those of yeast, filamentous fungi, plant, insect, amphibian or avian species, may also be useful in the present invention. Propagation of mammalian cells in culture is per se well known. Examples of commonly used mammalian host cell lines are VERO and HeLa cells, Chinese hamster ovary (CHO) cells, and WI38, BHK, and COS cell lines, although other cell lines may be appropriate, e.g., to provide higher expression. As used herein, "recombinant host cells", "host cells", "cells", "cell lines", "cell cultures", and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental or deliberate mutation.

Polynucleotide sequences of interest can be transcribed in vitro and the resulting RNA introduced into the host cell (eg. by injection), or the polynucleotide sequences can be introduced directly into host cells by methods which vary depending on the type of cellular host, including electroporation; transfection employing calcium chloride, rubidium chloride, calcium phosphate, DEAE-dextran, or other substances; microprojectile bombardment; lipofection; infection (where the vector is an infectious agent, such as a retroviral genome). "Transformation" refers to the insertion of an exogenous polynucleotide into a host cell, irrespective of the method used for the insertion, for example, direct uptake, transduction, f-mating or electroporation.

Vectors may replicate autonomously, or may replicate by being inserted into the genome of a host cell, in which case they include an insertion sequence. Expression and cloning vectors may contain a selectable marker, a gene encoding a protein necessary for the survival or growth of a host cell transformed with the vector. This gene ensures the growth of only those host cells which express the inserts. Conventional selection genes encode proteins that (a) confer resistance to antibiotics or other toxic substances, eg. ampicillin, neomycin, methotrexate, etc.; (b) complement auxotrophic deficiencies; or (c) supply critical nutrients not available from complex media, e.g. the gene encoding D-alanine racemase for bacilli. The choice of appropriate selectable marker will depend on the host cell. The transformed host cell can be cultured in accordance with known methods, and the expressed polypeptide may be recovered and isolated (eg. from the culture medium) using conventional protocols.

In one aspect, the present invention provides a method for producing an antigenic composition comprising (at least) a first mycobacterial antigen and optionally a second mycobacterial antigen, as defined above; said method comprising:

(a) expressing a polynucleotide sequence as defined above that encode said at least first and optionally second mycobacterial antigens; or (b) culturing a host cell as described above, whereby said cell produces said at least first and optionally second mycobacterial antigens;

and recovering the expressed antigen(s).

The invention also relates to antibodies that bind a first mycobacterial antigen (eg. polypeptide) as defined above and a second mycobacterial antigen (eg. polypeptide) as defined above. Thus, in one embodiment, the invention provides an immunogenic composition comprising a first antibody and optionally a second antibody, wherein said first antibody binds a first mycobacterial antigen and said second antibody binds a second mycobacterial antigen;

wherein said first mycobacterial antigen comprises:

(i) a polypeptide sequence as hereinbefore defined; or (ii) a polynucleotide sequence encoding a polypeptide sequence (i) as hereinbefore defined;

and wherein said second mycobacterial antigen is different from said first mycobacterial antigen.

In one embodiment, the immunogenic composition comprises a first antibody and a second antibody, wherein said first antibody binds a first mycobacterial antigenic polypeptide and said second antibody binds a second mycobacterial antigenic polypeptide as hereinbefore defined. Optionally, said immunogenic composition further comprises at least a third antibody (eg. at least a 3, 4, 5, 6, 7, 8 additional antibodies), wherein said third antibody binds a third mycobacterial antigen that is different from the first and second mycobacterial antigens.

The term 'antibody' encompasses any polypeptide that comprises an antigen binding fragment or an antigen-binding domain. Examples include, but are not limited to, polyclonal, monoclonal, specific, monospecific, polyspecific, non specific, humanized, human, single chain, chimeric, affibodies, synthetic, recombinant, hybrid, mutated, grafted, and in vitro generated antibodies. Unless preceded by the word "intact", the term "antibody" includes antibody fragments such as Fab, F(ab')2, Fv, scFv, Fd, dAb, and other antibody fragments that retain antigen binding function. In one embodiment the antibody belongs to the IgG, IgM or IgA isotype families. Reference to the IgA isotype includes the secretory form of this antibody (ie. sIgA). The secretory component (SC) of sIgA may be added in vitro or in vivo. In the latter case, the use of a patient's natural SC labeling machinery may be employed. In one embodiment, the antibody specifically binds the mycobacterial antigen in question. "Specific binding" is intended to mean the formation of a complex between two or more molecules that is relatively stable under physiologic conditions. Specific binding is characterized by a high affinity and a low to moderate capacity, as distinguished from non-specific binding which usually has a low affinity with a moderate to high capacity. Typically, binding between an antibody and an antigen is considered to be specific when the association constant KA is higher than 106 M 1. If necessary, nonspecific binding can be reduced without substantially affecting specific binding by varying the binding conditions. The appropriate binding conditions, such as antibody concentration, ionic strength of the solution, temperature, time allowed for binding, concentration of a blocking agent (e.g., serum albumin, milk casein), etc., may be optimized by a skilled person using routine techniques. In one embodiment, said first and second antibodies have been raised against the first and second mycobacterial antigens of the invention, as described herein, respectively. In one embodiment, said first and second antibodies have been raised against the first and second mycobacterial antigenic polypeptides of the invention, as described herein, respectively. In one embodiment, the invention provides antisera isolated from animals that have been immunized with an antigenic composition of the invention. As used herein, the term 'antisera' refers to antibodies in serum that possess detectable binding, e.g., by ELISA or flow cytometry, for a particular antigen. Methods of preparing immune sera are known in the art. For example, the first and second antibodies (and optional additional antibodies) of the invention, or immunogenic composition of the invention, can be administered to an animal (such as a mammal—eg. a horse or a human) until an antibody response (for instance, neutralizing antibody response) is generated to the first and second mycobacterial antigens.

Antibodies raised against antigenic fragments disclosed herein (eg. polypeptide fragments) may have the property of recognizing the full-length antigen (eg. full-length polypeptide) from which they are derived. In this regard, polypeptide fragments bear antigenic determinants that are detectable by conventional immunoassays. One or more antigenic determinants is shared by full-length antigens of the invention and fragments thereof, thus antibodies raised against an antigenic fragment may also bind corresponding full-length antigens of the invention. In one embodiment, the antibodies are provided in an isolated form. The antibodies may be tagged with a detectable or functional label. These labels include radiolabels (eg. 1311 or 99Tc), enzymatic labels (eg. horseradish peroxidase or alkaline phosphatase), and other chemical moieties (eg. biotin).

The above-described antibodies may provide improved survival when administered to a mammal, such as a human, prior to or shortly after exposure to mycobacteria such as *M. tuberculosis*. Accordingly, the first and second antibodies (and optional additional antibodies) of the invention (or immunogenic, antibody-containing composition of the invention) can be used as a passive immune serum to prevent mycobacterial infection, or to treat patients exposed to mycobacteria (such as *M. tuberculosis*). In one embodiment, binding of the antibodies to the mycobacterial antigens of the invention may initiate coating of a *mycobacterium* expressing said antigen. Coating of the *mycobacterium* preferably leads to opsonization thereof, which leads to the bacterium being destroyed. Opsonization by antibodies may influence cellular entry and spread of mycobacteria in phagocytic and non-phagocytic cells by preventing or modulating receptor-mediated entry and replication in macrophages. Without being bound by any theory, the inventors believe that macrophage lysis may result in bacilli release. It is at this stage that the mycobacteria are considered to be most vulnerable to antibody attack. Thus, the antibodies of the present invention may act on released bacilli, and thereby exert a post-infection effect. It is therefore possible that passive protection (ie. delivery of antibodies of the present invention) is facilitated by enhanced accessibility of the antibodies of the present invention to antigens on mycobacterial bacilli, and that antibody binding may block macrophage infection by steric hindrance or disruption of its oligomeric structure. Thus, antibodies acting on mycobacterial bacilli released from killed, infected macrophages may interfere with the spread of re-infection to fresh macrophages. This hypothesis involves a synergistic action between antibodies and cytotoxic T cells, acting early after infection, eg. NK T cells, but could later involve also CD8 and CD4 cytotoxic T cells.

In the context of the therapeutic uses and methods discussed below, a 'subject' is any animal subject that would benefit from stimulation of an immune response against mycobacteria, such as *M. tuberculosis*. Typical animal subjects are mammals, for example, human, bovine, porcine, ovine, caprine, equine, corvine, canine or feline subjects. In one embodiment, the subject is human, bovine, porcine or equine.

According to one aspect of the present invention, there is provided the use of a first mycobacterial antigen and (optionally) a second mycobacterial antigen for the manufacture of a medicament for stimulating an immune response in a subject, such as a mammalian subject, (eg. a human, bovine, porcine or equine subject); wherein said first mycobacterial antigen comprises:

(i) a polypeptide sequence as hereinbefore defined; or
(ii) a polynucleotide sequence as hereinbefore defined encoding a polypeptide sequence according to (i);

and wherein said optional second mycobacterial antigen is different from said first mycobacterial antigen.

The invention also provides a first mycobacterial antigen and (optionally) a second mycobacterial antigen for use in stimulating an immune response in a subject, such as a mammalian subject, (eg. a human, bovine, porcine or equine subject); wherein said first mycobacterial antigen comprises:

(i) a polypeptide sequence as hereinbefore defined; or
(ii) a polynucleotide sequence as hereinbefore defined encoding a polypeptide sequence according to (i);

and wherein said second mycobacterial antigen is different from said first mycobacterial antigen.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, the invention provides (a) a first mycobacterial antigenic polypeptide or a first mycobacterial polynucleotide, and optionally (b) a second mycobacterial antigenic polypeptide or a second mycobacterial polynucleotide, for use in stimulating an immune response in a subject; wherein (i) said first mycobacterial antigenic polypeptide comprises a polypeptide sequence as hereinbefore defined;
(ii) said first mycobacterial polynucleotide sequence as hereinbefore defined comprises a polynucleotide sequence encoding said first mycobacterial antigenic polypeptide;
(iii) said optional second mycobacterial antigenic polypeptide as hereinbefore defined; and
(iv) said second mycobacterial polynucleotide sequence as hereinbefore defined comprises a polynucleotide sequence encoding said second mycobacterial antigenic polypeptide.

In one embodiment, the invention provides (a) a first mycobacterial antigenic polypeptide or a first mycobacterial polynucleotide, and optionally (b) a second mycobacterial antigenic polypeptide or a second mycobacterial polynucleotide, for use in stimulating an immune response in a subject; wherein (i) said first mycobacterial antigenic polypeptide comprises a polypeptide sequence as hereinbefore defined;
(ii) said first mycobacterial polynucleotide sequence as hereinbefore comprises a polynucleotide sequence encoding said first mycobacterial antigenic polypeptide;
(iii) said optional second mycobacterial antigenic polypeptide comprises a polypeptide sequence as hereinbefore defined; and
(iv) said second mycobacterial polynucleotide sequence as hereinbefore defined comprises a polynucleotide sequence encoding said second mycobacterial antigenic polypeptide.

In one embodiment, immune stimulation is measured by a protective effect in an in vivo survival assay. In one embodiment, immune stimulation is measured by an increased frequency in immune cells such as T lymphocytes specific for the antigen in the vaccine—ie. an immune cell response (eg. T cell immune response). In one embodiment, the immune stimulation is a memory T cell immune response, such as a central memory T cell response (eg. a CCR7+ response). In one embodiment, immune stimulation is measured by an increase in antibody titer that is specific for the antigen in the vaccine.

In one embodiment, said medicament further comprises one or more additional mycobacterial antigens, as described herein. In one embodiment, one or more additional mycobacterial antigens, as described herein, are also for use with said first and second mycobacterial antigens. In one embodiment of this therapeutic use, said first and optional second (and optional additional mycobacterial antigen(s)) are provided in the form of an antigenic composition as described herein. In one embodiment, one or more of said first, second and/or optional additional mycobacterial antigens may be comprised within one or more vectors or cells as described herein. In one embodiment of this therapeutic use, said first and optional second mycobacterial antigens (and optional additional mycobacterial antigen(s)) are for administration to the subject substantially simultaneously, or sequentially. Simultaneous and sequential administration regimes are discussed in more detail below.

The present invention also provides the use of a first mycobacterial antigen and optionally a second mycobacterial antigen for the manufacture of a medicament for treating or preventing a mycobacterial infection (eg. *M. tuberculosis* infection) in a subject, such as a mammalian subject (eg. a human, bovine, porcine or equine subject); wherein said first mycobacterial antigen comprises:

(i) a polypeptide sequence as hereinbefore defined; or
(ii) a polynucleotide sequence as hereinbefore defined encoding a polypeptide sequence according to (i);

and wherein said second mycobacterial antigen is different from said first mycobacterial antigen.

The invention also provides a first mycobacterial antigen and optionally a second mycobacterial antigen for use in treating or preventing a mycobacterial infection (eg. *M. tuberculosis* infection) in a subject, such as a mammalian subject (eg. a human, bovine, porcine or equine subject); wherein said first mycobacterial antigen comprises:

(i) a polypeptide sequence as hereinbefore defined; or
(ii) a polynucleotide sequence encoding a polypeptide sequence as hereinbefore according to (i;

and wherein said second mycobacterial antigen is different from said first mycobacterial antigen.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, the invention provides (a) a first mycobacterial antigenic polypeptide or a first mycobacterial polynucleotide, and optionally (b) a second mycobacterial antigenic polypeptide or a second mycobacterial polynucleotide, for use in treating or preventing a mycobacterial infection (eg. *M. tuberculosis* infection) in a subject; wherein:

(i) said first mycobacterial antigenic polypeptide comprises a polypeptide sequence as hereinbefore defined;
(ii) said first mycobacterial polynucleotide sequence as hereinbefore defined comprises a polynucleotide sequence encoding said first mycobacterial antigenic polypeptide;
(iii) said optional second mycobacterial antigenic polypeptide comprises a polypeptide sequence as hereinbefore defined; and
(iv) said second mycobacterial polynucleotide sequence as hereinbefore defined comprises a polynucleotide sequence encoding said second mycobacterial antigenic polypeptide.

For example, said use or medicament may protect the subject against infection with mycobacteria, such as *M. tuberculosis*. For example, suitable subjects include human, bovine, porcine or equine subjects. In one embodiment, said medicament further comprises one or more additional mycobacterial antigens, as described herein. In one embodiment, one or more additional mycobacterial antigens, as described herein, are also for use with said first and second mycobacterial antigens.

In one embodiment of this therapeutic use, said first and second (and optional additional mycobacterial antigen(s)) are provided in the form of an antigenic composition as described herein. In one embodiment, one or more of said first, second and/or optional additional mycobacterial antigens may be comprised within one or more vectors or cells as described herein. In one embodiment of this therapeutic use, said first and second mycobacterial antigens (and optional additional mycobacterial antigen(s)) are for administration to the subject substantially simultaneously, or sequentially.

A related aspect includes a method for stimulating an immune response in a subject, comprising administering to a subject, such as a mammal (eg. a human, bovine, porcine or equine subject) an effective amount of a first mycobacterial antigen and optionally a second mycobacterial antigen;

wherein said first mycobacterial antigen comprises:

(i) a polypeptide sequence has hereinbefore defined; or
(ii) a polynucleotide sequence encoding a polypeptide sequence as hereinbefore defined according to (i);

and wherein said second mycobacterial antigen is different from said first mycobacterial antigen.

In one embodiment, said optional second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, the invention provides a method of stimulating an immune response in a subject, comprising administrating to said subject: (a) a first mycobacterial antigenic polypeptide or a first mycobacterial polynucleotide, and optionally (b) a second mycobacterial antigenic polypeptide or a second mycobacterial polynucleotide; wherein:

(i) said first mycobacterial antigenic polypeptide comprises a polypeptide sequence as hereinbefore defined;
(ii) said first mycobacterial polynucleotide as hereinbefore defined comprises a polynucleotide sequence encoding said first mycobacterial antigenic polypeptide;
(iii) said second mycobacterial antigenic polypeptide comprises a polypeptide sequence as hereinbefore defined; and
(iv) said second mycobacterial polynucleotide as hereinbefore defined comprises a polynucleotide sequence encoding said second mycobacterial polypeptide.

In one embodiment, immune stimulation is measured by a protective effect in an in vivo survival assay. In one embodiment, immune stimulation is measured by an increased frequency in immune cells such as T lymphocytes specific for the antigen in the vaccine—ie. an immune cell response (eg. a T cell immune response). In one embodiment, the immune stimulation is a memory T cell immune response, such as a central memory T cell response (eg. a CCR7+ response). In one embodiment, immune stimulation is measured by an increase in antibody titre that is specific for the antigen in the vaccine. In one embodiment, said method further comprises administering one or more additional mycobacterial antigens, as described herein. In one embodiment of this therapeutic method, said first and optional second (and optional additional mycobacterial antigen(s)) are provided in the form of an antigenic composition or formulation as described herein. In one embodiment, one or more of said first, second and/or optional additional mycobacterial antigens may be comprised within one or more vectors or cells as described herein. In one embodiment of this therapeutic method, any of the limitations described herein with respect to said first and/or second mycobacterial antigens (and/or optional additional mycobacterial antigens) apply equally to the therapeutic uses thereof. In one embodiment, the method comprises administering said first and second mycobacterial antigens to the subject substantially simultaneously, or sequentially. Simultaneous and sequential administration regimes are discussed in more detail below.

In a related aspect, there is provided a method of treating or preventing a mycobacterial infection (eg. an *M. tuberculosis* infection), comprising administering to a subject, such as a mammal (eg. a human, bovine, porcine or equine subject) an effective amount of a first mycobacterial antigen and optionally a second mycobacterial antigen;

wherein said first mycobacterial antigen comprises:

(i) a polypeptide sequence as hereinbefore defined; or
(ii) a polynucleotide sequence as hereinbefore defined encoding a polypeptide sequence according to (i);

and wherein said second mycobacterial antigen is different from said first mycobacterial antigen.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen). In one embodiment, the invention provides a method of treating or preventing a mycobacterial infection (eg. *M. tuberculosis* infection) in a subject; comprising administering to said subject: (a) a first mycobacterial antigenic polypeptide or a first mycobacterial polynucleotide, and optionally (b) a second mycobacterial antigenic polypeptide or a second mycobacterial polynucleotide; wherein:

(i) said first mycobacterial antigenic polypeptide comprises a polypeptide sequence as hereinbefore defined;

(ii) said first mycobacterial polynucleotide as hereinbefore defined comprises a polynucleotide sequence encoding said first mycobacterial antigenic polypeptide;

(iii) said second mycobacterial antigenic polypeptide comprises a polypeptide sequence as hereinbefore defined; and (iv) said second mycobacterial polynucleotide as hereinbefore defined.

For example, said method may protect the subject against infection with mycobacteria, such as *M. tuberculosis*. For example, said method may treat TB in the subject. In one embodiment, said method may protect the subject against an early stage infection with mycobacteria, such as *M. tuberculosis*. Early stage mycobacterial infection is defined above. In one embodiment, said method further comprises administering one or more additional mycobacterial antigens, as described herein. In one embodiment of this therapeutic method, said first and optional second (and optional additional mycobacterial antigen(s)) are provided in the form of an antigenic composition as described herein. In one embodiment, one or more of said first, second and/or optional additional mycobacterial antigens may be comprised within one or more vectors or cells as described herein. In one embodiment, the method comprises administering said first and second mycobacterial antigens to the subject substantially simultaneously, or sequentially. In a related aspect, the first and second (and optional additional) mycobacterial antigens, antigenic composition, antibodies, immunogenic composition or medicament of the present invention, as defined herein, may be useful in therapies (including preventative treatments) for a range of mycobacterial diseases not limited to tuberculosis (TB), leprosy, *M. avium* infection, *M. bovis* infection, *M. paratuberculosis* infection, *M. ulcerans* infection (eg. Buruli ulcer), or other non-tuberculosis mycobacterial infection.

The first and second (and optional additional) mycobacterial antigens, antigenic composition, antibodies, immunogenic composition or medicament of the present invention may be useful for inducing a range of immune responses and may therefore be useful in methods for treating a range of diseases. In one embodiment, the first and optional second (and optional additional) mycobacterial antigens, antigenic composition or medicament of the present invention is useful for treating or preventing a range of non-mycobacterial diseases in which mycobacteria are implicated. For example, diseases that may benefit from the medicament of the invention include inflammatory diseases such as autoimmune disease, cancer (eg. bladder cancer), inflammatory bowel disease, Crohn's Disease, Johne's Disease, Hansen's Disease, osteomyelitis, lymphadenitis, smallpox or monkeypox.

As used herein, the term "treatment" or "treating" embraces therapeutic or preventative/prophylactic measures, and includes post-infection therapy and amelioration/suppression of a mycobacterial infection. As used herein, the term "preventing" includes preventing the initiation of a mycobacterial infection and/or reducing the severity or intensity of a mycobacterial infection. As used herein, the term "vaccine efficacy" describes the ability of a vaccine to protect a subject (typically a mammalian subject eg. a human, bovine, porcine or equine subject) from challenge with mycobacteria such as *M. tuberculosis*. By way of example, "vaccine efficacy" may refer to the efficacy of a vaccine in preventing the initiation of a mycobacterial infection and/or reducing the severity/intensity of a mycobacterial infection.

A therapeutic/prophylactic composition or medicament may be administered to a subject (typically a mammalian subject such as a human, bovine, porcine or equine subject) already having a mycobacterial infection, condition or symptoms associated with a mycobacterial infection, to treat or prevent said mycobacterial infection. In one embodiment, the subject is suspected of having come in contact with mycobacteria, or has had known contact with mycobacteria, but is not yet showing symptoms of exposure. In one embodiment, the subject has an early-stage infection. When administered to a subject (eg. a mammal such as a human, bovine, porcine or equine subject) that already has a mycobacterial infection or disease, or is showing symptoms associated with a mycobacterial infection, the therapeutic composition/medicament can cure, delay, reduce the severity of, or ameliorate one or more symptoms, and/or prolong the survival of a subject beyond that expected in the absence of such treatment. Alternatively, a therapeutic/prophylactic composition or medicament may be administered to a subject (eg. a mammal such as a human, bovine, porcine or equine subject) who ultimately may acquire a mycobacterial infection, in order to prevent, cure, delay, reduce the severity of, or ameliorate one or more symptoms of said mycobacterial infection, or in order to prolong the survival of a subject beyond that expected in the absence of such treatment. In one embodiment, the subject has previously been exposed to mycobacteria. For example, the subject may have had a mycobacterial infection in the past (but is optionally not currently infected with mycobacteria). The subject may be latently infected with mycobacteria. Alternatively, or in addition, the subject may have been vaccinated against mycobacterial infection in the past (eg. the subject has previously received a BCG vaccination).

The treatments and preventative therapies of the present invention are applicable to a variety of different subjects of different ages. In the context of humans, the therapies are applicable to children (eg. infants, children under 5 years old, older children or teenagers) and adults. In the context of other animal subjects (eg. mammals such as bovine, porcine or equine subjects), the therapies are applicable to immature subjects (eg. calves, piglets, foals) and mature/adult subjects. The treatments and preventative therapies of the present invention are applicable to subjects who are immunocompromised or immunosuppressed (eg. human patients who have HIV or AIDS, or other animal patients with comparable immunodeficiency diseases), subjects who have undergone an organ transplant, bone marrow transplant, or who have genetic immuno-deficiencies.

The invention provides therapeutic formulations, medicaments and prophylactic formulations (eg. vaccines) comprising a pharmaceutically acceptable carrier, a first mycobacterial antigen of the invention as defined above, and a second mycobacterial antigen of the invention, as defined above (and optionally one or more additional mycobacterial antigens of the invention, as described above). In one embodiment, the invention provides a therapeutic or prophylactic formulation (eg. vaccine), comprising pharmaceutically acceptable carrier and:

(a) a first mycobacterial antigen, wherein said first mycobacterial antigen comprises:

(i) a polypeptide sequence as hereinbefore defined; or (ii) a polynucleotide sequence as hereinbefore defined encoding a polypeptide sequence according to (i);

and optionally (b) a second mycobacterial antigen, wherein said second mycobacterial antigen is different from said first mycobacterial antigen;

wherein said formulation is for simultaneous or sequential administration of said first and second mycobacterial antigens.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, said therapeutic or prophylactic formulation (eg. vaccine), comprises (a) a pharmaceutically acceptable carrier; (b) a first mycobacterial antigenic polypeptide or a first mycobacterial polynucleotide; and optionally (c) a second mycobacterial antigenic polypeptide or a second mycobacterial polynucleotide; wherein:

(i) said first mycobacterial antigenic polypeptide comprises a polypeptide sequence as hereinbefore defined;

(ii) said first mycobacterial polynucleotide as hereinbefore defined comprises a polynucleotide sequence encoding said first mycobacterial antigenic polypeptide;

(iii) said second mycobacterial antigenic polypeptide comprises a polypeptide sequence as hereinbefore defined; and (iv) said second mycobacterial polynucleotide as hereinbefore defined comprises a polynucleotide sequence encoding said second mycobacterial polypeptide;

wherein said formulation is for simultaneous or sequential administration of said first mycobacterial antigenic polypeptide or polynucleotide and said second mycobacterial antigenic polypeptide or polynucleotide.

In one embodiment, said therapeutic formulation, medicament or prophylactic formulation (eg. vaccine) of the invention comprises an antigenic composition of the invention, as defined above. In one embodiment, said therapeutic formulation, medicament or prophylactic formulation (eg. vaccine) comprises an antigenic composition comprising one or more vectors or cells, as described above, wherein said vectors or cells comprise at least one of the mycobacterial antigens. In one embodiment of said therapeutic formulation, medicament or prophylactic formulation (eg. vaccine), any of the limitations described herein with respect to said first and/or second (or additional) mycobacterial antigens apply equally to said therapeutic formulation, medicament or prophylactic formulation (eg. vaccine). In one embodiment, a vaccine of the invention is a "vectored vaccine" comprising one or more vectors as described above.

In one embodiment, the therapeutic formulations, medicaments or prophylactic formulations (eg. vaccines) of the invention are for simultaneous administration of said first and second (and/or optional additional) mycobacterial antigens. In an alternative embodiment, the therapeutic formulations, medicaments or prophylactic formulations (eg. vaccines) of the invention are for sequential administration of said first and second (and/or optional additional) mycobacterial antigens. Therapeutic formulations, medicaments and prophylactic formulations (eg. vaccines) of the invention comprise a pharmaceutically acceptable carrier, and optionally one or more of a salt, excipient, diluent and/or adjuvant. In one embodiment, the therapeutic formulation, medicament or prophylactic formulation (eg. vaccine) of the invention may comprise one or more immunoregulatory agents selected from, for example, immunoglobulins, antibiotics, interleukins (eg. IL-2, IL-12), and/or cytokines (eg. IFN-γ). In one embodiment, the therapeutic formulation, medicament or prophylactic formulation (eg. vaccine) of the invention may comprise one or more antimicrobial compounds, such as conventional anti-tuberculosis drugs (eg. rifampicin, isoniazid, ethambutol or pyrazinamide).

Accordingly, in one aspect, the invention provides a method for producing a therapeutic or prophylactic formulation (eg. vaccine), the method comprising combining a pharmaceutically acceptable carrier with a first mycobacterial antigen of the invention, as defined above; and a second mycobacterial antigen of the invention, as defined above (and optionally one or more additional mycobacterial antigens, as defined above).

Thus, in one embodiment, the invention provides a method for producing a therapeutic or prophylactic formulation (eg. vaccine), the method comprising combining a pharmaceutically acceptable carrier with:

(a) a first mycobacterial antigen, wherein said first mycobacterial antigen comprises:

(i) a polypeptide sequence as hereinbefore defined; or (ii) a polynucleotide sequence as hereinbefore defined encoding a polypeptide sequence according to (i);

and optionally (b) a second mycobacterial antigen, wherein said second mycobacterial antigen is different from said first mycobacterial antigen.

In one embodiment, said second mycobacterial antigen comprises or consists of a mycobacterial antigenic polypeptide or polynucleotide sequence, such as a mycobacterial antigenic polypeptide or polynucleotide sequence as defined in (i) or (ii) (wherein said second mycobacterial antigen is different from said first mycobacterial antigen).

In one embodiment, the invention provides a method for producing a therapeutic or prophylactic formulation (eg. vaccine), the method comprising:

combining a pharmaceutically acceptable carrier with either:

(i) a first mycobacterial antigenic polypeptide, wherein said first mycobacterial antigenic polypeptide comprises a polypeptide sequence as hereinbefore defined; or (ii) a first mycobacterial polynucleotide, wherein said first mycobacterial polynucleotide comprises a polynucleotide sequence as hereinbefore defined encoding said first mycobacterial antigenic polypeptide;

and optionally with either:

(iii) a second mycobacterial antigenic polypeptide, wherein said second mycobacterial antigenic polypeptide comprises a polypeptide sequence as hereinbefore defined; or (iv) a second mycobacterial polynucleotide, wherein said second mycobacterial polynucleotide as hereinbefore defined comprises a polynucleotide sequence encoding said second mycobacterial polypeptide.

In one embodiment, said mycobacterial antigens are in the form of an antigenic composition of the invention, as defined above. In one embodiment, the method further comprises combining said pharmaceutically acceptable carrier and mycobacterial antigens (or antigenic composition) with one or more of a salt, excipient, diluent, adjuvant, immunoregulatory agent and/or antimicrobial compound.

As used, herein, a "vaccine" is a formulation that, when administered to an animal subject such as a mammal (eg. a human, bovine, porcine, ovine, caprine, equine, corvine, canine or feline subject), stimulates a protective immune response against mycobacterial infection. The immune response may be a humoral and/or cell-mediated immune response (eg. a T cell response). A vaccine of the invention can be used, for example, to protect an animal from the effects of mycobacterial infection (eg. *M. tuberculosis* infection), such as an early-stage infection. The immunogenicity of the epitopes of the first and second mycobacterial antigens (eg. polypeptides) of the invention may be enhanced by preparing them in mammalian or yeast systems fused with or assembled with particle-forming proteins such as, for example, that associated with hepatitis B surface antigen. In one embodiment, the vaccine comprises at least one mycobacterial polypeptide that has been treated with a chemical modifying agent (such as formaldehyde) to give a vaccine of improved efficacy.

The polypeptides and/or polynucleotides of the invention may be formulated into a vaccine as neutral or salt forms. Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Administration of therapeutic formulations, medicaments and prophylactic formulations (eg. vaccines) is generally by conventional routes e.g. intravenous, subcutaneous, intraperitoneal, or mucosal (eg. intranasal) routes. The administration may be by parenteral injection, for example, a subcutaneous or intramuscular injection. Formulations comprising neutralizing antibodies may be particularly suited to administration intravenously, intramuscularly, intradermally, or subcutaneously. Accordingly, the therapeutic formulations, medicaments and prophylactic formulations (eg. vaccines) of the invention are typically prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules. The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, and/or adjuvants which enhance the effectiveness of the vaccine. Generally, the carrier is a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as BSA. In some embodiments, it may be desirable to formulate the composition with a preservative, such as thiomersal or sodium azide, to facilitate long term storage. Examples of adjuvants which may be effective include but are not limited to: complete Freunds adjuvant (CFA), Incomplete Freunds adjuvant (IVA), Saponin, a purified extract fraction of Saponin such as Quil A, a derivative of Saporin such as QS-21, lipid particles based on Saponin such as ISCOM/ISCOMATIX, *E. coli* heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryl oxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. Examples of buffering agents include, but are not limited to, sodium succinate (pH 6.5), and phosphate buffered saline (PBS; pH 6.5 and 7.5). Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

In the case of a mycobacterial respiratory infection (eg. a *M. tuberculosis* infection), efficient transmission of the therapeutic/prophylactic composition or medicament to the site of infection in the lungs may be achieved by oral or intra-nasal administration (i.n.). These modes of delivery correspond to the route of delivery of a *M. tuberculosis* infection. In the case of antibody-based compositions, these modes of delivery ensure that antibodies are present at the site of infection to combat the bacterium before it becomes intracellular and also during the period when it spreads between cells. Formulations for intranasal administration may in the form of nasal droplets or a nasal spray. An intranasal formulation may comprise droplets having approximate diameters in the range of 100-5000 μm, such as 500-4000 μm, 1000-3000 μm or 100-1000 μm. Alternatively, in terms of volume, the droplets may be in the range of about 0.001-100 μl, such as 0.1-50 μl or 1.0-25 μl, or such as 0.001-1 μl. Alternatively, the therapeutic/prophylactic formulation or medicament may be an aerosol formulation. The aerosol formulation may take the form of a powder, suspension or solution. The size of aerosol particles is relevant to the delivery capability of an aerosol. Smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli. In the case of aerosol delivery of the medicament, the particles may have diameters in the approximate range of 0.1-50 μm, preferably 1-25 μm, more preferably 1-5 μm. Aerosol particles may be for delivery using a nebulizer (eg. via the mouth) or nasal spray. An aerosol formulation may optionally contain a propellant and/or surfactant. It is possible that, following i.n. delivery of mycobacterial antigens or antibodies, their passage to the lungs is facilitated by a reverse flow of mucosal secretions, although mucociliary action in the respiratory tract is thought to take particles within the mucus out of the lungs. The relatively long persistence in lung lavage, fast clearance from the bile and lack of transport to the saliva of some antibodies suggests the role of mucosal site-specific mechanisms. By controlling the size of the droplets/particles to within the defined range of the present invention, it is possible to avoid (or minimize) inadvertent antigen delivery to the alveoli and thus avoid alveoli-associated pathological problems such as inflammation and fibrotic scarring of the lungs. I.n. vaccination engages both T and B cell mediated effector mechanisms in nasal and bronchus associated mucosal tissues, which differ from other mucosae-associated lymphoid tissues. The protective mechanisms invoked by the intranasal route of administration may include: the activation of T lymphocytes with preferential lung homing; up-regulation of co-stimulatory molecules (eg. B7.2); and/or activation of macrophages or secretory IgA antibodies. Intranasal delivery of antigens may facilitate the invoking of a mucosal antibody response, which is favoured by a shift in the T cell response toward the Th2 phenotype which helps antibody production. A mucosal response is characterised by enhanced IgA production, and a Th2 response is characterised by enhanced IL-4 production. Intranasal delivery of mycobacterial antigens of the invention allows targeting of the antigens to sub-mucosal B cells of the respiratory system. These B cells are the major local IgA-producing cells in mammals and intranasal delivery facilitates a rapid increase in IgA production by these cells against the mycobacterial antigens. In one embodiment, the therapeutic/prophylactic formulation or medicament of the invention stimulates a mucosal and/or Th2 immune response. In another embodiment, IgA antibody production is stimulated, and the IgA antibody binds to the mycobacterial antigen.

In one embodiment, the first and second (and optional additional) mycobacterial antigens or antibodies of the invention are for simultaneous administration. Thus, in one embodiment, the methods/uses of the invention comprise simultaneous administration of the first and second (and optional additional) mycobacterial antigens. Simultaneous administration means administration at (substantially) the same time. For example, in one embodiment the first and second (and optional additional) mycobacterial antigens are administered to the subject within 5 minutes of each other, such as within 4, 3, 2 or 1 minute of each other, for example within 30 seconds of each other. In one embodiment of ‘simultaneous administration’, at least two components (eg. antigens) of the invention are combined into one composition (eg. a single antigenic composition or immunogenic composition of the invention as defined herein). This composition is administered to the subject (such as a mammal—eg. a human, bovine, porcine, ovine, caprine, equine, corvine, canine or feline subject) thereby providing both components to the subject simultaneously. In an alternative embodiment of ‘simultaneous administration’, at least two of the components (eg. antigens) of the invention are provided separately from each other, but are administered to the subject (such as a mammal—eg. a human, bovine, porcine, ovine, caprine, equine, corvine, canine or feline subject) at (substantially) the same time. The concurrent/parallel administration of said separate compositions provides both components to the subject at (substantially) the same time. By way of example, the therapeutic or prophylactic formulation (eg. vaccine) of the invention may comprise a first mycobacterial antigen in a first composition and the second mycobacterial antigen in a second composition. In one embodiment, the first and second (and optional additional) mycobacterial antigens of the invention are for simultaneous administration at (substantially) the same site. Thus, in one embodiment, the methods/uses of the invention comprise simultaneous administration of the first and second (and optional additional) mycobacterial antigens at (substantially) the same site. In this regard, it is considered advantageous to administer each different antigenic component of conventional multivalent vaccines at different sites of the subject’s body, in order to stimulate different lymph nodes. Administration of different antigenic components of conventional multivalent vaccines at different sites is also considered advantageous in order to reduce or avoid undesirable antigenic competition.

In one embodiment, the present invention advantageously avoids the need to administer each different antigenic component to different sites/locations of the subject’s body. In this regard, in one embodiment, the first and second (and optional additional) antigens of the present invention (substantially) do not compete with each other, or are associated with relatively low levels of antigenic competition, as compared with the competitive effect that might have been expected in view of known multivalent vaccine compositions. If at least two components (eg. antigens) of the invention are combined into a single composition (eg. a single antigenic composition or immunogenic composition of the invention as defined herein), it is evident that all components of the invention are administered to the subject at the same site. In one embodiment, if the first and second (and optional additional) mycobacterial antigens of the invention are provided separately from each other, for simultaneous, parallel administration to the subject at (substantially) the same time, the separate compositions are administered at the same (or substantially the same) site on/in the subject.

In one embodiment, administration at (substantially) the same site on/in the subject means that the site at which each mycobacterial antigen of the invention is administered is in the vicinity of, or in close proximity to, the site at which the other mycobacterial antigens of the invention are administered. Alternatively, administration at (substantially) the same site on/in the subject means that the site at which each mycobacterial antigen of the invention is administered is at the precise site at which the other mycobacterial antigens of the invention are administered. By way of example, the first and second (and optional additional) mycobacterial antigens of the invention may be for administration to the same vein, artery or muscle of the subject, or via the same nostril of the subject; or to the same limb (eg. arm) of the subject (eg. to the same upper arm of the subject); or the first and second (and optional additional) mycobacterial antigens of the invention may all be for oral or sublingual administration. In one embodiment, the first and second (and optional additional) mycobacterial antigens of the invention may all be for administration at or in close proximity to the same lymph node. Alternatively, the mycobacterial antigens of the invention are for administration to the subject (eg. a mammal such as a human, bovine, porcine, ovine, caprine, equine, corvine, canine or feline subject) sequentially (ie. one after the other). In this embodiment, at least two of the components (eg. antigens) of the invention are provided separately from each other, and are administered sequentially to the subject. By way of example, the therapeutic or prophylactic formulation (eg. vaccine) of the invention may comprise a first mycobacterial antigen in a first composition and the second mycobacterial antigen in a second composition. The sequential administration of said first and second compositions provides both components to the subject one after the other. Thus, in one embodiment, the methods of the invention comprise administration of the first mycobacterial antigen, and then administration of the second mycobacterial antigen. Alternatively, the second mycobacterial antigen may be administered and then the first mycobacterial antigen is administered. Any additional mycobacterial antigens may be administered together with the first and/or second mycobacterial antigens. Alternatively, any additional mycobacterial antigens may be administered before or after the first and/or second mycobacterial antigens.

In one embodiment, each sequential administration of antigen is made immediately one after the other. In one embodiment, there is a time-gap or pause between one or more (eg. between each) of the administrations. A time-gap or pause between sequential administrations may be at least 5, 10, 15, or 30 minutes, or may be at least 1, 2, 5, 12, 18 or 24 hours, or may be at least 1, 2, or 5 days, or may be at least 1 or 2 weeks. In one embodiment, the first and second (and optional additional) mycobacterial antigens of the invention are for sequential administration at (substantially) the same site. Thus, in one embodiment, the methods/uses of the invention comprise sequential administration of the first and second (and optional additional) mycobacterial antigens at (substantially) the same site. In one embodiment, administration at (substantially) the same site on/in the subject means that the site at which the each mycobacterial antigen of the invention is administered is in the vicinity of, or in close proximity to, the site at which the other mycobacterial antigens of the invention are administered. Alternatively, administration at (substantially) the same site on/in the subject means that the site at which each mycobacterial antigen of the invention is administered is at the precise site at which the other mycobacterial antigens of the invention are administered. By way of example, the first and second (and optional additional) mycobacterial antigens of the invention may be for administration to the same vein, artery or muscle of the subject, or via the same nostril of the subject; or to the same limb (eg. arm) of the subject (eg. to the same upper arm of the subject); or the first and second (and optional additional) mycobacterial antigens of the invention may all be for oral or sublingual administration. In one embodiment, the first and second (and optional additional) mycobacterial antigens of the invention may all be for administration at or in close proximity to the same lymph node.

The therapeutic formulation, medicament or prophylactic formulation (eg. a vaccine) of the invention may be given in a single dose schedule (ie. the full dose is given at substantially one time). Alternatively, the therapeutic formulation, medicament or prophylactic formulation (eg. a vaccine) of the invention may be given in a multiple dose schedule. A multiple dose schedule is one in which a primary course of treatment (eg. vaccination) may be with 1-6 separate doses, followed by other doses given at subsequent time intervals required to maintain and or reinforce the immune response, for example (for human subjects), at 1-4 months for a second dose, and if needed, a subsequent dose(s) after a further 1-4 months. The dosage regimen will be determined, at least in part, by the need of the individual and be dependent upon the judgment of the practitioner (eg. doctor or veterinarian). In one embodiment, the vaccine of the present invention may be administered as part of a ‘prime-boost’ vaccination regime.

Prime-boost vaccination regimes involve: Priming—ie. exposing a subject to one or more antigens or a vaccine; and subsequently: Boosting—ie. exposing the subject to one or more antigens or a vaccine. The ‘boost’ antigens/vaccine is typically different from the ‘primer’ antigens/vaccine (known as “heterologous” prime-boost). In this regard, heterologous prime-boost immunization strategies have been shown to induce higher levels of immune cell responses (eg. effector T cell responses) in subjects as compared with homologous boosting with the same vaccine. For example, repeated vaccination with conventional vaccines such as BCG does not appear to further enhance protection against TB. However, incorporating BCG into a heterologous prime-boost regime may retain the protective effects of BCG. Thus, in one embodiment the invention provides a method of vaccination against mycobacterial infection comprising ‘priming’ a subject’s immune system by administration of a heterologous conventional vaccine (eg. BCG vaccine) and then ‘boosting’ the subject’s immune system by administration of the vaccine of the present invention. In one embodiment, the invention provides a method of vaccination against mycobacterial infection comprising administering the vaccine of the present invention to a subject that has been pre-exposed to a heterologous conventional vaccine such as BCG. Alternatively, a subject’s immune system may be ‘primed’ by administration of the vaccine of the present invention, and then ‘boosted’ by administration of a heterologous conventional vaccine (eg. BCG vaccine). Accordingly, in one embodiment, the vaccine is administered to a subject that is subsequently to be exposed to a heterologous conventional vaccine such as BCG. The ‘priming’ step may be carried out on the subject at any age—in the case of mammalian subjects (eg. human, bovine, porcine, ovine, caprine, equine, cervine, canine or feline subjects), priming with BCG is conventionally carried out neonatally, or during infancy, adolescence or adulthood. The ‘boosting’ step may be carried out at any time after the ‘priming’ step. In the case of mammalian subjects (eg. human, bovine, porcine, ovine, caprine, equine, cervine, canine or feline subjects), a boosting step may be carried out at least about 1, 2, 3, 4, 5, 6, 7, 8, 9 or 10 weeks after the priming step, or at least about 3, 6, 8 or 12 months after the priming step, or at least about 2, 5, 10, 15, 20, 25, 30, 35, or 40 or more years after the boosting step. In one embodiment, for a human subject, the priming step is carried out during infancy and the boosting step is carried out during adolescence. In one embodiment, the therapeutic formulation, medicament or prophylactic formulation (eg. a vaccine) of the invention can be administered to a subject such as a mammal (eg. a human, bovine, porcine, ovine, caprine, equine, corvine, canine or feline subject) in conjunction with (simultaneously or sequentially) one or more immunoregulatory agents selected from, for example, immunoglobulins, antibiotics, interleukins (eg. IL-2, IL-12), and/or cytokines (eg. IFNγ). In one embodiment, the therapeutic formulation, medicament or prophylactic formulation (eg. vaccine) of the invention can be administered to a subject such as a mammal (eg. a human, bovine, porcine, ovine, caprine, equine, corvine, canine or feline subject) in conjunction with (simultaneously or sequentially) one or more antimicrobial compounds, such as conventional anti-tuberculosis drugs (eg. rifampicin, isoniazid, ethambutol or pyrazinamide).

The therapeutic formulation, medicament or prophylactic formulation (eg. vaccine) may contain 5% to 95% of active ingredient, such as at least 10% or 25% of active ingredient, or at least 40% of active ingredient or at least 50, 55, 60, 70 or 75% active ingredient. The therapeutic formulation, medicament or prophylactic formulation (eg. a vaccine) is administered in a manner compatible with the dosage formulation, and in such amount as will be prophylactically and/or therapeutically effective. In this regard, as used herein, an “effective amount” is a dosage or amount that is sufficient to achieve a desired biological outcome. As used herein, a “therapeutically effective amount” is an amount which is effective, upon single or multiple dose administration to a subject (such as a mammal—eg. a human, bovine, porcine, ovine, caprine, equine, corvine, canine or feline subject) for treating, preventing, curing, delaying, reducing the severity of, ameliorating at least one symptom of a disorder or recurring disorder, or prolonging the survival of the subject beyond that expected in the absence of such treatment. Accordingly, the quantity of active ingredient to be administered, which is generally in the range of 5 micrograms to 250 micrograms of antigen per dose (or higher if delivered orally or in the form of viral vectors), depends on the subject to be treated, capacity of the subject's immune system to generate a protective immune response, and the degree of protection desired. Precise amounts of active ingredient required to be administered may depend on the judgment of the practitioner and may be particular to each subject.

According to a further aspect of the invention, the first and second mycobacterial antigens (and optional additional mycobacterial antigens) of the invention, as described herein, are useful in immunoassays to detect the presence in a test sample of antibodies to said first and second mycobacterial antigens. In one embodiment, said first and second mycobacterial antigens (and optional additional antigens) are used in the form of an antigenic composition, as described herein. According to another aspect of the invention, the first and second antibodies (and optional additional antibodies) of the invention, as described herein, are useful in immunoassays to detect the presence in a test sample of said first and second mycobacterial antigens. In one embodiment, said first and second antibodies (and optional additional antibodies) are used in the form of an immunogenic antibody-containing composition, as described herein.

A test sample may be a biological sample such as a clinical sample or environmental sample. As used herein, a 'clinical sample' refers to a sample of tissue or fluid isolated from an individual, including but not limited to, for example, plasma, serum, spinal fluid, lymph fluid, the external sections of the skin, respiratory, intestinal, and genitourinary tracts, tears, saliva, milk, blood cells, tumours, organs, and also samples of in vitro cell culture constituents (including but not limited to conditioned medium resulting from the growth of cells in cell culture medium, putatively infected cells, recombinant cells, and cell components). In the context of the diagnostic methods discussed below, a 'subject' is any animal subject that would benefit from detection of mycobacterial infection, such as *M. tuberculosis* infection. Typical animal subjects are mammals, for example, human, bovine, porcine, ovine, caprine, equine, corvine, canine or feline subjects. In one embodiment, the subject is human, bovine, porcine or equine.

Design of immunoassays is subject to a great deal of variation, and many formats are known in the art. Protocols may be based, for example, upon competition, direct reaction, or sandwich type assays. Protocols may also, for example, use solid supports, or may employ immuno-precipitation. Most assays involve the use of labeled antibodies or polypeptides; the labels may be, for example, enzymatic, fluorescent, chemiluminescent, radioactive, or dye molecules. Assays that comprise signal amplification are also known; for example, assays that utilize biotin and avidin, or enzyme-labeled and mediated immunoassays, such as ELISA assays. In one aspect of the invention, the first and second mycobacterial antigens (or antigenic composition) of the invention are useful for detecting the presence of a T-lymphocyte that has been previously exposed to an antigenic component of a mycobacterial infection in a patient.

Accordingly, in one embodiment, the invention provides an in vitro method of diagnosing a mycobacterial infection, such as an early stage mycobacterial infection, comprising incubating ('challenging') a test sample containing an immune cell such as a T-lymphocyte from a subject (eg. a mammal such as a human, bovine, porcine or equine subject) with a first mycobacterial antigen of the invention and a second mycobacterial antigen of the invention, as defined herein; or an antigenic composition of the invention, as defined herein; and detecting activation of said immune cell (eg. T-lymphocyte). Activation of said immune cell is indicative of a mycobacterial infection in the subject.

In one embodiment of said in vitro method, said first mycobacterial antigen is selected from (i) a first mycobacterial antigenic polypeptide comprising a polypeptide sequence having at least 70% amino acid sequence identity to the amino acid sequence of SEQ ID NO: 1 or 7, or a fragment thereof having at least 50 consecutive amino acids thereof; or (ii) a first mycobacterial polynucleotide sequence comprising a polynucleotide sequence encoding said first mycobacterial antigenic polypeptide. In one embodiment of said in vitro method, said second mycobacterial antigen is selected from (iii) a second mycobacterial antigenic polypeptide comprising a polypeptide sequence having at least 70% amino acid sequence identity to the amino acid sequence of SEQ ID NO: 5, or a fragment thereof having at least 7 consecutive amino acids thereof; or (iv) a second mycobacterial polynucleotide sequence comprising a polynucleotide sequence encoding said second mycobacterial antigenic polypeptide.

An immune cell, such as a T-lymphocyte, that has been previously exposed to one or both of the first and second mycobacterial antigens will become 'activated' on subsequent challenge by the same antigen. As such, activation of said immune cell (eg. T-lymphocyte) is indicative of a mycobacterial infection in the subject, and provides a means for identifying a positive diagnosis of mycobacterial infection. In contrast, the same activation is not achieved by an immune cell (eg. T-lymphocyte) that has not been previously exposed to the particular antigen. The above-described 'activation' of an immune cell (eg. T-lymphocyte) is sometimes referred to as a 'recall response' and may be measured, for example, by determining the release of interferon (eg. IFN-$\gamma$) from the activated immune cell (eg. T-lymphocyte). Thus, the presence of a mycobacterial infection in a patient may be determined by detecting activation of immune cell (eg. T-lymphocyte) in response to in vitro challenge with the first and second mycobacterial antigens (or antigenic composition) of the present invention—eg. by detecting the release of a minimum concentration of interferon from immune cell (eg. T-lymphocyte) after a defined time period following the challenge. The above immune cell (eg. T-lymphocyte) diagnostic assay may further include an antigen presenting cell (APC) expressing at least one major histocompatibility complex (MHC) class II molecule expressed by the patient in question. The APC may be inherently provided in the biological sample, or may be added exogenously. In one embodiment, the T-lymphocyte is a CD4 T-lymphocyte.

Alternative immunoassays for diagnosing mycobacterial infection depend upon detection of antibodies to the first and second mycobacterial antigens (eg. polypeptides) of the invention. Such assays may comprise the step of incubating a test sample (eg. a biological sample) suspected of containing the antibodies with said first and second antigens (or antigenic composition) of the invention. Accordingly, the invention also provides an in vitro method of diagnosing a mycobacterial infection, such as an early stage mycobacterial infection, comprising incubating a test sample from a subject (eg. a mammal such as a human, bovine, porcine or equine subject) with a first mycobacterial antigen and a second mycobacterial antigen of the invention, as defined herein; or an antigenic composition of the invention, as defined herein; wherein said incubating is performed under conditions that allow binding of said first and second mycobacterial antigens with antibodies in the sample to form antigen-antibody complexes; and then detecting the formation of such complexes. The presence of antigen-antibody complexes is indicative of a mycobacterial infection in the subject.

In one embodiment of said in vitro method, said first mycobacterial antigen is selected from (i) a first mycobacterial antigenic polypeptide comprising a polypeptide sequence as hereinbefore defined; or (ii) a first mycobacterial polynucleotide sequence comprising a polynucleotide sequence as hereinbefore defined encoding said first mycobacterial antigenic polypeptide; and optionally said second mycobacterial antigen is selected from (iii) a second mycobacterial antigenic polypeptide comprising a polypeptide sequence as hereinbefore defined; and (iv) a second mycobacterial polynucleotide sequence as hereinbefore defined comprising a polynucleotide sequence encoding said second mycobacterial antigenic polypeptide. Antigen-antibody complexes (or, in the case of competitive assays, the amount of competing antibody) may be detected by any of a number of known techniques, depending on the format. For example, unlabelled antibodies in the complex may be detected using a conjugate of anti-xenogeneic Ig complexed with a label (eg. an enzyme label). The immunoassay may be of a standard or competitive type. In one embodiment, the first and second mycobacterial antigens are bound to one or more solid supports to facilitate separation of the sample from the antigens after incubation. Examples of solid supports that can be used are nitrocellulose (eg. in membrane or microtitre well form), polyvinyl chloride (eg. in sheets or microtiter wells), polystyrene latex (eg. in beads or microtiter plates, polyvinylidine fluoride (known as Immulon), diazotized paper, nylon membranes, activated beads, and Protein A beads. For example, Dynatech Immulon microtiter plates or 60 mm diameter polystyrene beads (Precision Plastic Ball) may be used. The solid support(s) containing the first and second mycobacterial antigens is typically washed after separating it from the test sample, and prior to detection of bound antibodies. The invention also embraces immunoassays for detecting the presence of the first and second mycobacterial antigens (eg. polypeptides) of the invention in a test sample (eg. a biological sample). In such methods, a test sample suspected of containing said mycobacterial antigens may be incubated with antibodies directed against the first and second mycobacterial antigens.

Accordingly, the invention provides an in vitro method of diagnosing a mycobacterial infection, such as an early stage mycobacterial infection, comprising incubating a test sample from a subject (eg. a mammal such as a human, bovine, porcine or equine subject) with a first antibody and a second antibody of the invention, as defined herein; or an immunogenic composition of the invention, as defined herein; wherein said incubating is performed under conditions that allow binding of said first and second antibodies with antigens in the sample to form antigen-antibody complexes; and then detecting the formation of such complexes, wherein the presence of antigen-antibody complexes is indicative of a mycobacterial infection in the subject. In one embodiment of said in vitro method, said first antibody binds a first mycobacterial antigenic polypeptide; and said optional second antibody binds a second mycobacterial antigenic polypeptide. It may be desirable to treat the biological sample prior to testing, to release putative bacterial components. Various formats can be employed. For example, a "sandwich assay" may be employed, where antibodies bound to a solid support are incubated with the test sample; washed; incubated with second, labeled antibodies to the first and second antigens, and the support is washed again. The first and second mycobacterial antigens are detected by determining if the second antibody is bound to the support. In a competitive format, a test sample is usually incubated with antibodies and a labeled, competing antigen is also incubated, either sequentially or simultaneously.

In one aspect, the invention provides an immunoassay kit, comprising an antigenic composition of the invention, or antibodies to said first and second mycobacterial antigens.

The immunoassay kit may further comprise a buffer. The term "polypeptide" throughout this specification is synonymous with the terms "oligopeptide", "peptide" and "protein". These terms are used interchangeably and do not refer to a specific length of the product. These terms embrace post-translational modifications such as glycosylation, acetylation and phosphorylation. In one embodiment, the isolated polypeptides of the invention are substantially free from other proteins with which they are co-produced as well as from other contaminants. For instance, an isolated polypeptide is substantially free of material or other proteins from the cell, bacterial, or tissue source from which it was derived.

The present invention encompasses polypeptides that are substantially homologous to a polypeptide based on any one of the reference SEQ ID NOs identified in this application (including fragments thereof). The terms "sequence identity" and "sequence homology" are considered synonymous in this specification. By way of example, a polypeptide of interest may comprise an amino acid sequence having at least 70, 75, 80, 82, 84, 86, 88, 90, 92, 94, 96, 98, 99 or 100% amino acid sequence identity with the amino acid sequence of a reference polypeptide.

There are many established algorithms available to align two amino acid sequences. Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid sequences for comparison may be conducted, for example, by computer implemented algorithms (eg. GAP, BESTFIT, FASTA or TFASTA), BLAST and BLAST 2.0 algorithms, or BLOSUM62—Henikoff & Henikoff, Proc. Natl. Acad. Sci. USA 89:10915-10919, 1992; incorporated herein by reference). In a homology comparison, the identity may exist over a region of the sequences that is at least 50 amino acid residues in length (eg. at least 75, 100, 150, 200, 250, 300, 350, 400, 450, 500, 550, 600 or 650 amino acid residues in length—eg. up to the entire length of the reference sequence. Substantially homologous polypeptides have one or more amino acid substitutions, deletions, or additions. In many embodiments, those changes are of a minor nature, for example, involving only conservative amino acid substitutions. Conservative substitutions are those made by replacing one amino acid with another amino acid within the following groups: Basic: arginine, lysine, histidine; Acidic: glutamic acid, aspartic acid; Polar: glutamine, asparagine; Hydrophobic: leucine, isoleucine, valine; Aromatic: phenylalanine, tryptophan, tyrosine; Small: glycine, alanine, serine, threonine, methionine. Substantially homologous polypeptides also encompass those comprising other substitutions that do not significantly affect the folding or activity of the polypeptide; small deletions, typically of 1 to about 30 amino acids (such as 1-10, or 1-5 amino acids); and small amino- or carboxyl-terminal extensions, such as an amino-terminal methionine residue, a small linker peptide of up to about 20-25 residues, or an affinity tag.

The polypeptides of the present invention may also comprise non-naturally occurring amino acid residues. In this regard, in addition to the 20 standard amino acids, non-standard amino acids (such as 4-hydroxyproline, 6-N-methyl lysine, 2-aminoisobutyric acid, isovaline and a-methyl serine) may be substituted for amino acid residues of the mycobacterial polypeptides of the present invention. A limited number of non-conservative amino acids, amino acids that are not encoded by the genetic code, and unnatural amino acids may be substituted for mycobacterial polypeptide amino acid residues. Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethylhomo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine.

Routine deletion analyses of nucleic acid molecules can be performed to obtain functional fragments of a nucleic acid molecule that encodes a polypeptide of the invention. As an illustration, DNA molecules can be digested with Bal31 nuclease to obtain a series of nested deletions. These DNA fragments are then inserted into expression vectors in proper reading frame, and the expressed polypeptides are isolated and tested for the desired activity. An alternative to exonuclease digestion is to use oligonucleotide-directed mutagenesis to introduce deletions, or stop codons to specify production of a desired fragment. Alternatively, particular polynucleotide fragments can be synthesized using the polymerase chain reaction. A mutant of a polypeptide of the invention may contain one or more analogs of an amino acid (eg. an unnatural amino acid), or a substituted linkage, as compared with the sequence of the reference polypeptide. In a further embodiment, a polypeptide of interest may be a mimic of the reference polypeptide, which mimic reproduces at least one epitope of the reference polypeptide. Mutants of the disclosed polynucleotide and polypeptide sequences of the invention can be generated through DNA shuffling. Briefly, mutant DNAs are generated by in vitro homologous recombination by random fragmentation of a parent DNA followed by reassembly using PCR, resulting in randomly introduced point mutations. This technique can be modified by using a family of parent DNAs, to introduce additional variability into the process. Selection or screening for the desired activity, followed by additional iterations of mutagenesis and assay provides for rapid "evolution" of sequences by selecting for desirable mutations while simultaneously selecting against detrimental changes. Mutagenesis methods as disclosed above can be combined with high-throughput screening methods to detect activity of cloned mutant polypeptides. Mutagenized nucleic acid molecules that encode polypeptides of the invention, or fragments thereof, can be recovered from the host cells and rapidly sequenced using modern equipment. These methods allow the rapid determination of the importance of individual amino acid residues in a polypeptide of interest, and can be applied to polypeptides of unknown structure.

A "fragment" of a polypeptide of interest comprises a series of consecutive amino acid residues from the sequence of said polypeptide. By way of example, a "fragment" of a polypeptide of interest may comprise (or consist of) at least 50 consecutive amino acid residues from the sequence of said polypeptide (eg. at least 75, 100, 125, 150, 175, 200, 225, 250, 275, 300 consecutive amino acid residues of said polypeptide). A fragment includes at least one epitope of the polypeptide of interest.

As used herein, the terms "nucleic acid sequence" and "polynucleotide" are used interchangeably and do not imply any length restriction. As used herein, the terms "nucleic acid" and "nucleotide" are used interchangeably. The terms "nucleic acid sequence" and "polynucleotide" embrace DNA (including cDNA) and RNA sequences. The polynucleotide sequences of the present invention include nucleic acid sequences that have been removed from their naturally occurring environment, recombinant or cloned DNA isolates, and chemically synthesized analogues or analogues biologically synthesized by heterologous systems. The natural or synthetic DNA fragments coding for a desired fragment may be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines. The term "recombinant" as used herein intends a polynucleotide of genomic, cDNA, semi-synthetic, or synthetic origin which, by virtue of its origin or manipulation: (1) is not associated with all or a portion of a polynucleotide with which it is associated in nature; or (2) is linked to a polynucleotide other than that to which it is linked in nature; and (3) does not occur in nature. When applied to a nucleic acid sequence, the term "isolated" in the context of the present invention denotes that the polynucleotide sequence has been removed from its natural genetic milieu and is thus free of other extraneous or unwanted coding sequences (but may include naturally occurring 5' and 3' untranslated regions such as promoters and terminators), and is in a form suitable for use within genetically engineered protein production systems. Such isolated molecules are those that are separated from their natural environment. A "variant" nucleic acid sequence has substantial homology or substantial similarity to a reference nucleic acid sequence (or a fragment thereof). A nucleic acid sequence or fragment thereof is "substantially homologous" (or "substantially identical") to a reference sequence if, when optimally aligned (with appropriate nucleotide insertions or deletions) with the other nucleic acid (or its complementary strand), there is nucleotide sequence identity in at least about 70%, 75%, 80%, 82, 84, 86, 88, 90, 92, 94, 96, 98 or 99% of the nucleotide bases. Homology determination is performed as described supra for polypeptides. Alternatively, a "variant" nucleic acid sequence is substantially homologous with (or substantially identical to) a reference sequence (or a fragment thereof) if the "variant" and the reference sequence they are capable of hybridizing under stringent (eg. highly stringent) hybridization conditions. Nucleic acid sequence hybridization will be affected by such conditions as salt concentration (eg. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. The combination of parameters is much more important than any single parameter. A "fragment" of a polynucleotide of interest comprises a series of consecutive amino acid residues from the sequence of said full-length polynucleotide. By way of example, a "fragment" of a polynucleotide of interest may comprise (or consist of) at least 150 consecutive nucleic acid residues from the sequence of said polypeptide (eg. at least 200, 250, 300, 350, 400, 450, 500, 550, 600, 650, 700 or 750 consecutive nucleic acid residues of said polynucleotide). A fragment encodes at least one antigenic epitope of the corresponding polypeptide of interest.

SEQ ID No. 1

```
atgtggtggttccgccgccgagaccgggcgccgctgcgcgccaccagctcattatccctgcggtggcgggtcatgctgctggcgatgtccatg
gtcgcgatggtggttgtgctgatgtcgttcgccgtctatgcggtgatctcggccgcgctctacagcgacatcgacaaccaactgcagagccggg
cgcaactgctcatcgccagtggctcgctggcagctgatccgggtaaggcaatcgagggtaccgcctattcggatgtcaacgcgatgctggtca
accccggccagtccatctacaccgctcaacagccgggccagacgctgccggtcggtgctgccgagaaggcggtgatccgtggcgagttgtt
catgtcgcggcgcaccaccgccgaccaacgggtgcttgccatccgtctgaccaacggtagttcgctgctgatctccaaaagtctcaagccca
ccgaagcagtcatgaacaagctgcgttgggtgctattgatcgtgggtgggatcggggtggcggtcgccgcggtggccgggggggatggtcac
ccgggccgggctgaggccggtgggccgcctcaccgaagcggccgagcgggtggcgcgaaccgacgacctgcggcccatccccgtcttc
ggcagcgacgaattggccaggctgacagaggcattcaatttaatgctgcgggcgctggccgagtcacgggaacggcaggcaaggctggtt
accgacgccggacatgaattgcgtaccccgctaacgtcgctgcgcaccaatgtcgaactcttgatggcctcgatggcccgggggctccgcg
gctacccaagcaggagatggtcgacctgcgtgccgatgtgctggctcaaatcgaggaattgtccacactggtaggcgatttggtggacctgtc
ccgaggcgacgccggagaagtggtgcacgagccggtcgacatggctgacgtcgtcgaccgcagcctggagcgggtcaggcggcggcgc
aacgatatcctttttcgacgtcgaggtgattgggtggcaggtttatggcgataccgctggattgtcgcggatggcgcttaacctgatggacaacgc
cgcgaagtggagcccgccgggcggccacgtgggtgtcaggctgagccagctcgacgcgtcgcacgctgagctggtggtttccgaccgcgg
cccgggcattcccgtgcaggagcgccgtctggtgtttgaacggttttaccggtcggcatcggcacgggcgttgccgggttcgggcctcgggttg
gcgatcgtcaaacaggtggtgctcaaccacggcggattgctgcgcatcgaagacaccgacccaggcggccagcccccctggaacgtcgatt
tacgtgctgctccccggccgtcggatgccgattccgcagcttcccggtgcgacggctggcgctcggagcacggacatcgagaactctcgggg
ttcggcgaacgttatctcagtggaatctcagtccacgcgcgcaacctag
```

SEQ ID No. 2

```
MWWFRRRDRAPLRATSSLSLRWRVMLLAMSMVAMVVVLMSFAVYAVISAALYSDIDNQLQSRAQLL
IASGSLAADPGKAIEGTAYSDVNAMLVNPGQSIYTAQQPGQTLPVGAAEKAVIRGELFMSRRTTADQ
RVLAIRLTNGSSLLISKSLKPTEAVMNKLRWVLLIVGGIGVAVAAVAGGMVTRAGLRPVGRLTEAAER
VARTDDLRPIPVFGSDELARLTEAFNLMLRALAESRERQARLVTDAGHELRTPLTSLRTNVELLMASM
APGAPRLPKQEMVDLRADVLAQIEELSTLVGDLVDLSRGDAGEVVHEPVDMADVVDRSLERVRRRR
NDILFDVEVIGWQVYGDTAGLSRMALNLMDNAAKWSPPGGHVGVRLSQLDASHAELVVSDRGPGIP
VQERRLVFERFYRSASARALPGSGLGLAIVKQVVLNHGGLLRIEDTDPGGQPPGTSIYVLLPGRRMPI
PQLPGATAGARSTDIENSRGSANVISVESQSTRAT
```

SEQ ID No. 3

```
atgacggctccgggactgacagcagccgtcgaggggatcgcacacaacaagggcgagctgttcgcctcctttgacgtggacgcgttcgagg
ttccgcacggccgcgacgagatctggcggttcaccccgttgcggcggctgcgtggcctgcacgacggctccgcgcgggccaccggtagcg
ccacgatcacggtcagcgagcggccgggcgtatacacccagaccgtgcgccgcggcgatccacgactgggcgagggcggcgtacccac
cgaccgcgttgccgcccaagcgttttcgtcgttcaactccgcgactctggtcaccgtcgagcgcgacacccaggtcgtcgagccggtaggcat
caccgtgaccgggccgggggagggcgcggtggcctatgggcacctgcaggtgcgtatcgaggagcttggcgaggcggtcgtggtcatcga
ccaccggggcggcggaacctacgccgacaacgtcgagttcgttgtcgacgacgccgctcggctgaccgccgtgtggatcgccgactgggc
cgacaacaccgttcacctcagcgcgcaccatgctcggatcggcaaggacgcggtgctgcgccacgtcaccgtcatgttgggcggcgacgtg
gtgcgaatgtcggcgggcgtgcggttctgcggtgcgggtggggacgcggaactgctggggctgtatttcgccgacgacggccagcacctgg
agtcgcggctgctggtggaccacgcccaccccgactgcaagtcgaacgtgctgtataagggtgcactgcaaggtgatccggcgtcgtcgttg
cccgacgcacacacggtctgggtgggtgacgtgctgatccgtgcgcaggccaccggcaccgacaccttcgaggtgaaccggaacctggtg
ctcaccgacggcgcgcgtgccgactcggtgcccaacctggagatcgagaccggcgagatcgtcggcgccggacacgccagcgccaccg
gtcgcttcgacgatgagcaattgttctacctgcgttcgcgcggtattcccgaagcacaggcccgccggctggtggtccgcggcttcttcggtgag
atcatcgccaagatcgcggtgcccgaggtacgcgagcgcctgaccgcagccatcgaacacgagctggaaatcacggaatcaacggaaa
agacaacagtctcatga
```

SEQ ID No. 4

```
MTAPGLTAAVEGIAHNKGELFASFDVDAFEVPHGRDEIWRFTPLRRLRGLHDGSARATGSATITVSE
RPGVYTQTVRRGDPRLGEGGVPTDRVAAQAFSSFNSATLVTVERDTQVVEPVGITVTGPGEGAVAY
GHLQVRIEELGEAVVVIDHRGGGTYADNVEFVVDDAARLTAVWIADWADNTVHLSAHHARIGKDAVL
RHVTVMLGGDVVRMSAGVRFCGAGGDAELLGLYFADDGQHLESRLLVDHAHPDCKSNVLYKGALQ
GDPASSLPDAHTVWVGDVLIRAQATGTDTFEVNRNLVLTDGARADSVPNLEIETGEIVGAGHASATG
RFDDEQLFYLRSRGIPEAQARRLVVRGFFGEIIAKIAVPEVRERLTAAIEHELEITESTEKTTVS
```

SEQ ID No. 5

```
atggcggttcgtcaggtcaccgtcggctattcggacggcacgcacaagacgatgccggtgcggtgcgaccagacggtcctggatgccgccg
aggaacacggcgtggccatcgtcaacgaatgccaaagcgggatatgtggcacctgcgtggccacctgcaccgccggccgctaccagatg
ggacgcaccgagggactgtccgatgtcgagcgggcggcgcgaaagatcctcacctgccagacgtttgttacctccgattgccggatcgagct
gcagtatccggtcgacgacaacgccgccctgctggtcaccggtgacggtgtggtgaccgcggtcgagttggtgtcgcccagcaccgccatcc
tgcgggtggacacctctggcatggccggcgcgctgagataccgggccggccagttcgcccaattgcaggttcccggtaccaacgtatggcg
caactactcctacgcccatccggccgacggccgcggtgagtgcgagttcatcatcaggttgctgccggacggcgtgatgtcgaattatcttcgc
gaccgcgcccagcccggtgaccatatcgcgctgcgctgcagcaagggcagcttttatctgcgcccgatcgtgcgaccggtgatcctggtcgc
cggaggaaccggcctgtcagcgatcctggcgatggcccagagcctggatgccgatgtcgctcacccggtctacctgctctacggggtcgagc
gcaccgaagacctgtgcaagctcgacgaactcaccgagctgcgccgccgcgttggccgcctggaggtgcacgtcgtcgtcgctcgcccgg
accccgactgggatgggcgcaccgggctggtcaccgacctgctcgacgagcggatgctggcgagcggtgacgccgacgtgtatctgtgcg
gtccggtcgccatggtcgacgcagcccgaacctggctggaccacaatggctttcaccgtgtcgggttgtactacgagaagttcgtggccagcg
gggcggcgcgccgccgcaccccggctcggctggattacgcgggcgtggacattgccgaggtgtgccgccgcggccgcggcaccgcggtg
gtcatcggcggcagcatcgcgggcatcgcggcggcgaaaatgctcagcgagaccttcgatcgcgtcatcgtgctggagaaggacggcccg
caccgtcgccgcgagggcaggccgggcgcggcacagggttggcacctgcaccacctgctgaccgccgggcagatcgagctggagcgca
tcttccctggcatcgtcgacgacatggtgcgcgagggagcgttcaaggtcgacatggccgcgcagtaccgtatccggctgggcggcacctgg
```

-continued aagaagcccggcactagtgacatcgagatcgtctgcgcgggaaggccgctgctcgaatggtgtgtgcgccgccggctcgacgacgaaccg
cgcatcgacttccgctacgaatcggaggtggccgatctcgccttcgaccgcgccaacaatgccatcgtcggcgtcgccgtggacaatggcga
cgccgacggaggcgacggtttgcaggtggtgcccgccgagttcgtcgtggacgcgtcgggcaagaacacccgcgtgccggagttcttggag
cgtctcggtgttggcgctcccgaggccgagcaggacatcatcaactgcttctactccacgatgcagcaccgggttccgccggagcggcggtg
gcaggacaaggtgatggtgatctgctatgcgtaccgccctttcgaggatacctacgccgcgcagtactacaccgacagctcccgcaccatcct
gtccacctcactggtggcctacaactgctattcgccgccgcgtaccgcccgagaattccgcgcgttcgccgacctgatgccgtccccggtcatc
ggggagaacatcgacgggctggagccggcatcgcccatctacaatttccgctatcccaacatgctgcggctgcgctacgagaagaagcgc
aacctgccgcgggctttgctggcggtgggcgatgcctacaccagcgccgacccggtgtcgggtctgggtatgagcctggcgctcaaggaagt
tcgggagatgcaggcgctgctggctaaatacggcgccggtcaccgggatctgccgcgccggtactaccgggcgatcgccaagatggccga
cacggcctggttcgtgatccgcgagcagaacctgcgcttcgactggatgaaggacgtcgacaagaagcgcccgttctatttcggtgtgctgac
ctggtacatggaccgcgtgctggagctggtgcatgacgatctcgacgcgtaccgggaattcttggccgtcgtccatctggtcaagccgccgtcg
gcgctgatgcgacccaggatcgccagccgcgtcctcggcaaatgggcacgaacccgattgtcgggccagaagacgttgattgcccgcaac
tacgaaaatcatccgataccagccgaacccgcggaccaacttgtaaacgcttag SEQ ID No. 6

MAVRQVTVGYSDGTHKTMPVRCDQTVLDAAEEHGVAIVNECQSGICGTCVATCTAGRYQMGRTEG
LSDVERAARKILTCQTFVTSDCRIELQYPVDDNAALLVTGDGVVTAVELVSPSTAILRVDTSGMAGAL
RYRAGQFAQLQVPGTNVWRNYSYAHPADGRGECEFIIRLLPDGVMSNYLRDRAQPGDHIALRCSKG
SFYLRPIVRPVILVAGGTGLSAILAMAQSLDADVAHPVYLLYGVERTEDLCKLDELTELRRRVGRLEVH
VVVARPDPDWDGRTGLVTDLLDERMLASGDADVYLCGPVAMVDAARTWLDHNGFHRVGLYYEKFV
ASGAARRRTPARLDYAGVDIAEVCRRGRGTAVVIGGSIAGIAAAKMLSETFDRVIVLEKDGPHRRREG
RPGAAQGWHLHHLLTAGQIELERIFPGIVDDMVREGAFKVDMAAQYRIRLGGTWKKPGTSDIEIVCA
GRPLLEWCVRRRLDDEPRIDFRYESEVADLAFDRANNAIVGVAVDNGDADGGDGLQVVPAEFVVDA
SGKNTRVPEFLERLGVGAPEAEQDIINCFYSTMQHRVPPERRWQDKVMVICYAYRPFEDTYAAQYY
TDSSRTILSTSLVAYNCYSPPRTAREFRAFADLMPSPVIGENIDGLEPASPIYNFRYPNMLRLRYEKKR
NLPRALLAVGDAYTSADPVSGLGMSLALKEVREMQALLAKYGAGHRDLPRRYYRAIAKMADTAWFVI
REQNLRFDWMKDVDKKRPFYFGVLTWYMDRVLELVHDDLDAYREFLAVVHLVKPPSALMRPRIASR
VLGKWARTRLSGQKTLIARNYENHPIPAEPADQLVNA

SEQ ID No. 7 atgaccacaacgactacaacgatttctgggggatattacccaaggaataccaagatcttcgggatacggtggccgattttgcgcgcaccgtg
gtcgcgccggtatcggccaaacacgatgcggaacacagcttcccatacgaaattgtcgccaagatgggagagatgggcctgttcgggctgc
cgtttccggaggagtacggcggcatgggcggcgactacttcgcgctgtcgctggtacttgaggagctgggcaaggttgaccaatcggtagcg
atcacgctggaggccgcggtgggcctgggtgcgatgccgatctaccggttcggtaccgaggagcagaaacagaagtggttgcccgacttga
cgtctggccgtgcgctcgccggttttggtctcaccgagccgggagcgggatcggacgcgggcagcacccgcaccacggcgcgtctcgaag
gtgacgagtggatcatcaacggctccaagcaatttatcaccaactcgggcaccgacatcacatcgctggtcaccgtcactgcggttaccggg
accaccggaaccgctgcggatgccaagaaagagatttcgacgatcatcgtgcccagcggcacaccgggattcaccgtggaaccggtctat
aacaaggtcggctggaacgcctcggacacccacccactgacatttgccgatgcgcgggtcccgagggagaacctgctgggagcccgggg
gagcggctatgccaacttcttgtccatcctggacgagggccggattgcgattgcagcgctggccaccggcgcggcgcagggctgtgttgacg
agagcgtcaagtacgccaaccagcgtcagtcgtttggccagccgatcggcgcttatcaggcgatcggcttcaagatcgcgcggatggaggc
acgcgcccatgttgcccgcacagcgtactatgatgccgccgcaaagatgttggcgggcaagcccttcaagaaggaggcggcgatcgcgaa
gatgatctcctcggaggcggcgatggacaactcccgcgatgccacccagatacacggcggatacggctttatgaacgaatatccggtggcg
cgtcattaccgcgacagcaaggtgctcgagattggtgagggcaccacggaagtgcagctgatgcttatcgcgcgatcgttgggactgcagtg
a SEQ ID No. 8

MTTTTTTISGGILPKEYQDLRDTVADFARTVVAPVSAKHDAEHSFPYEIVAKMGEMGLFGLPFPEEYG
GMGGDYFALSLVLEELGKVDQSVAITLEAAVGLGAMPIYRFGTEEQKQKWLPDLTSGRALAGFGLTE
PGAGSDAGSTRTTARLEGDEWIINGSKQFITNSGTDITSLVTVTAVTGTTGTAADAKKEISTIIVPSGTP
GFTVEPVYNKVGWNASDTHPLTFADARVPRENLLGARGSGYANFLSILDEGRIAIAALATGAAQGCV
DESVKYANQRQSFGQPIGAYQAIGFKIARMEARAHVARTAYYDAAAKMLAGKPFKKEAAIAKMISSEA
AMDNSRDATQIHGGYGFMNEYPVARHYRDSKVLEIGEGTTEVQLMLIARSLGLQ

SEQ ID No. 9 atggacaaggtggtggccaccgccgcggaggcggtcgcagacatagccaacgggtcgtcgcttgcggttggtggattcgggctttgcggcat
ccccgaagcactgatcgcagcgttggtggatagcggtgtcaccgacctggaaacagtctcgaacaactgcggaatcgacggtgttggtctgg
gactattgttgcaacacaagcgaattcgccggacagtctcctcctacgtgggggagaacaaggagttcgcccgccagttcctcgcgggcgag
ctcgaggtggaactgaccccgcagggcacgctggccgagcggttgcgggccggagggatgggcataccggccttctatacaccggcagg
ggtcggtacccaggtcgccgacggcgggttgccgtggcgctacgacgcctcgggcggggtggcggtggtgtcgccggccaaggagactcg
ggagttcgatggtgtcacctatgtcctcgagcgggggatccggaccgacttcgcactggtgcatgcctggcaggggggaccggcacggcaac
ctgatgtaccgccacgccgcggccaacttcaacccggagtgcgcatccgcaggcaggatcacgatcgccgaggtcgagcacttggtcgag
ccgggtgagatcgaccctgccaccgtacacaccccgggcgtgtttgtgcaccgggtggttcatgtgcccaaccccgccaagaagatcgaga
gggagacggtgcggcaatga SEQ ID No. 10

MDKVVATAAEAVADIANGSSLAVGGFGLCGIPEALIAALVDSGVTDLETVSNNCGIDGVGLGLLLQHK
RIRRTVSSYVGENKEFARQFLAGELEVELTPQGTLAERLRAGGMGIPAFYTPAGVGTQVADGGLPW
RYDASGGVAVVSPAKETREFDGVTYVLERGIRTDFALVHAWQGDRHGNLMYRHAAANFNPECASA
GRITIAEVEHLVEPGEIDPATVHTPGVFVHRVVHVPNPAKKIERETVRQ

SEQ ID No. 11 atgaccctggaagtggtatcggacgcggccggacgcatgcgggtcaaagtcgactgggtccgttgcgattcccggcgcgcggtcgcggtcg
aagaggccgttgccaagcagaacggtgtgcgcgtcgtgcacgcctacccgcgcaccgggtccgtggtcgtgtggtattcacccagacgcgc
cgaccgcgcggcggtgctggcggcgatcaagggcgccgcgcacgtcgccgccgaactgatccccgcgcgtgcgccgcactcggccgag
atccgcaacaccgacgtgctccggatggtcatcggcggggtggcactggccttgctcggggtgcgccgctacgtgttcgcgcggccaccgct
gctcggaaccaccgggcggacggtggccaccggtgtcaccattttcaccgggtatccgttcctgcgtggcgcgctgcgctcgctgcgctccgg
aaaggccggcaccgatgccctggtctccgcggcgacggtggcaagcctcatcctgcgcgagaacgtggtcgcactcaccgtcctgtggttgc
tcaacatcggtgagtacctgcaggatctgacgctgcggcggacccggcgggccatctcggagctgctgcgcggcaaccaggacacggcct
gggtgcgcctcaccgatccttctgcaggctccgacgcggccaccgaaatccaggtcccgatcgacaccgtgcagatcggtgacgaggtggt
ggtccacgagcacgtcgcgataccggtcgacggtgaggtggtcgacggcgaagcgatcgtcaatcagtccgcgatcaccggggaaaacct
gccggtcagcgtcgtggtcggaacgcgcgtgcacgccggttcggtcgtggtgcgcggacgcgtggtggtgcgcgcccacgcggtaggcaa -continued ccaaaccaccatcggtcgcatcattagcagggtcgaagaggctcagctcgaccgggcacccatccagacggtgggcgagaacttctcccg
ccgcttcgttcccacctcgttcatcgtctcggccatcgcgttgctgatcaccggcgacgtgcggcgcgcgatgaccatgttgttgatcgcatgccc
gtgcgcggtgggactgtccaccccgaccgcgatcagcgcagcgatcggcaacggcgcgcgccgtggcatcctgatcaagggcggatccc
acctcgagcaggcgggccgcgtcgacgccatcgtgttcgacaagaccgggacgttgaccgtgggccgccccgtggtcaccaatatcgttgc
catgcataaagattgggagcccgagcaagtgctggcctatgccgccagctcggagatccactcacgtcatccgctggccgaggcggtgatc
cgctcgacggaggaacgccgcatcagcatcccaccacacgaggagtgcgaggtgctggtcggcctgggcatgcggacctgggccgacg
gtcggaccctgctgctgggcagtccgtcgttgctgcgcgccgaaaaagttcgggtgtccaagaaggcgtcggagtgggtcgacaagctgcg
ccgccaggcggagaccccgctgctgctcgcggtggacggcacgctggtcggcctgatcagcctgcgcgacgaggtgcgtccggaggcgg
cccaggtgctgacgaagctgcgggccaatgggattcgccggatcgtcatgctcaccggcgaccacccggagatcgcccaggttgtcgccga
cgaactggggattgatgagtggcgcgccgaggtcatgccggaggacaagctcgcggcggtgcgcgagctgcaggacgacggctacgtcg
tcgggatggtcggcgacggcatcaacgacgccccggcgctggccgccgccgatatcgggatcgccatgggccttgccggaaccgacgtcg
ccgtcgagaccgccgatgtcgcgctggccaacgacgacctgcaccgcctgctcgacgttggggacctgggcgagcgggcagtggatgtaa
tccggcagaactacggcatgtccatcgccgtcaacgcggccgggctgctgatcggcgcgggcggtgcgctctcgccggtgctggcggcgat
cctgcacaacgcgtcgtcggtggcggtggtggccaacagttcccggttgatccgctaccgcctggaccgctag SEQ ID No. 12

MTLEVVSDAAGRMRVKVDWVRCDSRRAVAVEEAVAKQNGVRVVHAYPRTGSVVVWYSPRRADRA
AVLAAIKGAAHVAAELIPARAPHSAEIRNTDVLRMVIGGVALALLGVRRYVFARPPLLGTTGRTVATGV
TIFTGYPFLRGALRSLRSGKAGTDALVSAATVASLILRENVVALTVLWLLNIGEYLQDLTLRRTRRAISE
LLRGNQDTAWVRLTDPSAGSDAATEIQVPIDTVQIGDEVVVHEHVAIPVDGEVVDGEAIVNQSAITGE
NLPVSVVVGTRVHAGSVVVRGRVVVRAHAVGNQTTIGRIISRVEEAQLDRAPIQTVGENFSRRFVPTS
FIVSAIALLITGDVRRAMTMLLIACPCAVGLSTPTAISAAIGNGARRGILIKGGSHLEQAGRVDAIVFDKT
GTLTVGRPVVTNIVAMHKDWEPEQVLAYAASSEIHSRHPLAEAVIRSTEERRISIPPHEECEVLVGLG
MRTWADGRTLLLGSPSLLRAEKVRVSKKASEWVDKLRRQAETPLLLAVDGTLVGLISLRDEVRPEAA
QVLTKLRANGIRRIVMLTGDHPEIAQVVADELGIDEWRAEVMPEDKLAAVRELQDDGYVVGMVGDGI
NDAPALAAADIGIAMGLAGTDVAVETADVALANDDLHRLLDVGDLGERAVDVIRQNYGMSIAVNAAGL
LIGAGGALSPVLAAILHNASSVAVVANSSRLIRYRLDR

SEQ ID No. 13 atgactgtgcaggagttcgacgtcgtggtggtcggcagcggcgccgccggcatggttgctgcgctggtcgccgctcaccgaggtctctcgacg
gtagtcgtcgagaaggccccgcactacggcggctccaccgcacgctcgggcggcggcgtctggatccccaacaacgaggtcctcaagcg
ccgcggcgttcgagatacaccggaggcggcacgcacctatctgcacggcatcgtcggcgaaatcgtcgagccggaacgcatcgatgctta
cctcgaccgcgggcccgagatgctgtcgttcgtgctgaagcacacgccgctgaagatgtgctgggtacccggctactccgactactaccccg
aggctccgggcggccgcccgggcggacgttcgatcgagccgaaaccgttcaacgcgcgcaagcttggtgccgacatggccgggctggag
cccgcgtatggcaaggttccgctcaatgtggttgtgatgcagcaggactacgttcgcctcaatcagctcaaacgtcaccccgtggcgtgctgc
gcagcatgaaggtcggcgcccgcacgatgtgggcgaaggcaacaggtaagaacctggtcggcatgggtcgagccctcattgggccgttgc
ggatcgggttgcagcgcgccggagtgccggtcgaactcaacaccgccttcaccgatcttttcgtcgaaaatggcgtcgtgtccggggtatacgt
ccgcgattcccacgaggcggaatccgctgagccgcagctgatccgggctcgccgcggcgtgatcctggcctgtggtggtttcgagcataacg
agcagatgcgaatcaagtaccagcgggcacccatcaccaccgagtggaccgtgggcgccagcgccaataccggtgacggcattctcgcc
gccgaaaagctcggcgcagcactggatctgatggatgacgcttggtggggcccgacggtaccgctggtcggcaaaccatggttcgcgctctc
ggagcgcaactctcccggttcgatcatcgtcaacatgtcaggcaagcgattcatgaacgaatcgatgccatacgtcgaagcctgtcatcatatg
tacggcggcgaacacggccaggggcccggaccgggcgagaacattccggcgtggctggtgttcgaccagcgataccgggaccgctacat
cttcgcgggactacaaccagggcaacgcattccgagcaggtggctggattccggcgtcatcgtccaggccgatacccttgcggagctggcc
ggcaaggccggtctacccgcggacgaactcactgccaccgtccagcgtttcaacgcattcgcccggtccggtgtcgacgaggactaccacc
gcggggaaagtgcctacgatcgctactacggcgacccgagcaacaagcccaatccgaacctcggcgaggtcggccacccgccctattatg
gcgccaagatggttccgggcgacctggggaccaagggcggtatccgcaccgatgtcaacggacgtgctctgcgggacgacggcagcatc
atcgacggcctttacgctgcaggcaatgtcagtgccccagtgatgggacacacctaccccggtccgggcggcacgataggcccggcgatg
acgttcgggtacctggcggcgctgcacattgccgatcaggcgggaaagcgctga SEQ ID No. 14

MTVQEFDVVVVGSGAAGMVAALVAAHRGLSTVVVEKAPHYGGSTARSGGGVWIPNNEVLKRRGVR
DTPEAARTYLHGIVGEIVEPERIDAYLDRGPEMLSFVLKHTPLKMCWVPGYSDYYPEAPGGRPGGRS
IEPKPFNARKLGADMAGLEPAYGKVPLNVVVMQQDYVRLNQLKRHPRGVLRSMKVGARTMWAKAT
GKNLVGMGRALIGPLRIGLQRAGVPVELNTAFTDLFVENGVVSGVYVRDSHEAESAEPQLIRARRGVI
LACGGFEHNEQMRIKYQRAPITTEWTVGASANTGDGILAAEKLGAALDLMDDAWWGPTVPLVGKPW
FALSERNSPGSIIVNMSGKRFMNESMPYVEACHHMYGGEHGQGPGPGENIPAWLVFDQRYRDRYIF
AGLQPGQRIPSRWLDSGVIVQADTLAELAGKAGLPADELTATVQRFNAFARSGVDEDYHRGESAYD
RYYGDPSNKPNPNLGEVGHPPYYGAKMVPGDLGTKGGIRTDVNGRALRDDGSIIDGLYAAGNVSAP
VMGHTYPGPGGTIGPAMTFGYLAALHIADQAGKR

SEQ ID No. 15 gtgagtccggcgcccgtgcaggtgatggggttctaaacgtcacggacgactctttctcggacggcgggtgttatctcgatctcgacgatgcgg
tgaagcacggtctggcgatggcagccgcaggtgcgggcatcgtcgacgtcggtggtgagtcgagccggcccggtgccactcgggttgaccc
ggcggtggagacgtctcgtgtcatacccgtcgtcaaagagcttgcagcacaaggcatcaccgtcagcatcgataccatgcgcgcggatgtcg
ctcgggcggcgttgcagaacggtgcccagatggtcaacgacgtgtcgggtgggcgggccgatccggcgatggggccgctgttggccgagg
ccgatgtgccgtgggtgttgatgcactggcgggcggtatcggccgataccccgcatgtgcctgtgcgctacggcaacgtggtggccgaggtcc
gtgccgacctgctggccagcgtcgccgacgcggtggccgcaggcgtcgacccggcaaggctggtgctcgatcccgggcttggattcgccaa
gacggcgcaacataattgggcgatcttgcatgcccttccggaactggtcgcgaccggaatcccagtgctggtgggtgcttcgcgcaagcgctt
cctcggtgcgttgttggccgggcccgacggcgtgatgcggccaaccgatgggcgtgacaccgcgacggcggtgatttccgcgctggccgca
ctgcacggggcctggggtgtgcgggtgcatgatgtgcgggcctcggtcgatgccatcaaggtggtcgaagcgtggatgggagcggaaagg
atagaacgcgatggctga SEQ ID No. 16

VSPAPVQVMGVLNVTDDSFSDGGCYLDLDDAVKHGLAMAAAGAGIVDVGGESSRPGATRVDPAVE
TSRVIPVVKELAAQGITVSIDTMRADVARAALQNGAQMVNDVSGGRADPAMGPLLAEADVPWVLMH
WRAVSADTPHVPVRYGNVVAEVRADLLASVADAVAAGVDPARLVLDPGLGFAKTAQHNWAILHALP
ELVATGIPVLVGASRKRFLGALLAGPDGVMRPTDGRDTATAVISALAALHGAWGVRVHDVRASVDAI
KVVEAWMGAERIERDG

-continued

SEQ ID No. 17 atgagtattaccaggccgacgggcagctatgccagacagatgctggatccgggcggctgggtggaagccgatgaagacactttctatgacc
gggcccaggaatatagccaggttttgcaaagggtcaccgatgtattggacacctgccgccagcagaaaggccacgtcttcgaaggcggcct
atggtccggcggcgccgccaatgctgccaacggcgccctgggtgcaaacatcaatcaattgatgacgctgcaggattatctcgccacggtga
ttacctggcacaggcatattgccgggttgattgagcaagctaaatccgatatcggcaataatgtggatggcgctcaacgggagatcgatatcct
ggagaatgaccctagcctggatgctgatgagcgccataccgccatcaattcattggtcacggcgacgcatggggccaatgtcagtctggtcgc
cgagaccgctgagcgggtgctggaatccaagaattggaaacctccgaagaacgcactcgaggatttgcttcagcagaagtcgccgccacc
cccagacgtgcctaccctggtcgtgccatccccgggcacaccgggcacaccgggaaccccgatcaccccgggaaccccgatcaccccgg
gaaccccaatcacacccatcccgggagcgccggtaactccgatcacaccaacgcccggcactcccgtcacgccggtgaccccgggcaa
gccggtcaccccggtgaccccggtcaaaccgggcacaccaggcgagccaaccccgatcacgccggtcaccccccggtcgccccggcc
acaccggcaaccccggccacgcccgttaccccagctcccgctccacacccgcagccggctccggcaccggcgccatcgcctgggcccca
gccggttacaccggccactcccggtccgtctggtccagcaacaccgggcaccccagggggcgagccggcgccgcacgtcaaacccgcg
gcgttggcggagcaacctggtgtgccgggccagcatgcgggcgggggacgcagtcggggcctgcccatgcggacgaatccgccgcgtc
ggtgacgccggctgcggcgtccggtgtcccgggcgcacgggcggcggccgccgcgccgagcggtaccgccgtgggagcgggcgcgcgt
tcgagcgtgggtacggccgcggcctcgggcgcggggtcgcatgctgccactgggcgggcgccggtggctacctcggacaaggcggcggc
accgagcacgcgggcggcctcggcgcggacggcacctcctgcccgcccgccgtcgaccgatcacatcgacaaacccgatcgcagcgag
tctgcagatgacggtacgccggtgtcgatgatcccggtgtcggcggctcgggcggcacgcgacgccgccactgcagctgccagcgcccgc
cagcgtggccgcggtgatgcgctgcggttggcgcgacgcatcgcggcggcgctcaacgcgtccgacaacaacgcgggcgactacgggtt
cttctggatcaccgcggtgaccaccgacggttccatcgtcgtggccaacagctatgggctggcctacatacccgacgggatggaattgccga
ataaggtgtacttggccagcgcggatcacgcaatcccggttgacgaaattgcacgctgtgccacctacccggttttggccgtgcaagcctggg
cggctttccacgacatgacgctgcgggcggtgatcggtaccgcggagcagttggccagttcggatcccggtgtggccaagattgtgctggag
ccagatgacattccggagagcggcaaaatgacgggccggtcgcggctggaggtcgtcgacccctcggcggcggctcagctggccgacac
taccgatcagcgtttgctcgacttgttgccgccggcgccggtggatgtcaatccaccgggcgatgagcggcacatgctgtggttcgagctgatg
aagcccatgaccagcaccgctaccggccgcgaggccgctcatctgcgggcgttccgggcctacgctgcccactcacaggagattgccctgc
accaagcgcacactgcgactgacgcggccgtccagcgtgtggccgtcgcggactggctgtactggcaatacgtcaccgggttgctcgaccg
ggccctggccgccgcatgctga SEQ ID No. 18

MSITRPTGSYARQMLDPGGWVEADEDTFYDRAQEYSQVLQRVTDVLDTCRQQKGHVFEGGLWSG
GAANAANGALGANINQLMTLQDYLATVITWHRHIAGLIEQAKSDIGNNVDGAQREIDILENDPSLDADE
RHTAINSLVTATHGANVSLVAETAERVLESKNWKPPKNALEDLLQQKSPPPPDVPTLVVPSPGTPGT
PGTPITPGTPITPGTPITPIPGAPVTPITPTPGTPVTPVTPGKPVTPVTPVKPGTPGEPTPITPVTPPVAP
ATPATPATPVTPAPAPHPQPAPAPAPSPGPQPVTPATPGPSGPATPGTPGGEPAPHVKPAALAEQP
GVPGQHAGGGTQSGPAHADESAASVTPAAASGVPGARAAAAAPSGTAVGAGARSSVGTAAASGA
GSHAATGRAPVATSDKAAAPSTRAASARTAPPARPPSTDHIDKPDRSESADDGTPVSMIPVSAARAA
RDAATAAASARQRGRGDALRLARRIAAALNASDNNAGDYGFFWITAVTTDGSIVVANSYGLAYIPDG
MELPNKVYLASADHAIPVDEIARCATYPVLAVQAWAAFHDMTLRAVIGTAEQLASSDPGVAKIVLEPD
DIPESGKMTGRSRLEVVDPSAAAQLADTTDQRLLDLLPPAPVDVNPPGDERHMLWFELMKPMTSTA
TGREAAHLRAFRAYAAHSQEIALHQAHTATDAAVQRVAVADWLYVVQYVTGLLDRALAAAC

SEQ ID NO: 19

MQLVDRVRGAVTGMSRRLVVGAVGAALVSGLVGAVGGTATAGAFSRPGLPVEYLQVPSPSMGRDI
KVQFQSGGANSPALYLLDGLRAQDDFSGWDINTPAFEWYDQSGLSVVMPVGGQSSFYSDWYQPA
CGKAGCQTYKWETFLTSELPGWLQANRHVKPTGSAVVGLSMAASSALTLAIYHPQQFVYAGAMSGL
LDPSQAMGPTLIGLAMGDAGGYKASDMWGPKEDPAWQRNDPLLNVGKLIANNTRVWVYCGNGKP
SDLGGNNLPAKFLEGFVRTSNIKFQDAYNAGGGHNGVFDFPDSGTHSWEYVVGAQLNAMKPDLQRA
LGATPNTGPAPQGA

SEQ ID NO: 20

MTDVSRKIRAWGRRLMIGTAAAVVLPGLVGLAGGAATAGAFSRPGLPVEYLQVPSPSMGRDIKVQF
QSGGNNSPAVYLLDGLRAQDDYNGWDINTPAFEWYYQSGLSIVMPVGGQSSFYSDWYSPACGKAG
CQTYKWETFLTSELPQWLSANRAVKPTGSAAIGLSMAGSSAMILAAYHPQQFIYAGSLSALLDPSQG
MGPSLIGLAMGDAGGYKAADMWGPSSDPAWERNDPTQQIPKLVANNTRLWVYCGNGTPNELGGA
NIPAEFLENFVRSSNLKFQDAYNAAGGHNAVFNFPPNGTHSWEYVVGAQLNAMKGDLQSSLGAG

SEQ ID NO: 21

MTEQQWNFAGIEAAASAIQGNVTSIHSLLDEGKQSLTKLAAAWGGSGSEAYQGVQQKVVDATATELN
NALQNLARTISEAGQAMASTEGNVTGMFA

SEQ ID NO: 22

MSQIMYNYPAMLGHAGDMAGYAGTLQSLGAEIAVEQAALQSAWQGDTGITYQAWQAQWNQAMED
LVRAYHAMSSTHEANTMAMMARDTAEAAKWGG

SEQ ID NO: 23

MSNSRRRSLRWSWLLSVLAAVGLGLATAPAQAAPPALSQDRFADFPALPLDPSAMVAQVGPQVVNI
NTKLGYNNAVGAGTGIVIDPNGVVLTNNHVIAGATDINAFSVGSGQTYGVDVVGYDRTQDVAVLQLR
GAGGLPSAAIGGGVAVGEPVVAMGNSGGQGGTPRAVPGRVVALGQTVQASDSLTGAEETLNGLIQ
FDAAIQPGDSGGPVVNGLGQVVGMNTAASDNFQLSQGGQGFAIPIGQAMAIAGQIRSGGGSPTVHI
GPTAFLGLGVVDNNGNGARVQRVVGSAPAASLGISTGDVITAVDGAPINSATAMADALNGHHPGDVI
SVTWQTKSGGTRTGNVTLAEGPPA

SEQ ID NO: 24

MVDFGALPPEINSARMYAGPGSASLVAAAQMWDSVASDLFSAASAFQSVVWGLTVGSWIGSSAGL
MVAAASPYVAWMSVTAGQAELTAAQVRVAAAAYETAYGLTVPPPVIAENRAELMILIATNLLGQNTPA
lAVNEAEYGEMWAQDAAAMFGYAAATATATATLLPFEEAPEMTSAGGLLEQAAAVEEASDTAAANQ
LMNNVPQALQQLAQPTQGTTPSSKLGGLWKTVSPHRSPISNMVSMANNHMSMTNSGVSMTNTLSS
MLKGFAPAAAAQAVQTAAQNGVRAMSSLGSSLGSSGLGGGVAANLGRAASVGSLSVPQAWAAAN
QAVTPAARALPLTSLTSAAERGPGQMLGGLPVGQMGARAGGGLSGVLRVPPRPYVMPHSPAAG

-continued

SEQ ID NO: 25

MRTPRRHCRRIAVLAAVSIAATVVAGCSSGSKPSGGPLPDAKPLVEEATAQTKALKSAHMVLTVNGKI
PGLSLKTLSGDLTTNPTAATGNVKLTLGGSDIDADFVVFDGILYATLTPNQWSDFGPAADIYDPAQVL
NPDTGLANVLANFADAKAEGRDTINGQNTIRISGKVSAQAVNQIAPPFNATQPVPATVWIQETGDHQL
AQAQLDRGSGNSVQMTLSKWGEKVQVTKPPVS

SEQ ID NO: 26

MAKTIAYDEEARRGLERGLNALADAVKVTLGPKGRNVVLEKKWGAPTITNDGVSIAKEIELEDPYEKIG
AELVKEVAKKTDDVAGDGTTTATVLAQALVREGLRNVAAGANPLGLKRGIEKAVEKVTETLLKGAKEV
ETKEQIAATAAISAGDQSIGDLIAEAMDKVGNEGVITVEESNTFGLQLELTEGMRFDKGYISGYFVTDP
ERQEAVLEDPYILLVSSKVSTVKDLLPLLEKVIGAGKPLLIIAEDVEGEALSTLVVNKIRGTFKSVAVKAP
GFGDRRKAMLQDMAILTGGQVISEEVGLTLENADLSLLGKARKVVVTKDETTIVEGAGDTDAIAGRVA
QIRQEIENSDSDYDREKLQERLAKLAGGVAVIKAGAATEVELKERKHRIEDAVRNAKAAVEEGIVAGG
GVTLLQAAPTLDELKLEGDEATGANIVKVALEAPLKQIAFNSGLEPGVVAEKVRNLPAGHGLNAQTGV
YEDLLAAGVADPVKVTRSALQNAASIAGLFLTTEAVVADKPEKEKASVPGGGDMGGMDF

SEQ ID NO: 27

MAENSNIDDIKAPLLAALGAADLALATVNELITNLRERAEETRTDTRSRVEESRARLTKLQEDLPEQLT
ELREKFTAEELRKAAEGYLEAATSRYNELVERGEAALERLRSQQSFEEVSARAEGYVDQAVELTQEA
LGTVASQTRAVGERAAKLVGIELPKKAAPAKKAAPAKKAAPAKKAAAKKAPAKKAAAKKVTQK

SEQ ID NO: 28

VTQTGKRQRRKFGRIRQFNSGRWQASYTGPDGRVYIAPKTFNAKIDAEAWLTDRRREIDRQLWSPA
SGQEDRPGAPFGEYAEGWLKQRGIKDRTRAHYRKLLDNHILATFADTDLRDITPAAVRRWYATTAVG
TPTMRAHSYSLLRAIMQTALADDLIDSNPCRISGASTARRVHKIRPATLDELETITKAMPDPYQAFVLM
AAWLAMRYGELTELRRKDIDLHGEVARVRRAVVRVGEGFKVTTPKSDAGVRDISIPPHLIPAIEDHLH
KHVNPGRESLLFPSVNDPNRHLAPSALYRMFYKARKAAGRPDLRVHDLRHSGAVLAASTGATLAEL
MQRLGHSTAGAALRYQHAAKGRDREIAALLSKLAENQEM

SEQ ID NO: 29

VIAGVDQALAATGQASQRAAGASGGVTVGVGVGTEQRNLSVVAPSQFTFSSRSPDFVDETAGQSW
CAILGLNQFH

SEQ ID NO: 30

MATTLPVQRHPRSLFPEFSELFAAFPSFAGLRPTFDTRLMRLEDEMKEGRYEVRAELPGVDPDKDV
DIMVRDGQLTIKAERTEQKDFDGRSEFAYGSFVRTVSLPVGADEDDIKATYDKGILTVSVAVSEGKPT
EKHIQIRSTN

SEQ ID NO: 31

MSGRHRKPTTSNVSVAKIAFTGAVLGGGGIAMAAQATAATDGEWDQVARCESGGNWSINTGNGYL
GGLQFTQSTWAAHGGGEFAPSAQLASREQQIAVGERVLATQGRGAWPVCGRGLSNATPREVLPAS
AAMDAPLDAAAVNGEPAPLAPPPADPAPPVELAANDLPAPLGEPLPAAPADPAPPADLAPPAPADVA
PPVELAVNDLPAPLGEPLPAAPADPAPPADLAPPAPADLAPPAPADLAPPAPADLAPPVELAVNDLPA
PLGEPLPAAPAELAPPADLAPASADLAPPAPADLAPPAPAELAPPAPADLAPPAAVNEQTAPGDQPA
TAPGGPVGLATDLELPEPDPQPADAPPPGDVTEAPAETPQVSNIAYTKKLWQAIRAQDVCGNDALDS
LAQPYVIG

SEQ ID NO: 32

MLRLVVGALLLVLAFAGGYAVAACKTVTLTVDGTAMRVTTMKSRVIDIVEENGFSVDDRDDLYPAAG
VQVHDADTIVLRRSRPLQISLDGHDAKQVWTTASTVDEALAQLAMTDTAPAAASRASRVPLSGMALP
VVSAKTVQLNDGGLVRTVHLPAPNVAGLLSAAGVPLLQSDHVVPAATAPIVEGMQIQVTRNRIKKVTE
RLPLPPNARRVEDPEMNMSREVVEDPGVPGTQDVTFAVAEVNGVETGRLPVANVVVTPAHEAVVR
VGTKPGTEVPPVIDGSIWDAIAGCEAGGNWAINTGNGYYGGVQFDQGTWEANGGLRYAPRADLAT
REEQIAVAEVTRLRQGWGAWPVCAARAGAR

SEQ ID NO: 33

VHPLPADHGRSRCNRHPISPLSLIGNASATSGDMSSMTRIAKPLIKSAMAAGLVTASMSLSTAVAHAG
PSPNWDAVAQCESGGNWAANTGNGKYGGLQFKPATWAAFGGVGNPAAASREQQIAVANRVLAEQ
GLDAWPTCGAASGLPIALWSKPAQGIKQIINEIIWAGIQASIPR

SEQ ID NO: 34

MTPGLLTTAGAGRPRDRCARIVCTVFIETAVVATMFVALLGLSTISSKADDIDWDAIAQCESGGNWAA
NTGNGLYGGLQISQATWDSNGGVGSPAAASPQQQIEVADNIMKTQGPGAWPKCSSCSQGDAPLGS
LTHILTFLAAETGGCSGSRDD

SEQ ID NO: 35

LKNARTTLIAAAIAGTLVTTSPAGIANADDAGLDPNAAAGPDAVGFDPNLPPAPDAAPVDTPPAPEDA
GFDPNLPPPLAPDFLSPPAEEAPPVPVAYSVNWDAIAQCESGGNWSINTGNGYYGGLRFTAGTWRA
NGGSGSAANASREEQIRVAENVLRSQGIRAWPVCGRRG

SEQ ID NO: 36

MIATTRDREGATMITFRLRLPCRTILRVFSRNPLVRGTDRLEAVVMLLAVTVSLLTIPFAAAAGTAVQD
SRSHVYAHQAQTRHPATATVIDHEGVIDSNTTATSAPPRTKITVPARWVVNGIERSGEVNAKPGTKS
GDRVGIWVDSAGQLVDEPAPPARAIADAALAALGLWLSVAAVAGALLALTRAILIRVRNASWQHDIDS
LFCTQR

SEQ ID NO: 37

MTEPAAWDEGKPRIITLTMNPALDITTSVDVVRPTEKMRCGAPRYDPGGGGINVARIVHVLGGCSTAL
FPAGGSTGSLLMALLGDAGVPFRVIPIAASTRESFTVNESRTAKQYRFVLPGPSLTVAEQEQCLDELR
GAAASAAFVVASGSLPPGVAADYYQRVADICRRSSTPLILDTSGGGLQHISSGVFLLKASVRELRECV

-continued

GSELLTEPEQLAAAHELIDRGRAEVVVVSLGSQGALLATRHASHRFSSIPMTAVSGVGAGDAMVAAIT
VGLSRGWSLIKSVRLGNAAGAAMLLTPGTAACNRDDVERFFELAAEPTEVGQDQYVWHPIVNPEAS
P

SEQ ID NO: 38

MPDTMVTTDVIKSAVQLACRAPSLHNSQPWRWIAEDHTVALFLDKDRVLYATDHSGREALLGCGAVL
DHFRVAMAAAGTTANVERFPNPNDPLHLASIDFSPADFVTEGHRLRADAILLRRTDRLPFAEPPDWD
LVESQLRTTVTADTVRIDVIADDMRPELAAASKLTESLRLYDSSYHAELFWWTGAFETSEGIPHSSLV
SAAESDRVTFGRDFPVVANTDRRPEFGHDRSKVLVLSTYDNERASLLRCGEMLSAVLLDATMAGLA
TCTLTHITELHASRDLVAALIGQPATPQALVRVGLAPEMEEPPPATPRRPIDEVFHVRAKDHR

SEQ ID NO: 39

MTTARDIMNAGVTCVGEHETLTAAAQYMREHDIGALPICGDDDRLHGMLTDRDIVIKGLAAGLDPNTA
TAGELARDSIYYVDANASIQEMLNVMEEHQVRRVPVISEHRLVGIVTEADIARHLPEHAIVQFVKAICS
PMALAS

SEQ ID NO: 40

MASSASDGTHERSAFRLSPPVLSGAMGPFMHTGLYVAQSWRDYLGQQPDKLPIARPTIALAAQAFR
DEIVLLGLKARRPVSNHRVFERISQEVAAGLEFYGNRRWLEKPSGFFAQPPPLTEVAVRKVKDRRRS
FYRIFFDSGFTPHPGEPGSQRWLSYTANNREYALLLRHPEPRPWLVCVHGTEMGRAPLDLAVFRAW
KLHDELGLNIVMPVLPMHGPRGQGLPKGAVFPGEDVLDDVHGTAQAVWDIRRLLSWIRSQEEESLIG
LNGLSLGGYIASLVASLEEGLACAILGVPVADLIELLGRHCGLRHKDPRRHTVKMAEPIGRMISPLSLT
PLVPMPGRFIYAGIADRLVHPREQVTRLWEHWGKPEIVWYPGGHTGFFQSRPVRRFVQAALEQSGL
LDAPRTQRDRSA

SEQ ID NO: 41

MSTQRPRHSGIRAVGPYAWAGRCGRIGRWGVHQEAMMNLAIWHPRKVQSATIYQVTDRSHDGRTA
RVPGDEITSTVSGWLSELGTQSPLADELARAVRIGDWPAAYAIGEHLSVEIAVAV

SEQ ID NO: 42 atgcagcttgttgacagggttcgtggcgccgtcacgggtatgtcgcgtcgactcgtggtcggggccgtcggcgcggccctagtgtcgggtctgg
tcggcgccgtcggtggcacggcgaccgcgggggcattttcccggccgggcttgccggtggagtacctgcaggtgccgtcgccgtcgatggg
ccgtgacatcaaggtccaattccaaagtggtggtgccaactcgcccgccctgtacctgctcgacggcctgcgcgcgcaggacgacttcagcg
gctgggacatcaacaccccggcgttcgagtggtacgaccagtcgggcctgtcggtggtcatgccggtgggtggccagtcaagcttctactccg
actggtaccagcccgcctgcggcaaggccggttgccagacttacaagtgggagaccttcctgaccagcgagctgccggggtggctgcagg
ccaacaggcacgtcaagcccaccggaagcgccgtcgtcggtctttcgatggctgcttcttcggcgctgacgctggcgatctatcacccccagc
agttcgtctacgcgggagcgatgtcgggcctgttggacccctcccaggcgatgggtcccaccctgatcggcctggcgatgggtgacgctggc
ggctacaaggcctccgacatgtggggcccgaaggaggacccggcgtggcagcgcaacgacccgctgttgaacgtcgggaagctgatcgc
caacaacacccgcgtctgggtgtactgcggcaacggcaagccgtcggatctgggtggcaacaacctgccggccaagttcctcgagggcttc
gtgcggaccagcaacatcaagttccaagacgcctacaacgccggtggcggccacaacggcgtgttcgacttcccggacagcggtacgcac
agctgggagtactggggcgcgcagctcaacgctatgaagcccgacctgcaacgggcactgggtgccacgcccaacaccgggcccgcgc
cccagggcgcctag

SEQ ID NO: 43 atgacagacgtgagccgaaagattcgagcttggggacgccgattgatgatcggcacggcagcggctgtagtccttccgggcctggtggggct
tgccggcggagcggcaaccgcgggcgcgttctcccggccggggctgccggtcgagtacctgcaggtgccgtcgccgtcgatgggccgcga
catcaaggttcagttccagagcggtgggaacaactcacctgcggtttatctgctcgacggcctgcgcgcccaagacgactacaacggctggg
atatcaacaccccggcgttcgagtggtactaccagtcgggactgtcgatagtcatgccggtcggcgggcagtccagcttctacagcgactggt
acagcccggcctgcggtaaggctggctgccagacttacaagtgggaaaccttcctgaccagcgagctgccgcaatggttgtccgccaacag
ggccgtgaagcccaccggcagcgctgcaatcggcttgtcgatggccggctcgtcggcaatgatcttggccgcctaccacccccagcagttca
tctacgccggctcgctgtcggccctgctggacccctctcaggggatggggcctagcctgatcggcctcgcgatgggtgacgccggcggttaca
aggccgcagacatgtggggtccctcgagtgacccggcatgggagcgcaacgaccctacgcagcagatccccaagctggtcgcaaacaa
cacccggctatgggtttattgcgggaacggcaccccgaacgagttgggcggtgccaacatacccgccgagttcttggagaacttcgttcgtag
cagcaacctgaagttccaggatgcgtacaacgccgcgggcgggcacaacgccgtgttcaacttcccgcccaacggcacgcacagctggg
agtactggggcgctcagctcaacgccatgaagggtgacctgcagagttcgttaggcgccggctga

SEQ ID NO: 44 atgacagagcagcagtggaatttcgcgggtatcgaggccgcggcaagcgcaatccagggaaatgtcacgtccattcattccctccttgacga
ggggaagcagtccctgaccaagctcgcagcggcctggggcggtagcggttcggaggcgtaccagggtgtccagcaaaaatgggacgcc
acggctaccgagctgaacaacgcgctgcagaacctggcgcggacgatcagcgaagccggtcaggcaatggcttcgaccgaaggcaacg
tcactgggatgttcgcatag

SEQ ID NO: 45 atgtcgcaaatcatgtacaactaccccgcgatgttgggtcacgccggggatatggccggatatgccggcacgctgcagagcttgggtgccga
gatcgccgtggagcaggccgcgttgcagagtgcgtggcagggcgataccgggatcacgtatcaggcgtggcaggcacagtggaaccagg
ccatggaagatttggtgcgggcctatcatgcgatgtccagcacccatgaagccaacaccatggcgatgatggcccgcgacacggccgaag
ccgccaaatggggcggctag

SEQ ID NO: 46 atgagcaattcgcgccgccgctcactcaggtggtcatggttgctgagcgtgctggctgccgtcgggctgggcctggccacggcgccggccca
ggcggccccgccggccttgtcgcaggaccggttcgccgacttccccgcgctgcccctcgacccgtccgcgatggtcgcccaagtggggcca
caggtggtcaacatcaacaccaaactgggctacaacaacgccgtgggcgccgggaccggcatcgtcatcgatcccaacggtgtcgtgctg
accaacaaccacgtgatcgcgggcgccaccgacatcaatgcgttcagcgtcggctccggccaaacctacggcgtcgatgtggtcgggtatg
accgcacccaggatgtcgcggtgctgcagctgcgcggtgccggtggcctgccgtcggcggcgatcggtggcggcgtcgcggttggtgagcc
cgtcgtcgcgatgggcaacagcggtgggcagggcggaacgccccgtgcggtgcctggcagggtggtcgcgctcggccaaaccgtgcagg
cgtcggattcgctgaccggtgccgaagagacattgaacgggttgatccagttcgatgccgcgatccagcccggtgattcgggcgggcccgtc
gtcaacggcctaggacaggtggtcggtatgaacacggccgcgtccgataacttccagctgtcccagggtggcagggattcgccattccgat
cgggcaggcgatggcgatcgcgggccagatccgatcgggtggggggtcacccaccgttcatatcgggcctaccgccttcctcggcttgggtg
ttgtcgacaacaacggcaacggcgcacgagtccaacgcgtggtcgggagcgctccggcggcaagtctcggcatctccaccggcgacgtg
atcaccgcggtcgacggcgctccgatcaactcggccaccgcgatggcggacgcgcttaacgggcatcatcccggtgacgtcatctcggtga
cctggcaaaccaagtcgggcggcacgcgtacagggaacgtgacattggccgagggacccccggcctga -continued

SEQ ID NO: 47 atggtggatttcggggcgttaccaccggagatcaactccgcgaggatgtacgccggcccgggttcggcctcgctggtggccgcggctcagat
gtgggacagcgtggcgagtgacctgttttcggccgcgtcggcgtttcagtcggtggtctggggtctgacggtggggtcgtggataggttcgtcgg
cgggtctgatggtggcggcggcctcgccgtatgtggcgtggatgagcgtcaccgcggggcaggccgagctgaccgccgcccaggtccggg
ttgctgcggcggcctacgagacggcgtatgggctgacggtgcccccgccggtgatcgccgagaaccgtgctgaactgatgattctgatagcg
accaacctcttggggcaaaacaccccggcgatcgcggtcaacgaggccgaatacggcgagatgtgggcccaagacgccgccgcgatgtt
tggctacgccgcggcgacggcgacggcgacggcgacgttgctgccgttcgaggaggcgccggagatgaccagcgcgggtgggctcctcg
agcaggccgccgcggtcgaggaggcctccgacaccgccgcggcgaaccagttgatgaacaatgtgccccaggcgctgcaacagctggc
ccagcccacgcagggcaccacgccttcttccaagctgggtggcctgtggaagacggtctcgccgcatcggtcgccgatcagcaacatggtgt
cgatggccaacaaccacatgtcgatgaccaactcgggtgtgtcgatgaccaacaccttgagctcgatgttgaagggctttgctccggcggcgg
ccgcccaggccgtgcaaaccgcggcgcaaaacggggtccgggcgatgagctcgctgggcagctcgctgggttcttcgggtctgggcggtg
ggtggccgccaacttgggtcgggcggcctcggtcggttcgttgtcggtgccgcaggcctgggccgcggccaaccaggcagtcaccccggc
ggcgcgggcgctgccgctgaccagcctgaccagcgccgcggaaagagggcccgggcagatgctgggcgggctgccggtggggcagat
gggcgccagggccggtggtgggctcagtggtgtgctgcgtgttccgccgcgaccctatgtgatgccgcattctccggcggccggctag

SEQ ID NO: 48 atgcggacccccagacgccactgccgtcgcatcgccgtcctcgccgccgttagcatcgccgccactgtcgttgccggctgctcgtcgggctcg
aagccaagcggcggaccacttccggacgcgaagccgctggtcgaggaggccaccgcgcagaccaaggctctcaagagcgcgcacatg
gtgctgacggtcaacggcaagatcccgggactgtctctgaagacgctgagcggcgatctcaccaccaacccccaccgccgcgacgggaaa
cgtcaagctcacgctgggtgggtctgatatcgatgccgacttcgtggtgttcgacgggatcctgtacgccaccctgacgcccaaccagtggag
cgatttcggtcccgccgccgacatctacgacccccgcccaggtgctgaatccggataccggcctggccaacgtgctggcgaatttcgccgacg
caaaagccgaagggcgggataccatcaacggccagaacaccatccgcatcagcgggaaggtatcggcacaggcggtgaaccagatag
cgccgccgttcaacgcgacgcagccggtgccggcgaccgtctggattcaggagaccggcgatcatcaactggcacaggcccagttggacc
gcggctcgggcaattccgtccagatgaccttgtcgaaatggggcgagaaggtccaggtcacgaagcccccggtgagctga

SEQ ID NO: 49 atggccaagacaattgcgtacgacgaagaggcccgtcgcggcctcgagcggggcttgaacgccctcgccgatgcggtaaaggtgacattg
ggccccaagggccgcaacgtcgtcctggaaaagaagtggggtgcccccacgatcaccaacgatggtgtgtccatcgccaaggagatcga
gctggaggatccgtacgagaagatcggcgccgagctggtcaaagaggtagccaagaagaccgatgacgtcgccggtgacggcaccacg
acggccaccgtgctggcccaggcgttggttcgcgagggcctgcgcaacgtcgcggccggcgccaacccgctcggtctcaaacgcggcatc
gaaaaggccgtggagaaggtcaccgagaccctgctcaagggcgccaaggaggtcgagaccaaggagcagattgcggccaccgcagc
gatttcggcgggtgaccagtccatcggtgacctgatcgccgaggcgatggacaaggtgggcaacgagggcgtcatcaccgtcgaggagtc
caacacctttgggctgcagctcgagctcaccgagggtatgcggttcgacaagggctacatctcggggtacttcgtgaccgacccggagcgtc
aggaggcggtcctggaggacccctacatcctgctggtcagctccaaggtgtccactgtcaaggatctgctgccgctgctcgagaaggtcatcg
gagccggtaagccgctgctgatcatcgccgaggacgtcgagggcgaggcgctgtccaccctggtcgtcaacaagatccgcggcaccttca
agtcggtggcggtcaaggctcccggcttcggcgaccgccgcaaggcgatgctgcaggatatggccattctcaccggtggtcaggtgatcagc
gaagaggtcggcctgacgctggagaacgccgacctgtcgctgctaggcaaggcccgcaaggtcgtggtcaccaaggacgagaccaccat
cgtcgagggcgccggtgacaccgacgccatcgccggacgagtggcccagatccgccaggagatcgagaacagcgactccgactacgac
cgtgagaagctgcaggagcggctggccaagctggccggtggtgtcgcggtgatcaaggccggtgccgccaccgaggtcgaactcaagga
gcgcaagcaccgcatcgaggatgcggttcgcaatgccaaggccgccgtcgaggagggcatcgtcgccggtgggggtgtgacgctgttgca
agcggccccgaccctggacgagctgaagctcgaaggcgacgaggcgaccggcgccaacatcgtgaaggtggcgctggaggccccgct
gaagcagatcgccttcaactccgggctggagccgggcgtggtggccgagaaggtgcgcaacctgccggctggccacggactgaacgctc
agaccggtgtctacgaggatctgctcgctgccggcgttgctgacccggtcaaggtgacccgttcggcgctgcagaatgcggcgtccatcgcg
ggctgttcctgaccaccgaggccgtcgttgccgacaagccggaaaaggagaaggcttccgttcccggtggcggcgacatgggtggcatg
gatttctga

SEQ ID NO: 50 atggctgaaaactcgaacattgatgacatcaaggctccgttgcttgccgcgcttggagcggccgacctggccttggccactgtcaacgagttga
tcacgaacctgcgtgagcgtgcggaggagactcgtacggacacccgcagccgggtcgaggagagccgtgctcgcctgaccaagctgcag
gaagatctgcccgagcagctcaccgagctgcgtgagaagttcaccgccgaggagctgcgtaaggccgccgagggctacctcgaggccgc
gactagccggtacaacgagctggtcgagcgcggtgaggccgctctagagcggctgcgcagccagcagagcttcgaggaagtgtcggcgc
gcgccgaaggctacgtggaccaggcggtggagttgacccaggaggcgttgggtacggtcgcatcgcagacccgcgcggtcggtgagcgt
gccgccaagctggtcggcatcgagctgcctaagaaggctgctccggccaagaaggccgctccggccaagaaggccgctccggccaaga
aggcggcggccaagaaggcgcccgcgaagaaggcggcggccaagaaggtcacccagaagtag

SEQ ID NO: 51 gtgacgcaaaccggcaagcgtcagagacgcaaattcggtcgcatccgacagttcaactccggccgctggcaagccagctacaccggccc
cgacggccgcgtgtacatcgcccccaaaaccttcaacgccaagatcgacgccgaagcatggctcaccgaccgccgccgcgaaatcgacc
gacaactatggtccccggcatcgggtcaggaagaccgccccggagccccattcggtgagtacgccgaaggatggctgaagcagcgtgga
atcaaggaccgcacccgcgcccactatcgcaaactgctggacaaccacatcctggccaccttcgctgacaccgacctacgcgacatcacc
ccggccgccgtgcgccgctggtacgccaccaccgccgtgggcacaccgaccatgcgggcacactcctacagcttgctgcgcgcaatcatg
cagaccgccttggccgacgacctgatcgactccaacccctgccgcatctcaggcgcgtccaccgcccgccgcgtccacaagatcaggccc
gccaccctcgacgagctggaaaccatcaccaaagccatgcccgacccctaccaggcgttcgtgctgatggcggcatggctggccatgcgct
acggcgagctgaccgaattacgccgcaaagacatcgacctgcacggcgaggttgcgcgggtgcggcgggctgtcgttcgggtgggcgaa
ggcttcaaggtgacgacaccgaaaagcgatgcgggagtgcgcgacataagtatcccgccacatctgatacccgccatcgaagaccacctt
cacaaacacgtcaaccccggccgggagtccctgctgttcccatcggtcaacgaccccaaccgtcacctagcaccctcggcgctgtaccgca
tgttctacaaggcccgaaaagccgccggccgaccagacttacgggtgcacgaccttcgacactccggcgccgtgttggctgcatccaccgg
cgccacactggccgaactgatgcagcggctaggacacagcacagccggcgccgcactccgctaccagcacgccgccaagggccggga
ccgcgaaatcgccgcactgttaagcaaactggccgagaaccaggagatgtga

SEQ ID NO: 52 gtgatagcgggcgtcgaccaggcgcttgcagcaacaggccaggctagccagcgggcggcaggcgcatctggtggggtcaccgtcggtgtc
ggcgtgggcacggaacagaggaacctttcggtggttgcaccgagtcagttcacatttagttcacgcagcccagattttgtggatgaaaccgca
ggtcaatcgtggtgcgcgatactgggattgaaccagtttcactag

SEQ ID NO: 53 atggccaccacccttcccgttcagcgccacccgcggtccctcttccccgagttttctgagctgttcgcggccttcccgtcattcgccggactccgg
cccaccttcgacacccggttgatgcggctggaagacgagatgaaagaggggcgctacgaggtacgcgcggagcttcccggggtcgaccc -continued cgacaaggacgtcgacattatggtccgcgatggtcagctgaccatcaaggccgagcgcaccgagcagaaggacttcgacggtcgctcgga
attcgcgtacggttccttcgttcgcacggtgtcgctgccggtaggtgctgacgaggacgacattaaggccacctacgacaagggcattcttactg
tgtcggtggcggtttcggaagggaagccaaccgaaaagcacattcagatccggtccaccaactga

SEQ ID NO: 54 atgagtggacgccaccgtaagcccaccacatccaacgtcagcgtcgccaagatcgcctttaccggcgcagtactcggtggcggcggcatcg
ccatggccgctcaggcgaccgcggccaccgacggggaatgggatcaggtggcccgctgcgagtcgggcggcaactggtcgatcaacac
cggcaacggttacctcggtggcttgcagttcactcaaagcacctgggccgcacatggtggcggcgagttcgccccgtcggctcagctggcca
gccgggagcagcagattgccgtcggtgagcgggtgctggccacccagggtcgcggcgcctggccggtgtgcggccgcgggttatcgaacg
caacaccccgcgaagtgcttcccgcttcggcagcgatggacgctccgttggacgcggccgcggtcaacggcgaaccagcaccgctggccc
cgccgcccgccgacccggcgccacccgtggaacttgccgctaacgacctgcccgcaccgctgggtgaacccctcccggcagctcccgcc
gacccggcaccacccgccgacctggcaccacccgcgcccgccgacgtcgcgccacccgtggaacttgccgtaaacgacctgcccgcac
cgctgggtgaacccctcccggcagctcccgccgacccggcaccacccgccgacctggcaccacccgcgcccgccgacctggcgccacc
cgcgcccgccgacctggcgccacccgcgcccgccgacctggcaccacccgtggaacttgccgtaaacgacctgcccgcgccgctgggtg
aacccctcccggcagctcccgccgaactggcgccacccgccgatctggcacccgcgtccgccgacctggcgccacccgcgcccgccgac
ctggcgccacccgcgcccgccgaactggcgccacccgcgcccgccgacctggcaccacccgctgcggtgaacgagcaaaccgcgccg
ggcgatcagcccgccacagctccaggcggcccggttggccttgccaccgatttggaactccccgagcccgacccccaaccagctgacgca
ccgccgcccggcgacgtcaccgaggcgcccgccgaaacgccccaagtctcgaacatcgcctatacgaagaagctgtggcaggcgattcg
ggcccaggacgtctgcggcaacgatgcgctggactcgctcgcacagccgtacgtcatcggctga

SEQ ID NO: 55 atgttgcgcctggtagtcggtgcgctgctgctggtgttggcgttcgccggtggctatgcggtcgccgcatgcaaaacggtgacgttgaccgtcga
cggaaccgcgatgcgggtgaccacgatgaaatcgcgggtgatcgacatcgtcgaagagaacgggttctcagtcgacgaccgcgacgacc
tgtatcccgcggccggcgtgcaggtccatgacgccgacaccatcgtgctgcggcgtagccgtccgctgcagatctcgctggatggtcacgac
gctaagcaggtgtggacgaccgcgtcgacggtggacgaggcgctggcccaactcgcgatgaccgacacggcgccggccgcggcttctcg
cgccagccgcgtcccgctgtccgggatggcgctaccggtcgtcagcgccaagacggtgcagctcaacgacggcgggttggtgcgcacggt
gcacttgccggcccccaatgtcgcggggctgctgagtgcggccggcgtgccgctgttgcaaagcgaccacgtggtgcccgccgcgacggc
cccgatcgtcgaaggcatgcagatccaggtgacccgcaatcggatcaagaaggtcaccgagcggctgccgctgccgccgaacgcgcgtc
gtgtcgaggacccggagatgaacatgagccgggaggtcgtcgaagacccgggggttccggggacccaggatgtgacgttcgcggtagctg
aggtcaacggcgtcgagaccggccgtttgcccgtcgccaacgtcgtggtgaccccggcccacgaagccgtggtgcgggtgggcaccaagc
ccggtaccgaggtgcccccggtgatcgacggaagcatctgggacgcgatcgccggctgtgaggccggtggcaactgggcgatcaacacc
ggcaacgggtattacggtggtgtgcagtttgaccagggcacctgggaggccaacggcgggctgcggtatgcaccccgcgctgacctcgcca
cccgcgaagagcagatcgccgttgccgaggtgacccgactgcgtcaaggttggggcgcctggccggtatgtgctgcacgagcgggtgcgc
gctga

SEQ ID NO: 56 gtgcatcctttgccggccgaccacggccggtcgcggtgcaatagacacccgatctcaccactctctctaatcggtaacgcttcggccacttccg
gcgatatgtcgagcatgacaagaatcgccaagccgctcatcaagtccgccatggccgcaggactcgtcacggcatccatgtcgctctccacc
gccgttgcccacgccggtcccagcccgaactgggacgccgtcgcgcagtgcgaatccgggggcaactgggcggccaacaccggaaacg
gcaaatacggcggactgcagttcaagccggccacctgggccgcattcggcggtgtcggcaacccagcagctgcctctcgggaacaacaa
atcgcagttgccaatcgggttctcgccgaacagggattggacgcgtggccgacgtgcggcgccgcctctggccttccgatcgcactgtggtcg
aaacccgcgcagggcatcaagcaaatcatcaacgagatcatttgggcaggcattcaggcaagtattccgcgctga

SEQ ID NO: 57 atgacaccgggtttgcttactactgcgggtgctggccgaccacgtgacaggtgcgccaggatcgtatgcacggtgttcatcgaaaccgccgttg
tcgcgaccatgtttgtcgcgttgttgggtctgtccaccatcagctcgaaagccgacgacatcgattgggacgccatcgcgcaatgcgaatccgg
cggcaattgggcggccaacaccggtaacgggttatacggtggtctgcagatcagccaggcgacgtgggattccaacggtggtgtcgggtcg
ccggcggccgcgagtccccagcaacagatcgaggtcgcagacaacattatgaaaacccaaggcccgggtgcgtggccgaaatgtagttct
tgtagtcagggagacgcaccgctgggctcgctcacccacatcctgacgttcctcgcggccgagactggaggttgttcggggagcagggacg
attga

SEQ ID NO: 58 ttgaagaacgcccgtacgacgctcatcgccgccgcgattgccgggacgttggtgaccacgtcaccagccggtatcgccaatgccgacgacg
cgggcttggacccaaacgccgcagccggcccggatgccgtgggctttgacccgaacctgccgccggccccggacgctgcacccgtcgata
ctccgccggctccggaggacgcgggctttgatcccaacctcccccgccgctggccccggacttcctgtccccgcctgcggaggaagcgcct
cccgtgcccgtggcctacagcgtgaactgggacgcgatcgcgcagtgcgagtccggtggaaactggtcgatcaacaccggtaacggttact
acggcggcctgcggttcaccgccggcacctggcgtgccaacggtggctcggggtccgcggccaacgcgagccgggaggagcagatccg
ggtggctgagaacgtgctgcgttcgcagggtatccgcgcctggccggtctgcggccgccgcggctga

SEQ ID NO: 59 atgatcgccacaacccgcgatcgtgaaggagccaccatgatcacgtttaggctgcgcttgccgtgccggacgatactgcgggtgttcagccg
caatccgctggtgcgtgggacggatcgactcgaggcggtcgtcatgctgctggccgtcacggtctcgctgctgactatcccgttcgccgccgcg
gccggcaccgcagtccaggattcccgcagccacgtctatgcccaccaggcccagacccgccatcccgcaaccgcgaccgtgatcgatcac
gagggggtgatcgacagcaacacgaccgccacgtcagcgccgccgcgcacgaagatcaccgtgcctgcccgatgggtcgtgaacggaa
tagaacgcagcggtgaggtcaacgcgaagccgggaaccaaatccggtgaccgcgtcggcatttgggtcgacagtgccggtcagctggtcg
atgaaccagctccgccggcccgtgccattgcggatgcggccctggccgccttgggactctggttgagcgtcgccgcggttgcgggcgccctg
ctggcgctcactcgggcgattctgatccgcgttcgcaacgccagttggcaacacgacatcgacagcctgttctgcacgcagcggtga

SEQ ID NO: 60 atgacggagccagcggcgtgggacgaaggcaagccgcgaatcatcactttgaccatgaaccccgccttggacatcacgacgagcgtcga
cgtggtgcgcccgaccgagaaaatgcgttgtggcgcacctcgctacgatcccggcggcggcggtatcaatgtcgcccgcattgtgcatgtcct
cggcggttgctcgacagcactgttcccggccggcgggtcgaccgggagcctgctgatggcgctgctcggtgatgcgggagtgccatttcgcgt
cattccgatcgcggcctcgacgcgggagagcttcacggtcaacgagtccaggaccgccaagcagtatcgtttcgtgcttccggggccgtcgct
gaccgtcgcggagcaggagcaatgcctcgacgaactgcgcggtgcggcggcttcggccgcctttgtggtggccagtggcagcctgccgcc
aggtgtggctgccgactactatcagcgggttgccgacatctgccgccgatcgagcactccgctgatcctggatacatctggtggcgggttgcag
cacatttcgtccggggtgtttcttctcaaggcgagcgtgcgggaactgcgcgagtgcgtcggatccgaactgctgaccgagcccgaacaactg
gccgccgcacacgaactcattgaccgtgggcgcgccgaggtcgtggtggtctcgcttggatctcagggcgcgctattggccacacgacatgc
gagccatcgattttcgtcgattccgatgaccgcggttagcggtgtcggcgccggcgacgcgatggtggccgcgattaccgtgggcctcagccg
tggctggtcgctcatcaagtccgttcgcttgggaaacgcggcaggtgcagccatgctgctgacgccaggcaccgcggcctgcaatcgcgac
gatgtggagaggttcttcgagctggcggccgaacccaccgaagtcgggcaggatcaatacgtttggcacccgatcgttaacccggaagcctc
gccatga -continued

SEQ ID NO: 61

```
atgccggacaccatggtgaccaccgatgtcatcaagagcgcggtgcagttggcctgccgcgcaccgtcgctccacaacagccagccctgg
cgctggatagccgaggaccacacggttgcgctgttcctcgacaaggatcgggtgctttacgcgaccgaccactccggccgggaagcgctgc
tggggtgcggcgccgtactcgaccactttcgggtggcgatggcggccgcgggtaccaccgccaatgtggaacggtttcccaaccccaacga
tcctttgcatctggcgtcaattgacttcagcccggccgatttcgtcaccgagggccaccgtctaagggcggatgcgatcctactgcgccgtaccg
accggctgcctttcgccgagccgccggattgggacttggtggagtcgcagttgcgcacgaccgtcaccgccgacacggtgcgcatcgacgtc
atcgccgacgatatgcgtcccgaactggcggcggcgtccaaactcaccgaatcgctgcggctctacgattcgtcgtatcatgccgaactcttttg
gtggacaggggcttttgagacttctgagggcataccgcacagttcattggtatcggcggccgaaagtgaccgggtcaccttcggacgcgactt
cccggtcgtcgccaacaccgataggcgcccggagtttggccacgaccgctctaaggtcctggtgctctccacctacgacaacgaacgcgcc
agcctactgcgctgcggcgagatgctttccgccgtattgcttgacgccaccatggctgggcttgccacctgcacgctgacccacatcaccgaa
ctgcacgccagccgagacctggtcgcagcgctgattgggcagcccgcaactccgcaagccttggttcgcgtcggtctggccccggagatgg
aagagccgccaccggcaacgcctcggcgaccaatcgatgaagtgtttcacgttcgggctaaggatcaccggtag
```

SEQ ID NO: 62

```
atgaccaccgcacgcgacatcatgaacgcaggtgtgacctgtgttggcgaacacgagacgctaaccgctgccgctcaatacatgcgtgagc
acgacatcggcgcgttgccgatctgcggggacgacgaccggctgcacggcatgctcaccgaccgcgacattgtgatcaaaggcctggctg
cgggcctagacccgaataccgccacggctggcgagttggcccgggacagcatctactacgtcgatgcgaacgcaagcatccaggagatg
ctcaacgtcatggaagaacatcaggtccgccgtgttccggtcatctcagagcaccgcttggtcggaatcgtcaccgaagccgacatcgcccg
acacctgcccgagcacgccattgtgcagttcgtcaaggcaatctgctcgcccatggccctcgccagctag
```

SEQ ID NO: 63

```
atggcaagttctgcgagcgacggcacccacgaacgctcggcttttcgcctgagtccaccggtcttgagcggcgccatgggaccgttcatgcac
accggtctgtacgtcgctcaatcgtggcgcgactatctgggtcaacagcccgataaactgccgatcgcacggcccactattgccttagcggcg
caagcctttcgagacgaaatcgtcctgctgggcctcaaggcacgacgtccggtcagcaatcatcgagtgttcgagcgcatcagccaagaagt
ggccgctggactggagttctatgggaatcgcagatggctggagaagcctagcggatttttgcccagcccccaccgctcaccgaggtcgcggt
ccgaaaggtcaaggaccgcagacgctccttttatcgcatcttcttcgacagtgggtttacgccgcatccgggtgaaccgggcagccaacggtg
gctctcatacactgcgaacaatcgcgagtacgccctgttactgcggcacccagagccgcgtccctggctggtttgtgtacacggcaccgagat
gggcagggccccgttggatctcgcggtgttccgcgcctggaagctgcatgacgaactcggcctgaacattgtcatgccggttcttccgatgcat
ggtccccgcgggcaaggtctgccgaagggcgccgtttttcccggagaagatgttctcgacgatgtgcatgggacggctcaagcggtgtggga
tatccggcggctgttgtcctggatacgatcgcaggaggaggagtcgctgatcgggttgaacggtctctcgctgggcggctacatcgcgtcattg
gtcgccagcctcgaagaaggtctcgcctgcgcgattctcggtgtcccagtggctgatctgatcgagttgttgggccgccactgcggtcttcggca
caaagaccccgccgccacaccgtcaagatggccgaaccgatcggccgaatgatctcgccgctctcacttacgccactggtgcccatg
ccgggccgctttatctacgcgggcattgccgaccgactcgtgcatccacgcgaacaggtgactcgcctctgggagcactggggcaaacccg
aaatcgtgtggtatccaggcggtcacactggcttcttccagtcgcggccggtacgacggtttgtccaggctgcgctggagcagtcgggcctgttg
gacgcgccacggacacagcgcgaccgttccgcctaa
```

SEQ ID NO: 64

```
atgtccacgcaacgaccgaggcactccggtattcgggctgttggcccctacgcatgggccggccgatgtggtcggataggcaggtgggggg
tgcaccaggaggcgatgatgaatctagcgatatggcacccgcgcaaggtgcaatccgccaccatctatcaggtgaccgatcgctcgcacga
cgggcgcacagcacgggtgcctggtgacgagatcactagcaccgtgtccggttggttgtcggagttgggcacccaaagcccgttggccgatg
agcttgcgcgtgcggtgcggatcggcgactggcccgctgcgtacgcaatcggtgagcacctgtccgttgagattgccgttgcggtctaa
```

SEQ ID NO: 65

```
LDFATLPPEINSARMYSGAGSAPMLAAASAWHGLSAELRASALSYSSVLSTLTGEEWHGPASASMT
AAAAPYVAWMSVTAVRAEQAGAQAEAAAAAYEAAFAATVPPPVIEANRAQLMALIATNVLGQNAPAI
AATEAQYAEMWSQDAMAMYGYAGASAAATQLTPFTEPVQTTNASGLAAQSAAIAHATGASAGAQQ
TTLSQLIAAIPSVLQGLSSSTAATFASGPSGLLGIVGSGSSWLDKLWALLDPNSNFWNTIASSGLFLPS
NTIAPFLGLLGGVAAADAAGDVLGEATSGGLGGALVAPLGSAGGLGGTVAAGLGNAATVGTLSVPPS
WTAAAPLASPLGSALGGTPMVAPPPAVAAGMPGMPFGTMGGQGFGRAVPQYGFRPNFVARPPAA
G
```

EXAMPLES

The invention will be further clarified by the following examples, which are intended to be purely exemplary of the invention and in no way limiting.

Example 1—Sub-Unit Vaccines Containing Polypeptides of the Invention

To prepare sub-unit vaccines comprising polypeptides it is first of all necessary to obtain a supply of polypeptide to prepare the vaccine. This can be achieved by purifying proteins of interest from TB culture, or by cloning the gene of interest and producing a recombinant protein. The coding sequences for the genes of interest are amplified by PCR with restriction sites inserted at the N terminus and C terminus to permit cloning in-frame into a protein expression vector such as pET-15b. The genes are inserted behind an inducible promoter such as lacZ. The vector is then transformed into *E. coli* which is grown in culture. The recombinant protein is over-expressed and is purified. One of the common purification methods is to produce a recombinant protein with an N-terminal tag for purification eg a His-tag. The protein can then be purified on the basis of the affinity of the His-tag for metal ions on a Ni-NTA column after which the His-tag is cleaved. The purified protein is then administered to animals in a suitable adjuvant.

Example 2—Use of BCG as a Microbial Carrier

The polynucleotide sequence of interest is amplified by PCR. The amplified product is purified and cloned into a plasmid (pMV306) that integrates site specifically into the mycobacterial genome at the attachment site (attB) for mycobacteriophage L5. BCG is transformed with the plasmid by electroporation, which involves damaging the cell envelope with high voltage electrical pulses, resulting in uptake of the DNA. The plasmid integrates into the BCG chromosome at the attB site, generating stable recombinants. Recombinants are selected and are checked by PCR or Southern blotting to ensure that the gene has been integrated. The recombinant strain is then used for protection studies.

Figure 4:
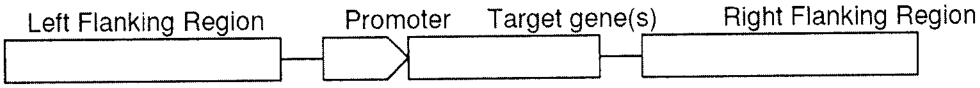
FIG. 4 schematically illustrates an exemplary vector construct expressing target gene(s), according to some embodiments of the present disclosure.

Example 3—Viral Vectors (Eg. Attenuated Vaccinia Virus) Expressing Mycobacterial Genes Methodologies permitting recombination of foreign or target genes into the genome of MVA are well known in the art [1,2]. Insertion of the target gene(s) is mediated by transfer DNA with features similar to those shown in FIG. 4. The transfer DNA may be in the form of a plasmid that can be propagated in a bacterial strain optimised for routine cloning procedures.

The target gene(s) is introduced to the cassette downstream of a promoter such as mH5, p7.5 or another. The target gene(s) may comprise one or more of nucleotide Seq IDs 1-18 and/or fragments thereof. The target gene(s) may also comprise adjuvanting cofactors such as B7-1 or IL-12 as is well described in the art [3]. The target gene(s) would be positioned downstream and in frame with an optimised Kozak sequence e.g. GCCACCATGG (SEQ ID NO: 66). The target gene(s) may also be positioned downstream and in frame with a leader sequence e.g. tPA. The target gene(s) may be positioned upstream of an in-frame tag e.g. V5, HIS or another. Transfer of the cassette into the genome of MVA is mediated by homologous flanking regions well known in the art e.g. Del I-VI.

1. Generation of recombinant vaccinia viruses. (2001) Earl P L et al. Current Protocols in Protein Science
2. Preparation of cell cultures and vaccine virus stocks. (2001) Earl P L et al. Current Protocols in Protein Science
3. Construction and characterisation of a triple-recombinant vaccine virus encoding B7-1, Interleukin 12 and a model tumor antigen. (1998) Carroll M W et al. Journal of the National Cancer Institute Dec. 16, 1998; 90(24): 1881-1887

Example 4—Preparation of DNA Expression Vectors

DNA vaccines consist of a nucleic acid sequence of interest cloned into a bacterial plasmid. The plasmid vector pVAX1 is commonly used in the preparation of DNA vaccines. The vector is designed to facilitate high copy number replication in *E. coli* and high level transient expression of the peptide of interest in most mammalian cells (for details see manufacturer's protocol for pVAX1 (Invitrogen catalog No. V260-20).

The vector contains the following elements:

- Human cytomegalovirus immediate-early (CMV) promoter for high-level expression in a variety of mammalian cells
- T7 promoter/priming site to allow in vitro transcription in the sense orientation and sequencing through the insert
- Bovine growth hormone (BGH) polyadenylation signal for efficient transcription termination and polyadenylation of mRNA
- Kanamycin resistance gene for selection in *E. coli*
- A multiple cloning site
- pUC origin for high-copy number replication and growth in *E. coli*
- BGH reverse priming site to permit sequencing through the insert Vectors may be prepared by means of standard recombinant techniques that are known in the art, for example Sambrook et al. (1989). Key stages in preparing the vaccine are as follows:

- The polynucleotide of interest is ligated into pVAX1 via one of the multiple cloning sites
- The ligation mixture is then transformed into a competent *E. coli* strain (e.g. TOP10) and LB plates containing 50 μg/ml kanamycin are used to select transformants.
- Clones are selected and may be sequenced to confirm the presence and orientation of the gene of interest.
- Once the presence of the gene has been verified, the vector can be used to transfect a mammalian cell line to check for protein expression. Methods for transfection are known in the art and include, for example, electroporation, calcium phosphate, and lipofection.
- Once polypeptide expression has been confirmed, large quantities of the vector can be produced and purified from the appropriate cell host, eg. *E. coli*.

pVAX1 does not integrate into the host chromosome. All non-essential sequences have been removed to minimise the possibility of integration. When constructing a specific vector, a leader sequence may be included to direct secretion of the encoded protein when expressed inside the eukaryotic cell. Other examples of vectors that can be used include V1Jns.tPA and pCMV4. Expression vectors may be used that integrate into the genome of the host, however, it is more common and more preferable to use a vector that does not integrate. Integration would lead to the generation of a genetically modified host which raises other issues.

Example 5—Plasmid DNA Vaccines Carrying Mycobacterial Polynucleotides

A polynucleotide sequence of interest is amplified by PCR, purified and inserted into specialized vectors developed for vaccine development, such as pVAX1. As above (Example 4), these vectors contain promoter sequences (eg. CMV or SV40 promoters), which direct strong expression of the introduced polynucleotide (encoding the candidate antigen) in eukaryotic cells; and polyadenylation signals (eg. SV40 or bovine growth hormone) to stabilize the mRNA transcript. The target gene(s) would be positioned downstream and in frame with an optimised Kozak sequence e.g. GCCACCATGG (SEQ ID NO: 66). The target gene(s) may also be positioned downstream and in frame with a leader sequence e.g. tPA. The target gene(s) may be positioned upstream of an in-frame tag e.g. V5. The vector is transformed into *E. coli* and transformants are selected using a marker, such as kanamycin resistance, encoded by the plasmid. The plasmid is then recovered from transformed colonies and is sequenced to check that the polynucleotide of interest is present and encoded properly without PCR generated mutations. Large quantities of the plasmid are then produced in *E. coli* and the plasmid is recovered and purified using commercially available kits (e.g. Qiagen Endofree-plasmid preparation). The vaccine is then administered to animals (e.g. by intramuscular injection) in the presence or absence of an adjuvant.

Example 6—RNA Vaccine

RNA can be introduced directly into the host. Thus, a vector construct may be used to generate RNA in vitro and the purified RNA is then injected into the host. The RNA then serves as a template for translation in the host cell. In this embodiment, integration would not normally occur.

An alternative option is to use an infectious agent such as the retroviral genome carrying RNA corresponding to the gene of interest. In this embodiment, integration into the host genome will occur. Another option is the use of RNA replicon vaccines which can be derived from virus vectors such as Sindbis virus or Semliki Forest virus. These vaccines are self-replicating and self-limiting and may be administered as either RNA or DNA which is then transcribed into RNA replicons in vivo. The vector eventually causes lysis of the transfected cells thereby reducing concerns about integration into the host genome.

Example 7—Diagnostic Assays Based on Assessing T Cell Responses

For a diagnostic assay based on assessing T cell responses it would be sufficient to obtain a sample of blood from the patient. Mononuclear cells (monocytes, T and B lymphocytes) can be separated from the blood using density gradients such as Ficoll gradients.

Both monocytes and B-lymphocytes are both able to present antigen, although less efficiently than professional antigen presenting cells (APCs) such as dendritic cells. The latter are more localized in lymphoid tissue.

The simplest approach would be to add antigen to the separated mononuclear cells and incubate for a week and then assess the amount of proliferation. If the individual had been exposed to the antigen previously through infection, then T-cell closes specific to the antigen should be more prevalent in the sample and should respond. It is also possible to separate the different cellular populations should it be desired to control the ratio of T cells to APCs. Another variation of this type of assay is to measure cytokine production by the responding lymphocytes as a measure of response. The ELISPOT assay is a suitable example of this assay.

Example 8—Detection of Latent Mycobacteria

The presence of latent mycobacteria-associated antigen may be detected either by detecting antigen-specific antibody, or by detecting T-cells in blood samples.

A 96 well plate is coated with cytokine (e.g. interferon-γ, IL-2)-specific antibody. Peripheral blood monocytes are then isolated from patient whole blood and are applied to the wells. Antigen is added to stimulate specific T cells that may be present and the plates are incubated for 24 h. The antigen stimulates the T-cells to produce cytokines, which bind a specific antibody. The plates are washed leaving a footprint where antigen-specific T cells were present. A second antibody coupled with a suitable detection system, e.g. enzyme, is then added and the number of spots is enumerated after the appropriate substrate has been added. The number of spots, each corresponding to a single antigen-specific T cell, is related to the total number of cells originally added. The above-described assay may also be used to distinguish TB-infected individuals from BCG-vaccinated individuals.

Example 9—Antigenic Activity

Mice are immunised with a mycobacterial antigen. Delivery systems include, but are not restricted to DNA vaccines, recombinant MVA, adjuvanted protein. Delivery routes include, but are not restricted to sub-cutaneous, intra-dermal, intra-muscular or aerosol administration. The immunisation regimen sometimes involves heterologous prime-boosting e.g. DNA vaccine followed by MVA vaccine. The immunisation regimen may also involve multiple doses.

After vaccination e.g. 2 weeks later, splenocytes are removed from the vaccinated animals and stimulated with polypeptide representative of the immunising antigen. An immune response is measurable through antigen-specific induction of cytokine release e.g. IFN-γ, and is evidence for immunisation against the target antigen.

Example 10—Demonstrating Vaccine Efficacy in an Experimental Model

Figure 2:
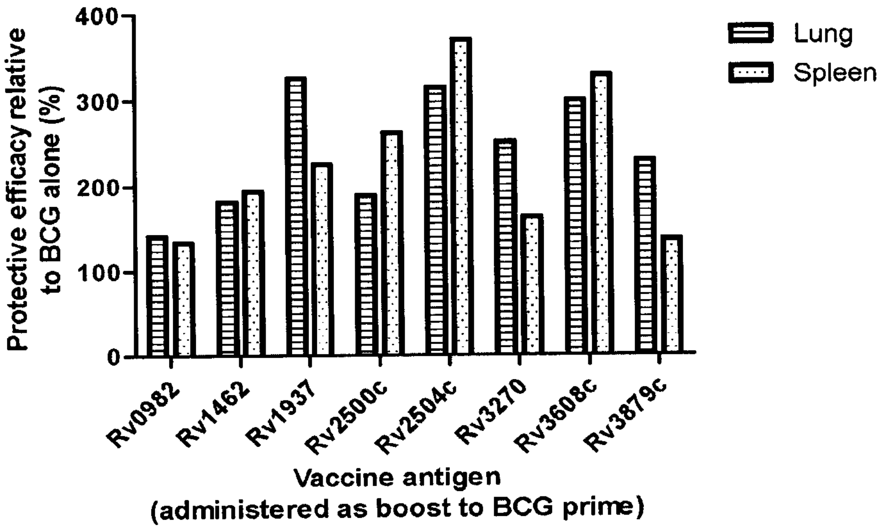
FIG. 2 graphically illustrates the protective efficacy (%) relative to BCG alone in lung and spleen for various vaccine antigens. The vaccine antigens were administered as a boost to a BCG prime vaccine.

Vaccine candidate efficacy in guinea pigs or mice may be assessed on the basis of reducing the bacterial burden of *M. tuberculosis* in the lungs and/or spleens at 6-24 weeks post-aerosol challenge—see FIGS. 1 & 2.

The mycobacterial antigens are delivered as sub-unit DNA vaccines or protein in a Th1-inducing adjuvant such as DDA/MPL, or by expression vectors such as recombinant viruses or BCG (see examples 1-4). The mycobacterial antigens may be delivered as a boost to an initial prime provided by BCG. There may be additional boosts provided by repeat inoculation of either DNA, polypeptide or viral vector or (less commonly) recombinant BCG. Groups of six to eight animals are immunised and then rested for 6 weeks prior to challenge. A group of positive control animals are inoculated sub-cutaneously with $5\times10^4$ colony forming units (CFU) of BCG Danish (1331), and a group of negative control animals remain unvaccinated. Six weeks following the final vaccination, fine particle aerosols of *M. tuberculosis* (2 μm mean diameter; generated in a Collison nebuliser), are delivered directly to the animal snout using a contained Henderson apparatus. 6 weeks post-aerosol challenge, the animals are euthanised and the lungs and spleen removed for CFU determination. Homogenised samples are serially diluted and plated on Middlebrook 7H11 selective agar and the mean CFU for each treatment group is determined. Vaccine efficacy is assessed in terms of reduction in bacterial counts in lungs or spleens compared to the unvaccinated control group. The reduction in bacterial load of test groups can be expressed as a proportion of the reduction achieved by BCG alone. Protective efficacy in animal models is indicative of the ability of the mycobacterial antigen to protect humans and animals from pathogenic mycobacterial infection.

Example 11—Demonstrating Vaccine Efficacy in an Experimental Model

Figure 3:
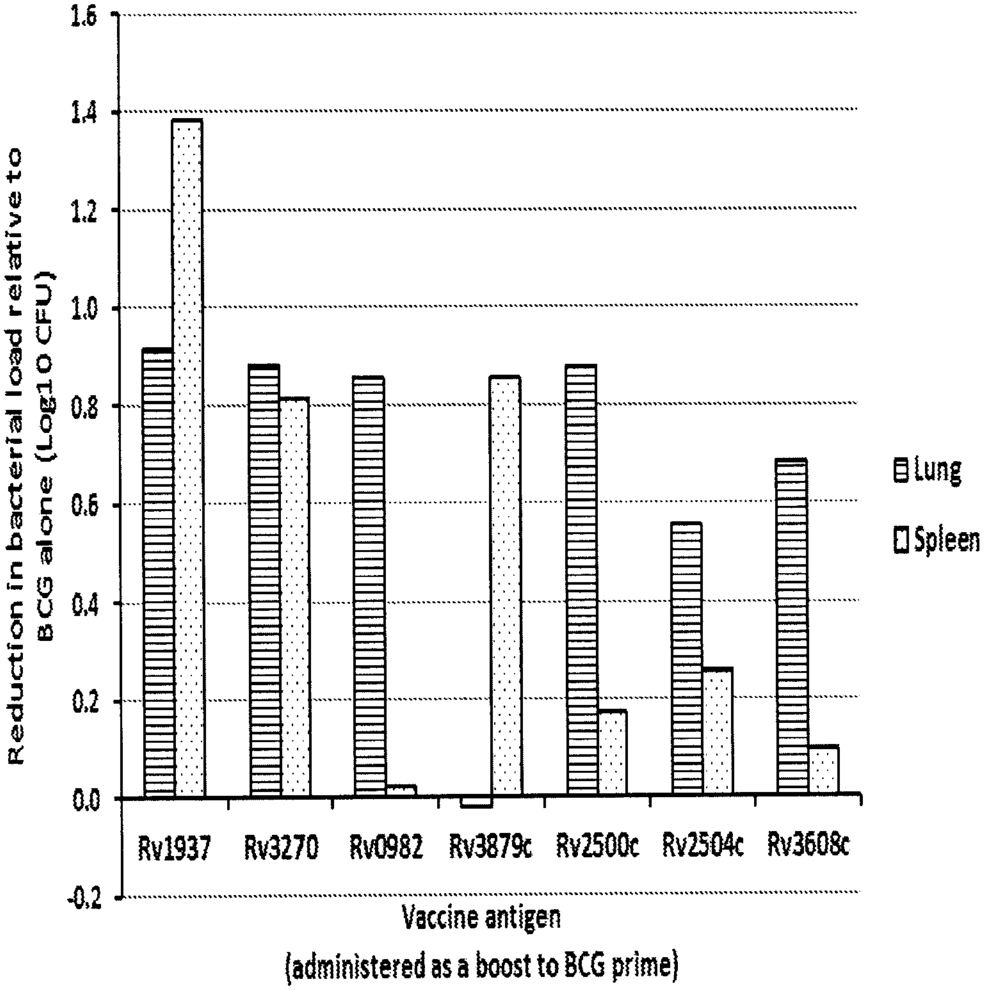
FIG. 3 graphically illustrates the protective efficacy ($Log^{10}$ CFU) relative to BCG alone in lung and spleen for various vaccine antigens. The vaccine antigens were administered as a boost to a BCG prime vaccine.

Vaccine candidate efficacy in guinea pigs or mice may be assessed on the basis of reducing the bacterial burden of *M. tuberculosis* in the lungs and/or spleens at 6-24 weeks post-aerosol challenge—see FIG. 3.

The mycobacterial antigens are delivered as sub-unit DNA vaccines or protein in a Th1-inducing adjuvant such as DDA/MPL, or by expression vectors such as recombinant viruses or BCG (see examples 1-4). The mycobacterial antigens may be delivered as a boost to an initial prime provided by BCG. There may be additional boosts provided by repeat inoculation of either DNA, polypeptide or viral vector or (less commonly) recombinant BCG. Groups of six to eight animals are immunised and then rested for 6 weeks prior to challenge. A group of positive control animals are inoculated sub-cutaneously with $5\times10^4$ colony forming units (CFU) of BCG Danish (1331), and a group of negative control animals remain unvaccinated. Six weeks following the final vaccination, fine particle aerosols of *M. tuberculosis* (2 μm mean diameter; generated in a Collison nebuliser), are delivered directly to the animal snout using a contained Henderson apparatus. 24 weeks post-aerosol challenge, the animals are euthanised and the lungs and spleen removed for CFU determination. Homogenised samples are serially diluted and plated on Middlebrook 7H11 selective agar and the mean CFU for each treatment group is determined. Vaccine efficacy is assessed in terms of reduction in bacterial counts in lungs or spleens compared to the unvaccinated control group. The reduction in bacterial load of test groups can be expressed as a proportion of the reduction achieved by BCG alone, or as the additional reduction in bacterial burden achieved. Protective efficacy in animal models is indicative of the ability of the mycobacterial antigen to protect humans and animals from pathogenic mycobacterial infection.

The invention claimed is:

1. An antigenic composition comprising a first mycobacterial polynucleotide, wherein said first mycobacterial polynucleotide comprises a polynucleotide sequence having at least 90% identity to SEQ ID NO: 7 or a fragment thereof having at least 450 consecutive nucleotides thereof;

wherein said antigenic composition induces an immune response in a subject; and wherein A) said antigenic composition comprises at least one vector and wherein said mycobacterial polynucleotide is incorporated into said at least one vector; wherein said vector is an expression vector, or a viral vector, or a plasmid; or B) said antigenic composition comprises an immunologically useful adjuvant.

2. The antigenic composition according to claim 1, further comprising at least one additional (second) mycobacterial polynucleotide encoding a second mycobacterial antigenic polypeptide, wherein said second mycobacterial polypeptide is different from said first mycobacterial polypeptide.

3. The antigenic composition according to claim 1, wherein said antigenic composition comprises at least one vector and wherein said mycobacterial polynucleotide(s) is/are incorporated into said at least one vector.

4. The antigenic composition according to claim 3, wherein said vector is an expression vector or a viral vector.

5. The antigenic composition of claim 3, wherein said vector is a plasmid.

6. The antigenic composition according to claim 1, wherein said antigenic composition comprises at least one cell, and wherein said cell comprises at least one of said mycobacterial polynucleotides.

7. The antigenic composition of claim 6, wherein said cell is an attenuated microbial carrier.

8. The antigenic composition of claim 7, wherein said attenuated microbial carrier is attenuated *salmonella*, attenuated *M. bovis* or attenuated *M. tuberculosis*.

9. The antigenic composition of claim 8, wherein said attenuated *M. bovis* is a BCG strain of *M. bovis*.

10. The antigenic composition of claim 1, wherein said viral vector is an attenuated vaccinia virus vector or an adenoviral vector.

* * * * *

SEQUENCE LISTING

```
<160> NUMBER OF SEQ ID NOS: 65

<210> SEQ ID NO 1
<211> LENGTH: 1515
<212> TYPE: DNA
<213> ORGANISM: Mycobacterium tuberculosis

<400> SEQUENCE: 1

atgtggtggt tccgccgccg agaccgggcg ccgctgcgcg ccaccagctc attatccctg     60

cggtggcggg tcatgctgct ggcgatgtcc atggtcgcga tggtggttgt gctgatgtcg    120

ttcgccgtct atgcggtgat ctcggccgcg ctctacagcg acatcgacaa ccaactgcag    180

agccgggcgc aactgctcat cgccagtggc tcgctggcag ctgatccggg taaggcaatc    240

gagggtaccg cctattcgga tgtcaacgcg atgctggtca accccggcca gtccatctac    300

accgctcaac agccgggcca gacgctgccg gtcggtgctg ccgagaaggc ggtgatccgt    360

ggcgagttgt tcatgtcgcg gcgcaccacc gccgaccaac gggtgcttgc catccgtctg    420

accaacggta gttcgctgct gatctccaaa agtctcaagc ccaccgaagc agtcatgaac    480

aagctgcgtt gggtgctatt gatcgtgggt gggatcgggg tggcggtcgc cgcggtggcc    540

ggggggatgg tcacccgggc cgggctgagg ccggtgggcc gcctcaccga agcggccgag    600

cgggtggcgc gaaccgacga cctgcggccc atccccgtct tcggcagcga cgaattggcc    660

aggctgacag aggcattcaa tttaatgctg cgggcgctgg ccgagtcacg ggaacggcag    720

gcaaggctgg ttaccgacgc cggacatgaa ttgcgtaccc cgctaacgtc gctgcgcacc    780

aatgtcgaac tcttgatggc ctcgatggcc ccgggggctc cgcggctacc caagcaggag    840

atggtcgacc tgcgtgccga tgtgctggct caaatcgagg aattgtccac actggtaggc    900

gatttggtgg acctgtcccg aggcgacgcc ggagaagtgg tgcacgagcc ggtcgacatg    960

gctgacgtcg tcgaccgcag cctggagcgg gtcaggcggc ggcgcaacga tatccttttc   1020

gacgtcgagg tgattgggtg gcaggtttat ggcgataccg ctggattgtc gcggatggcg   1080

cttaacctga tggacaacgc cgcgaagtgg agcccgccgg gcggccacgt gggtgtcagg   1140

ctgagccagc tcgacgcgtc gcacgctgag ctggtggttt ccgaccgcgg cccgggcatt   1200

cccgtgcagg agcgccgtct ggtgtttgaa cggttttacc ggtcggcatc ggcacgggcg   1260

ttgccgggtt cgggcctcgg gttggcgatc gtcaaacagg tggtgctcaa ccacggcgga   1320

ttgctgcgca tcgaagacac cgacccaggc ggccagcccc ctggaacgtc gatttacgtg   1380

ctgctccccg gccgtcggat gccgattccg cagcttcccg gtgcgacggc tggcgctcgg   1440

agcacggaca tcgagaactc tcggggttcg gcgaacgtta tctcagtgga atctcagtcc   1500

acgcgcgcaa cctag                                                    1515


<210> SEQ ID NO 2
<211> LENGTH: 504
<212> TYPE: PRT
<213> ORGANISM: Mycobacterium tuberculosis

<400> SEQUENCE: 2

Met Trp Trp Phe Arg Arg Arg Asp Arg Ala Pro Leu Arg Ala Thr Ser
1               5                   10                  15
```

-continued

```
Ser Leu Ser Leu Arg Trp Arg Val Met Leu Leu Ala Met Ser Met Val
            20                  25                  30

Ala Met Val Val Val Leu Met Ser Phe Ala Val Tyr Ala Val Ile Ser
        35                  40                  45

Ala Ala Leu Tyr Ser Asp Ile Asp Asn Gln Leu Gln Ser Arg Ala Gln
    50                  55                  60

Leu Leu Ile Ala Ser Gly Ser Leu Ala Ala Asp Pro Gly Lys Ala Ile
65                  70                  75                  80

Glu Gly Thr Ala Tyr Ser Asp Val Asn Ala Met Leu Val Asn Pro Gly
                85                  90                  95

Gln Ser Ile Tyr Thr Ala Gln Gln Pro Gly Gln Thr Leu Pro Val Gly
            100                 105                 110

Ala Ala Glu Lys Ala Val Ile Arg Gly Glu Leu Phe Met Ser Arg Arg
        115                 120                 125

Thr Thr Ala Asp Gln Arg Val Leu Ala Ile Arg Leu Thr Asn Gly Ser
    130                 135                 140

Ser Leu Leu Ile Ser Lys Ser Leu Lys Pro Thr Glu Ala Val Met Asn
145                 150                 155                 160

Lys Leu Arg Trp Val Leu Leu Ile Val Gly Gly Ile Gly Val Ala Val
                165                 170                 175

Ala Ala Val Ala Gly Gly Met Val Thr Arg Ala Gly Leu Arg Pro Val
            180                 185                 190

Gly Arg Leu Thr Glu Ala Ala Glu Arg Val Ala Arg Thr Asp Asp Leu
        195                 200                 205

Arg Pro Ile Pro Val Phe Gly Ser Asp Glu Leu Ala Arg Leu Thr Glu
    210                 215                 220

Ala Phe Asn Leu Met Leu Arg Ala Leu Ala Glu Ser Arg Glu Arg Gln
225                 230                 235                 240

Ala Arg Leu Val Thr Asp Ala Gly His Glu Leu Arg Thr Pro Leu Thr
                245                 250                 255

Ser Leu Arg Thr Asn Val Glu Leu Leu Met Ala Ser Met Ala Pro Gly
            260                 265                 270

Ala Pro Arg Leu Pro Lys Gln Glu Met Val Asp Leu Arg Ala Asp Val
        275                 280                 285

Leu Ala Gln Ile Glu Glu Leu Ser Thr Leu Val Gly Asp Leu Val Asp
    290                 295                 300

Leu Ser Arg Gly Asp Ala Gly Glu Val Val His Glu Pro Val Asp Met
305                 310                 315                 320

Ala Asp Val Val Asp Arg Ser Leu Glu Arg Val Arg Arg Arg Arg Asn
                325                 330                 335

Asp Ile Leu Phe Asp Val Glu Val Ile Gly Trp Gln Val Tyr Gly Asp
            340                 345                 350

Thr Ala Gly Leu Ser Arg Met Ala Leu Asn Leu Met Asp Asn Ala Ala
        355                 360                 365

Lys Trp Ser Pro Pro Gly Gly His Val Gly Val Arg Leu Ser Gln Leu
    370                 375                 380

Asp Ala Ser His Ala Glu Leu Val Val Ser Asp Arg Gly Pro Gly Ile
385                 390                 395                 400

Pro Val Gln Glu Arg Arg Leu Val Phe Glu Arg Phe Tyr Arg Ser Ala
                405                 410                 415

Ser Ala Arg Ala Leu Pro Gly Ser Gly Leu Gly Leu Ala Ile Val Lys
            420                 425                 430

Gln Val Val Leu Asn His Gly Gly Leu Leu Arg Ile Glu Asp Thr Asp
```

```
        435                 440                 445

Pro Gly Gly Gln Pro Pro Gly Thr Ser Ile Tyr Val Leu Leu Pro Gly
    450                 455                 460

Arg Arg Met Pro Ile Pro Gln Leu Pro Gly Ala Thr Ala Gly Ala Arg
465                 470                 475                 480

Ser Thr Asp Ile Glu Asn Ser Arg Gly Ser Ala Asn Val Ile Ser Val
                485                 490                 495

Glu Ser Gln Ser Thr Arg Ala Thr
            500


<210> SEQ ID NO 3
<211> LENGTH: 1194
<212> TYPE: DNA
<213> ORGANISM: Mycobacterium tuberculosis

<400> SEQUENCE: 3

atgacggctc cgggactgac agcagccgtc gaggggatcg cacacaacaa gggcgagctg      60

ttcgcctcct ttgacgtgga cgcgttcgag gttccgcacg gccgcgacga gatctggcgg     120

ttcaccccgt tgcggcggct gcgtggcctg cacgacggct ccgcgcgggc caccggtagc     180

gccacgatca cggtcagcga gcggccgggc gtatacaccc agaccgtgcg ccgcggcgat     240

ccacgactgg gcgagggcgg cgtacccacc gaccgcgttg ccgcccaagc gttttcgtcg     300

ttcaactccg cgactctggt caccgtcgag cgcgacaccc aggtcgtcga gccggtaggc     360

atcaccgtga ccgggccggg ggagggcgcg gtggcctatg ggcacctgca ggtgcgtatc     420

gaggagcttg gcgaggcggt cgtggtcatc gaccaccggg gcggcggaac ctacgccgac     480

aacgtcgagt tcgttgtcga cgacgccgct cggctgaccg ccgtgtggat cgccgactgg     540

gccgacaaca ccgttcacct cagcgcgcac catgctcgga tcggcaagga cgcggtgctg     600

cgccacgtca ccgtcatgtt gggcggcgac gtggtgcgaa tgtcggcggg cgtgcggttc     660

tgcggtgcgg gtggggacgc ggaactgctg gggctgtatt tcgccgacga cggccagcac     720

ctggagtcgc ggctgctggt ggaccacgcc caccccgact gcaagtcgaa cgtgctgtat     780

aagggtgcac tgcaaggtga tccggcgtcg tcgttgcccg acgcacacac ggtctgggtg     840

ggtgacgtgc tgatccgtgc gcaggccacc ggcaccgaca ccttcgaggt gaaccggaac     900

ctggtgctca ccgacggcgc gcgtgccgac tcggtgccca acctggagat cgagaccggc     960

gagatcgtcg gcgccggaca cgccagcgcc accggtcgct tcgacgatga gcaattgttc    1020

tacctgcgtt cgcgcggtat tcccgaagca caggcccgcc ggctggtggt ccgcggcttc    1080

ttcggtgaga tcatcgccaa gatcgcggtg cccgaggtac gcgagcgcct gaccgcagcc    1140

atcgaacacg agctggaaat cacggaatca acggaaaaga caacagtctc atga          1194


<210> SEQ ID NO 4
<211> LENGTH: 397
<212> TYPE: PRT
<213> ORGANISM: Mycobacterium tuberculosis

<400> SEQUENCE: 4

Met Thr Ala Pro Gly Leu Thr Ala Ala Val Glu Gly Ile Ala His Asn
1               5                   10                  15

Lys Gly Glu Leu Phe Ala Ser Phe Asp Val Asp Ala Phe Glu Val Pro
            20                  25                  30

His Gly Arg Asp Glu Ile Trp Arg Phe Thr Pro Leu Arg Arg Leu Arg
        35                  40                  45
```

-continued

```
Gly Leu His Asp Gly Ser Ala Arg Ala Thr Gly Ser Ala Thr Ile Thr
    50                  55                  60

Val Ser Glu Arg Pro Gly Val Tyr Thr Gln Thr Val Arg Arg Gly Asp
65                  70                  75                  80

Pro Arg Leu Gly Glu Gly Gly Val Pro Thr Asp Arg Val Ala Ala Gln
                85                  90                  95

Ala Phe Ser Ser Phe Asn Ser Ala Thr Leu Val Thr Val Glu Arg Asp
            100                 105                 110

Thr Gln Val Val Glu Pro Val Gly Ile Thr Val Thr Gly Pro Gly Glu
        115                 120                 125

Gly Ala Val Ala Tyr Gly His Leu Gln Val Arg Ile Glu Glu Leu Gly
    130                 135                 140

Glu Ala Val Val Val Ile Asp His Arg Gly Gly Gly Thr Tyr Ala Asp
145                 150                 155                 160

Asn Val Glu Phe Val Val Asp Asp Ala Ala Arg Leu Thr Ala Val Trp
                165                 170                 175

Ile Ala Asp Trp Ala Asp Asn Thr Val His Leu Ser Ala His His Ala
            180                 185                 190

Arg Ile Gly Lys Asp Ala Val Leu Arg His Val Thr Val Met Leu Gly
        195                 200                 205

Gly Asp Val Val Arg Met Ser Ala Gly Val Arg Phe Cys Gly Ala Gly
    210                 215                 220

Gly Asp Ala Glu Leu Leu Gly Leu Tyr Phe Ala Asp Asp Gly Gln His
225                 230                 235                 240

Leu Glu Ser Arg Leu Leu Val Asp His Ala His Pro Asp Cys Lys Ser
                245                 250                 255

Asn Val Leu Tyr Lys Gly Ala Leu Gln Gly Asp Pro Ala Ser Ser Leu
            260                 265                 270

Pro Asp Ala His Thr Val Trp Val Gly Asp Val Leu Ile Arg Ala Gln
        275                 280                 285

Ala Thr Gly Thr Asp Thr Phe Glu Val Asn Arg Asn Leu Val Leu Thr
    290                 295                 300

Asp Gly Ala Arg Ala Asp Ser Val Pro Asn Leu Glu Ile Glu Thr Gly
305                 310                 315                 320

Glu Ile Val Gly Ala Gly His Ala Ser Ala Thr Gly Arg Phe Asp Asp
                325                 330                 335

Glu Gln Leu Phe Tyr Leu Arg Ser Arg Gly Ile Pro Glu Ala Gln Ala
            340                 345                 350

Arg Arg Leu Val Val Arg Gly Phe Phe Gly Glu Ile Ile Ala Lys Ile
        355                 360                 365

Ala Val Pro Glu Val Arg Glu Arg Leu Thr Ala Ala Ile Glu His Glu
    370                 375                 380

Leu Glu Ile Thr Glu Ser Thr Glu Lys Thr Thr Val Ser
385                 390                 395
```

<210> SEQ ID NO 5
<211> LENGTH: 2520
<212> TYPE: DNA
<213> ORGANISM: Mycobacterium tuberculosis

<400> SEQUENCE: 5

```
atggcggttc gtcaggtcac cgtcggctat tcggacggca cgcacaagac gatgccggtg      60

cggtgcgacc agacggtcct ggatgccgcc gaggaacacg gcgtggccat cgtcaacgaa     120

tgccaaagcg ggatatgtgg cacctgcgtg gccacctgca ccgccggccg ctaccagatg     180
```

-continued

```
ggacgcaccg agggactgtc cgatgtcgag cgggcggcgc gaaagatcct cacctgccag    240
acgtttgtta cctccgattg ccggatcgag ctgcagtatc cggtcgacga caacgccgcc    300
ctgctggtca ccggtgacgg tgtggtgacc gcggtcgagt tggtgtcgcc cagcaccgcc    360
atcctgcggg tggacacctc tggcatggcc ggcgcgctga gataccgggc cggccagttc    420
gcccaattgc aggttcccgg taccaacgta tggcgcaact actcctacgc ccatccggcc    480
gacggccgcg gtgagtgcga gttcatcatc aggttgctgc cggacggcgt gatgtcgaat    540
tatcttcgcg accgcgccca gcccggtgac catatcgcgc tgcgctgcag caagggcagc    600
ttttatctgc gcccgatcgt gcgaccggtg atcctggtcg ccggaggaac cggcctgtca    660
gcgatcctgg cgatggccca gagcctggat gccgatgtcg ctcacccggt ctacctgctc    720
tacggggtcg agcgcaccga agacctgtgc aagctcgacg aactcaccga gctgcgccgc    780
cgcgttggcc gcctggaggt gcacgtcgtc gtcgctcgcc cggaccccga ctgggatggg    840
cgcaccgggc tggtcaccga cctgctcgac gagcggatgc tggcgagcgg tgacgccgac    900
gtgtatctgt gcggtccggt cgccatggtc gacgcagccc gaacctggct ggaccacaat    960
ggctttcacc gtgtcgggtt gtactacgag aagttcgtgg ccagcggggc ggcgcgccgc   1020
cgcaccccgg ctcggctgga ttacgcgggc gtggacattg ccgaggtgtg ccgccgcggc   1080
cgcggcaccg cggtggtcat cggcggcagc atcgcgggca tcgcggcggc gaaaatgctc   1140
agcgagacct tcgatcgcgt catcgtgctg gagaaggacg gcccgcaccg tcgccgcgag   1200
ggcaggccgg gcgcggcaca gggttggcac ctgcaccacc tgctgaccgc cgggcagatc   1260
gagctggagc gcatcttccc tggcatcgtc gacgacatgg tgcgcgaggg agcgttcaag   1320
gtcgacatgg ccgcgcagta ccgtatccgg ctgggcggca cctggaagaa gcccggcact   1380
agtgacatcg agatcgtctg cgcgggaagg ccgctgctcg aatggtgtgt gcgccgccgg   1440
ctcgacgacg aaccgcgcat cgacttccgc tacgaatcgg aggtggccga tctcgccttc   1500
gaccgcgcca acaatgccat cgtcggcgtc gccgtggaca atggcgacgc cgacggaggc   1560
gacggtttgc aggtggtgcc cgccgagttc gtcgtggacg cgtcgggcaa gaacacccgc   1620
gtgccggagt tcttggagcg tctcggtgtt ggcgctcccg aggccgagca ggacatcatc   1680
aactgcttct actccacgat gcagcaccgg gttccgccgg agcggcggtg gcaggacaag   1740
gtgatggtga tctgctatgc gtaccgccct ttcgaggata cctacgccgc gcagtactac   1800
accgacagct cccgcaccat cctgtccacc tcactggtgg cctacaactg ctattcgccg   1860
ccgcgtaccg cccgagaatt ccgcgcgttc gccgacctga tgccgtcccc ggtcatcggg   1920
gagaacatcg acgggctgga gccggcatcg cccatctaca atttccgcta tcccaacatg   1980
ctgcggctgc gctacgagaa gaagcgcaac ctgccgcggg ctttgctggc ggtgggcgat   2040
gcctacacca gcgccgaccc ggtgtcgggt ctgggtatga gcctggcgct caaggaagtt   2100
cgggagatgc aggcgctgct ggctaaatac ggcgccggtc accgggatct gccgcgccgg   2160
tactaccggg cgatcgccaa gatggccgac acggcctggt tcgtgatccg cgagcagaac   2220
ctgcgcttcg actggatgaa ggacgtcgac aagaagcgcc cgttctattt cggtgtgctg   2280
acctggtaca tggaccgcgt gctggagctg gtgcatgacg atctcgacgc gtaccgggaa   2340
ttcttggccg tcgtccatct ggtcaagccg ccgtcggcgc tgatgcgacc caggatcgcc   2400
agccgcgtcc tcggcaaatg ggcacgaacc cgattgtcgg gccagaagac gttgattgcc   2460
cgcaactacg aaaatcatcc gataccagcc gaacccgcgg accaacttgt aaacgcttag   2520
```

<210> SEQ ID NO 6
<211> LENGTH: 839
<212> TYPE: PRT
<213> ORGANISM: Mycobacterium tuberculosis

<400> SEQUENCE: 6

```
Met Ala Val Arg Gln Val Thr Val Gly Tyr Ser Asp Gly Thr His Lys
1               5                   10                  15

Thr Met Pro Val Arg Cys Asp Gln Thr Val Leu Asp Ala Ala Glu Glu
            20                  25                  30

His Gly Val Ala Ile Val Asn Glu Cys Gln Ser Gly Ile Cys Gly Thr
        35                  40                  45

Cys Val Ala Thr Cys Thr Ala Gly Arg Tyr Gln Met Gly Arg Thr Glu
    50                  55                  60

Gly Leu Ser Asp Val Glu Arg Ala Ala Arg Lys Ile Leu Thr Cys Gln
65                  70                  75                  80

Thr Phe Val Thr Ser Asp Cys Arg Ile Glu Leu Gln Tyr Pro Val Asp
                85                  90                  95

Asp Asn Ala Ala Leu Leu Val Thr Gly Asp Gly Val Val Thr Ala Val
            100                 105                 110

Glu Leu Val Ser Pro Ser Thr Ala Ile Leu Arg Val Asp Thr Ser Gly
        115                 120                 125

Met Ala Gly Ala Leu Arg Tyr Arg Ala Gly Gln Phe Ala Gln Leu Gln
    130                 135                 140

Val Pro Gly Thr Asn Val Trp Arg Asn Tyr Ser Tyr Ala His Pro Ala
145                 150                 155                 160

Asp Gly Arg Gly Glu Cys Glu Phe Ile Ile Arg Leu Leu Pro Asp Gly
                165                 170                 175

Val Met Ser Asn Tyr Leu Arg Asp Arg Ala Gln Pro Gly Asp His Ile
            180                 185                 190

Ala Leu Arg Cys Ser Lys Gly Ser Phe Tyr Leu Arg Pro Ile Val Arg
        195                 200                 205

Pro Val Ile Leu Val Ala Gly Gly Thr Gly Leu Ser Ala Ile Leu Ala
    210                 215                 220

Met Ala Gln Ser Leu Asp Ala Asp Val Ala His Pro Val Tyr Leu Leu
225                 230                 235                 240

Tyr Gly Val Glu Arg Thr Glu Asp Leu Cys Lys Leu Asp Glu Leu Thr
                245                 250                 255

Glu Leu Arg Arg Arg Val Gly Arg Leu Glu Val His Val Val Val Ala
            260                 265                 270

Arg Pro Asp Pro Asp Trp Asp Gly Arg Thr Gly Leu Val Thr Asp Leu
        275                 280                 285

Leu Asp Glu Arg Met Leu Ala Ser Gly Asp Ala Asp Val Tyr Leu Cys
    290                 295                 300

Gly Pro Val Ala Met Val Asp Ala Ala Arg Thr Trp Leu Asp His Asn
305                 310                 315                 320

Gly Phe His Arg Val Gly Leu Tyr Tyr Glu Lys Phe Val Ala Ser Gly
                325                 330                 335

Ala Ala Arg Arg Arg Thr Pro Ala Arg Leu Asp Tyr Ala Gly Val Asp
            340                 345                 350

Ile Ala Glu Val Cys Arg Arg Gly Arg Gly Thr Ala Val Val Ile Gly
        355                 360                 365

Gly Ser Ile Ala Gly Ile Ala Ala Ala Lys Met Leu Ser Glu Thr Phe
    370                 375                 380
```

Asp Arg Val Ile Val Leu Glu Lys Asp Gly Pro His Arg Arg Arg Glu
385 390 395 400

Gly Arg Pro Gly Ala Ala Gln Gly Trp His Leu His His Leu Leu Thr
405 410 415

Ala Gly Gln Ile Glu Leu Glu Arg Ile Phe Pro Gly Ile Val Asp Asp
420 425 430

Met Val Arg Glu Gly Ala Phe Lys Val Asp Met Ala Ala Gln Tyr Arg
435 440 445

Ile Arg Leu Gly Gly Thr Trp Lys Lys Pro Gly Thr Ser Asp Ile Glu
450 455 460

Ile Val Cys Ala Gly Arg Pro Leu Leu Glu Trp Cys Val Arg Arg Arg
465 470 475 480

Leu Asp Asp Glu Pro Arg Ile Asp Phe Arg Tyr Glu Ser Glu Val Ala
485 490 495

Asp Leu Ala Phe Asp Arg Ala Asn Asn Ala Ile Val Gly Val Ala Val
500 505 510

Asp Asn Gly Asp Ala Asp Gly Gly Asp Gly Leu Gln Val Val Pro Ala
515 520 525

Glu Phe Val Val Asp Ala Ser Gly Lys Asn Thr Arg Val Pro Glu Phe
530 535 540

Leu Glu Arg Leu Gly Val Gly Ala Pro Glu Ala Glu Gln Asp Ile Ile
545 550 555 560

Asn Cys Phe Tyr Ser Thr Met Gln His Arg Val Pro Pro Glu Arg Arg
565 570 575

Trp Gln Asp Lys Val Met Val Ile Cys Tyr Ala Tyr Arg Pro Phe Glu
580 585 590

Asp Thr Tyr Ala Ala Gln Tyr Tyr Thr Asp Ser Ser Arg Thr Ile Leu
595 600 605

Ser Thr Ser Leu Val Ala Tyr Asn Cys Tyr Ser Pro Pro Arg Thr Ala
610 615 620

Arg Glu Phe Arg Ala Phe Ala Asp Leu Met Pro Ser Pro Val Ile Gly
625 630 635 640

Glu Asn Ile Asp Gly Leu Glu Pro Ala Ser Pro Ile Tyr Asn Phe Arg
645 650 655

Tyr Pro Asn Met Leu Arg Leu Arg Tyr Glu Lys Lys Arg Asn Leu Pro
660 665 670

Arg Ala Leu Leu Ala Val Gly Asp Ala Tyr Thr Ser Ala Asp Pro Val
675 680 685

Ser Gly Leu Gly Met Ser Leu Ala Leu Lys Glu Val Arg Glu Met Gln
690 695 700

Ala Leu Leu Ala Lys Tyr Gly Ala Gly His Arg Asp Leu Pro Arg Arg
705 710 715 720

Tyr Tyr Arg Ala Ile Ala Lys Met Ala Asp Thr Ala Trp Phe Val Ile
725 730 735

Arg Glu Gln Asn Leu Arg Phe Asp Trp Met Lys Asp Val Asp Lys Lys
740 745 750

Arg Pro Phe Tyr Phe Gly Val Leu Thr Trp Tyr Met Asp Arg Val Leu
755 760 765

Glu Leu Val His Asp Asp Leu Asp Ala Tyr Arg Glu Phe Leu Ala Val
770 775 780

Val His Leu Val Lys Pro Pro Ser Ala Leu Met Arg Pro Arg Ile Ala
785 790 795 800

```
Ser Arg Val Leu Gly Lys Trp Ala Arg Thr Arg Leu Ser Gly Gln Lys
                805                 810                 815

Thr Leu Ile Ala Arg Asn Tyr Glu Asn His Pro Ile Pro Ala Glu Pro
            820                 825                 830

Ala Asp Gln Leu Val Asn Ala
        835


<210> SEQ ID NO 7
<211> LENGTH: 1185
<212> TYPE: DNA
<213> ORGANISM: Mycobacterium tuberculosis

<400> SEQUENCE: 7

atgaccacaa cgactacaac gatttctggg gggatattac ccaaggaata ccaagatctt      60

cgggatacgg tggccgattt tgcgcgcacc gtggtcgcgc cggtatcggc caaacacgat     120

gcggaacaca gcttcccata cgaaattgtc gccaagatgg gagagatggg cctgttcggg     180

ctgccgtttc cggaggagta cggcggcatg ggcggcgact acttcgcgct gtcgctggta     240

cttgaggagc tgggcaaggt tgaccaatcg gtagcgatca cgctggaggc cgcggtgggc     300

ctgggtgcga tgccgatcta ccggttcggt accgaggagc agaaacagaa gtggttgccc     360

gacttgacgt ctggccgtgc gctcgccggt tttggtctca ccgagccggg agcgggatcg     420

gacgcgggca gcacccgcac cacggcgcgt ctcgaaggtg acgagtggat catcaacggc     480

tccaagcaat ttatcaccaa ctcgggcacc gacatcacat cgctggtcac cgtcactgcg     540

gttaccggga ccaccggaac cgctgcggat gccaagaaag agatttcgac gatcatcgtg     600

cccagcggca caccgggatt caccgtggaa ccggtctata acaaggtcgg ctggaacgcc     660

tcggacaccc acccactgac atttgccgat gcgcgggtcc cgagggagaa cctgctggga     720

gcccggggga gcggctatgc caacttcttg tccatcctgg acgagggccg gattgcgatt     780

gcagcgctgg ccaccggcgc ggcgcagggc tgtgttgacg agagcgtcaa gtacgccaac     840

cagcgtcagt cgtttggcca gccgatcggc gcttatcagg cgatcggctt caagatcgcg     900

cggatggagg cacgcgccca tgttgcccgc acagcgtact atgatgccgc cgcaaagatg     960

ttggcgggca agcccttcaa gaaggaggcg gcgatcgcga agatgatctc ctcggaggcg    1020

gcgatggaca actcccgcga tgccacccag atacacggcg gatacggctt tatgaacgaa    1080

tatccggtgg cgcgtcatta ccgcgacagc aaggtgctcg agattggtga gggcaccacg    1140

gaagtgcagc tgatgcttat cgcgcgatcg ttgggactgc agtga                    1185


<210> SEQ ID NO 8
<211> LENGTH: 394
<212> TYPE: PRT
<213> ORGANISM: Mycobacterium tuberculosis

<400> SEQUENCE: 8

Met Thr Thr Thr Thr Thr Thr Ile Ser Gly Gly Ile Leu Pro Lys Glu
1               5                   10                  15

Tyr Gln Asp Leu Arg Asp Thr Val Ala Asp Phe Ala Arg Thr Val Val
            20                  25                  30

Ala Pro Val Ser Ala Lys His Asp Ala Glu His Ser Phe Pro Tyr Glu
        35                  40                  45

Ile Val Ala Lys Met Gly Glu Met Gly Leu Phe Gly Leu Pro Phe Pro
    50                  55                  60

Glu Glu Tyr Gly Gly Met Gly Gly Asp Tyr Phe Ala Leu Ser Leu Val
65                  70                  75                  80
```

```
Leu Glu Glu Leu Gly Lys Val Asp Gln Ser Val Ala Ile Thr Leu Glu
                85                  90                  95

Ala Ala Val Gly Leu Gly Ala Met Pro Ile Tyr Arg Phe Gly Thr Glu
            100                 105                 110

Glu Gln Lys Gln Lys Trp Leu Pro Asp Leu Thr Ser Gly Arg Ala Leu
        115                 120                 125

Ala Gly Phe Gly Leu Thr Glu Pro Gly Ala Gly Ser Asp Ala Gly Ser
    130                 135                 140

Thr Arg Thr Thr Ala Arg Leu Glu Gly Asp Glu Trp Ile Ile Asn Gly
145                 150                 155                 160

Ser Lys Gln Phe Ile Thr Asn Ser Gly Thr Asp Ile Thr Ser Leu Val
                165                 170                 175

Thr Val Thr Ala Val Thr Gly Thr Thr Gly Thr Ala Ala Asp Ala Lys
            180                 185                 190

Lys Glu Ile Ser Thr Ile Ile Val Pro Ser Gly Thr Pro Gly Phe Thr
        195                 200                 205

Val Glu Pro Val Tyr Asn Lys Val Gly Trp Asn Ala Ser Asp Thr His
    210                 215                 220

Pro Leu Thr Phe Ala Asp Ala Arg Val Pro Arg Glu Asn Leu Leu Gly
225                 230                 235                 240

Ala Arg Gly Ser Gly Tyr Ala Asn Phe Leu Ser Ile Leu Asp Glu Gly
                245                 250                 255

Arg Ile Ala Ile Ala Ala Leu Ala Thr Gly Ala Ala Gln Gly Cys Val
            260                 265                 270

Asp Glu Ser Val Lys Tyr Ala Asn Gln Arg Gln Ser Phe Gly Gln Pro
        275                 280                 285

Ile Gly Ala Tyr Gln Ala Ile Gly Phe Lys Ile Ala Arg Met Glu Ala
    290                 295                 300

Arg Ala His Val Ala Arg Thr Ala Tyr Tyr Asp Ala Ala Ala Lys Met
305                 310                 315                 320

Leu Ala Gly Lys Pro Phe Lys Lys Glu Ala Ala Ile Ala Lys Met Ile
                325                 330                 335

Ser Ser Glu Ala Ala Met Asp Asn Ser Arg Asp Ala Thr Gln Ile His
            340                 345                 350

Gly Gly Tyr Gly Phe Met Asn Glu Tyr Pro Val Ala Arg His Tyr Arg
        355                 360                 365

Asp Ser Lys Val Leu Glu Ile Gly Glu Gly Thr Thr Glu Val Gln Leu
    370                 375                 380

Met Leu Ile Ala Arg Ser Leu Gly Leu Gln
385                 390
```

<210> SEQ ID NO 9
<211> LENGTH: 747
<212> TYPE: DNA
<213> ORGANISM: Mycobacterium tuberculosis

<400> SEQUENCE: 9

```
atggacaagg tggtggccac cgccgcggag gcggtcgcag acatagccaa cgggtcgtcg      60

cttgcggttg gtggattcgg gctttgcggc atccccgaag cactgatcgc agcgttggtg     120

gatagcggtg tcaccgacct ggaaacagtc tcgaacaact gcggaatcga cggtgttggt     180

ctgggactat tgttgcaaca caagcgaatt cgccggacag tctcctccta cgtgggggag     240

aacaaggagt tcgcccgcca gttcctcgcg ggcgagctcg aggtggaact gaccccgcag     300
```

-continued ggcacgctgg ccgagcggtt gcgggccgga gggatgggca taccggcctt ctatacaccg 360
gcaggggtcg gtacccaggt cgccgacggc gggttgccgt ggcgctacga cgcctcgggc 420
ggggtggcgg tggtgtcgcc ggccaaggag actcgggagt tcgatggtgt cacctatgtc 480
ctcgagcggg ggatccggac cgacttcgca ctggtgcatg cctggcaggg ggaccggcac 540
ggcaacctga tgtaccgcca cgccgcggcc aacttcaacc cggagtgcgc atccgcaggc 600
aggatcacga tcgccgaggt cgagcacttg gtcgagccgg gtgagatcga ccctgccacc 660
gtacacaccc cgggcgtgtt tgtgcaccgg gtggttcatg tgcccaaccc cgccaagaag 720
atcgagaggg agacggtgcg gcaatga 747

<210> SEQ ID NO 10
<211> LENGTH: 248
<212> TYPE: PRT
<213> ORGANISM: Mycobacterium tuberculosis

<400> SEQUENCE: 10

Met Asp Lys Val Val Ala Thr Ala Ala Glu Ala Val Ala Asp Ile Ala
1               5                   10                  15

Asn Gly Ser Ser Leu Ala Val Gly Gly Phe Gly Leu Cys Gly Ile Pro
            20                  25                  30

Glu Ala Leu Ile Ala Ala Leu Val Asp Ser Gly Val Thr Asp Leu Glu
        35                  40                  45

Thr Val Ser Asn Asn Cys Gly Ile Asp Gly Val Gly Leu Gly Leu Leu
    50                  55                  60

Leu Gln His Lys Arg Ile Arg Arg Thr Val Ser Ser Tyr Val Gly Glu
65                  70                  75                  80

Asn Lys Glu Phe Ala Arg Gln Phe Leu Ala Gly Glu Leu Glu Val Glu
                85                  90                  95

Leu Thr Pro Gln Gly Thr Leu Ala Glu Arg Leu Arg Ala Gly Gly Met
            100                 105                 110

Gly Ile Pro Ala Phe Tyr Thr Pro Ala Gly Val Gly Thr Gln Val Ala
        115                 120                 125

Asp Gly Gly Leu Pro Trp Arg Tyr Asp Ala Ser Gly Gly Val Ala Val
    130                 135                 140

Val Ser Pro Ala Lys Glu Thr Arg Glu Phe Asp Gly Val Thr Tyr Val
145                 150                 155                 160

Leu Glu Arg Gly Ile Arg Thr Asp Phe Ala Leu Val His Ala Trp Gln
                165                 170                 175

Gly Asp Arg His Gly Asn Leu Met Tyr Arg His Ala Ala Ala Asn Phe
            180                 185                 190

Asn Pro Glu Cys Ala Ser Ala Gly Arg Ile Thr Ile Ala Glu Val Glu
        195                 200                 205

His Leu Val Glu Pro Gly Glu Ile Asp Pro Ala Thr Val His Thr Pro
    210                 215                 220

Gly Val Phe Val His Arg Val Val His Val Pro Asn Pro Ala Lys Lys
225                 230                 235                 240

Ile Glu Arg Glu Thr Val Arg Gln
                245

<210> SEQ ID NO 11
<211> LENGTH: 2157
<212> TYPE: DNA
<213> ORGANISM: Mycobacterium tuberculosis

<400> SEQUENCE: 11

-continued

```
atgaccctgg aagtggtatc ggacgcggcc ggacgcatgc gggtcaaagt cgactgggtc     60
cgttgcgatt cccggcgcgc ggtcgcggtc gaagaggccg ttgccaagca gaacggtgtg    120
cgcgtcgtgc acgcctaccc gcgcaccggg tccgtggtcg tgtggtattc acccagacgc    180
gccgaccgcg cggcggtgct ggcggcgatc aagggcgccg cgcacgtcgc cgccgaactg    240
atccccgcgc gtgcgccgca ctcggccgag atccgcaaca ccgacgtgct ccggatggtc    300
atcggcgggg tggcactggc cttgctcggg gtgcgccgct acgtgttcgc gcggccaccg    360
ctgctcggaa ccaccgggcg gacggtggcc accggtgtca ccattttcac cgggtatccg    420
ttcctgcgtg gcgcgctgcg ctcgctgcgc tccggaaagg ccggcaccga tgccctggtc    480
tccgcggcga cggtggcaag cctcatcctg cgcgagaacg tggtcgcact caccgtcctg    540
tggttgctca acatcggtga gtacctgcag gatctgacgc tgcggcggac ccggcgggcc    600
atctcggagc tgctgcgcgg caaccaggac acggcctggg tgcgcctcac cgatccttct    660
gcaggctccg acgcggccac cgaaatccag gtcccgatcg acaccgtgca gatcggtgac    720
gaggtggtgg tccacgagca cgtcgcgata ccggtcgacg gtgaggtggt cgacggcgaa    780
gcgatcgtca atcagtccgc gatcaccggg gaaaacctgc cggtcagcgt cgtggtcgga    840
acgcgcgtgc acgccggttc ggtcgtggtg cgcggacgcg tggtggtgcg cgcccacgcg    900
gtaggcaacc aaaccaccat cggtcgcatc attagcaggg tcgaagaggc tcagctcgac    960
cgggcaccca tccagacggt gggcgagaac ttctcccgcc gcttcgttcc cacctcgttc   1020
atcgtctcgg ccatcgcgtt gctgatcacc ggcgacgtgc ggcgcgcgat gaccatgttg   1080
ttgatcgcat gcccgtgcgc ggtgggactg tccaccccga ccgcgatcag cgcagcgatc   1140
ggcaacggcg cgcgccgtgg catcctgatc aagggcggat cccacctcga gcaggcgggc   1200
cgcgtcgacg ccatcgtgtt cgacaagacc gggacgttga ccgtgggccg ccccgtggtc   1260
accaatatcg ttgccatgca taaagattgg gagcccgagc aagtgctggc ctatgccgcc   1320
agctcggaga tccactcacg tcatccgctg gccgaggcgg tgatccgctc gacggaggaa   1380
cgccgcatca gcatcccacc acacgaggag tgcgaggtgc tggtcggcct gggcatgcgg   1440
acctgggccg acggtcggac cctgctgctg ggcagtccgt cgttgctgcg cgccgaaaaa   1500
gttcgggtgt ccaagaaggc gtcggagtgg gtcgacaagc tgcgccgcca ggcggagacc   1560
ccgctgctgc tcgcggtgga cggcacgctg gtcggcctga tcagcctgcg cgacgaggtg   1620
cgtccggagg cggcccaggt gctgacgaag ctgcgggcca atgggattcg ccggatcgtc   1680
atgctcaccg gcgaccaccc ggagatcgcc caggttgtcg ccgacgaact ggggattgat   1740
gagtggcgcg ccgaggtcat gccggaggac aagctcgcgg cggtgcgcga gctgcaggac   1800
gacggctacg tcgtcgggat ggtcggcgac ggcatcaacg acgccccggc gctggccgcc   1860
gccgatatcg ggatcgccat gggccttgcc ggaaccgacg tcgccgtcga gaccgccgat   1920
gtcgcgctgg ccaacgacga cctgcaccgc ctgctcgacg ttggggacct gggcgagcgg   1980
gcagtggatg taatccggca gaactacggc atgtccatcg ccgtcaacgc ggccgggctg   2040
ctgatcggcg cgggcggtgc gctctcgccg gtgctggcgg cgatcctgca caacgcgtcg   2100
tcggtggcgg tggtggccaa cagttcccgg ttgatccgct accgcctgga ccgctag      2157
```

<210> SEQ ID NO 12
<211> LENGTH: 718
<212> TYPE: PRT
<213> ORGANISM: Mycobacterium tuberculosis

<400> SEQUENCE: 12

Met Thr Leu Glu Val Val Ser Asp Ala Ala Gly Arg Met Arg Val Lys
1               5                   10                  15

Val Asp Trp Val Arg Cys Asp Ser Arg Arg Ala Val Ala Val Glu Glu
            20                  25                  30

Ala Val Ala Lys Gln Asn Gly Val Arg Val Val His Ala Tyr Pro Arg
        35                  40                  45

Thr Gly Ser Val Val Val Trp Tyr Ser Pro Arg Arg Ala Asp Arg Ala
    50                  55                  60

Ala Val Leu Ala Ala Ile Lys Gly Ala Ala His Val Ala Ala Glu Leu
65                  70                  75                  80

Ile Pro Ala Arg Ala Pro His Ser Ala Glu Ile Arg Asn Thr Asp Val
                85                  90                  95

Leu Arg Met Val Ile Gly Gly Val Ala Leu Ala Leu Leu Gly Val Arg
            100                 105                 110

Arg Tyr Val Phe Ala Arg Pro Pro Leu Leu Gly Thr Thr Gly Arg Thr
        115                 120                 125

Val Ala Thr Gly Val Thr Ile Phe Thr Gly Tyr Pro Phe Leu Arg Gly
    130                 135                 140

Ala Leu Arg Ser Leu Arg Ser Gly Lys Ala Gly Thr Asp Ala Leu Val
145                 150                 155                 160

Ser Ala Ala Thr Val Ala Ser Leu Ile Leu Arg Glu Asn Val Val Ala
                165                 170                 175

Leu Thr Val Leu Trp Leu Leu Asn Ile Gly Glu Tyr Leu Gln Asp Leu
            180                 185                 190

Thr Leu Arg Arg Thr Arg Arg Ala Ile Ser Glu Leu Leu Arg Gly Asn
        195                 200                 205

Gln Asp Thr Ala Trp Val Arg Leu Thr Asp Pro Ser Ala Gly Ser Asp
    210                 215                 220

Ala Ala Thr Glu Ile Gln Val Pro Ile Asp Thr Val Gln Ile Gly Asp
225                 230                 235                 240

Glu Val Val Val His Glu His Val Ala Ile Pro Val Asp Gly Glu Val
                245                 250                 255

Val Asp Gly Glu Ala Ile Val Asn Gln Ser Ala Ile Thr Gly Glu Asn
            260                 265                 270

Leu Pro Val Ser Val Val Val Gly Thr Arg Val His Ala Gly Ser Val
        275                 280                 285

Val Val Arg Gly Arg Val Val Val Arg Ala His Ala Val Gly Asn Gln
    290                 295                 300

Thr Thr Ile Gly Arg Ile Ile Ser Arg Val Glu Glu Ala Gln Leu Asp
305                 310                 315                 320

Arg Ala Pro Ile Gln Thr Val Gly Glu Asn Phe Ser Arg Arg Phe Val
                325                 330                 335

Pro Thr Ser Phe Ile Val Ser Ala Ile Ala Leu Leu Ile Thr Gly Asp
            340                 345                 350

Val Arg Arg Ala Met Thr Met Leu Leu Ile Ala Cys Pro Cys Ala Val
        355                 360                 365

Gly Leu Ser Thr Pro Thr Ala Ile Ser Ala Ala Ile Gly Asn Gly Ala
    370                 375                 380

Arg Arg Gly Ile Leu Ile Lys Gly Gly Ser His Leu Glu Gln Ala Gly
385                 390                 395                 400

Arg Val Asp Ala Ile Val Phe Asp Lys Thr Gly Thr Leu Thr Val Gly
                405                 410                 415

Arg Pro Val Val Thr Asn Ile Val Ala Met His Lys Asp Trp Glu Pro
420 425 430

Glu Gln Val Leu Ala Tyr Ala Ala Ser Ser Glu Ile His Ser Arg His
435 440 445

Pro Leu Ala Glu Ala Val Ile Arg Ser Thr Glu Glu Arg Arg Ile Ser
450 455 460

Ile Pro Pro His Glu Glu Cys Glu Val Leu Val Gly Leu Gly Met Arg
465 470 475 480

Thr Trp Ala Asp Gly Arg Thr Leu Leu Leu Gly Ser Pro Ser Leu Leu
485 490 495

Arg Ala Glu Lys Val Arg Val Ser Lys Lys Ala Ser Glu Trp Val Asp
500 505 510

Lys Leu Arg Arg Gln Ala Glu Thr Pro Leu Leu Leu Ala Val Asp Gly
515 520 525

Thr Leu Val Gly Leu Ile Ser Leu Arg Asp Glu Val Arg Pro Glu Ala
530 535 540

Ala Gln Val Leu Thr Lys Leu Arg Ala Asn Gly Ile Arg Arg Ile Val
545 550 555 560

Met Leu Thr Gly Asp His Pro Glu Ile Ala Gln Val Val Ala Asp Glu
565 570 575

Leu Gly Ile Asp Glu Trp Arg Ala Glu Val Met Pro Glu Asp Lys Leu
580 585 590

Ala Ala Val Arg Glu Leu Gln Asp Asp Gly Tyr Val Val Gly Met Val
595 600 605

Gly Asp Gly Ile Asn Asp Ala Pro Ala Leu Ala Ala Ala Asp Ile Gly
610 615 620

Ile Ala Met Gly Leu Ala Gly Thr Asp Val Ala Val Glu Thr Ala Asp
625 630 635 640

Val Ala Leu Ala Asn Asp Asp Leu His Arg Leu Leu Asp Val Gly Asp
645 650 655

Leu Gly Glu Arg Ala Val Asp Val Ile Arg Gln Asn Tyr Gly Met Ser
660 665 670

Ile Ala Val Asn Ala Ala Gly Leu Leu Ile Gly Ala Gly Gly Ala Leu
675 680 685

Ser Pro Val Leu Ala Ala Ile Leu His Asn Ala Ser Ser Val Ala Val
690 695 700

Val Ala Asn Ser Ser Arg Leu Ile Arg Tyr Arg Leu Asp Arg
705 710 715

<210> SEQ ID NO 13
<211> LENGTH: 1692
<212> TYPE: DNA
<213> ORGANISM: Mycobacterium tuberculosis

<400> SEQUENCE: 13
atgactgtgc aggagttcga cgtcgtggtg gtcggcagcg gcgccgccgg catggttgct 60
gcgctggtcg ccgctcaccg aggtctctcg acggtagtcg tcgagaaggc cccgcactac 120
ggcggctcca ccgcacgctc gggcggcggc gtctggatcc ccaacaacga ggtcctcaag 180
cgccgcggcg ttcgagatac accggaggcg gcacgcacct atctgcacgg catcgtcggc 240
gaaatcgtcg agccggaacg catcgatgct tacctcgacc gcgggcccga gatgctgtcg 300
ttcgtgctga agcacacgcc gctgaagatg tgctgggtac ccggctactc cgactactac 360
cccgaggctc cgggcggccg cccgggcgga cgttcgatcg agccgaaacc gttcaacgcg 420

```
cgcaagcttg gtgccgacat ggccgggctg gagcccgcgt atggcaaggt tccgctcaat    480

gtggttgtga tgcagcagga ctacgttcgc ctcaatcagc tcaaacgtca cccccgtggc    540

gtgctgcgca gcatgaaggt cggcgcccgc acgatgtggg cgaaggcaac aggtaagaac    600

ctggtcggca tgggtcgagc cctcattggg ccgttgcgga tcgggttgca gcgcgccgga    660

gtgccggtcg aactcaacac cgccttcacc gatcttttcg tcgaaaatgg cgtcgtgtcc    720

ggggtatacg tccgcgattc ccacgaggcg gaatccgctg agccgcagct gatccgggct    780

cgccgcggcg tgatcctggc ctgtggtggt ttcgagcata acgagcagat gcgaatcaag    840

taccagcggg cacccatcac caccgagtgg accgtgggcg ccagcgccaa taccggtgac    900

ggcattctcg ccgccgaaaa gctcggcgca gcactggatc tgatggatga cgcttggtgg    960

ggcccgacgg taccgctggt cggcaaacca tggttcgcgc tctcggagcg caactctccc   1020

ggttcgatca tcgtcaacat gtcaggcaag cgattcatga acgaatcgat gccatacgtc   1080

gaagcctgtc atcatatgta cggcggcgaa cacggccagg ggcccggacc gggcgagaac   1140

attccggcgt ggctggtgtt cgaccagcga taccgggacc gctacatctt cgcgggacta   1200

caaccagggc aacgcattcc gagcaggtgg ctggattccg gcgtcatcgt ccaggccgat   1260

acccttgcgg agctggccgg caaggccggt ctacccgcgg acgaactcac tgccaccgtc   1320

cagcgtttca acgcattcgc ccggtccggt gtcgacgagg actaccaccg cggggaaagt   1380

gcctacgatc gctactacgg cgacccgagc aacaagccca atccgaacct cggcgaggtc   1440

ggccacccgc cctattatgg cgccaagatg gttccgggcg acctggggac caagggcggt   1500

atccgcaccg atgtcaacgg acgtgctctg cgggacgacg gcagcatcat cgacggcctt   1560

tacgctgcag gcaatgtcag tgccccagtg atgggacaca cctaccccgg tccgggcggc   1620

acgataggcc cggcgatgac gttcgggtac ctggcggcgc tgcacattgc cgatcaggcg   1680

ggaaagcgct ga                                                       1692
```

<210> SEQ ID NO 14
<211> LENGTH: 563
<212> TYPE: PRT
<213> ORGANISM: Mycobacterium tuberculosis

<400> SEQUENCE: 14

```
Met Thr Val Gln Glu Phe Asp Val Val Val Val Gly Ser Gly Ala Ala
1               5                   10                  15

Gly Met Val Ala Ala Leu Val Ala Ala His Arg Gly Leu Ser Thr Val
            20                  25                  30

Val Val Glu Lys Ala Pro His Tyr Gly Gly Ser Thr Ala Arg Ser Gly
        35                  40                  45

Gly Gly Val Trp Ile Pro Asn Asn Glu Val Leu Lys Arg Arg Gly Val
    50                  55                  60

Arg Asp Thr Pro Glu Ala Ala Arg Thr Tyr Leu His Gly Ile Val Gly
65                  70                  75                  80

Glu Ile Val Glu Pro Glu Arg Ile Asp Ala Tyr Leu Asp Arg Gly Pro
                85                  90                  95

Glu Met Leu Ser Phe Val Leu Lys His Thr Pro Leu Lys Met Cys Trp
            100                 105                 110

Val Pro Gly Tyr Ser Asp Tyr Tyr Pro Glu Ala Pro Gly Gly Arg Pro
        115                 120                 125

Gly Gly Arg Ser Ile Glu Pro Lys Pro Phe Asn Ala Arg Lys Leu Gly
    130                 135                 140
```

-continued

```
Ala Asp Met Ala Gly Leu Glu Pro Ala Tyr Gly Lys Val Pro Leu Asn
145                 150                 155                 160

Val Val Val Met Gln Gln Asp Tyr Val Arg Leu Asn Gln Leu Lys Arg
                165                 170                 175

His Pro Arg Gly Val Leu Arg Ser Met Lys Val Gly Ala Arg Thr Met
            180                 185                 190

Trp Ala Lys Ala Thr Gly Lys Asn Leu Val Gly Met Gly Arg Ala Leu
        195                 200                 205

Ile Gly Pro Leu Arg Ile Gly Leu Gln Arg Ala Gly Val Pro Val Glu
    210                 215                 220

Leu Asn Thr Ala Phe Thr Asp Leu Phe Val Glu Asn Gly Val Val Ser
225                 230                 235                 240

Gly Val Tyr Val Arg Asp Ser His Glu Ala Glu Ser Ala Glu Pro Gln
                245                 250                 255

Leu Ile Arg Ala Arg Arg Gly Val Ile Leu Ala Cys Gly Gly Phe Glu
            260                 265                 270

His Asn Glu Gln Met Arg Ile Lys Tyr Gln Arg Ala Pro Ile Thr Thr
        275                 280                 285

Glu Trp Thr Val Gly Ala Ser Ala Asn Thr Gly Asp Gly Ile Leu Ala
    290                 295                 300

Ala Glu Lys Leu Gly Ala Ala Leu Asp Leu Met Asp Asp Ala Trp Trp
305                 310                 315                 320

Gly Pro Thr Val Pro Leu Val Gly Lys Pro Trp Phe Ala Leu Ser Glu
                325                 330                 335

Arg Asn Ser Pro Gly Ser Ile Ile Val Asn Met Ser Gly Lys Arg Phe
            340                 345                 350

Met Asn Glu Ser Met Pro Tyr Val Glu Ala Cys His His Met Tyr Gly
        355                 360                 365

Gly Glu His Gly Gln Gly Pro Gly Pro Gly Glu Asn Ile Pro Ala Trp
    370                 375                 380

Leu Val Phe Asp Gln Arg Tyr Arg Asp Arg Tyr Ile Phe Ala Gly Leu
385                 390                 395                 400

Gln Pro Gly Gln Arg Ile Pro Ser Arg Trp Leu Asp Ser Gly Val Ile
                405                 410                 415

Val Gln Ala Asp Thr Leu Ala Glu Leu Ala Gly Lys Ala Gly Leu Pro
            420                 425                 430

Ala Asp Glu Leu Thr Ala Thr Val Gln Arg Phe Asn Ala Phe Ala Arg
        435                 440                 445

Ser Gly Val Asp Glu Asp Tyr His Arg Gly Glu Ser Ala Tyr Asp Arg
    450                 455                 460

Tyr Tyr Gly Asp Pro Ser Asn Lys Pro Asn Pro Asn Leu Gly Glu Val
465                 470                 475                 480

Gly His Pro Pro Tyr Tyr Gly Ala Lys Met Val Pro Gly Asp Leu Gly
                485                 490                 495

Thr Lys Gly Gly Ile Arg Thr Asp Val Asn Gly Arg Ala Leu Arg Asp
            500                 505                 510

Asp Gly Ser Ile Ile Asp Gly Leu Tyr Ala Ala Gly Asn Val Ser Ala
        515                 520                 525

Pro Val Met Gly His Thr Tyr Pro Gly Pro Gly Gly Thr Ile Gly Pro
    530                 535                 540

Ala Met Thr Phe Gly Tyr Leu Ala Ala Leu His Ile Ala Asp Gln Ala
545                 550                 555                 560
```

Gly Lys Arg

<210> SEQ ID NO 15
<211> LENGTH: 843
<212> TYPE: DNA
<213> ORGANISM: Mycobacterium tuberculosis

<400> SEQUENCE: 15

```
gtgagtccgg cgcccgtgca ggtgatgggg gttctaaacg tcacggacga ctctttctcg     60

gacggcgggt gttatctcga tctcgacgat gcggtgaagc acggtctggc gatggcagcc    120

gcaggtgcgg gcatcgtcga cgtcggtggt gagtcgagcc ggcccggtgc cactcgggtt    180

gacccggcgg tggagacgtc tcgtgtcata cccgtcgtca aagagcttgc agcacaaggc    240

atcaccgtca gcatcgatac catgcgcgcg gatgtcgctc gggcggcgtt gcagaacggt    300

gcccagatgg tcaacgacgt gtcgggtggg cgggccgatc cggcgatggg gccgctgttg    360

gccgaggccg atgtgccgtg ggtgttgatg cactggcggg cggtatcggc cgataccccg    420

catgtgcctg tgcgctacgg caacgtggtg gccgaggtcc gtgccgacct gctggccagc    480

gtcgccgacg cggtggccgc aggcgtcgac ccggcaaggc tggtgctcga tcccgggctt    540

ggattcgcca agacggcgca acataattgg gcgatcttgc atgcccttcc ggaactggtc    600

gcgaccggaa tcccagtgct ggtgggtgct tcgcgcaagc gcttcctcgg tgcgttgttg    660

gccgggcccg acggcgtgat gcggccaacc gatgggcgtg acaccgcgac ggcggtgatt    720

tccgcgctgg ccgcactgca cggggcctgg ggtgtgcggg tgcatgatgt gcgggcctcg    780

gtcgatgcca tcaaggtggt cgaagcgtgg atgggagcgg aaaggataga acgcgatggc    840

tga                                                                   843
```

<210> SEQ ID NO 16
<211> LENGTH: 280
<212> TYPE: PRT
<213> ORGANISM: Mycobacterium tuberculosis

<400> SEQUENCE: 16

```
Val Ser Pro Ala Pro Val Gln Val Met Gly Val Leu Asn Val Thr Asp
1               5                   10                  15

Asp Ser Phe Ser Asp Gly Gly Cys Tyr Leu Asp Leu Asp Asp Ala Val
            20                  25                  30

Lys His Gly Leu Ala Met Ala Ala Ala Gly Ala Gly Ile Val Asp Val
        35                  40                  45

Gly Gly Glu Ser Ser Arg Pro Gly Ala Thr Arg Val Asp Pro Ala Val
    50                  55                  60

Glu Thr Ser Arg Val Ile Pro Val Val Lys Glu Leu Ala Ala Gln Gly
65                  70                  75                  80

Ile Thr Val Ser Ile Asp Thr Met Arg Ala Asp Val Ala Arg Ala Ala
                85                  90                  95

Leu Gln Asn Gly Ala Gln Met Val Asn Asp Val Ser Gly Gly Arg Ala
            100                 105                 110

Asp Pro Ala Met Gly Pro Leu Leu Ala Glu Ala Asp Val Pro Trp Val
        115                 120                 125

Leu Met His Trp Arg Ala Val Ser Ala Asp Thr Pro His Val Pro Val
    130                 135                 140

Arg Tyr Gly Asn Val Val Ala Glu Val Arg Ala Asp Leu Leu Ala Ser
145                 150                 155                 160

Val Ala Asp Ala Val Ala Ala Gly Val Asp Pro Ala Arg Leu Val Leu
```

```
                165                 170                 175

Asp Pro Gly Leu Gly Phe Ala Lys Thr Ala Gln His Asn Trp Ala Ile
            180                 185                 190

Leu His Ala Leu Pro Glu Leu Val Ala Thr Gly Ile Pro Val Leu Val
        195                 200                 205

Gly Ala Ser Arg Lys Arg Phe Leu Gly Ala Leu Leu Ala Gly Pro Asp
    210                 215                 220

Gly Val Met Arg Pro Thr Asp Gly Arg Asp Thr Ala Thr Ala Val Ile
225                 230                 235                 240

Ser Ala Leu Ala Ala Leu His Gly Ala Trp Gly Val Arg Val His Asp
                245                 250                 255

Val Arg Ala Ser Val Asp Ala Ile Lys Val Val Glu Ala Trp Met Gly
            260                 265                 270

Ala Glu Arg Ile Glu Arg Asp Gly
        275                 280


<210> SEQ ID NO 17
<211> LENGTH: 2190
<212> TYPE: DNA
<213> ORGANISM: Mycobacterium tuberculosis

<400> SEQUENCE: 17

atgagtatta ccaggccgac gggcagctat gccagacaga tgctggatcc gggcggctgg     60

gtggaagccg atgaagacac tttctatgac cgggcccagg aatatagcca ggttttgcaa    120

agggtcaccg atgtattgga cacctgccgc cagcagaaag gccacgtctt cgaaggcggc    180

ctatggtccg gcggcgccgc caatgctgcc aacggcgccc tgggtgcaaa catcaatcaa    240

ttgatgacgc tgcaggatta tctcgccacg gtgattacct ggcacaggca tattgccggg    300

ttgattgagc aagctaaatc cgatatcggc aataatgtgg atggcgctca acgggagatc    360

gatatcctgg agaatgaccc tagcctggat gctgatgagc gccataccgc catcaattca    420

ttggtcacgg cgacgcatgg ggccaatgtc agtctggtcg ccgagaccgc tgagcgggtg    480

ctggaatcca agaattggaa acctccgaag aacgcactcg aggatttgct tcagcagaag    540

tcgccgccac ccccagacgt gcctaccctg gtcgtgccat ccccgggcac accgggcaca    600

ccgggaaccc cgatcacccc gggaaccccg atcaccccgg gaaccccaat cacacccatc    660

ccgggagcgc cggtaactcc gatcacacca acgcccggca ctcccgtcac gccggtgacc    720

ccgggcaagc cggtcacccc ggtgaccccg gtcaaaccgg gcacaccagg cgagccaacc    780

ccgatcacgc cggtcacccc cccggtcgcc ccggccacac cggcaacccc ggccacgccc    840

gttaccccag ctcccgctcc acacccgcag ccggctccgg caccggcgcc atcgcctggg    900

ccccagccgg ttacaccggc cactcccggt ccgtctggtc cagcaacacc gggcacccca    960

gggggcgagc cggcgccgca cgtcaaaccc gcggcgttgg cggagcaacc tggtgtgccg   1020

ggccagcatg cgggcggggg gacgcagtcg gggcctgccc atgcggacga atccgccgcg   1080

tcggtgacgc cggctgcggc gtccggtgtc ccgggcgcac gggcggcggc cgccgcgccg   1140

agcggtaccg ccgtgggagc gggcgcgcgt tcgagcgtgg gtacggccgc ggcctcgggc   1200

gcggggtcgc atgctgccac tgggcgggcg ccggtggcta cctcggacaa ggcggcggca   1260

ccgagcacgc gggcggcctc ggcgcggacg gcacctcctg cccgcccgcc gtcgaccgat   1320

cacatcgaca aacccgatcg cagcgagtct gcagatgacg gtacgccggt gtcgatgatc   1380

ccggtgtcgg cggctcgggc ggcacgcgac gccgccactg cagctgccag cgcccgccag   1440
```

-continued

```
cgtggccgcg gtgatgcgct gcggttggcg cgacgcatcg cggcggcgct caacgcgtcc   1500

gacaacaacg cgggcgacta cgggttcttc tggatcaccg cggtgaccac cgacggttcc   1560

atcgtcgtgg ccaacagcta tggctggcc tacatacccg acgggatgga attgccgaat   1620

aaggtgtact tggccagcgc ggatcacgca atcccggttg acgaaattgc acgctgtgcc   1680

acctacccgg ttttggccgt gcaagcctgg gcggctttcc acgacatgac gctgcgggcg   1740

gtgatcggta ccgcggagca gttggccagt tcggatcccg gtgtggccaa gattgtgctg   1800

gagccagatg acattccgga gagcggcaaa atgacgggcc ggtcgcggct ggaggtcgtc   1860

gacccctcgg cggcggctca gctggccgac actaccgatc agcgtttgct cgacttgttg   1920

ccgccggcgc cggtggatgt caatccaccg ggcgatgagc ggcacatgct gtggttcgag   1980

ctgatgaagc ccatgaccag caccgctacc ggccgcgagg ccgctcatct gcgggcgttc   2040

cgggcctacg ctgcccactc acaggagatt gccctgcacc aagcgcacac tgcgactgac   2100

gcggccgtcc agcgtgtggc cgtcgcggac tggctgtact ggcaatacgt caccgggttg   2160

ctcgaccggg ccctggccgc cgcatgctga                                    2190
```

<210> SEQ ID NO 18
<211> LENGTH: 729
<212> TYPE: PRT
<213> ORGANISM: Mycobacterium tuberculosis

<400> SEQUENCE: 18

```
Met Ser Ile Thr Arg Pro Thr Gly Ser Tyr Ala Arg Gln Met Leu Asp
1               5                   10                  15

Pro Gly Gly Trp Val Glu Ala Asp Glu Asp Thr Phe Tyr Asp Arg Ala
            20                  25                  30

Gln Glu Tyr Ser Gln Val Leu Gln Arg Val Thr Asp Val Leu Asp Thr
        35                  40                  45

Cys Arg Gln Gln Lys Gly His Val Phe Glu Gly Gly Leu Trp Ser Gly
    50                  55                  60

Gly Ala Ala Asn Ala Ala Asn Gly Ala Leu Gly Ala Asn Ile Asn Gln
65                  70                  75                  80

Leu Met Thr Leu Gln Asp Tyr Leu Ala Thr Val Ile Thr Trp His Arg
                85                  90                  95

His Ile Ala Gly Leu Ile Glu Gln Ala Lys Ser Asp Ile Gly Asn Asn
            100                 105                 110

Val Asp Gly Ala Gln Arg Glu Ile Asp Ile Leu Glu Asn Asp Pro Ser
        115                 120                 125

Leu Asp Ala Asp Glu Arg His Thr Ala Ile Asn Ser Leu Val Thr Ala
    130                 135                 140

Thr His Gly Ala Asn Val Ser Leu Val Ala Glu Thr Ala Glu Arg Val
145                 150                 155                 160

Leu Glu Ser Lys Asn Trp Lys Pro Pro Lys Asn Ala Leu Glu Asp Leu
                165                 170                 175

Leu Gln Gln Lys Ser Pro Pro Pro Pro Asp Val Pro Thr Leu Val Val
            180                 185                 190

Pro Ser Pro Gly Thr Pro Gly Thr Pro Gly Thr Pro Ile Thr Pro Gly
        195                 200                 205

Thr Pro Ile Thr Pro Gly Thr Pro Ile Thr Pro Ile Pro Gly Ala Pro
    210                 215                 220

Val Thr Pro Ile Thr Pro Thr Pro Gly Thr Pro Val Thr Pro Val Thr
225                 230                 235                 240
```

-continued

```
Pro Gly Lys Pro Val Thr Pro Val Thr Pro Val Lys Pro Gly Thr Pro
                245                 250                 255

Gly Glu Pro Thr Pro Ile Thr Pro Val Thr Pro Pro Val Ala Pro Ala
            260                 265                 270

Thr Pro Ala Thr Pro Ala Thr Pro Val Thr Pro Ala Pro Ala Pro His
        275                 280                 285

Pro Gln Pro Ala Pro Ala Pro Ala Pro Ser Pro Gly Pro Gln Pro Val
    290                 295                 300

Thr Pro Ala Thr Pro Gly Pro Ser Gly Pro Ala Thr Pro Gly Thr Pro
305                 310                 315                 320

Gly Gly Glu Pro Ala Pro His Val Lys Pro Ala Ala Leu Ala Glu Gln
                325                 330                 335

Pro Gly Val Pro Gly Gln His Ala Gly Gly Gly Thr Gln Ser Gly Pro
            340                 345                 350

Ala His Ala Asp Glu Ser Ala Ala Ser Val Thr Pro Ala Ala Ala Ser
        355                 360                 365

Gly Val Pro Gly Ala Arg Ala Ala Ala Ala Ala Pro Ser Gly Thr Ala
    370                 375                 380

Val Gly Ala Gly Ala Arg Ser Ser Val Gly Thr Ala Ala Ala Ser Gly
385                 390                 395                 400

Ala Gly Ser His Ala Ala Thr Gly Arg Ala Pro Val Ala Thr Ser Asp
                405                 410                 415

Lys Ala Ala Ala Pro Ser Thr Arg Ala Ala Ser Ala Arg Thr Ala Pro
            420                 425                 430

Pro Ala Arg Pro Pro Ser Thr Asp His Ile Asp Lys Pro Asp Arg Ser
        435                 440                 445

Glu Ser Ala Asp Asp Gly Thr Pro Val Ser Met Ile Pro Val Ser Ala
    450                 455                 460

Ala Arg Ala Ala Arg Asp Ala Ala Thr Ala Ala Ala Ser Ala Arg Gln
465                 470                 475                 480

Arg Gly Arg Gly Asp Ala Leu Arg Leu Ala Arg Arg Ile Ala Ala Ala
                485                 490                 495

Leu Asn Ala Ser Asp Asn Asn Ala Gly Asp Tyr Gly Phe Phe Trp Ile
            500                 505                 510

Thr Ala Val Thr Thr Asp Gly Ser Ile Val Val Ala Asn Ser Tyr Gly
        515                 520                 525

Leu Ala Tyr Ile Pro Asp Gly Met Glu Leu Pro Asn Lys Val Tyr Leu
    530                 535                 540

Ala Ser Ala Asp His Ala Ile Pro Val Asp Glu Ile Ala Arg Cys Ala
545                 550                 555                 560

Thr Tyr Pro Val Leu Ala Val Gln Ala Trp Ala Ala Phe His Asp Met
                565                 570                 575

Thr Leu Arg Ala Val Ile Gly Thr Ala Glu Gln Leu Ala Ser Ser Asp
            580                 585                 590

Pro Gly Val Ala Lys Ile Val Leu Glu Pro Asp Asp Ile Pro Glu Ser
        595                 600                 605

Gly Lys Met Thr Gly Arg Ser Arg Leu Glu Val Val Asp Pro Ser Ala
    610                 615                 620

Ala Ala Gln Leu Ala Asp Thr Thr Asp Gln Arg Leu Leu Asp Leu Leu
625                 630                 635                 640

Pro Pro Ala Pro Val Asp Val Asn Pro Pro Gly Asp Glu Arg His Met
                645                 650                 655

Leu Trp Phe Glu Leu Met Lys Pro Met Thr Ser Thr Ala Thr Gly Arg
```

```
            660                 665                 670

Glu Ala Ala His Leu Arg Ala Phe Arg Ala Tyr Ala Ala His Ser Gln
        675                 680                 685

Glu Ile Ala Leu His Gln Ala His Thr Ala Thr Asp Ala Ala Val Gln
    690                 695                 700

Arg Val Ala Val Ala Asp Trp Leu Tyr Trp Gln Tyr Val Thr Gly Leu
705                 710                 715                 720

Leu Asp Arg Ala Leu Ala Ala Ala Cys
                725


<210> SEQ ID NO 19
<211> LENGTH: 338
<212> TYPE: PRT
<213> ORGANISM: Mycobacterium tuberculosis

<400> SEQUENCE: 19

Met Gln Leu Val Asp Arg Val Arg Gly Ala Val Thr Gly Met Ser Arg
1               5                   10                  15

Arg Leu Val Val Gly Ala Val Gly Ala Ala Leu Val Ser Gly Leu Val
            20                  25                  30

Gly Ala Val Gly Gly Thr Ala Thr Ala Gly Ala Phe Ser Arg Pro Gly
        35                  40                  45

Leu Pro Val Glu Tyr Leu Gln Val Pro Ser Pro Ser Met Gly Arg Asp
    50                  55                  60

Ile Lys Val Gln Phe Gln Ser Gly Gly Ala Asn Ser Pro Ala Leu Tyr
65                  70                  75                  80

Leu Leu Asp Gly Leu Arg Ala Gln Asp Asp Phe Ser Gly Trp Asp Ile
                85                  90                  95

Asn Thr Pro Ala Phe Glu Trp Tyr Asp Gln Ser Gly Leu Ser Val Val
            100                 105                 110

Met Pro Val Gly Gly Gln Ser Ser Phe Tyr Ser Asp Trp Tyr Gln Pro
        115                 120                 125

Ala Cys Gly Lys Ala Gly Cys Gln Thr Tyr Lys Trp Glu Thr Phe Leu
    130                 135                 140

Thr Ser Glu Leu Pro Gly Trp Leu Gln Ala Asn Arg His Val Lys Pro
145                 150                 155                 160

Thr Gly Ser Ala Val Val Gly Leu Ser Met Ala Ala Ser Ser Ala Leu
                165                 170                 175

Thr Leu Ala Ile Tyr His Pro Gln Gln Phe Val Tyr Ala Gly Ala Met
            180                 185                 190

Ser Gly Leu Leu Asp Pro Ser Gln Ala Met Gly Pro Thr Leu Ile Gly
        195                 200                 205

Leu Ala Met Gly Asp Ala Gly Gly Tyr Lys Ala Ser Asp Met Trp Gly
    210                 215                 220

Pro Lys Glu Asp Pro Ala Trp Gln Arg Asn Asp Pro Leu Leu Asn Val
225                 230                 235                 240

Gly Lys Leu Ile Ala Asn Asn Thr Arg Val Trp Val Tyr Cys Gly Asn
                245                 250                 255

Gly Lys Pro Ser Asp Leu Gly Gly Asn Asn Leu Pro Ala Lys Phe Leu
            260                 265                 270

Glu Gly Phe Val Arg Thr Ser Asn Ile Lys Phe Gln Asp Ala Tyr Asn
        275                 280                 285

Ala Gly Gly Gly His Asn Gly Val Phe Asp Phe Pro Asp Ser Gly Thr
    290                 295                 300
```

His Ser Trp Glu Tyr Trp Gly Ala Gln Leu Asn Ala Met Lys Pro Asp
305 310 315 320

Leu Gln Arg Ala Leu Gly Ala Thr Pro Asn Thr Gly Pro Ala Pro Gln
325 330 335

Gly Ala

<210> SEQ ID NO 20
<211> LENGTH: 325
<212> TYPE: PRT
<213> ORGANISM: Mycobacterium tuberculosis

<400> SEQUENCE: 20

Met Thr Asp Val Ser Arg Lys Ile Arg Ala Trp Gly Arg Arg Leu Met
1 5 10 15

Ile Gly Thr Ala Ala Ala Val Val Leu Pro Gly Leu Val Gly Leu Ala
20 25 30

Gly Gly Ala Ala Thr Ala Gly Ala Phe Ser Arg Pro Gly Leu Pro Val
35 40 45

Glu Tyr Leu Gln Val Pro Ser Pro Ser Met Gly Arg Asp Ile Lys Val
50 55 60

Gln Phe Gln Ser Gly Gly Asn Asn Ser Pro Ala Val Tyr Leu Leu Asp
65 70 75 80

Gly Leu Arg Ala Gln Asp Asp Tyr Asn Gly Trp Asp Ile Asn Thr Pro
85 90 95

Ala Phe Glu Trp Tyr Tyr Gln Ser Gly Leu Ser Ile Val Met Pro Val
100 105 110

Gly Gly Gln Ser Ser Phe Tyr Ser Asp Trp Tyr Ser Pro Ala Cys Gly
115 120 125

Lys Ala Gly Cys Gln Thr Tyr Lys Trp Glu Thr Phe Leu Thr Ser Glu
130 135 140

Leu Pro Gln Trp Leu Ser Ala Asn Arg Ala Val Lys Pro Thr Gly Ser
145 150 155 160

Ala Ala Ile Gly Leu Ser Met Ala Gly Ser Ser Ala Met Ile Leu Ala
165 170 175

Ala Tyr His Pro Gln Gln Phe Ile Tyr Ala Gly Ser Leu Ser Ala Leu
180 185 190

Leu Asp Pro Ser Gln Gly Met Gly Pro Ser Leu Ile Gly Leu Ala Met
195 200 205

Gly Asp Ala Gly Gly Tyr Lys Ala Ala Asp Met Trp Gly Pro Ser Ser
210 215 220

Asp Pro Ala Trp Glu Arg Asn Asp Pro Thr Gln Gln Ile Pro Lys Leu
225 230 235 240

Val Ala Asn Asn Thr Arg Leu Trp Val Tyr Cys Gly Asn Gly Thr Pro
245 250 255

Asn Glu Leu Gly Gly Ala Asn Ile Pro Ala Glu Phe Leu Glu Asn Phe
260 265 270

Val Arg Ser Ser Asn Leu Lys Phe Gln Asp Ala Tyr Asn Ala Ala Gly
275 280 285

Gly His Asn Ala Val Phe Asn Phe Pro Pro Asn Gly Thr His Ser Trp
290 295 300

Glu Tyr Trp Gly Ala Gln Leu Asn Ala Met Lys Gly Asp Leu Gln Ser
305 310 315 320

Ser Leu Gly Ala Gly
325

<210> SEQ ID NO 21
<211> LENGTH: 95
<212> TYPE: PRT
<213> ORGANISM: Mycobacterium tuberculosis

<400> SEQUENCE: 21

Met Thr Glu Gln Gln Trp Asn Phe Ala Gly Ile Glu Ala Ala Ala Ser
1 5 10 15

Ala Ile Gln Gly Asn Val Thr Ser Ile His Ser Leu Leu Asp Glu Gly
20 25 30

Lys Gln Ser Leu Thr Lys Leu Ala Ala Ala Trp Gly Gly Ser Gly Ser
35 40 45

Glu Ala Tyr Gln Gly Val Gln Gln Lys Trp Asp Ala Thr Ala Thr Glu
50 55 60

Leu Asn Asn Ala Leu Gln Asn Leu Ala Arg Thr Ile Ser Glu Ala Gly
65 70 75 80

Gln Ala Met Ala Ser Thr Glu Gly Asn Val Thr Gly Met Phe Ala
85 90 95

<210> SEQ ID NO 22
<211> LENGTH: 96
<212> TYPE: PRT
<213> ORGANISM: Mycobacterium tuberculosis

<400> SEQUENCE: 22

Met Ser Gln Ile Met Tyr Asn Tyr Pro Ala Met Leu Gly His Ala Gly
1 5 10 15

Asp Met Ala Gly Tyr Ala Gly Thr Leu Gln Ser Leu Gly Ala Glu Ile
20 25 30

Ala Val Glu Gln Ala Ala Leu Gln Ser Ala Trp Gln Gly Asp Thr Gly
35 40 45

Ile Thr Tyr Gln Ala Trp Gln Ala Gln Trp Asn Gln Ala Met Glu Asp
50 55 60

Leu Val Arg Ala Tyr His Ala Met Ser Ser Thr His Glu Ala Asn Thr
65 70 75 80

Met Ala Met Met Ala Arg Asp Thr Ala Glu Ala Ala Lys Trp Gly Gly
85 90 95

<210> SEQ ID NO 23
<211> LENGTH: 355
<212> TYPE: PRT
<213> ORGANISM: Mycobacterium tuberculosis

<400> SEQUENCE: 23

Met Ser Asn Ser Arg Arg Arg Ser Leu Arg Trp Ser Trp Leu Leu Ser
1 5 10 15

Val Leu Ala Ala Val Gly Leu Gly Leu Ala Thr Ala Pro Ala Gln Ala
20 25 30

Ala Pro Pro Ala Leu Ser Gln Asp Arg Phe Ala Asp Phe Pro Ala Leu
35 40 45

Pro Leu Asp Pro Ser Ala Met Val Ala Gln Val Gly Pro Gln Val Val
50 55 60

Asn Ile Asn Thr Lys Leu Gly Tyr Asn Asn Ala Val Gly Ala Gly Thr
65 70 75 80

Gly Ile Val Ile Asp Pro Asn Gly Val Val Leu Thr Asn Asn His Val
85 90 95

Ile Ala Gly Ala Thr Asp Ile Asn Ala Phe Ser Val Gly Ser Gly Gln

```
            100                 105                 110

Thr Tyr Gly Val Asp Val Val Gly Tyr Asp Arg Thr Gln Asp Val Ala
        115                 120                 125

Val Leu Gln Leu Arg Gly Ala Gly Gly Leu Pro Ser Ala Ala Ile Gly
    130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
                165                 170                 175

Gly Gln Thr Val Gln Ala Ser Asp Ser Leu Thr Gly Ala Glu Glu Thr
            180                 185                 190

Leu Asn Gly Leu Ile Gln Phe Asp Ala Ala Ile Gln Pro Gly Asp Ser
        195                 200                 205

Gly Gly Pro Val Val Asn Gly Leu Gly Gln Val Val Gly Met Asn Thr
    210                 215                 220

Ala Ala Ser Asp Asn Phe Gln Leu Ser Gln Gly Gly Gln Gly Phe Ala
225                 230                 235                 240

Ile Pro Ile Gly Gln Ala Met Ala Ile Ala Gly Gln Ile Arg Ser Gly
                245                 250                 255

Gly Gly Ser Pro Thr Val His Ile Gly Pro Thr Ala Phe Leu Gly Leu
            260                 265                 270

Gly Val Val Asp Asn Asn Gly Asn Gly Ala Arg Val Gln Arg Val Val
        275                 280                 285

Gly Ser Ala Pro Ala Ala Ser Leu Gly Ile Ser Thr Gly Asp Val Ile
    290                 295                 300

Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Thr Trp Gln
                325                 330                 335

Thr Lys Ser Gly Gly Thr Arg Thr Gly Asn Val Thr Leu Ala Glu Gly
            340                 345                 350

Pro Pro Ala
        355


<210> SEQ ID NO 24
<211> LENGTH: 391
<212> TYPE: PRT
<213> ORGANISM: Mycobacterium tuberculosis

<400> SEQUENCE: 24

Met Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Ala Gln Met Trp
            20                  25                  30

Asp Ser Val Ala Ser Asp Leu Phe Ser Ala Ala Ser Ala Phe Gln Ser
        35                  40                  45

Val Val Trp Gly Leu Thr Val Gly Ser Trp Ile Gly Ser Ser Ala Gly
    50                  55                  60

Leu Met Val Ala Ala Ala Ser Pro Tyr Val Ala Trp Met Ser Val Thr
65                  70                  75                  80

Ala Gly Gln Ala Glu Leu Thr Ala Ala Gln Val Arg Val Ala Ala Ala
                85                  90                  95

Ala Tyr Glu Thr Ala Tyr Gly Leu Thr Val Pro Pro Pro Val Ile Ala
            100                 105                 110
```

```
Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
            180                 185                 190

Asp Thr Ala Ala Ala Asn Gln Leu Met Asn Asn Val Pro Gln Ala Leu
        195                 200                 205

Gln Gln Leu Ala Gln Pro Thr Gln Gly Thr Thr Pro Ser Ser Lys Leu
    210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
            260                 265                 270

Ala Ala Ala Gln Ala Val Gln Thr Ala Ala Gln Asn Gly Val Arg Ala
        275                 280                 285

Met Ser Ser Leu Gly Ser Ser Leu Gly Ser Ser Gly Leu Gly Gly Gly
    290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
            340                 345                 350

Gln Met Leu Gly Gly Leu Pro Val Gly Gln Met Gly Ala Arg Ala Gly
        355                 360                 365

Gly Gly Leu Ser Gly Val Leu Arg Val Pro Pro Arg Pro Tyr Val Met
    370                 375                 380

Pro His Ser Pro Ala Ala Gly
385                 390
```

<210> SEQ ID NO 25
<211> LENGTH: 236
<212> TYPE: PRT
<213> ORGANISM: Mycobacterium tuberculosis

<400> SEQUENCE: 25

```
Met Arg Thr Pro Arg Arg His Cys Arg Arg Ile Ala Val Leu Ala Ala
1               5                   10                  15

Val Ser Ile Ala Ala Thr Val Val Ala Gly Cys Ser Ser Gly Ser Lys
            20                  25                  30

Pro Ser Gly Gly Pro Leu Pro Asp Ala Lys Pro Leu Val Glu Glu Ala
        35                  40                  45

Thr Ala Gln Thr Lys Ala Leu Lys Ser Ala His Met Val Leu Thr Val
    50                  55                  60

Asn Gly Lys Ile Pro Gly Leu Ser Leu Lys Thr Leu Ser Gly Asp Leu
65                  70                  75                  80

Thr Thr Asn Pro Thr Ala Ala Thr Gly Asn Val Lys Leu Thr Leu Gly
                85                  90                  95
```

Gly Ser Asp Ile Asp Ala Asp Phe Val Val Phe Asp Gly Ile Leu Tyr
100 105 110

Ala Thr Leu Thr Pro Asn Gln Trp Ser Asp Phe Gly Pro Ala Ala Asp
115 120 125

Ile Tyr Asp Pro Ala Gln Val Leu Asn Pro Asp Thr Gly Leu Ala Asn
130 135 140

Val Leu Ala Asn Phe Ala Asp Ala Lys Ala Glu Gly Arg Asp Thr Ile
145 150 155 160

Asn Gly Gln Asn Thr Ile Arg Ile Ser Gly Lys Val Ser Ala Gln Ala
165 170 175

Val Asn Gln Ile Ala Pro Pro Phe Asn Ala Thr Gln Pro Val Pro Ala
180 185 190

Thr Val Trp Ile Gln Glu Thr Gly Asp His Gln Leu Ala Gln Ala Gln
195 200 205

Leu Asp Arg Gly Ser Gly Asn Ser Val Gln Met Thr Leu Ser Lys Trp
210 215 220

Gly Glu Lys Val Gln Val Thr Lys Pro Pro Val Ser
225 230 235

<210> SEQ ID NO 26
<211> LENGTH: 540
<212> TYPE: PRT
<213> ORGANISM: Mycobacterium tuberculosis

<400> SEQUENCE: 26

Met Ala Lys Thr Ile Ala Tyr Asp Glu Glu Ala Arg Arg Gly Leu Glu
1 5 10 15

Arg Gly Leu Asn Ala Leu Ala Asp Ala Val Lys Val Thr Leu Gly Pro
20 25 30

Lys Gly Arg Asn Val Val Leu Glu Lys Lys Trp Gly Ala Pro Thr Ile
35 40 45

Thr Asn Asp Gly Val Ser Ile Ala Lys Glu Ile Glu Leu Glu Asp Pro
50 55 60

Tyr Glu Lys Ile Gly Ala Glu Leu Val Lys Glu Val Ala Lys Lys Thr
65 70 75 80

Asp Asp Val Ala Gly Asp Gly Thr Thr Thr Ala Thr Val Leu Ala Gln
85 90 95

Ala Leu Val Arg Glu Gly Leu Arg Asn Val Ala Ala Gly Ala Asn Pro
100 105 110

Leu Gly Leu Lys Arg Gly Ile Glu Lys Ala Val Glu Lys Val Thr Glu
115 120 125

Thr Leu Leu Lys Gly Ala Lys Glu Val Glu Thr Lys Glu Gln Ile Ala
130 135 140

Ala Thr Ala Ala Ile Ser Ala Gly Asp Gln Ser Ile Gly Asp Leu Ile
145 150 155 160

Ala Glu Ala Met Asp Lys Val Gly Asn Glu Gly Val Ile Thr Val Glu
165 170 175

Glu Ser Asn Thr Phe Gly Leu Gln Leu Glu Leu Thr Glu Gly Met Arg
180 185 190

Phe Asp Lys Gly Tyr Ile Ser Gly Tyr Phe Val Thr Asp Pro Glu Arg
195 200 205

Gln Glu Ala Val Leu Glu Asp Pro Tyr Ile Leu Leu Val Ser Ser Lys
210 215 220

Val Ser Thr Val Lys Asp Leu Leu Pro Leu Leu Glu Lys Val Ile Gly

```
225                 230                 235                 240

Ala Gly Lys Pro Leu Leu Ile Ile Ala Glu Asp Val Glu Gly Glu Ala
                245                 250                 255

Leu Ser Thr Leu Val Val Asn Lys Ile Arg Gly Thr Phe Lys Ser Val
            260                 265                 270

Ala Val Lys Ala Pro Gly Phe Gly Asp Arg Arg Lys Ala Met Leu Gln
        275                 280                 285

Asp Met Ala Ile Leu Thr Gly Gly Gln Val Ile Ser Glu Glu Val Gly
    290                 295                 300

Leu Thr Leu Glu Asn Ala Asp Leu Ser Leu Leu Gly Lys Ala Arg Lys
305                 310                 315                 320

Val Val Val Thr Lys Asp Glu Thr Thr Ile Val Glu Gly Ala Gly Asp
                325                 330                 335

Thr Asp Ala Ile Ala Gly Arg Val Ala Gln Ile Arg Gln Glu Ile Glu
            340                 345                 350

Asn Ser Asp Ser Asp Tyr Asp Arg Glu Lys Leu Gln Glu Arg Leu Ala
        355                 360                 365

Lys Leu Ala Gly Gly Val Ala Val Ile Lys Ala Gly Ala Ala Thr Glu
    370                 375                 380

Val Glu Leu Lys Glu Arg Lys His Arg Ile Glu Asp Ala Val Arg Asn
385                 390                 395                 400

Ala Lys Ala Ala Val Glu Glu Gly Ile Val Ala Gly Gly Gly Val Thr
                405                 410                 415

Leu Leu Gln Ala Ala Pro Thr Leu Asp Glu Leu Lys Leu Glu Gly Asp
            420                 425                 430

Glu Ala Thr Gly Ala Asn Ile Val Lys Val Ala Leu Glu Ala Pro Leu
        435                 440                 445

Lys Gln Ile Ala Phe Asn Ser Gly Leu Glu Pro Gly Val Val Ala Glu
    450                 455                 460

Lys Val Arg Asn Leu Pro Ala Gly His Gly Leu Asn Ala Gln Thr Gly
465                 470                 475                 480

Val Tyr Glu Asp Leu Leu Ala Ala Gly Val Ala Asp Pro Val Lys Val
                485                 490                 495

Thr Arg Ser Ala Leu Gln Asn Ala Ala Ser Ile Ala Gly Leu Phe Leu
            500                 505                 510

Thr Thr Glu Ala Val Val Ala Asp Lys Pro Glu Lys Glu Lys Ala Ser
        515                 520                 525

Val Pro Gly Gly Gly Asp Met Gly Gly Met Asp Phe
    530                 535                 540


<210> SEQ ID NO 27
<211> LENGTH: 199
<212> TYPE: PRT
<213> ORGANISM: Mycobacterium tuberculosis

<400> SEQUENCE: 27

Met Ala Glu Asn Ser Asn Ile Asp Asp Ile Lys Ala Pro Leu Leu Ala
1               5                   10                  15

Ala Leu Gly Ala Ala Asp Leu Ala Leu Ala Thr Val Asn Glu Leu Ile
            20                  25                  30

Thr Asn Leu Arg Glu Arg Ala Glu Glu Thr Arg Thr Asp Thr Arg Ser
        35                  40                  45

Arg Val Glu Glu Ser Arg Ala Arg Leu Thr Lys Leu Gln Glu Asp Leu
    50                  55                  60
```

```
Pro Glu Gln Leu Thr Glu Leu Arg Glu Lys Phe Thr Ala Glu Glu Leu
65                  70                  75                  80

Arg Lys Ala Ala Glu Gly Tyr Leu Glu Ala Ala Thr Ser Arg Tyr Asn
                85                  90                  95

Glu Leu Val Glu Arg Gly Glu Ala Ala Leu Glu Arg Leu Arg Ser Gln
            100                 105                 110

Gln Ser Phe Glu Glu Val Ser Ala Arg Ala Glu Gly Tyr Val Asp Gln
        115                 120                 125

Ala Val Glu Leu Thr Gln Glu Ala Leu Gly Thr Val Ala Ser Gln Thr
    130                 135                 140

Arg Ala Val Gly Glu Arg Ala Ala Lys Leu Val Gly Ile Glu Leu Pro
145                 150                 155                 160

Lys Lys Ala Ala Pro Ala Lys Lys Ala Ala Pro Ala Lys Lys Ala Ala
                165                 170                 175

Pro Ala Lys Lys Ala Ala Ala Lys Lys Ala Pro Ala Lys Lys Ala Ala
            180                 185                 190

Ala Lys Lys Val Thr Gln Lys
        195


<210> SEQ ID NO 28
<211> LENGTH: 375
<212> TYPE: PRT
<213> ORGANISM: Mycobacterium tuberculosis

<400> SEQUENCE: 28

Val Thr Gln Thr Gly Lys Arg Gln Arg Arg Lys Phe Gly Arg Ile Arg
1               5                   10                  15

Gln Phe Asn Ser Gly Arg Trp Gln Ala Ser Tyr Thr Gly Pro Asp Gly
            20                  25                  30

Arg Val Tyr Ile Ala Pro Lys Thr Phe Asn Ala Lys Ile Asp Ala Glu
        35                  40                  45

Ala Trp Leu Thr Asp Arg Arg Arg Glu Ile Asp Arg Gln Leu Trp Ser
    50                  55                  60

Pro Ala Ser Gly Gln Glu Asp Arg Pro Gly Ala Pro Phe Gly Glu Tyr
65                  70                  75                  80

Ala Glu Gly Trp Leu Lys Gln Arg Gly Ile Lys Asp Arg Thr Arg Ala
                85                  90                  95

His Tyr Arg Lys Leu Leu Asp Asn His Ile Leu Ala Thr Phe Ala Asp
            100                 105                 110

Thr Asp Leu Arg Asp Ile Thr Pro Ala Ala Val Arg Arg Trp Tyr Ala
        115                 120                 125

Thr Thr Ala Val Gly Thr Pro Thr Met Arg Ala His Ser Tyr Ser Leu
    130                 135                 140

Leu Arg Ala Ile Met Gln Thr Ala Leu Ala Asp Asp Leu Ile Asp Ser
145                 150                 155                 160

Asn Pro Cys Arg Ile Ser Gly Ala Ser Thr Ala Arg Arg Val His Lys
                165                 170                 175

Ile Arg Pro Ala Thr Leu Asp Glu Leu Glu Thr Ile Thr Lys Ala Met
            180                 185                 190

Pro Asp Pro Tyr Gln Ala Phe Val Leu Met Ala Ala Trp Leu Ala Met
        195                 200                 205

Arg Tyr Gly Glu Leu Thr Glu Leu Arg Arg Lys Asp Ile Asp Leu His
    210                 215                 220

Gly Glu Val Ala Arg Val Arg Arg Ala Val Val Arg Val Gly Glu Gly
225                 230                 235                 240
```

```
Phe Lys Val Thr Thr Pro Lys Ser Asp Ala Gly Val Arg Asp Ile Ser
                245                 250                 255

Ile Pro Pro His Leu Ile Pro Ala Ile Glu Asp His Leu His Lys His
            260                 265                 270

Val Asn Pro Gly Arg Glu Ser Leu Leu Phe Pro Ser Val Asn Asp Pro
        275                 280                 285

Asn Arg His Leu Ala Pro Ser Ala Leu Tyr Arg Met Phe Tyr Lys Ala
    290                 295                 300

Arg Lys Ala Ala Gly Arg Pro Asp Leu Arg Val His Asp Leu Arg His
305                 310                 315                 320

Ser Gly Ala Val Leu Ala Ala Ser Thr Gly Ala Thr Leu Ala Glu Leu
                325                 330                 335

Met Gln Arg Leu Gly His Ser Thr Ala Gly Ala Ala Leu Arg Tyr Gln
            340                 345                 350

His Ala Ala Lys Gly Arg Asp Arg Glu Ile Ala Ala Leu Leu Ser Lys
        355                 360                 365

Leu Ala Glu Asn Gln Glu Met
    370                 375


<210> SEQ ID NO 29
<211> LENGTH: 75
<212> TYPE: PRT
<213> ORGANISM: Mycobacterium tuberculosis

<400> SEQUENCE: 29

Val Ile Ala Gly Val Asp Gln Ala Leu Ala Ala Thr Gly Gln Ala Ser
1               5                   10                  15

Gln Arg Ala Ala Gly Ala Ser Gly Gly Val Thr Val Gly Val Gly Val
            20                  25                  30

Gly Thr Glu Gln Arg Asn Leu Ser Val Val Ala Pro Ser Gln Phe Thr
        35                  40                  45

Phe Ser Ser Arg Ser Pro Asp Phe Val Asp Glu Thr Ala Gly Gln Ser
    50                  55                  60

Trp Cys Ala Ile Leu Gly Leu Asn Gln Phe His
65                  70                  75


<210> SEQ ID NO 30
<211> LENGTH: 144
<212> TYPE: PRT
<213> ORGANISM: Mycobacterium tuberculosis

<400> SEQUENCE: 30

Met Ala Thr Thr Leu Pro Val Gln Arg His Pro Arg Ser Leu Phe Pro
1               5                   10                  15

Glu Phe Ser Glu Leu Phe Ala Ala Phe Pro Ser Phe Ala Gly Leu Arg
            20                  25                  30

Pro Thr Phe Asp Thr Arg Leu Met Arg Leu Glu Asp Glu Met Lys Glu
        35                  40                  45

Gly Arg Tyr Glu Val Arg Ala Glu Leu Pro Gly Val Asp Pro Asp Lys
    50                  55                  60

Asp Val Asp Ile Met Val Arg Asp Gly Gln Leu Thr Ile Lys Ala Glu
65                  70                  75                  80

Arg Thr Glu Gln Lys Asp Phe Asp Gly Arg Ser Glu Phe Ala Tyr Gly
                85                  90                  95

Ser Phe Val Arg Thr Val Ser Leu Pro Val Gly Ala Asp Glu Asp Asp
            100                 105                 110
```

Ile Lys Ala Thr Tyr Asp Lys Gly Ile Leu Thr Val Ser Val Ala Val
115 120 125

Ser Glu Gly Lys Pro Thr Glu Lys His Ile Gln Ile Arg Ser Thr Asn
130 135 140

<210> SEQ ID NO 31
<211> LENGTH: 407
<212> TYPE: PRT
<213> ORGANISM: Mycobacterium tuberculosis

<400> SEQUENCE: 31

Met Ser Gly Arg His Arg Lys Pro Thr Thr Ser Asn Val Ser Val Ala
1 5 10 15

Lys Ile Ala Phe Thr Gly Ala Val Leu Gly Gly Gly Gly Ile Ala Met
20 25 30

Ala Ala Gln Ala Thr Ala Ala Thr Asp Gly Glu Trp Asp Gln Val Ala
35 40 45

Arg Cys Glu Ser Gly Gly Asn Trp Ser Ile Asn Thr Gly Asn Gly Tyr
50 55 60

Leu Gly Gly Leu Gln Phe Thr Gln Ser Thr Trp Ala Ala His Gly Gly
65 70 75 80

Gly Glu Phe Ala Pro Ser Ala Gln Leu Ala Ser Arg Glu Gln Gln Ile
85 90 95

Ala Val Gly Glu Arg Val Leu Ala Thr Gln Gly Arg Gly Ala Trp Pro
100 105 110

Val Cys Gly Arg Gly Leu Ser Asn Ala Thr Pro Arg Glu Val Leu Pro
115 120 125

Ala Ser Ala Ala Met Asp Ala Pro Leu Asp Ala Ala Ala Val Asn Gly
130 135 140

Glu Pro Ala Pro Leu Ala Pro Pro Pro Ala Asp Pro Ala Pro Pro Val
145 150 155 160

Glu Leu Ala Ala Asn Asp Leu Pro Ala Pro Leu Gly Glu Pro Leu Pro
165 170 175

Ala Ala Pro Ala Asp Pro Ala Pro Pro Ala Asp Leu Ala Pro Pro Ala
180 185 190

Pro Ala Asp Val Ala Pro Pro Val Glu Leu Ala Val Asn Asp Leu Pro
195 200 205

Ala Pro Leu Gly Glu Pro Leu Pro Ala Ala Pro Ala Asp Pro Ala Pro
210 215 220

Pro Ala Asp Leu Ala Pro Pro Ala Pro Ala Asp Leu Ala Pro Pro Ala
225 230 235 240

Pro Ala Asp Leu Ala Pro Pro Ala Pro Ala Asp Leu Ala Pro Pro Val
245 250 255

Glu Leu Ala Val Asn Asp Leu Pro Ala Pro Leu Gly Glu Pro Leu Pro
260 265 270

Ala Ala Pro Ala Glu Leu Ala Pro Pro Ala Asp Leu Ala Pro Ala Ser
275 280 285

Ala Asp Leu Ala Pro Pro Ala Pro Ala Asp Leu Ala Pro Pro Ala Pro
290 295 300

Ala Glu Leu Ala Pro Pro Ala Pro Ala Asp Leu Ala Pro Pro Ala Ala
305 310 315 320

Val Asn Glu Gln Thr Ala Pro Gly Asp Gln Pro Ala Thr Ala Pro Gly
325 330 335

Gly Pro Val Gly Leu Ala Thr Asp Leu Glu Leu Pro Glu Pro Asp Pro

```
            340                 345                 350

Gln Pro Ala Asp Ala Pro Pro Pro Gly Asp Val Thr Glu Ala Pro Ala
        355                 360                 365

Glu Thr Pro Gln Val Ser Asn Ile Ala Tyr Thr Lys Lys Leu Trp Gln
    370                 375                 380

Ala Ile Arg Ala Gln Asp Val Cys Gly Asn Asp Ala Leu Asp Ser Leu
385                 390                 395                 400

Ala Gln Pro Tyr Val Ile Gly
                405


<210> SEQ ID NO 32
<211> LENGTH: 362
<212> TYPE: PRT
<213> ORGANISM: Mycobacterium tuberculosis

<400> SEQUENCE: 32

Met Leu Arg Leu Val Val Gly Ala Leu Leu Leu Val Leu Ala Phe Ala
1               5                   10                  15

Gly Gly Tyr Ala Val Ala Ala Cys Lys Thr Val Thr Leu Thr Val Asp
            20                  25                  30

Gly Thr Ala Met Arg Val Thr Thr Met Lys Ser Arg Val Ile Asp Ile
        35                  40                  45

Val Glu Glu Asn Gly Phe Ser Val Asp Asp Arg Asp Asp Leu Tyr Pro
    50                  55                  60

Ala Ala Gly Val Gln Val His Asp Ala Asp Thr Ile Val Leu Arg Arg
65                  70                  75                  80

Ser Arg Pro Leu Gln Ile Ser Leu Asp Gly His Asp Ala Lys Gln Val
                85                  90                  95

Trp Thr Thr Ala Ser Thr Val Asp Glu Ala Leu Ala Gln Leu Ala Met
            100                 105                 110

Thr Asp Thr Ala Pro Ala Ala Ala Ser Arg Ala Ser Arg Val Pro Leu
        115                 120                 125

Ser Gly Met Ala Leu Pro Val Val Ser Ala Lys Thr Val Gln Leu Asn
    130                 135                 140

Asp Gly Gly Leu Val Arg Thr Val His Leu Pro Ala Pro Asn Val Ala
145                 150                 155                 160

Gly Leu Leu Ser Ala Ala Gly Val Pro Leu Leu Gln Ser Asp His Val
                165                 170                 175

Val Pro Ala Ala Thr Ala Pro Ile Val Glu Gly Met Gln Ile Gln Val
            180                 185                 190

Thr Arg Asn Arg Ile Lys Lys Val Thr Glu Arg Leu Pro Leu Pro Pro
        195                 200                 205

Asn Ala Arg Arg Val Glu Asp Pro Glu Met Asn Met Ser Arg Glu Val
    210                 215                 220

Val Glu Asp Pro Gly Val Pro Gly Thr Gln Asp Val Thr Phe Ala Val
225                 230                 235                 240

Ala Glu Val Asn Gly Val Glu Thr Gly Arg Leu Pro Val Ala Asn Val
                245                 250                 255

Val Val Thr Pro Ala His Glu Ala Val Val Arg Val Gly Thr Lys Pro
            260                 265                 270

Gly Thr Glu Val Pro Pro Val Ile Asp Gly Ser Ile Trp Asp Ala Ile
        275                 280                 285

Ala Gly Cys Glu Ala Gly Gly Asn Trp Ala Ile Asn Thr Gly Asn Gly
    290                 295                 300
```

Tyr Tyr Gly Gly Val Gln Phe Asp Gln Gly Thr Trp Glu Ala Asn Gly
305 310 315 320

Gly Leu Arg Tyr Ala Pro Arg Ala Asp Leu Ala Thr Arg Glu Glu Gln
325 330 335

Ile Ala Val Ala Glu Val Thr Arg Leu Arg Gln Gly Trp Gly Ala Trp
340 345 350

Pro Val Cys Ala Ala Arg Ala Gly Ala Arg
355 360

<210> SEQ ID NO 33
<211> LENGTH: 176
<212> TYPE: PRT
<213> ORGANISM: Mycobacterium tuberculosis

<400> SEQUENCE: 33

Val His Pro Leu Pro Ala Asp His Gly Arg Ser Arg Cys Asn Arg His
1 5 10 15

Pro Ile Ser Pro Leu Ser Leu Ile Gly Asn Ala Ser Ala Thr Ser Gly
20 25 30

Asp Met Ser Ser Met Thr Arg Ile Ala Lys Pro Leu Ile Lys Ser Ala
35 40 45

Met Ala Ala Gly Leu Val Thr Ala Ser Met Ser Leu Ser Thr Ala Val
50 55 60

Ala His Ala Gly Pro Ser Pro Asn Trp Asp Ala Val Ala Gln Cys Glu
65 70 75 80

Ser Gly Gly Asn Trp Ala Ala Asn Thr Gly Asn Gly Lys Tyr Gly Gly
85 90 95

Leu Gln Phe Lys Pro Ala Thr Trp Ala Ala Phe Gly Gly Val Gly Asn
100 105 110

Pro Ala Ala Ala Ser Arg Glu Gln Gln Ile Ala Val Ala Asn Arg Val
115 120 125

Leu Ala Glu Gln Gly Leu Asp Ala Trp Pro Thr Cys Gly Ala Ala Ser
130 135 140

Gly Leu Pro Ile Ala Leu Trp Ser Lys Pro Ala Gln Gly Ile Lys Gln
145 150 155 160

Ile Ile Asn Glu Ile Ile Trp Ala Gly Ile Gln Ala Ser Ile Pro Arg
165 170 175

<210> SEQ ID NO 34
<211> LENGTH: 154
<212> TYPE: PRT
<213> ORGANISM: Mycobacterium tuberculosis

<400> SEQUENCE: 34

Met Thr Pro Gly Leu Leu Thr Thr Ala Gly Ala Gly Arg Pro Arg Asp
1 5 10 15

Arg Cys Ala Arg Ile Val Cys Thr Val Phe Ile Glu Thr Ala Val Val
20 25 30

Ala Thr Met Phe Val Ala Leu Leu Gly Leu Ser Thr Ile Ser Ser Lys
35 40 45

Ala Asp Asp Ile Asp Trp Asp Ala Ile Ala Gln Cys Glu Ser Gly Gly
50 55 60

Asn Trp Ala Ala Asn Thr Gly Asn Gly Leu Tyr Gly Gly Leu Gln Ile
65 70 75 80

Ser Gln Ala Thr Trp Asp Ser Asn Gly Gly Val Gly Ser Pro Ala Ala
85 90 95

-continued

```
Ala Ser Pro Gln Gln Gln Ile Glu Val Ala Asp Asn Ile Met Lys Thr
            100                 105                 110

Gln Gly Pro Gly Ala Trp Pro Lys Cys Ser Ser Cys Ser Gln Gly Asp
        115                 120                 125

Ala Pro Leu Gly Ser Leu Thr His Ile Leu Thr Phe Leu Ala Ala Glu
    130                 135                 140

Thr Gly Gly Cys Ser Gly Ser Arg Asp Asp
145                 150


<210> SEQ ID NO 35
<211> LENGTH: 172
<212> TYPE: PRT
<213> ORGANISM: Mycobacterium tuberculosis

<400> SEQUENCE: 35

Leu Lys Asn Ala Arg Thr Thr Leu Ile Ala Ala Ala Ile Ala Gly Thr
1               5                   10                  15

Leu Val Thr Thr Ser Pro Ala Gly Ile Ala Asn Ala Asp Asp Ala Gly
            20                  25                  30

Leu Asp Pro Asn Ala Ala Ala Gly Pro Asp Ala Val Gly Phe Asp Pro
        35                  40                  45

Asn Leu Pro Pro Ala Pro Asp Ala Ala Pro Val Asp Thr Pro Pro Ala
    50                  55                  60

Pro Glu Asp Ala Gly Phe Asp Pro Asn Leu Pro Pro Pro Leu Ala Pro
65                  70                  75                  80

Asp Phe Leu Ser Pro Pro Ala Glu Glu Ala Pro Pro Val Pro Val Ala
                85                  90                  95

Tyr Ser Val Asn Trp Asp Ala Ile Ala Gln Cys Glu Ser Gly Gly Asn
            100                 105                 110

Trp Ser Ile Asn Thr Gly Asn Gly Tyr Tyr Gly Gly Leu Arg Phe Thr
        115                 120                 125

Ala Gly Thr Trp Arg Ala Asn Gly Gly Ser Gly Ser Ala Ala Asn Ala
    130                 135                 140

Ser Arg Glu Glu Gln Ile Arg Val Ala Glu Asn Val Leu Arg Ser Gln
145                 150                 155                 160

Gly Ile Arg Ala Trp Pro Val Cys Gly Arg Arg Gly
                165                 170


<210> SEQ ID NO 36
<211> LENGTH: 210
<212> TYPE: PRT
<213> ORGANISM: Mycobacterium tuberculosis

<400> SEQUENCE: 36

Met Ile Ala Thr Thr Arg Asp Arg Glu Gly Ala Thr Met Ile Thr Phe
1               5                   10                  15

Arg Leu Arg Leu Pro Cys Arg Thr Ile Leu Arg Val Phe Ser Arg Asn
            20                  25                  30

Pro Leu Val Arg Gly Thr Asp Arg Leu Glu Ala Val Val Met Leu Leu
        35                  40                  45

Ala Val Thr Val Ser Leu Leu Thr Ile Pro Phe Ala Ala Ala Ala Gly
    50                  55                  60

Thr Ala Val Gln Asp Ser Arg Ser His Val Tyr Ala His Gln Ala Gln
65                  70                  75                  80

Thr Arg His Pro Ala Thr Ala Thr Val Ile Asp His Glu Gly Val Ile
                85                  90                  95
```

-continued

```
Asp Ser Asn Thr Thr Ala Thr Ser Ala Pro Pro Arg Thr Lys Ile Thr
            100                 105                 110

Val Pro Ala Arg Trp Val Val Asn Gly Ile Glu Arg Ser Gly Glu Val
        115                 120                 125

Asn Ala Lys Pro Gly Thr Lys Ser Gly Asp Arg Val Gly Ile Trp Val
    130                 135                 140

Asp Ser Ala Gly Gln Leu Val Asp Glu Pro Ala Pro Pro Ala Arg Ala
145                 150                 155                 160

Ile Ala Asp Ala Ala Leu Ala Ala Leu Gly Leu Trp Leu Ser Val Ala
                165                 170                 175

Ala Val Ala Gly Ala Leu Leu Ala Leu Thr Arg Ala Ile Leu Ile Arg
            180                 185                 190

Val Arg Asn Ala Ser Trp Gln His Asp Ile Asp Ser Leu Phe Cys Thr
        195                 200                 205

Gln Arg
    210


<210> SEQ ID NO 37
<211> LENGTH: 339
<212> TYPE: PRT
<213> ORGANISM: Mycobacterium tuberculosis

<400> SEQUENCE: 37

Met Thr Glu Pro Ala Ala Trp Asp Glu Gly Lys Pro Arg Ile Ile Thr
1               5                   10                  15

Leu Thr Met Asn Pro Ala Leu Asp Ile Thr Thr Ser Val Asp Val Val
            20                  25                  30

Arg Pro Thr Glu Lys Met Arg Cys Gly Ala Pro Arg Tyr Asp Pro Gly
        35                  40                  45

Gly Gly Gly Ile Asn Val Ala Arg Ile Val His Val Leu Gly Gly Cys
    50                  55                  60

Ser Thr Ala Leu Phe Pro Ala Gly Gly Ser Thr Gly Ser Leu Leu Met
65                  70                  75                  80

Ala Leu Leu Gly Asp Ala Gly Val Pro Phe Arg Val Ile Pro Ile Ala
                85                  90                  95

Ala Ser Thr Arg Glu Ser Phe Thr Val Asn Glu Ser Arg Thr Ala Lys
            100                 105                 110

Gln Tyr Arg Phe Val Leu Pro Gly Pro Ser Leu Thr Val Ala Glu Gln
        115                 120                 125

Glu Gln Cys Leu Asp Glu Leu Arg Gly Ala Ala Ala Ser Ala Ala Phe
    130                 135                 140

Val Val Ala Ser Gly Ser Leu Pro Pro Gly Val Ala Ala Asp Tyr Tyr
145                 150                 155                 160

Gln Arg Val Ala Asp Ile Cys Arg Arg Ser Ser Thr Pro Leu Ile Leu
                165                 170                 175

Asp Thr Ser Gly Gly Gly Leu Gln His Ile Ser Ser Gly Val Phe Leu
            180                 185                 190

Leu Lys Ala Ser Val Arg Glu Leu Arg Glu Cys Val Gly Ser Glu Leu
        195                 200                 205

Leu Thr Glu Pro Glu Gln Leu Ala Ala Ala His Glu Leu Ile Asp Arg
    210                 215                 220

Gly Arg Ala Glu Val Val Val Val Ser Leu Gly Ser Gln Gly Ala Leu
225                 230                 235                 240

Leu Ala Thr Arg His Ala Ser His Arg Phe Ser Ser Ile Pro Met Thr
                245                 250                 255
```

```
Ala Val Ser Gly Val Gly Ala Gly Asp Ala Met Val Ala Ala Ile Thr
            260                 265                 270

Val Gly Leu Ser Arg Gly Trp Ser Leu Ile Lys Ser Val Arg Leu Gly
        275                 280                 285

Asn Ala Ala Gly Ala Ala Met Leu Leu Thr Pro Gly Thr Ala Ala Cys
    290                 295                 300

Asn Arg Asp Asp Val Glu Arg Phe Phe Glu Leu Ala Ala Glu Pro Thr
305                 310                 315                 320

Glu Val Gly Gln Asp Gln Tyr Val Trp His Pro Ile Val Asn Pro Glu
                325                 330                 335

Ala Ser Pro


<210> SEQ ID NO 38
<211> LENGTH: 331
<212> TYPE: PRT
<213> ORGANISM: Mycobacterium tuberculosis

<400> SEQUENCE: 38

Met Pro Asp Thr Met Val Thr Thr Asp Val Ile Lys Ser Ala Val Gln
1               5                   10                  15

Leu Ala Cys Arg Ala Pro Ser Leu His Asn Ser Gln Pro Trp Arg Trp
            20                  25                  30

Ile Ala Glu Asp His Thr Val Ala Leu Phe Leu Asp Lys Asp Arg Val
        35                  40                  45

Leu Tyr Ala Thr Asp His Ser Gly Arg Glu Ala Leu Leu Gly Cys Gly
    50                  55                  60

Ala Val Leu Asp His Phe Arg Val Ala Met Ala Ala Ala Gly Thr Thr
65                  70                  75                  80

Ala Asn Val Glu Arg Phe Pro Asn Pro Asn Asp Pro Leu His Leu Ala
                85                  90                  95

Ser Ile Asp Phe Ser Pro Ala Asp Phe Val Thr Glu Gly His Arg Leu
            100                 105                 110

Arg Ala Asp Ala Ile Leu Leu Arg Arg Thr Asp Arg Leu Pro Phe Ala
        115                 120                 125

Glu Pro Pro Asp Trp Asp Leu Val Glu Ser Gln Leu Arg Thr Thr Val
    130                 135                 140

Thr Ala Asp Thr Val Arg Ile Asp Val Ile Ala Asp Asp Met Arg Pro
145                 150                 155                 160

Glu Leu Ala Ala Ala Ser Lys Leu Thr Glu Ser Leu Arg Leu Tyr Asp
                165                 170                 175

Ser Ser Tyr His Ala Glu Leu Phe Trp Trp Thr Gly Ala Phe Glu Thr
            180                 185                 190

Ser Glu Gly Ile Pro His Ser Ser Leu Val Ser Ala Ala Glu Ser Asp
        195                 200                 205

Arg Val Thr Phe Gly Arg Asp Phe Pro Val Val Ala Asn Thr Asp Arg
    210                 215                 220

Arg Pro Glu Phe Gly His Asp Arg Ser Lys Val Leu Val Leu Ser Thr
225                 230                 235                 240

Tyr Asp Asn Glu Arg Ala Ser Leu Leu Arg Cys Gly Glu Met Leu Ser
                245                 250                 255

Ala Val Leu Leu Asp Ala Thr Met Ala Gly Leu Ala Thr Cys Thr Leu
            260                 265                 270

Thr His Ile Thr Glu Leu His Ala Ser Arg Asp Leu Val Ala Ala Leu
        275                 280                 285
```

```
Ile Gly Gln Pro Ala Thr Pro Gln Ala Leu Val Arg Val Gly Leu Ala
    290                 295                 300

Pro Glu Met Glu Glu Pro Pro Pro Ala Thr Pro Arg Arg Pro Ile Asp
305                 310                 315                 320

Glu Val Phe His Val Arg Ala Lys Asp His Arg
                325                 330


<210> SEQ ID NO 39
<211> LENGTH: 143
<212> TYPE: PRT
<213> ORGANISM: Mycobacterium tuberculosis

<400> SEQUENCE: 39

Met Thr Thr Ala Arg Asp Ile Met Asn Ala Gly Val Thr Cys Val Gly
1               5                   10                  15

Glu His Glu Thr Leu Thr Ala Ala Ala Gln Tyr Met Arg Glu His Asp
            20                  25                  30

Ile Gly Ala Leu Pro Ile Cys Gly Asp Asp Asp Arg Leu His Gly Met
        35                  40                  45

Leu Thr Asp Arg Asp Ile Val Ile Lys Gly Leu Ala Ala Gly Leu Asp
    50                  55                  60

Pro Asn Thr Ala Thr Ala Gly Glu Leu Ala Arg Asp Ser Ile Tyr Tyr
65                  70                  75                  80

Val Asp Ala Asn Ala Ser Ile Gln Glu Met Leu Asn Val Met Glu Glu
                85                  90                  95

His Gln Val Arg Arg Val Pro Val Ile Ser Glu His Arg Leu Val Gly
            100                 105                 110

Ile Val Thr Glu Ala Asp Ile Ala Arg His Leu Pro Glu His Ala Ile
        115                 120                 125

Val Gln Phe Val Lys Ala Ile Cys Ser Pro Met Ala Leu Ala Ser
    130                 135                 140


<210> SEQ ID NO 40
<211> LENGTH: 413
<212> TYPE: PRT
<213> ORGANISM: Mycobacterium tuberculosis

<400> SEQUENCE: 40

Met Ala Ser Ser Ala Ser Asp Gly Thr His Glu Arg Ser Ala Phe Arg
1               5                   10                  15

Leu Ser Pro Pro Val Leu Ser Gly Ala Met Gly Pro Phe Met His Thr
            20                  25                  30

Gly Leu Tyr Val Ala Gln Ser Trp Arg Asp Tyr Leu Gly Gln Gln Pro
        35                  40                  45

Asp Lys Leu Pro Ile Ala Arg Pro Thr Ile Ala Leu Ala Ala Gln Ala
    50                  55                  60

Phe Arg Asp Glu Ile Val Leu Leu Gly Leu Lys Ala Arg Arg Pro Val
65                  70                  75                  80

Ser Asn His Arg Val Phe Glu Arg Ile Ser Gln Glu Val Ala Ala Gly
                85                  90                  95

Leu Glu Phe Tyr Gly Asn Arg Arg Trp Leu Glu Lys Pro Ser Gly Phe
            100                 105                 110

Phe Ala Gln Pro Pro Pro Leu Thr Glu Val Ala Val Arg Lys Val Lys
        115                 120                 125

Asp Arg Arg Arg Ser Phe Tyr Arg Ile Phe Phe Asp Ser Gly Phe Thr
    130                 135                 140
```

-continued

```
Pro His Pro Gly Glu Pro Gly Ser Gln Arg Trp Leu Ser Tyr Thr Ala
145                 150                 155                 160

Asn Asn Arg Glu Tyr Ala Leu Leu Leu Arg His Pro Glu Pro Arg Pro
                165                 170                 175

Trp Leu Val Cys Val His Gly Thr Glu Met Gly Arg Ala Pro Leu Asp
            180                 185                 190

Leu Ala Val Phe Arg Ala Trp Lys Leu His Asp Glu Leu Gly Leu Asn
        195                 200                 205

Ile Val Met Pro Val Leu Pro Met His Gly Pro Arg Gly Gln Gly Leu
    210                 215                 220

Pro Lys Gly Ala Val Phe Pro Gly Glu Asp Val Leu Asp Asp Val His
225                 230                 235                 240

Gly Thr Ala Gln Ala Val Trp Asp Ile Arg Arg Leu Leu Ser Trp Ile
                245                 250                 255

Arg Ser Gln Glu Glu Glu Ser Leu Ile Gly Leu Asn Gly Leu Ser Leu
            260                 265                 270

Gly Gly Tyr Ile Ala Ser Leu Val Ala Ser Leu Glu Glu Gly Leu Ala
        275                 280                 285

Cys Ala Ile Leu Gly Val Pro Val Ala Asp Leu Ile Glu Leu Leu Gly
    290                 295                 300

Arg His Cys Gly Leu Arg His Lys Asp Pro Arg Arg His Thr Val Lys
305                 310                 315                 320

Met Ala Glu Pro Ile Gly Arg Met Ile Ser Pro Leu Ser Leu Thr Pro
                325                 330                 335

Leu Val Pro Met Pro Gly Arg Phe Ile Tyr Ala Gly Ile Ala Asp Arg
            340                 345                 350

Leu Val His Pro Arg Glu Gln Val Thr Arg Leu Trp Glu His Trp Gly
        355                 360                 365

Lys Pro Glu Ile Val Trp Tyr Pro Gly Gly His Thr Gly Phe Phe Gln
    370                 375                 380

Ser Arg Pro Val Arg Arg Phe Val Gln Ala Ala Leu Glu Gln Ser Gly
385                 390                 395                 400

Leu Leu Asp Ala Pro Arg Thr Gln Arg Asp Arg Ser Ala
                405                 410


<210> SEQ ID NO 41
<211> LENGTH: 120
<212> TYPE: PRT
<213> ORGANISM: Mycobacterium tuberculosis

<400> SEQUENCE: 41

Met Ser Thr Gln Arg Pro Arg His Ser Gly Ile Arg Ala Val Gly Pro
1               5                   10                  15

Tyr Ala Trp Ala Gly Arg Cys Gly Arg Ile Gly Arg Trp Gly Val His
            20                  25                  30

Gln Glu Ala Met Met Asn Leu Ala Ile Trp His Pro Arg Lys Val Gln
        35                  40                  45

Ser Ala Thr Ile Tyr Gln Val Thr Asp Arg Ser His Asp Gly Arg Thr
    50                  55                  60

Ala Arg Val Pro Gly Asp Glu Ile Thr Ser Thr Val Ser Gly Trp Leu
65                  70                  75                  80

Ser Glu Leu Gly Thr Gln Ser Pro Leu Ala Asp Glu Leu Ala Arg Ala
                85                  90                  95

Val Arg Ile Gly Asp Trp Pro Ala Ala Tyr Ala Ile Gly Glu His Leu
```

-continued 100 105 110

Ser Val Glu Ile Ala Val Ala Val
115 120

<210> SEQ ID NO 42
<211> LENGTH: 1017
<212> TYPE: DNA
<213> ORGANISM: Mycobacterium tuberculosis

<400> SEQUENCE: 42
atgcagcttg ttgacagggt tcgtggcgcc gtcacgggta tgtcgcgtcg actcgtggtc 60
ggggccgtcg gcgcggccct agtgtcgggt ctggtcggcg ccgtcggtgg cacggcgacc 120
gcgggggcat tttcccggcc gggcttgccg gtggagtacc tgcaggtgcc gtcgccgtcg 180
atgggccgtg acatcaaggt ccaattccaa agtggtggtg ccaactcgcc cgccctgtac 240
ctgctcgacg gcctgcgcgc gcaggacgac ttcagcggct gggacatcaa caccccggcg 300
ttcgagtggt acgaccagtc gggcctgtcg gtggtcatgc cggtgggtgg ccagtcaagc 360
ttctactccg actggtacca gcccgcctgc ggcaaggccg gttgccagac ttacaagtgg 420
gagaccttcc tgaccagcga gctgccgggg tggctgcagg ccaacaggca cgtcaagccc 480
accggaagcg ccgtcgtcgg tctttcgatg gctgcttctt cggcgctgac gctggcgatc 540
tatcaccccc agcagttcgt ctacgcggga gcgatgtcgg gcctgttgga cccctcccag 600
gcgatgggtc ccaccctgat cggcctggcg atgggtgacg ctggcggcta caaggcctcc 660
gacatgtggg gcccgaagga ggacccggcg tggcagcgca acgacccgct gttgaacgtc 720
gggaagctga tcgccaacaa cacccgcgtc tgggtgtact gcggcaacgg caagccgtcg 780
gatctgggtg gcaacaacct gccggccaag ttcctcgagg gcttcgtgcg gaccagcaac 840
atcaagttcc aagacgccta caacgccggt ggcggccaca acggcgtgtt cgacttcccg 900
gacagcggta cgcacagctg ggagtactgg ggcgcgcagc tcaacgctat gaagcccgac 960
ctgcaacggg cactgggtgc cacgcccaac accgggcccg cgccccaggg cgcctag 1017

<210> SEQ ID NO 43
<211> LENGTH: 978
<212> TYPE: DNA
<213> ORGANISM: Mycobacterium tuberculosis

<400> SEQUENCE: 43
atgacagacg tgagccgaaa gattcgagct tggggacgcc gattgatgat cggcacggca 60
gcggctgtag tccttccggg cctggtgggg cttgccggcg gagcggcaac cgcgggcgcg 120
ttctcccggc cggggctgcc ggtcgagtac ctgcaggtgc cgtcgccgtc gatgggccgc 180
gacatcaagg ttcagttcca gagcggtggg aacaactcac ctgcggttta tctgctcgac 240
ggcctgcgcg cccaagacga ctacaacggc tgggatatca acaccccggc gttcgagtgg 300
tactaccagt cgggactgtc gatagtcatg ccggtcggcg ggcagtccag cttctacagc 360
gactggtaca gcccggcctg cggtaaggct ggctgccaga cttacaagtg ggaaaccttc 420
ctgaccagcg agctgccgca atggttgtcc gccaacaggg ccgtgaagcc caccggcagc 480
gctgcaatcg gcttgtcgat ggccggctcg tcggcaatga tcttggccgc ctaccacccc 540
cagcagttca tctacgccgg ctcgctgtcg gccctgctgg acccctctca ggggatgggg 600
cctagcctga tcggcctcgc gatgggtgac gccggcggtt acaaggccgc agacatgtgg 660
ggtccctcga gtgacccggc atgggagcgc aacgacccta cgcagcagat ccccaagctg 720
gtcgcaaaca acacccggct atgggtttat tgcgggaacg gcaccccgaa cgagttgggc 780
ggtgccaaca tacccgccga gttcttggag aacttcgttc gtagcagcaa cctgaagttc 840
caggatgcgt acaacgccgc gggcgggcac aacgccgtgt tcaacttccc gcccaacggc 900
acgcacagct gggagtactg gggcgctcag ctcaacgcca tgaagggtga cctgcagagt 960
tcgttaggcg ccggctga 978

<210> SEQ ID NO 44
<211> LENGTH: 288
<212> TYPE: DNA
<213> ORGANISM: Mycobacterium tuberculosis

<400> SEQUENCE: 44
atgacagagc agcagtggaa tttcgcgggt atcgaggccg cggcaagcgc aatccaggga 60
aatgtcacgt ccattcattc cctccttgac gaggggaagc agtccctgac caagctcgca 120
gcggcctggg gcggtagcgg ttcggaggcg taccagggtg tccagcaaaa atgggacgcc 180
acggctaccg agctgaacaa cgcgctgcag aacctggcgc ggacgatcag cgaagccggt 240
caggcaatgg cttcgaccga aggcaacgtc actgggatgt tcgcatag 288

<210> SEQ ID NO 45
<211> LENGTH: 291
<212> TYPE: DNA
<213> ORGANISM: Mycobacterium tuberculosis

<400> SEQUENCE: 45
atgtcgcaaa tcatgtacaa ctaccccgcg atgttgggtc acgccgggga tatggccgga 60
tatgccggca cgctgcagag cttgggtgcc gagatcgccg tggagcaggc cgcgttgcag 120
agtgcgtggc agggcgatac cgggatcacg tatcaggcgt ggcaggcaca gtggaaccag 180
gccatggaag atttggtgcg ggcctatcat gcgatgtcca gcacccatga agccaacacc 240
atggcgatga tggcccgcga cacggccgaa gccgccaaat ggggcggcta g 291

<210> SEQ ID NO 46
<211> LENGTH: 1068
<212> TYPE: DNA
<213> ORGANISM: Mycobacterium tuberculosis

<400> SEQUENCE: 46
atgagcaatt cgcgccgccg ctcactcagg tggtcatggt tgctgagcgt gctggctgcc 60
gtcgggctgg gcctggccac ggcgccggcc caggcggccc cgccggcctt gtcgcaggac 120
cggttcgccg acttccccgc gctgcccctc gacccgtccg cgatggtcgc ccaagtgggg 180
ccacaggtgg tcaacatcaa caccaaactg ggctacaaca acgccgtggg cgccgggacc 240
ggcatcgtca tcgatcccaa cggtgtcgtg ctgaccaaca accacgtgat cgcgggcgcc 300
accgacatca atgcgttcag cgtcggctcc ggccaaacct acggcgtcga tgtggtcggg 360
tatgaccgca cccaggatgt cgcggtgctg cagctgcgcg gtgccggtgg cctgccgtcg 420
gcggcgatcg gtggcggcgt cgcggttggt gagcccgtcg tcgcgatggg caacagcggt 480
gggcagggcg gaacgccccg tgcggtgcct ggcagggtgg tcgcgctcgg ccaaaccgtg 540
caggcgtcgg attcgctgac cggtgccgaa gagacattga acgggttgat ccagttcgat 600
gccgcgatcc agcccggtga ttcgggcggg cccgtcgtca acggcctagg acaggtggtc 660
ggtatgaaca cggccgcgtc cgataacttc cagctgtccc agggtgggca gggattcgcc 720
attccgatcg ggcaggcgat ggcgatcgcg ggccagatcc gatcgggtgg ggggtcaccc 780

| | |
|---|---|
| accgttcata tcgggcctac cgccttcctc ggcttgggtg ttgtcgacaa caacggcaac | 840 |
| ggcgcacgag tccaacgcgt ggtcgggagc gctccggcgg caagtctcgg catctccacc | 900 |
| ggcgacgtga tcaccgcggt cgacggcgct ccgatcaact cggccaccgc gatggcggac | 960 |
| gcgcttaacg ggcatcatcc cggtgacgtc atctcggtga cctggcaaac caagtcgggc | 1020 |
| ggcacgcgta cagggaacgt gacattggcc gagggacccc cggcctga | 1068 |

<210> SEQ ID NO 47
<211> LENGTH: 1176
<212> TYPE: DNA
<213> ORGANISM: Mycobacterium tuberculosis

<400> SEQUENCE: 47

| | |
|---|---|
| atggtggatt tcggggcgtt accaccggag atcaactccg cgaggatgta cgccggcccg | 60 |
| ggttcggcct cgctggtggc cgcggctcag atgtgggaca gcgtggcgag tgacctgttt | 120 |
| tcggccgcgt cggcgtttca gtcggtggtc tggggtctga cggtggggtc gtggataggt | 180 |
| tcgtcggcgg gtctgatggt ggcggcggcc tcgccgtatg tggcgtggat gagcgtcacc | 240 |
| gcggggcagg ccgagctgac cgccgcccag gtccgggttg ctgcggcggc ctacgagacg | 300 |
| gcgtatgggc tgacggtgcc cccgccggtg atcgccgaga accgtgctga actgatgatt | 360 |
| ctgatagcga ccaacctctt ggggcaaaac accccggcga tcgcggtcaa cgaggccgaa | 420 |
| tacggcgaga tgtgggccca agacgccgcc gcgatgtttg gctacgccgc ggcgacggcg | 480 |
| acggcgacgg cgacgttgct gccgttcgag gaggcgccgg agatgaccag cgcgggtggg | 540 |
| ctcctcgagc aggccgccgc ggtcgaggag gcctccgaca ccgccgcggc gaaccagttg | 600 |
| atgaacaatg tgccccaggc gctgcaacag ctggcccagc ccacgcaggg caccacgcct | 660 |
| tcttccaagc tgggtggcct gtggaagacg gtctcgccgc atcggtcgcc gatcagcaac | 720 |
| atggtgtcga tggccaacaa ccacatgtcg atgaccaact cgggtgtgtc gatgaccaac | 780 |
| accttgagct cgatgttgaa gggctttgct ccggcggcgg ccgcccaggc cgtgcaaacc | 840 |
| gcggcgcaaa acggggtccg ggcgatgagc tcgctgggca gctcgctggg ttcttcgggt | 900 |
| ctgggcggtg gggtggccgc caacttgggt cgggcggcct cggtcggttc gttgtcggtg | 960 |
| ccgcaggcct gggccgcggc caaccaggca gtcaccccgg cggcgcgggc gctgccgctg | 1020 |
| accagcctga ccagcgccgc ggaaagaggg cccgggcaga tgctgggcgg gctgccggtg | 1080 |
| gggcagatgg gcgccagggc cggtggtggg ctcagtggtg tgctgcgtgt tccgccgcga | 1140 |
| ccctatgtga tgccgcattc tccggcggcc ggctag | 1176 |

<210> SEQ ID NO 48
<211> LENGTH: 711
<212> TYPE: DNA
<213> ORGANISM: Mycobacterium tuberculosis

<400> SEQUENCE: 48

| | |
|---|---|
| atgcggaccc ccagacgcca ctgccgtcgc atcgccgtcc tcgccgccgt tagcatcgcc | 60 |
| gccactgtcg ttgccggctg ctcgtcgggc tcgaagccaa gcggcggacc acttccggac | 120 |
| gcgaagccgc tggtcgagga ggccaccgcg cagaccaagg ctctcaagag cgcgcacatg | 180 |
| gtgctgacgg tcaacggcaa gatcccggga ctgtctctga agacgctgag cggcgatctc | 240 |
| accaccaacc ccaccgccgc gacgggaaac gtcaagctca cgctgggtgg gtctgatatc | 300 |
| gatgccgact tcgtggtgtt cgacgggatc ctgtacgcca ccctgacgcc caaccagtgg | 360 |

-continued

```
agcgatttcg gtcccgccgc cgacatctac gaccccgccc aggtgctgaa tccggatacc    420

ggcctggcca acgtgctggc gaatttcgcc gacgcaaaag ccgaagggcg ggataccatc    480

aacggccaga acaccatccg catcagcggg aaggtatcgg cacaggcggt gaaccagata    540

gcgccgccgt tcaacgcgac gcagccggtg ccggcgaccg tctggattca ggagaccggc    600

gatcatcaac tggcacaggc ccagttggac cgcggctcgg gcaattccgt ccagatgacc    660

ttgtcgaaat ggggcgagaa ggtccaggtc acgaagcccc cggtgagctg a             711
```

<210> SEQ ID NO 49
<211> LENGTH: 1623
<212> TYPE: DNA
<213> ORGANISM: Mycobacterium tuberculosis

<400> SEQUENCE: 49

```
atggccaaga caattgcgta cgacgaagag gcccgtcgcg gcctcgagcg ggcttgaac      60

gccctcgccg atgcggtaaa ggtgacattg ggccccaagg gccgcaacgt cgtcctggaa    120

aagaagtggg gtgcccccac gatcaccaac gatggtgtgt ccatcgccaa ggagatcgag    180

ctggaggatc cgtacgagaa gatcggcgcc gagctggtca aagaggtagc caagaagacc    240

gatgacgtcg ccggtgacgg caccacgacg gccaccgtgc tggcccaggc gttggttcgc    300

gagggcctgc gcaacgtcgc ggccggcgcc aacccgctcg gtctcaaacg cggcatcgaa    360

aaggccgtgg agaaggtcac cgagaccctg ctcaagggcg ccaaggaggt cgagaccaag    420

gagcagattg cggccaccgc agcgatttcg gcgggtgacc agtccatcgg tgacctgatc    480

gccgaggcga tggacaaggt gggcaacgag ggcgtcatca ccgtcgagga gtccaacacc    540

tttgggctgc agctcgagct caccgagggt atgcggttcg acaagggcta catctcgggg    600

tacttcgtga ccgacccgga gcgtcaggag gcggtcctgg aggaccccta catcctgctg    660

gtcagctcca aggtgtccac tgtcaaggat ctgctgccgc tgctcgagaa ggtcatcgga    720

gccggtaagc cgctgctgat catcgccgag gacgtcgagg gcgaggcgct gtccaccctg    780

gtcgtcaaca agatccgcgg caccttcaag tcggtggcgg tcaaggctcc cggcttcggc    840

gaccgccgca aggcgatgct gcaggatatg gccattctca ccggtggtca ggtgatcagc    900

gaagaggtcg gcctgacgct ggagaacgcc gacctgtcgc tgctaggcaa ggcccgcaag    960

gtcgtggtca ccaaggacga gaccaccatc gtcgagggcg ccggtgacac cgacgccatc   1020

gccggacgag tggcccagat ccgccaggag atcgagaaca gcgactccga ctacgaccgt   1080

gagaagctgc aggagcggct ggccaagctg gccggtggtg tcgcggtgat caaggccggt   1140

gccgccaccg aggtcgaact caaggagcgc aagcaccgca tcgaggatgc ggttcgcaat   1200

gccaaggccg ccgtcgagga gggcatcgtc gccggtgggg gtgtgacgct gttgcaagcg   1260

gccccgaccc tggacgagct gaagctcgaa ggcgacgagg cgaccggcgc caacatcgtg   1320

aaggtggcgc tggaggcccc gctgaagcag atcgccttca actccgggct ggagccgggc   1380

gtggtggccg agaaggtgcg caacctgccg gctggccacg gactgaacgc tcagaccggt   1440

gtctacgagg atctgctcgc tgccggcgtt gctgacccgg tcaaggtgac ccgttcggcg   1500

ctgcagaatg cggcgtccat cgcggggctg ttcctgacca ccgaggccgt cgttgccgac   1560

aagccggaaa aggagaaggc ttccgttccc ggtggcggcg acatgggtgg catggatttc   1620

tga                                                                 1623
```

<210> SEQ ID NO 50
<211> LENGTH: 600

-continued

<212> TYPE: DNA
<213> ORGANISM: Mycobacterium tuberculosis

<400> SEQUENCE: 50
atggctgaaa actcgaacat tgatgacatc aaggctccgt tgcttgccgc gcttggagcg 60
gccgacctgg ccttggccac tgtcaacgag ttgatcacga acctgcgtga gcgtgcggag 120
gagactcgta cggacacccg cagccgggtc gaggagagcc gtgctcgcct gaccaagctg 180
caggaagatc tgcccgagca gctcaccgag ctgcgtgaga agttcaccgc cgaggagctg 240
cgtaaggccg ccgagggcta cctcgaggcc gcgactagcc ggtacaacga gctggtcgag 300
cgcggtgagg ccgctctaga gcggctgcgc agccagcaga gcttcgagga agtgtcggcg 360
cgcgccgaag gctacgtgga ccaggcggtg gagttgaccc aggaggcgtt gggtacggtc 420
gcatcgcaga cccgcgcggt cggtgagcgt gccgccaagc tggtcggcat cgagctgcct 480
aagaaggctg ctccggccaa gaaggccgct ccggccaaga aggccgctcc ggccaagaag 540
gcggcggcca agaaggcgcc cgcgaagaag gcggcggcca agaaggtcac ccagaagtag 600

<210> SEQ ID NO 51
<211> LENGTH: 1128
<212> TYPE: DNA
<213> ORGANISM: Mycobacterium tuberculosis

<400> SEQUENCE: 51
gtgacgcaaa ccggcaagcg tcagagacgc aaattcggtc gcatccgaca gttcaactcc 60
ggccgctggc aagccagcta caccggcccc gacggccgcg tgtacatcgc ccccaaaacc 120
ttcaacgcca agatcgacgc cgaagcatgg ctcaccgacc gccgccgcga aatcgaccga 180
caactatggt ccccggcatc gggtcaggaa gaccgccccg gagccccatt cggtgagtac 240
gccgaaggat ggctgaagca gcgtggaatc aaggaccgca cccgcgccca ctatcgcaaa 300
ctgctggaca accacatcct ggccaccttc gctgacaccg acctacgcga catcaccccg 360
gccgccgtgc gccgctggta cgccaccacc gccgtgggca caccgaccat gcgggcacac 420
tcctacagct tgctgcgcgc aatcatgcag accgccttgg ccgacgacct gatcgactcc 480
aacccctgcc gcatctcagg cgcgtccacc gcccgccgcg tccacaagat caggcccgcc 540
accctcgacg agctggaaac catcaccaaa gccatgcccg acccctacca ggcgttcgtg 600
ctgatggcgg catggctggc catgcgctac ggcgagctga ccgaattacg ccgcaaagac 660
atcgacctgc acggcgaggt tgcgcgggtg cggcgggctg tcgttcgggt gggcgaaggc 720
ttcaaggtga cgacaccgaa aagcgatgcg ggagtgcgcg acataagtat cccgccacat 780
ctgatacccg ccatcgaaga ccaccttcac aaacacgtca accccggccg ggagtccctg 840
ctgttcccat cggtcaacga ccccaaccgt cacctagcac cctcggcgct gtaccgcatg 900
ttctacaagg cccgaaaagc cgccggccga ccagacttac gggtgcacga ccttcgacac 960
tccggcgccg tgttggctgc atccaccggc gccacactgg ccgaactgat gcagcggcta 1020
ggacacagca cagccggcgc cgcactccgc taccagcacg ccgccaaggg ccgggaccgc 1080
gaaatcgccg cactgttaag caaactggcc gagaaccagg agatgtga 1128

<210> SEQ ID NO 52
<211> LENGTH: 228
<212> TYPE: DNA
<213> ORGANISM: Mycobacterium tuberculosis

<400> SEQUENCE: 52

-continued gtgatagcgg gcgtcgacca ggcgcttgca gcaacaggcc aggctagcca gcgggcggca 60
ggcgcatctg gtggggtcac cgtcggtgtc ggcgtgggca cggaacagag gaacctttcg 120
gtggttgcac cgagtcagtt cacatttagt tcacgcagcc cagattttgt ggatgaaacc 180
gcaggtcaat cgtggtgcgc gatactggga ttgaaccagt ttcactag 228

<210> SEQ ID NO 53
<211> LENGTH: 435
<212> TYPE: DNA
<213> ORGANISM: Mycobacterium tuberculosis

<400> SEQUENCE: 53
atggccacca cccttcccgt tcagcgccac ccgcggtccc tcttccccga gttttctgag 60
ctgttcgcgg ccttcccgtc attcgccgga ctccggccca ccttcgacac ccggttgatg 120
cggctggaag acgagatgaa agaggggcgc tacgaggtac gcgcggagct tcccggggtc 180
gaccccgaca aggacgtcga cattatggtc cgcgatggtc agctgaccat caaggccgag 240
cgcaccgagc agaaggactt cgacggtcgc tcggaattcg cgtacggttc cttcgttcgc 300
acggtgtcgc tgccggtagg tgctgacgag gacgacatta aggccaccta cgacaagggc 360
attcttactg tgtcggtggc ggtttcggaa gggaagccaa ccgaaaagca cattcagatc 420
cggtccacca actga 435

<210> SEQ ID NO 54
<211> LENGTH: 1224
<212> TYPE: DNA
<213> ORGANISM: Mycobacterium tuberculosis

<400> SEQUENCE: 54
atgagtggac gccaccgtaa gcccaccaca tccaacgtca gcgtcgccaa gatcgccttt 60
accggcgcag tactcggtgg cggcggcatc gccatggccg ctcaggcgac cgcggccacc 120
gacggggaat gggatcaggt ggcccgctgc gagtcgggcg gcaactggtc gatcaacacc 180
ggcaacggtt acctcggtgg cttgcagttc actcaaagca cctgggccgc acatggtggc 240
ggcgagttcg ccccgtcggc tcagctggcc agccgggagc agcagattgc cgtcggtgag 300
cgggtgctgg ccacccaggg tcgcggcgcc tggccggtgt gcggccgcgg gttatcgaac 360
gcaacacccc gcgaagtgct tcccgcttcg gcagcgatgg acgctccgtt ggacgcggcc 420
gcggtcaacg gcgaaccagc accgctggcc ccgccgcccg ccgacccggc gccacccgtg 480
gaacttgccg ctaacgacct gcccgcaccg ctgggtgaac ccctcccggc agctcccgcc 540
gacccggcac cacccgccga cctggcacca cccgcgcccg ccgacgtcgc gccacccgtg 600
gaacttgccg taaacgacct gcccgcaccg ctgggtgaac ccctcccggc agctcccgcc 660
gacccggcac cacccgccga cctggcacca cccgcgcccg ccgacctggc gccacccgcg 720
cccgccgacc tggcgccacc cgcgcccgcc gacctggcac cacccgtgga acttgccgta 780
aacgacctgc ccgcgccgct gggtgaaccc ctcccggcag ctcccgccga actggcgcca 840
cccgccgatc tggcacccgc gtccgccgac ctggcgccac ccgcgcccgc cgacctggcg 900
ccacccgcgc ccgccgaact ggcgccaccc gcgcccgccg acctggcacc acccgctgcg 960
gtgaacgagc aaaccgcgcc gggcgatcag cccgccacag ctccaggcgg cccggttggc 1020
cttgccaccg atttggaact ccccgagccc gacccccaac cagctgacgc accgccgccc 1080
ggcgacgtca ccgaggcgcc cgccgaaacg ccccaagtct cgaacatcgc ctatacgaag 1140
aagctgtggc aggcgattcg ggcccaggac gtctgcggca acgatgcgct ggactcgctc 1200
gcacagccgt acgtcatcgg ctga 1224

<210> SEQ ID NO 55
<211> LENGTH: 1089
<212> TYPE: DNA
<213> ORGANISM: Mycobacterium tuberculosis

<400> SEQUENCE: 55
atgttgcgcc tggtagtcgg tgcgctgctg ctggtgttgg cgttcgccgg tggctatgcg 60
gtcgccgcat gcaaaacggt gacgttgacc gtcgacggaa ccgcgatgcg ggtgaccacg 120
atgaaatcgc gggtgatcga catcgtcgaa gagaacgggt tctcagtcga cgaccgcgac 180
gacctgtatc ccgcggccgg cgtgcaggtc catgacgccg acaccatcgt gctgcggcgt 240
agccgtccgc tgcagatctc gctggatggt cacgacgcta agcaggtgtg gacgaccgcg 300
tcgacggtgg acgaggcgct ggcccaactc gcgatgaccg acacggcgcc ggccgcggct 360
tctcgcgcca gccgcgtccc gctgtccggg atggcgctac cggtcgtcag cgccaagacg 420
gtgcagctca acgacggcgg gttggtgcgc acggtgcact tgccggcccc caatgtcgcg 480
gggctgctga gtgcggccgg cgtgccgctg ttgcaaagcg accacgtggt gcccgccgcg 540
acggccccga tcgtcgaagg catgcagatc caggtgaccc gcaatcggat caagaaggtc 600
accgagcggc tgccgctgcc gccgaacgcg cgtcgtgtcg aggacccgga gatgaacatg 660
agccgggagg tcgtcgaaga cccgggggtt ccggggaccc aggatgtgac gttcgcggta 720
gctgaggtca acggcgtcga gaccggccgt ttgcccgtcg ccaacgtcgt ggtgaccccg 780
gcccacgaag ccgtggtgcg ggtgggcacc aagcccggta ccgaggtgcc cccggtgatc 840
gacggaagca tctgggacgc gatcgccggc tgtgaggccg gtggcaactg ggcgatcaac 900
accggcaacg ggtattacgg tggtgtgcag tttgaccagg gcacctggga ggccaacggc 960
gggctgcggt atgcaccccg cgctgacctc gccacccgcg aagagcagat cgccgttgcc 1020
gaggtgaccc gactgcgtca aggttggggc gcctggccgg tatgtgctgc acgagcgggt 1080
gcgcgctga 1089

<210> SEQ ID NO 56
<211> LENGTH: 531
<212> TYPE: DNA
<213> ORGANISM: Mycobacterium tuberculosis

<400> SEQUENCE: 56
gtgcatcctt tgccggccga ccacggccgg tcgcggtgca atagacaccc gatctcacca 60
ctctctctaa tcggtaacgc ttcggccact tccggcgata tgtcgagcat gacaagaatc 120
gccaagccgc tcatcaagtc cgccatggcc gcaggactcg tcacggcatc catgtcgctc 180
tccaccgccg ttgcccacgc cggtcccagc ccgaactggg acgccgtcgc gcagtgcgaa 240
tccgggggca actgggcggc caacaccgga aacggcaaat acggcggact gcagttcaag 300
ccggccacct gggccgcatt cggcggtgtc ggcaacccag cagctgcctc tcgggaacaa 360
caaatcgcag ttgccaatcg ggttctcgcc gaacagggat tggacgcgtg gccgacgtgc 420
ggcgccgcct ctggccttcc gatcgcactg tggtcgaaac ccgcgcaggg catcaagcaa 480
atcatcaacg agatcatttg ggcaggcatt caggcaagta ttccgcgctg a 531

<210> SEQ ID NO 57
<211> LENGTH: 465
<212> TYPE: DNA

<213> ORGANISM: Mycobacterium tuberculosis

<400> SEQUENCE: 57
atgacaccgg gtttgcttac tactgcgggt gctggccgac cacgtgacag gtgcgccagg 60
atcgtatgca cggtgttcat cgaaaccgcc gttgtcgcga ccatgtttgt cgcgttgttg 120
ggtctgtcca ccatcagctc gaaagccgac gacatcgatt gggacgccat cgcgcaatgc 180
gaatccggcg gcaattgggc ggccaacacc ggtaacgggt tatacggtgg tctgcagatc 240
agccaggcga cgtgggattc caacggtggt gtcgggtcgc cggcggccgc gagtccccag 300
caacagatcg aggtcgcaga caacattatg aaaacccaag gcccgggtgc gtggccgaaa 360
tgtagttctt gtagtcaggg agacgcaccg ctgggctcgc tcacccacat cctgacgttc 420
ctcgcggccg agactggagg ttgttcgggg agcagggacg attga 465

<210> SEQ ID NO 58
<211> LENGTH: 519
<212> TYPE: DNA
<213> ORGANISM: Mycobacterium tuberculosis

<400> SEQUENCE: 58
ttgaagaacg cccgtacgac gctcatcgcc gccgcgattg ccgggacgtt ggtgaccacg 60
tcaccagccg gtatcgccaa tgccgacgac gcgggcttgg acccaaacgc cgcagccggc 120
ccggatgccg tgggctttga cccgaacctg ccgccggccc cggacgctgc acccgtcgat 180
actccgccgg ctccggagga cgcgggcttt gatcccaacc tccccccgcc gctggccccg 240
gacttcctgt ccccgcctgc ggaggaagcg cctcccgtgc ccgtggccta cagcgtgaac 300
tgggacgcga tcgcgcagtg cgagtccggt ggaaactggt cgatcaacac cggtaacggt 360
tactacggcg gcctgcggtt caccgccggc acctggcgtg ccaacggtgg ctcggggtcc 420
gcggccaacg cgagccggga ggagcagatc cgggtggctg agaacgtgct gcgttcgcag 480
ggtatccgcg cctggccggt ctgcggccgc cgcggctga 519

<210> SEQ ID NO 59
<211> LENGTH: 633
<212> TYPE: DNA
<213> ORGANISM: Mycobacterium tuberculosis

<400> SEQUENCE: 59
atgatcgcca caacccgcga tcgtgaagga gccaccatga tcacgtttag gctgcgcttg 60
ccgtgccgga cgatactgcg ggtgttcagc cgcaatccgc tggtgcgtgg gacggatcga 120
ctcgaggcgg tcgtcatgct gctggccgtc acggtctcgc tgctgactat cccgttcgcc 180
gccgcggccg gcaccgcagt ccaggattcc cgcagccacg tctatgccca ccaggcccag 240
acccgccatc ccgcaaccgc gaccgtgatc gatcacgagg gggtgatcga cagcaacacg 300
accgccacgt cagcgccgcc gcgcacgaag atcaccgtgc ctgcccgatg ggtcgtgaac 360
ggaatagaac gcagcggtga ggtcaacgcg aagccgggaa ccaaatccgg tgaccgcgtc 420
ggcatttggg tcgacagtgc cggtcagctg gtcgatgaac cagctccgcc ggcccgtgcc 480
attgcggatg cggccctggc cgccttggga ctctggttga gcgtcgccgc ggttgcgggc 540
gccctgctgg cgctcactcg ggcgattctg atccgcgttc gcaacgccag ttggcaacac 600
gacatcgaca gcctgttctg cacgcagcgg tga 633

<210> SEQ ID NO 60
<211> LENGTH: 1020

<212> TYPE: DNA
<213> ORGANISM: Mycobacterium tuberculosis

<400> SEQUENCE: 60
atgacggagc cagcggcgtg ggacgaaggc aagccgcgaa tcatcacttt gaccatgaac 60
cccgccttgg acatcacgac gagcgtcgac gtggtgcgcc cgaccgagaa aatgcgttgt 120
ggcgcacctc gctacgatcc cggcggcggc ggtatcaatg tcgcccgcat tgtgcatgtc 180
ctcggcggtt gctcgacagc actgttcccg gccggcgggt cgaccgggag cctgctgatg 240
gcgctgctcg gtgatgcggg agtgccattt cgcgtcattc cgatcgcggc ctcgacgcgg 300
gagagcttca cggtcaacga gtccaggacc gccaagcagt atcgtttcgt gcttccgggg 360
ccgtcgctga ccgtcgcgga gcaggagcaa tgcctcgacg aactgcgcgg tgcggcggct 420
tcggccgcct ttgtggtggc cagtggcagc ctgccgccag gtgtggctgc cgactactat 480
cagcgggttg ccgacatctg ccgccgatcg agcactccgc tgatcctgga tacatctggt 540
ggcgggttgc agcacatttc gtccggggtg tttcttctca aggcgagcgt gcgggaactg 600
cgcgagtgcg tcggatccga actgctgacc gagcccgaac aactggccgc cgcacacgaa 660
ctcattgacc gtgggcgcgc cgaggtcgtg gtggtctcgc ttggatctca gggcgcgcta 720
ttggccacac gacatgcgag ccatcgattt tcgtcgattc cgatgaccgc ggttagcggt 780
gtcggcgccg gcgacgcgat ggtggccgcg attaccgtgg gcctcagccg tggctggtcg 840
ctcatcaagt ccgttcgctt gggaaacgcg gcaggtgcag ccatgctgct gacgccaggc 900
accgcggcct gcaatcgcga cgatgtggag aggttcttcg agctggcggc cgaacccacc 960
gaagtcgggc aggatcaata cgtttggcac ccgatcgtta acccggaagc ctcgccatga 1020

<210> SEQ ID NO 61
<211> LENGTH: 996
<212> TYPE: DNA
<213> ORGANISM: Mycobacterium tuberculosis

<400> SEQUENCE: 61
atgccggaca ccatggtgac caccgatgtc atcaagagcg cggtgcagtt ggcctgccgc 60
gcaccgtcgc tccacaacag ccagccctgg cgctggatag ccgaggacca cacggttgcg 120
ctgttcctcg acaaggatcg ggtgctttac gcgaccgacc actccggccg ggaagcgctg 180
ctggggtgcg gcgccgtact cgaccacttt cgggtggcga tggcggccgc gggtaccacc 240
gccaatgtgg aacggtttcc caaccccaac gatcctttgc atctggcgtc aattgacttc 300
agcccggccg atttcgtcac cgagggccac cgtctaaggg cggatgcgat cctactgcgc 360
cgtaccgacc ggctgccttt cgccgagccg ccggattggg acttggtgga gtcgcagttg 420
cgcacgaccg tcaccgccga cacggtgcgc atcgacgtca tcgccgacga tatgcgtccc 480
gaactggcgg cggcgtccaa actcaccgaa tcgctgcggc tctacgattc gtcgtatcat 540
gccgaactct tttggtggac aggggctttt gagacttctg agggcatacc gcacagttca 600
ttggtatcgg cggccgaaag tgaccgggtc accttcggac gcgacttccc ggtcgtcgcc 660
aacaccgata ggcgcccgga gtttggccac gaccgctcta aggtcctggt gctctccacc 720
tacgacaacg aacgcgccag cctactgcgc tgcggcgaga tgctttccgc cgtattgctt 780
gacgccacca tggctgggct tgccacctgc acgctgaccc acatcaccga actgcacgcc 840
agccgagacc tggtcgcagc gctgattggg cagcccgcaa ctccgcaagc cttggttcgc 900
gtcggtctgg ccccggagat ggaagagccg ccaccggcaa cgcctcggcg accaatcgat 960

-continued gaagtgtttc acgttcgggc taaggatcac cggtag 996

<210> SEQ ID NO 62
<211> LENGTH: 432
<212> TYPE: DNA
<213> ORGANISM: Mycobacterium tuberculosis

<400> SEQUENCE: 62
atgaccaccg cacgcgacat catgaacgca ggtgtgacct gtgttggcga acacgagacg 60
ctaaccgctg ccgctcaata catgcgtgag cacgacatcg gcgcgttgcc gatctgcggg 120
gacgacgacc ggctgcacgg catgctcacc gaccgcgaca ttgtgatcaa aggcctggct 180
gcgggcctag acccgaatac cgccacggct ggcgagttgg cccgggacag catctactac 240
gtcgatgcga acgcaagcat ccaggagatg ctcaacgtca tggaagaaca tcaggtccgc 300
cgtgttccgg tcatctcaga gcaccgcttg gtcggaatcg tcaccgaagc cgacatcgcc 360
cgacacctgc ccgagcacgc cattgtgcag ttcgtcaagg caatctgctc gcccatggcc 420
ctcgccagct ag 432

<210> SEQ ID NO 63
<211> LENGTH: 1242
<212> TYPE: DNA
<213> ORGANISM: Mycobacterium tuberculosis

<400> SEQUENCE: 63
atggcaagtt ctgcgagcga cggcacccac gaacgctcgg cttttcgcct gagtccaccg 60
gtcttgagcg gcgccatggg accgttcatg cacaccggtc tgtacgtcgc tcaatcgtgg 120
cgcgactatc tgggtcaaca gcccgataaa ctgccgatcg cacggcccac tattgcctta 180
gcggcgcaag cctttcgaga cgaaatcgtc ctgctgggcc tcaaggcacg acgtccggtc 240
agcaatcatc gagtgttcga gcgcatcagc caagaagtgg ccgctggact ggagttctat 300
gggaatcgca gatggctgga gaagcctagc ggattttttg cccagccccc accgctcacc 360
gaggtcgcgg tccgaaaggt caaggaccgc agacgctcct tttatcgcat cttcttcgac 420
agtgggttta cgccgcatcc gggtgaaccg ggcagccaac ggtggctctc atacactgcg 480
aacaatcgcg agtacgccct gttactgcgg cacccagagc cgcgtccctg gctggtttgt 540
gtacacggca ccgagatggg cagggccccg ttggatctcg cggtgttccg cgcctggaag 600
ctgcatgacg aactcggcct gaacattgtc atgccggttc ttccgatgca tggtccccgc 660
gggcaaggtc tgccgaaggg cgccgttttt cccggagaag atgttctcga cgatgtgcat 720
gggacggctc aagcggtgtg ggatatccgg cggctgttgt cctggatacg atcgcaggag 780
gaggagtcgc tgatcgggtt gaacggtctc tcgctgggcg gctacatcgc gtcattggtc 840
gccagcctcg aagaaggtct cgcctgcgcg attctcggtg tcccagtggc tgatctgatc 900
gagttgttgg gccgccactg cggtcttcgg cacaaagacc cccgccgcca caccgtcaag 960
atggccgaac cgatcggccg aatgatctcg ccgctctcac ttacgccact ggtgcccatg 1020
ccgggccgct ttatctacgc gggcattgcc gaccgactcg tgcatccacg cgaacaggtg 1080
actcgcctct gggagcactg gggcaaaccc gaaatcgtgt ggtatccagg cggtcacact 1140
ggcttcttcc agtcgcggcc ggtacgacgg tttgtccagg ctgcgctgga gcagtcgggc 1200
ctgttggacg cgccacggac acagcgcgac cgttccgcct aa 1242

<210> SEQ ID NO 64
<211> LENGTH: 363

<212> TYPE: DNA
<213> ORGANISM: Mycobacterium tuberculosis

<400> SEQUENCE: 64
atgtccacgc aacgaccgag gcactccggt attcgggctg ttggccccta cgcatgggcc 60
ggccgatgtg gtcggatagg caggtggggg gtgcaccagg aggcgatgat gaatctagcg 120
atatggcacc cgcgcaaggt gcaatccgcc accatctatc aggtgaccga tcgctcgcac 180
gacgggcgca cagcacgggt gcctggtgac gagatcacta gcaccgtgtc cggttggttg 240
tcggagttgg gcacccaaag cccgttggcc gatgagcttg cgcgtgcggt gcggatcggc 300
gactggcccg ctgcgtacgc aatcggtgag cacctgtccg ttgagattgc cgttgcggtc 360
taa 363

<210> SEQ ID NO 65
<211> LENGTH: 399
<212> TYPE: PRT
<213> ORGANISM: Mycobacterium tuberculosis

<400> SEQUENCE: 65

Leu Asp Phe Ala Thr Leu Pro Pro Glu Ile Asn Ser Ala Arg Met Tyr
1               5                   10                  15

Ser Gly Ala Gly Ser Ala Pro Met Leu Ala Ala Ala Ser Ala Trp His
            20                  25                  30

Gly Leu Ser Ala Glu Leu Arg Ala Ser Ala Leu Ser Tyr Ser Ser Val
        35                  40                  45

Leu Ser Thr Leu Thr Gly Glu Glu Trp His Gly Pro Ala Ser Ala Ser
    50                  55                  60

Met Thr Ala Ala Ala Ala Pro Tyr Val Ala Trp Met Ser Val Thr Ala
65                  70                  75                  80

Val Arg Ala Glu Gln Ala Gly Ala Gln Ala Glu Ala Ala Ala Ala Ala
                85                  90                  95

Tyr Glu Ala Ala Phe Ala Ala Thr Val Pro Pro Pro Val Ile Glu Ala
            100                 105                 110

Asn Arg Ala Gln Leu Met Ala Leu Ile Ala Thr Asn Val Leu Gly Gln
        115                 120                 125

Asn Ala Pro Ala Ile Ala Ala Thr Glu Ala Gln Tyr Ala Glu Met Trp
    130                 135                 140

Ser Gln Asp Ala Met Ala Met Tyr Gly Tyr Ala Gly Ala Ser Ala Ala
145                 150                 155                 160

Ala Thr Gln Leu Thr Pro Phe Thr Glu Pro Val Gln Thr Thr Asn Ala
                165                 170                 175

Ser Gly Leu Ala Ala Gln Ser Ala Ala Ile Ala His Ala Thr Gly Ala
            180                 185                 190

Ser Ala Gly Ala Gln Gln Thr Thr Leu Ser Gln Leu Ile Ala Ala Ile
        195                 200                 205

Pro Ser Val Leu Gln Gly Leu Ser Ser Ser Thr Ala Ala Thr Phe Ala
    210                 215                 220

Ser Gly Pro Ser Gly Leu Leu Gly Ile Val Gly Ser Gly Ser Ser Trp
225                 230                 235                 240

Leu Asp Lys Leu Trp Ala Leu Leu Asp Pro Asn Ser Asn Phe Trp Asn
                245                 250                 255

Thr Ile Ala Ser Ser Gly Leu Phe Leu Pro Ser Asn Thr Ile Ala Pro
            260                 265                 270

Phe Leu Gly Leu Leu Gly Gly Val Ala Ala Ala Asp Ala Ala Gly Asp

-continued

```
        275                 280                 285

Val Leu Gly Glu Ala Thr Ser Gly Gly Leu Gly Gly Ala Leu Val Ala
    290                 295                 300

Pro Leu Gly Ser Ala Gly Gly Leu Gly Gly Thr Val Ala Ala Gly Leu
305                 310                 315                 320

Gly Asn Ala Ala Thr Val Gly Thr Leu Ser Val Pro Pro Ser Trp Thr
                325                 330                 335

Ala Ala Ala Pro Leu Ala Ser Pro Leu Gly Ser Ala Leu Gly Gly Thr
            340                 345                 350

Pro Met Val Ala Pro Pro Pro Ala Val Ala Ala Gly Met Pro Gly Met
        355                 360                 365

Pro Phe Gly Thr Met Gly Gly Gln Gly Phe Gly Arg Ala Val Pro Gln
    370                 375                 380

Tyr Gly Phe Arg Pro Asn Phe Val Ala Arg Pro Pro Ala Ala Gly
385                 390                 395
```